US012668818B2

(12) United States Patent
Owens et al.

(10) Patent No.: US 12,668,818 B2
(45) Date of Patent: Jun. 30, 2026

(54) MUSCLE-SPECIFIC EXPRESSION CASSETTES

(71) Applicant: Precision BioSciences, Inc., Durham, NC (US)

(72) Inventors: Gary Owens, Durham, NC (US); Matt Jordan-Steele, Durham, NC (US)

(73) Assignee: Precision BioSciences, Inc., Durham, NC (US)

( * ) Notice: Subject to any disclaimer, the term of this patent is extended or adjusted under 35 U.S.C. 154(b) by 0 days.

(21) Appl. No.: 19/355,669

(22) Filed: Oct. 10, 2025

(65) Prior Publication Data

US 2026/0078408 A1 Mar. 19, 2026

Related U.S. Application Data

(63) Continuation of application No. PCT/US2024/024385, filed on Apr. 12, 2024.

(60) Provisional application No. 63/503,337, filed on May 19, 2023, provisional application No. 63/496,114, filed on Apr. 14, 2023.

(51) Int. Cl.
*C12N 15/86* (2006.01)
*A61K 48/00* (2006.01)

(52) U.S. Cl.
CPC .......... *C12N 15/86* (2013.01); *A61K 48/0058* (2013.01); *C12N 2750/14143* (2013.01); *C12N 2830/008* (2013.01)

(58) Field of Classification Search
None
See application file for complete search history.

(56) References Cited

FOREIGN PATENT DOCUMENTS

| WO | WO 2017/072590 A1 | 5/2017 |
| WO | WO 2022/056291 A1 | 3/2022 |
| WO | WO 02/29056 A2 | 4/2022 |
| WO | WO 2022/104062 A1 | 5/2022 |
| WO | WO 2022/216988 A2 | 10/2022 |

*Primary Examiner* — Peter Paras, Jr.
*Assistant Examiner* — Khoa Nhat Tran
(74) *Attorney, Agent, or Firm* — Womble Bond Dickinson (US) LLP

(57) ABSTRACT

The present disclosure encompasses nucleic acid expression constructs that regulate the expression of a heterologous protein specifically in muscle tissues (e.g., skeletal muscle and cardiac muscle tissue). In particular embodiments of the disclosure, muscle-specific expression constructs are described that encode a heterologous protein. These heterologous proteins can be any protein that is desired to be expressed in a muscle cell. In particular embodiments of the disclosure, proteins are described for the treatment of Duchenne Muscular Dystrophy (e.g., engineered nucleases such as engineered meganucleases).

4 Claims, 37 Drawing Sheets

Specification includes a Sequence Listing.

Meganuclease Expression (MSD)
MHCK7 vs  tMCK AAV9

- MHCK7 AAV9 1e14
- tMCK AAV9 1e14
- PBS

Meganuclease Expression (MSD)
MHCK7 vs  tMCK AAVrh74

- MHCK7 AAVrh74 1e14
- tMCK AAVrh74 1e14
- PBS

Dystrophin Restortation (WES)
MHCK7 vs tMCK AAV9

- MHCK7 AAV9 1e14
- tMCK AAV9 1e14
- PBS

Dystrophin Restoration (WES)
MHCK7 vs tMCK AAVrh74

- MHCK7 AAVrh74 1e14
- tMCK AAVrh74 1e14
- PBS

Total Ligation in Liver with Various Promoters

Table 3: Potential Group Associated Heart Lesions

| | Group | | | | | | | | | | |
|---|---|---|---|---|---|---|---|---|---|---|---|
| | 1 | 2 | 3 | 4 | 5 | 6 | 7 | 8 | 9 | 10 | 11 |
| *Number examined* | 3 | 3 | 3 | 3 | 3 | 3 | 3 | 3 | 3 | 3 | 3 |
| Necrosis/inflammatory cell infiltrate, cardiomyocyte | 3 | 3 | 3 | 1 | 0 | 0 | 1 | 0 | 2 | 3 | 2 |
| Minimal | 0 | 0 | 3 | 1 | 0 | 0 | 1 | 0 | 1 | 1 | 1 |
| Mild | 0 | 0 | 0 | 0 | 0 | 0 | 0 | 0 | 1 | 2 | 1 |
| Moderate | 0 | 0 | 0 | 0 | 0 | 0 | 0 | 0 | 0 | 0 | 0 |
| Marked | 3 | 3 | 0 | 0 | 0 | 0 | 0 | 0 | 0 | 0 | 0 |
| Vacuolation, cardiomyocyte | 3 | 3 | 3 | 1 | 0 | 0 | 0 | 0 | 2 | 1 | 1 |
| Minimal | 0 | 1 | 3 | 1 | 0 | 0 | 0 | 0 | 2 | 1 | 1 |
| Mild | 3 | 2 | 0 | 0 | 0 | 0 | 0 | 0 | 0 | 0 | 0 |
| | | | | | | | | | | | |
| *Number examined** | 3 | 3 | 2 | 1 | 3 | 1 | 2 | 3 | 2 | 2 | 2 |
| Inflammatory cell infiltrate, acute, atria | 3 | 3 | 0 | 0 | 0 | 0 | 0 | 0 | 0 | 0 | 0 |
| Minimal | 2 | 2 | 0 | 0 | 0 | 0 | 0 | 0 | 0 | 0 | 0 |
| Mild | 1 | 1 | 0 | 0 | 0 | 0 | 0 | 0 | 0 | 0 | 0 |
| Atrial Thrombus** | 0 | 1 | 0 | 0 | 0 | 0 | 0 | 0 | 0 | 0 | 0 |

* atria not present on all submitted slides; **atrial thrombus scored as present/not present

FIGURE 7

Quadricep Dystrophin Restoration (WES)

Tibialis Anterior Dystrophin Restoration (WES)

Heart Total Ligation (ddPCR)

Diaphragm Total Ligation (ddPCR)

Quadricep meganuclease Expression (MSD)

Heart meganuclease Expression (MSD)

Gastrocnemius meganuclease Expression (MSD)

Diaphragm meganuclease Expression (MSD)

Tibialis Anterior meganuclease Expression (MSD)

Liver meganuclease Expression (MSD)

Quadricep Total Ligation (ddPCR)

Gastrocnemius Total Ligation (ddPCR)

Heart Total Ligation (ddPCR)

Tibialis Anterior Total Ligation (ddPCR)

Diaphragm Total Ligation (ddPCR)

Liver Total Ligation (ddPCR)

Quadricep Dystrophin Restoration (WES)

Gastrocnemius Dystrophin Restoration (WES)

Heart Dystrophin Restoration (WES)

Tibialis Anterior Dystrophin Restoration (WES)

Quadricep Total Ligation (ddPCR)

Gastrocnemius Total Ligation (ddPCR)

Heart Total Ligation (ddPCR)

Tibialis Anterior Total Ligation (ddPCR)

Quadricep Dystrophin Restoration (WES)

Gastrocnemius Dystrophin Restoration (WES)

Heart Dystrophin Restoration (WES)

Tibialis Anterior Dystrophin Restoration (WES)

Quadricep Dystrophin Restoration (WES)

Heart Dystrophin Restoration (WES)

Diaphragm Dystrophin Restoration (WES)

Gastrocnemius Dystrophin Restoration (WES)

- B-301
- MTF1
- SPDEF1
- Enhancer F
- Enhancer G
- Enhancer I
- MHCK7

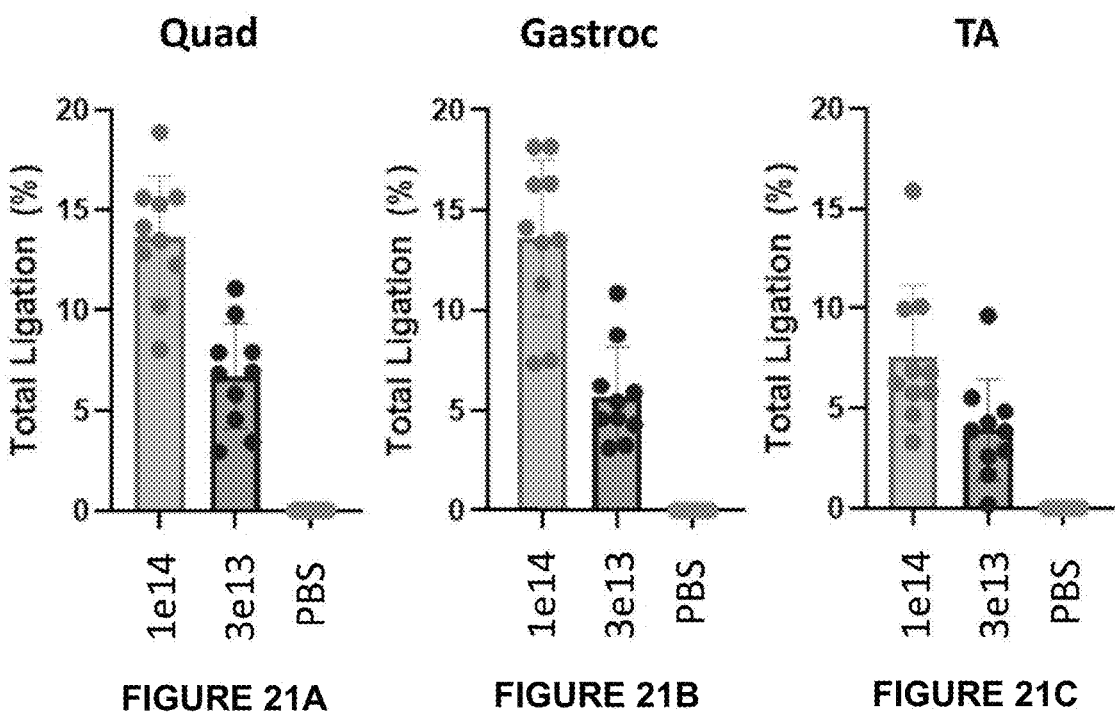
FIGURE 21A     FIGURE 21B     FIGURE 21C
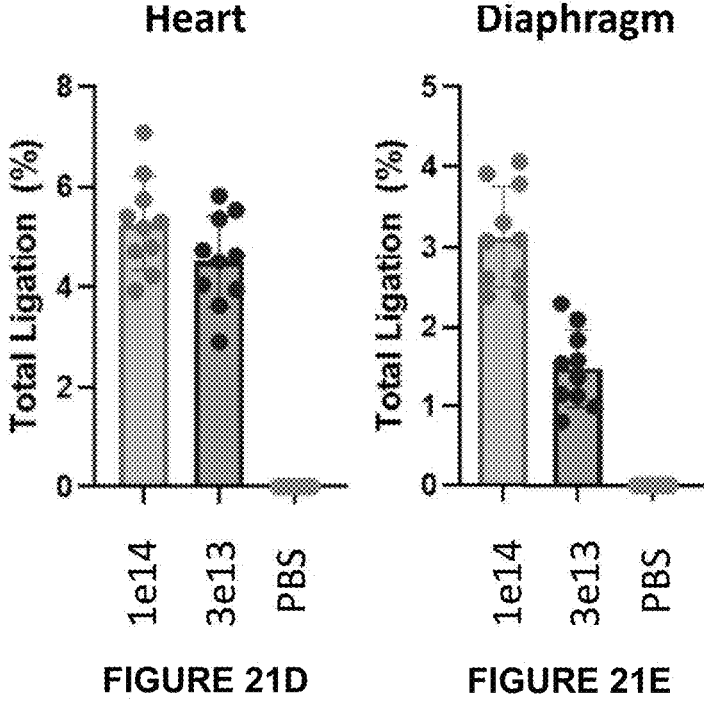
FIGURE 21D     FIGURE 21E

Brain

Liver

Lung

MUSCLE-SPECIFIC EXPRESSION CASSETTES

CROSS-REFERENCE TO RELATED APPLICATIONS

This application is a continuation of International Application No. PCT/US2024/024385, filed Apr. 12, 2024, which was published by the International Bureau in English on Oct. 17, 2024, and which claims priority to U.S. Provisional Application No. 63/496,114, filed Apr. 14, 2023, and U.S. Provisional Application No. 63/503,337, filed May 19, 2023, the disclosures of which are incorporated herein by referenced in their entirety.

TECHNICAL FIELD

The disclosure relates to the field of molecular biology and recombinant nucleic acid technology. In particular aspects, the disclosure relates to expression constructs that regulate the expression of a heterologous protein in muscle tissues (e.g., skeletal muscle and cardiac muscle tissue). Such muscle-specific expression constructs are useful for the expression of a heterologous protein, such as engineered nucleases, for the treatment of muscle disorders (e.g., Duchenne Muscular Dystrophy).

REFERENCE TO A SEQUENCE LISTING SUBMITTED AS AN XML (ST.26) FILE VIA USPTO PATENT CENTER

The instant application contains a Sequence Listing which has been submitted in xml (ST.26) format via USPTO Patent Center and is hereby incorporated by reference in its entirety. Said xml (ST.26) copy, created on Apr. 11, 2024, is named "PBIO-074PCTSeqList.xml" and is 186,779 bytes in size.

BACKGROUND

Gene therapy is a potentially curative approach to muscular disorders having known gene mutations. However, to date, gene therapy approaches have been unsuccessful due to difficulty in delivering and expressing therapeutic proteins in muscle tissue in vivo. One such muscular disorder, Duchenne Muscular Dystrophy (DMD) is a rare, X-linked muscle degenerative disorder that affects about 1 in every 3500 boys worldwide. The disease is caused by mutations in the dystrophin gene, which is the largest known gene. The dystrophin gene spans 2.2 Mb of the X chromosome and encodes predominantly a 14-kb transcript derived from 79 exons. The full-length dystrophin protein, as expressed in skeletal muscle, smooth muscle, and cardiac muscle, is 3685 amino acids and has a molecular weight of 427 kD. The severe Duchenne phenotype is generally associated with the loss of full-length dystrophin protein from skeletal and cardiac muscle, which leads to debilitating muscle degeneration and, ultimately, heart failure. A large number of different dystrophin gene mutations have been described, many of them resulting in either the severe DMD or the milder Becker Muscular Dystrophy.

There are several gene therapy strategies being pursued for the treatment of DMD, which involve the expression of a heterologous protein specifically in muscle tissue. One strategy involves "gene replacement" (Oshima et al. (2009) *J. Am. Soc. Gene Ther.* 17:73-80; Liu et al. (2005) *Mol. Ther.* 11:245-56; Lai et al. (2006) *Hum Gene Ther.* 17:1036-42;

Odom et al. (2008) *Mol. Ther.* 16:1539-45). This approach involves delivering a functional copy of the dystrophin gene such as "micro dystrophin" to patients using a viral delivery vector, typically adeno-associated virus (AAV).

Another strategy involves "gene editing," which includes correcting gene expression at the level of the genomic DNA or causing an exon skipping such that the deleterious mutations (e.g., an out of frame exon) of the DMD gene are not present in the mRNA. These approaches utilize engineered nucleases to either excise portions of the mutated dystrophin gene or edit individual portions of the gene. Such engineered nucleases include the clustered regularly interspaced short palindromic repeats (CRISPR) Cas9 enzyme, Transcription activator-like effector nucleases (TALENs) and zinc-finger nucleases (ZFNs), engineered meganucleases, CRISPR Cas9 base editors, and CRISPR Cas9 prime editors. (Erkut and Yokota (2022) *Int J Mol Sci* 23:3). Another approach is utilizing multiple meganucleases to excise specific exons from the dystrophin coding sequence. This strategy is described in PCT International Patent Application Publication No. WO/2022/104062.

Each of these gene therapy strategies requires the expression of a heterologous protein in a patient. In the case of DMD, the therapeutic heterologous protein must be expressed in muscle tissues to have any therapeutic effect. Indeed, in the case of gene editing, the expression of engineered nucleases proteins must be carefully controlled to muscle tissue in which the gene editing is desired. Such muscle tissue tropism can be affected by utilizing muscle tissue tropic AAVs. A secondary level of expression control can arise from the use of tissue specific promoters. However, prior to the present disclosure, precise control of expression of heterologous genes in muscle tissue has not been adequately achieved to result in therapeutically relevant muscle protein expression levels.

BRIEF SUMMARY

The present disclosure provides muscle-specific expression cassettes that specifically regulate gene expression to muscle tissues including skeletal and cardiac muscle tissues for treating muscle disorders. In particular embodiments, muscle-specific cassettes are described that encode engineered nucleases (e.g., engineered meganucleases) that bind and cleave recognition sequences in a dystrophin gene (e.g., a human dystrophin gene), as well as compositions comprising such engineered nucleases and methods of their use. In some embodiments disclosed herein are muscle-specific expression cassettes that encode pairs of engineered nucleases (e.g., engineered meganucleases) are used to remove multiple exons from a dystrophin gene by generating a first cleavage site in an intron upstream of a first exon and a second cleavage site in an intron downstream of a second exon. In particular examples described herein, the first cleavage site is generated in the intron 5' upstream of exon 45 of the dystrophin gene, while the second cleavage site is generated in the intron 3' downstream of exon 55. This process allows for excision and removal of exons 45-55 from the dystrophin gene following annealment of the two cleavage sites and repair of the genome. The recognition sequences targeted by the disclosed engineered meganucleases are selected to have identical four basepair center sequences, such that the first and second cleavage sites will have complementary four basepair 3' overhangs that can perfectly ligate to one another (i.e., each basepair of one overhang pairs with its complement on the other overhang). By removing exons 45-55 from a mutant dystrophin gene that lacks one or more of these exons, this approach results in a restoration of the normal (i.e., wild-type) reading frame of the dystrophin gene. Cells so treated will express a shortened modified form of the dystrophin protein in which a portion of the central spectrin repeat domain is absent but the amino (N)- and carboxy (C)-terminal domains are intact. This will, in many cases, reduce the severity of the disease. In some cases, it will result in a milder Becker phenotype. Although specific embodiments and examples disclosed herein relate to the above-described strategy for treatment of DMD, it is envisioned that these muscle-specific expression cassettes can be useful for treatment of any muscle disorder where expression of a heterologous transgene is desired in the muscle tissue. Specific embodiments of the disclosure are provided and summarized below.

Accordingly, one aspect of the disclosure described herein is a muscle-specific expression cassette comprising a nucleic acid sequence encoding a heterologous protein operably linked to a muscle-specific promoter. In some embodiments described herein, the muscle-specific promoter is a muscle creatine kinase (MCK) promoter.

In some embodiments, the muscle-specific expression cassette described herein comprises a muscle-specific enhancer. In some embodiments, the muscle-specific expression cassette described herein comprises a Kozak sequence. In some embodiments, the muscle-specific expression cassette described herein comprises a post transcriptional regulatory element. In some embodiments, the post transcriptional regulatory element comprises a Woodchuck Hepatitis virus post-transcriptional regulatory element (WPRE).

In some embodiments of the muscle-specific expression cassette described herein the muscle-specific enhancer comprises a nucleic acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 1. In some embodiments the muscle-specific enhancer comprises a nucleic acid sequence according to a sequence set forth in SEQ ID NO: 1.

In some embodiments of the muscle-specific expression cassette described herein, the MCK promoter is a truncated MCK (tMCK) promoter. In some embodiments, the tMCK promoter comprises a basal promoter and one or more MCK enhancer elements. In some embodiments, the basal promoter comprises a nucleic acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 3. In some embodiments, the basal promoter comprises a nucleic acid sequence according to a sequence set forth in SEQ ID NO: 3.

In some embodiments of the muscle-specific expression cassette described herein, the MCK enhancer element comprises a MCK-R control element. In some embodiments, the MCK enhancer element comprises two MCK-R control elements. In some embodiments, the MCK-R control element comprises a nucleic acid sequence according to a sequence set forth in any one of SEQ ID NOs: 4-17.

In some embodiments of the muscle-specific expression cassette described herein the MCK enhancer element comprises a nucleic acid sequence having at least at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 21. In some embodiments, the MCK enhancer element comprises a nucleic acid sequence according to a sequence set forth in SEQ ID NO: 21.

In some embodiments of the muscle-specific expression cassette described herein, the MCK promoter is a tMCK promoter comprising three MCK enhancer elements.

In some embodiments of the muscle-specific expression cassette described herein, the MCK promoter is a tMCK promoter comprising a nucleic acid sequence having at least at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 22. In some embodiments, the MCK promoter is a tMCK promoter comprising a nucleic acid sequence according to a sequence set forth in SEQ ID NO: 22.

In some embodiments of the muscle-specific expression cassette described herein the heterologous protein is a nucleoprotein. In some embodiments, the heterologous protein comprises a nuclear localization sequence (NLS). In some embodiments, the NLS is positioned at the N-terminus of the heterologous protein. In some embodiments, the NLS is positioned at the C-terminus of the heterologous protein. In some embodiments, the heterologous protein comprises a first NLS at the N-terminus and a second NLS at the C-terminus of the heterologous protein. In some embodiments, the first NLS and the second NLS are identical. In some embodiments, the first NLS and the second NLS are not identical. In some embodiments, the NLS comprises an SV40 NLS, a c-myc NLS or an NLS5 NLS. In some embodiments, the NLS comprises an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in any one of SEQ ID NOs: 25-28. In some embodiments, the NLS comprises an amino acid sequence according to a sequence set forth in any one of SEQ ID NOs: 25-28.

In some embodiments, the SV40 NLS sequence comprises a nucleic acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 106. In some embodiments, the SV40 NLS sequence comprises a nucleic acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 107.

In some embodiments, the c-myc NLS sequence comprises a nucleic acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 108. In some embodiments, the c-myc NLS sequence comprises a nucleic acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 109.

In some embodiments, the SV40 NLS sequence comprises a nucleic acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 110. In some embodiments, the SV40 NLS sequence comprises a nucleic acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 111.

In some embodiments, the c-myc NLS sequence comprises a nucleic acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 112. In some embodiments, the c-myc NLS sequence comprises a nucleic acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 113.

In some embodiments of the muscle-specific expression cassette described herein, the expression cassette comprises a first nucleic acid sequence encoding a first heterologous protein and a second nucleic acid sequence encoding a second heterologous protein. In some embodiments, the first nucleic acid sequence and the second nucleic acid sequence are separated by an IRES or 2A sequence. In some embodiments, the 2A sequence further comprises a furin cleavage motif and a GSG linker sequence. In some embodiments, the 2A sequence is a T2A, P2A, E2A, or F2A sequence. In some embodiments, the 2A sequence further comprises a furin cleavage motif and a GSG linker sequence that comprises an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 103. In some embodiments, the 2A sequence comprising a furin cleavage motif and a GSG linker sequence comprises a nucleic acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 104. In some embodiments, the 2A sequence comprising a furin cleavage motif and a GSG linker sequence comprises a nucleic acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 105. In some embodiments, the heterologous protein is an engineered nuclease. In some embodiments, the first heterologous protein and the second heterologous protein are an engineered nuclease. In some embodiments, the engineered nuclease is an engineered meganuclease, a TALEN, a zinc finger nuclease, a CRISPR system nuclease, a compact TALEN, a megaTAL, a base editor, or a prime editor. In some embodiments, the engineered nuclease is an engineered meganuclease. In some embodiments, the engineered meganuclease comprises an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in any one of SEQ ID NOs: 43-59. In some embodiments, the engineered meganuclease comprises an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 50. In some embodiments, the engineered meganuclease comprises an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 58. In some embodiments, the engineered meganuclease comprises an amino acid sequence according to a sequence set forth in any one of SEQ ID NOs: 43-59. In some embodiments, the engineered meganuclease comprises an amino acid sequence according to a sequence set forth in SEQ ID NO: 50. In some embodiments, the engineered meganuclease comprises an amino acid sequence according to a sequence set forth in SEQ ID NO: 58. In some embodiments, the first heterologous protein is an engineered meganuclease comprising a nucleic acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 99 or 100. In some embodiments, the second heterologous protein is an engineered meganuclease comprising a nucleic acid sequence having at least at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 99 or 100. In some embodiments, the first heterologous protein is an engineered meganuclease comprising a nucleic acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 99. In some embodiments, the first heterologous protein is an engineered meganuclease comprising a nucleic acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 100. In some embodiments, the second heterologous protein is an engineered meganuclease comprising a nucleic acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 99. In some embodiments, the second heterologous protein is an engineered meganuclease comprising a nucleic acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 100.

In some embodiments, the first heterologous protein is an engineered meganuclease comprising a nucleic acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 101 or 102. In some embodiments, the second heterologous protein is an engineered meganuclease comprising a nucleic acid sequence having at least at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 101 or 102. In some embodiments, the first heterologous protein is an engineered meganuclease comprising a nucleic acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 101. In some embodiments, the first heterologous protein is an engineered meganuclease comprising a nucleic acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 102. In some embodiments, the second heterologous protein is an engineered meganuclease comprising a nucleic acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 101. In some embodiments, the second heterologous protein is an engineered meganuclease comprising a nucleic acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 102.

In some embodiments of the muscle-specific expression cassette described herein, the expression cassette comprises a SV40 polyadenylation signal sequence that comprises a nucleic acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 114. In some embodiments of the muscle-specific expression cassette described herein comprises from 5' to 3': a) a tMCK promoter according to a sequence set forth in SEQ ID NO: 22, b) a Kozak sequence, c) a first nucleic acid sequence encoding a first heterologous protein, d) a 2A sequence, e) a second nucleic acid sequence encoding a second heterologous protein, and f) a WPRE sequence.

In some embodiments, the first heterologous protein is an engineered nuclease. In some embodiments, the second heterologous protein is an engineered nuclease. In some embodiments, the engineered nuclease is an engineered meganuclease, a TALEN, a zinc finger nuclease, a CRISPR system nuclease, a compact TALEN, a megaTAL, a base editor, or a prime editor.

In some embodiments, the first heterologous protein is an engineered meganuclease. In some embodiments, the second heterologous protein is an engineered meganuclease.

In some embodiments, the first heterologous protein is an engineered meganuclease comprising an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to any one of SEQ ID NOs: 43-51 or SEQ ID NOs: 52-59. In some embodiments, the first heterologous protein is an engineered meganuclease comprising an amino acid sequence according to any one of SEQ ID NOs: 43-51 or SEQ ID NOs: 52-59. In some embodiments, the second heterologous protein is an engineered meganuclease comprising an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to any one of SEQ ID NOs: 43-51 or SEQ ID NOs: 52-59. In some embodiments, the second heterologous protein is an engineered meganuclease comprising an amino acid sequence according to any one of SEQ ID NOs: 43-51 or SEQ ID NOs: 52-59. In some embodiments, the first heterologous protein is an engineered meganuclease comprising an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 50 or 58. In some embodiments, the second heterologous protein is an engineered meganuclease comprising an amino acid sequence having at least at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 50 or 58. In some embodiments, the first heterologous protein is an engineered meganuclease comprising an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 50. In some embodiments, the first heterologous protein is an engineered meganuclease comprising an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 58. In some embodiments, the second heterologous protein is an engineered meganuclease comprising an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 50. In some embodiments, the second heterologous protein is an engineered meganuclease comprising an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 58.

In some embodiments, the first nucleic acid sequence and the second nucleic acid sequence has been modified to reduce CpG content. In some embodiments, the first nucleic acid sequence or the second nucleic acid sequence has been codon modified to reduce the percent sequence identity between the first nucleic acid sequence and the second nucleic acid sequence, wherein the codon modification does not alter the amino acid sequence of the first heterologous protein or the second heterologous protein. In some embodiments, the first nucleic acid sequence has no more than about 30% to about 90% sequence identity to the second nucleic acid sequence. In some embodiments, the first nucleic acid sequence has no more than about 40% to about 60% sequence identity to the second nucleic acid sequence. In some embodiments, the first nucleic acid sequence has no more than about 30%, about 35%, about 40%, about 45%, about 50%, about 55%, about 60%, about 65%, about 70%, about 75%, about 80%, about 85%, or about 90% sequence identity to the second nucleic acid sequence. In some embodiments, the first nucleic acid sequence has no more than about 40% sequence identity to the second nucleic acid sequence. In some embodiments, the first nucleic acid sequence has no more than about 50% sequence identity to the second nucleic acid sequence. In some embodiments, the first nucleic acid sequence has no more than about 60% sequence identity to the second nucleic acid sequence.

In some embodiments, the expression cassette comprises a nucleic acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in any one of SEQ ID NOs: 78-87. In some embodiments, the expression cassette comprises a nucleic acid sequence according to a sequence set forth in any one of SEQ ID NOs: 78-87.

In another aspect described herein is a muscle-specific expression cassette comprising a nucleic acid sequence encoding a heterologous protein operably linked to a muscle-specific promoter wherein the expression cassette comprises from 5' to 3': a) a muscle-specific enhancer element according to SEQ ID NO: 1, b) a tMCK promoter according to SEQ ID NO: 22, c) a Kozak sequence, d) a first nucleic acid sequence encoding a first heterologous protein, c) a 2A sequence comprising a furin cleavage motif and GSG linker, f) a second nucleic acid sequence encoding a second heterologous protein, and g) a WPRE sequence.

In some embodiments, the first heterologous protein is an engineered meganuclease comprising an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in any one of SEQ ID NOs: 43-51 or SEQ ID NOs: 52-59. In some embodiments, the first heterologous protein is an engineered meganuclease comprising an amino acid sequence according to a sequence set forth in any one of SEQ ID NOs: 43-51 or SEQ ID NOs: 52-59. In some embodiments, the second heterologous protein is an engineered meganuclease com- prising an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in any one of SEQ ID NOs: 43-51 or SEQ ID NOs: 52-59. In some embodiments, the second heterologous pro- tein is an engineered meganuclease comprising an amino acid sequence according to a sequence set forth in any one of SEQ ID NOs: 43-51 or SEQ ID NOs: 52-59. In some embodiments, the first heterologous protein is an engineered meganuclease comprising an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 50 or 58. In some embodiments, the second heterologous protein is an engi- neered meganuclease comprising an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 50 or 58. In some embodiments, the first heterologous protein is an engineered meganuclease comprising an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 50. In some embodiments, the first heterologous protein is an engineered meganuclease comprising an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 58. In some embodiments, the second heterologous protein is an engineered meganuclease comprising an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 50. In some embodiments, the second heterologous protein is an engineered meganuclease comprising an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 58.

In some embodiments, the first nucleic acid sequence and the second nucleic acid sequence has been modified to reduce CpG content. In some embodiments, the first nucleic acid sequence or the second nucleic acid sequence has been codon modified to reduce the percent sequence identity between the first nucleic acid sequence and the second nucleic acid sequence, wherein the codon modification does not alter the amino acid sequence of the first heterologous protein or the second heterologous protein. In some embodi- ments, the first nucleic acid sequence has no more than about 30% to about 90% sequence identity to the second nucleic acid sequence. In some embodiments, the first nucleic acid sequence has no more than about 40% to about 60% sequence identity to the second nucleic acid sequence. In some embodiments, the first nucleic acid sequence has no more than about 30%, about 35%, about 40%, about 45%, about 50%, about 55%, about 60%, about 65%, about 70%, about 75%, about 80%, about 85%, or about 90% sequence identity to the second nucleic acid sequence. In some embodiments, the first nucleic acid sequence has no more than about 40% sequence identity to the second nucleic acid sequence. In some embodiments, the first nucleic acid sequence has no more than about 50% sequence identity to the second nucleic acid sequence. In some embodiments, the first nucleic acid sequence has no more than about 60% sequence identity to the second nucleic acid sequence. In some embodiments, the expression cassette comprises a nucleic acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in any one of SEQ ID NOs: 78-87. In some embodiments, the expression cassette comprises a nucleic acid sequence according to a sequence set forth in any one of SEQ ID NOs: 78-87.

In another aspect described herein is a muscle-specific expression cassette comprising a nucleic acid sequence encoding a heterologous protein operably linked to a muscle-specific promoter wherein the expression cassette comprises from 5' to 3': a) a muscle-specific enhancer element according to SEQ ID NO: 1, b) a tMCK promoter according to SEQ ID NO: 22, c) a Kozak sequence, d) a first nucleic acid sequence encoding a first engineered meganuclease comprising an amino acid sequence according to any one of SEQ ID NOs: 43-51 or SEQ ID NOs: 52-59, e) a 2A sequence comprising a furin cleavage motif and GSG linker, f) a second nucleic acid sequence encoding a second engineered meganuclease comprising an amino acid sequence according to any one of SEQ ID NOs: 43-51 or SEQ ID NOs: 52-59, and g) a WPRE sequence.

In some embodiments, the first nucleic acid sequence and the second nucleic acid sequence has been modified to reduce CpG content. In some embodiments, the first nucleic acid sequence or the second nucleic acid sequence has been codon modified to reduce the percent sequence identity between the first nucleic acid sequence and the second nucleic acid sequence, wherein the codon modification does not alter the amino acid sequence of the first heterologous protein or the second heterologous protein. In some embodiments, the first nucleic acid sequence has no more than about 30% to about 90% sequence identity to the second nucleic acid sequence. In some embodiments, the first nucleic acid sequence has no more than about 40% to about 60% sequence identity to the second nucleic acid sequence. In some embodiments, the first nucleic acid sequence has no more than about 30%, about 35%, about 40%, about 45%, about 50%, about 55%, about 60%, about 65%, about 70%, about 75%, about 80%, about 85%, or about 90% sequence identity to the second nucleic acid sequence. In some embodiments, the first nucleic acid sequence has no more than about 40% sequence identity to the second nucleic acid sequence. In some embodiments, the first nucleic acid sequence has no more than about 50% sequence identity to the second nucleic acid sequence. In some embodiments, the first nucleic acid sequence has no more than about 60% sequence identity to the second nucleic acid sequence.

In some embodiments, the first engineered meganuclease comprises an amino acid sequence according to SEQ ID NO: 50. In some embodiments, the second engineered meganuclease comprises an amino acid sequence according to SEQ ID NO: 58.

In some embodiments, the expression cassette comprises a nucleic acid sequence having at least at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in any one of SEQ ID NOs: 78-87. In some embodiments, the expression cassette comprises a nucleic acid sequence according to a sequence set forth in any one of SEQ ID NOs: 78-87. In another aspect described herein is a muscle-specific expression cassette comprising a nucleic acid sequence encoding: (a) an engineered meganuclease comprising an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in any one of SEQ ID NOs: 43-51, wherein the engineered meganuclease binds and cleaves a recognition sequence comprising SEQ ID NO: 37 in a dystrophin gene; or (b) an engineered meganuclease comprising an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in any one of SEQ ID NOs: 52-59, wherein the engineered meganuclease binds and cleaves a recognition sequence comprising SEQ ID NO: 39 in a dystrophin gene; wherein the nucleic acid sequence encoding the engineered meganuclease is operably linked to a MCK promoter.

In some embodiments, the muscle-specific expression cassette described herein comprises a muscle-specific enhancer. In some embodiments, the muscle-specific expression cassette described herein comprises a Kozak sequence. In some embodiments, the muscle-specific expression cassette described herein comprises a post transcriptional regulatory element. In some embodiments, the post transcriptional regulatory element comprises a WPRE.

In some embodiments of the muscle-specific expression cassette described herein the muscle-specific enhancer comprises a nucleic acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 1. In some embodiments the muscle-specific enhancer comprises a nucleic acid sequence according to a sequence set forth in SEQ ID NO: 1.

In some embodiments of the muscle-specific expression cassette described herein, the MCK promoter is a tMCK promoter. In some embodiments, the tMCK promoter comprises a basal promoter and one or more MCK enhancer elements. In some embodiments, the basal promoter comprises a nucleic acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 3. In some embodiments, the basal promoter comprises a nucleic acid sequence according to a sequence set forth in SEQ ID NO: 3.

In some embodiments of the muscle-specific expression cassette described herein, the MCK enhancer element comprises a MCK-R control element. In some embodiments, the MCK enhancer element comprises two MCK-R control elements. In some embodiments, the MCK-R control element comprises a nucleic acid sequence according to a sequence set forth in any one of SEQ ID NOs: 4-17.

In some embodiments of the muscle-specific expression cassette described herein the MCK enhancer element comprises a nucleic acid sequence having at least at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 21. In some embodiments, the MCK enhancer element comprises a nucleic acid sequence according to a sequence set forth in SEQ ID NO: 21.

In some embodiments of the muscle-specific expression cassette described herein, the MCK promoter is a tMCK promoter comprising three MCK enhancer elements.

In some embodiments of the muscle-specific expression cassette described herein the MCK promoter is a tMCK promoter comprising a nucleic acid sequence having at least at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 22. In some embodiments, the MCK promoter is a tMCK promoter comprising a nucleic acid sequence according to a sequence set forth in SEQ ID NO: 22.

In some embodiments, the engineered meganuclease comprises a nuclear localization sequence (NLS). In some embodiments, the NLS is positioned at the N-terminus of the engineered meganuclease. In some embodiments, the NLS is positioned at the C-terminus of the engineered meganuclease. In some embodiments, the engineered meganuclease comprises a first NLS at the N-terminus and a second NLS at the C-terminus of the engineered meganuclease. In some embodiments, the first NLS and the second NLS are identical. In some embodiments, the first NLS and the second NLS are not identical. In some embodiments, the NLS comprises an SV40 NLS, a c-myc NLS or an NLS5 NLS. In some embodiments, the NLS comprises an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in any one of SEQ ID NOs: 25-28. In some embodiments, the NLS comprises an amino acid sequence according to a sequence set forth in any one of SEQ ID NOs: 25-28.

In some embodiments of the muscle-specific expression cassette described herein, the expression cassette comprises a first nucleic acid sequence encoding a first engineered meganuclease and a second nucleic acid sequence encoding a second engineered meganuclease. In some embodiments, the first nucleic acid sequence and the second nucleic acid sequence are separated by an IRES or 2A sequence. In some embodiments, the 2A sequence further comprises a furin cleavage motif and a GSG linker sequence. In some embodiments, the 2A sequence is a T2A, P2A, E2A, or F2A sequence.

In some embodiments, the first engineered meganuclease comprises an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity set forth in any one of SEQ ID NOs: 43-51. In some embodiments, the second engineered meganuclease comprises an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity set forth in any one of SEQ ID NOs: 43-51. In some embodiments, the first engineered meganuclease comprises an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity set forth in any one of SEQ ID NOs: 52-59. In some embodiments, the second engineered meganuclease comprises an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity set forth in any one of SEQ ID NOs: 52-59.

In some embodiments, the first engineered meganuclease comprises an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 50. In some embodiments, the second engineered meganuclease comprises an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 50. In some embodiments, the first engineered meganuclease comprises an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 58. In some embodiments, the second engineered meganuclease comprises an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 58.

In some embodiments, the first engineered meganuclease comprises an amino acid sequence set forth in any one of SEQ ID NOs: 43-51. In some embodiments, the first engineered meganuclease comprises an amino acid sequence set forth in any one of SEQ ID NOs: 52-59. In some embodiments, the second engineered meganuclease comprises an amino acid sequence set forth in any one of SEQ ID NOs: 43-51. In some embodiments, the second engineered meganuclease comprises an amino acid sequence set forth in any one of SEQ ID NOs: 52-59.

In some embodiments, the first engineered meganuclease comprises an amino acid sequence set forth in SEQ ID NO: 50. In some embodiments, the first engineered meganuclease comprises an amino acid sequence set forth in SEQ ID NO: 58. In some embodiments, the second engineered meganuclease comprises an amino acid sequence set forth in SEQ ID NO: 50. In some embodiments, the second engineered meganuclease comprises an amino acid sequence set forth in SEQ ID NO: 58.

In some embodiments, the first nucleic acid sequence and the second nucleic acid sequence has been modified to reduce CpG content. In some embodiments, the first nucleic acid sequence or the second nucleic acid sequence has been codon modified to reduce the percent sequence identity between the first nucleic acid sequence and the second nucleic acid sequence, wherein the codon modification does not alter the amino acid sequence of the first heterologous protein or the second heterologous protein. In some embodiments, the first nucleic acid sequence has no more than about 30% to about 90% sequence identity to the second nucleic acid sequence. In some embodiments, the first nucleic acid sequence has no more than about 40% to about 60% sequence identity to the second nucleic acid sequence. In some embodiments, the first nucleic acid sequence has no more than about 30%, about 35%, about 40%, about 45%, about 50%, about 55%, about 60%, about 65%, about 70%, about 75%, about 80%, about 85%, or about 90% sequence identity to the second nucleic acid sequence. In some embodiments, the first nucleic acid sequence has no more than about 40% sequence identity to the second nucleic acid sequence. In some embodiments, the first nucleic acid sequence has no more than about 50% sequence identity to the second nucleic acid sequence. In some embodiments, the first nucleic acid sequence has no more than about 60% sequence identity to the second nucleic acid sequence.

In another aspect described herein is a muscle-specific expression cassette comprising from 5' to 3': a) a tMCK promoter according to a sequence set forth in SEQ ID NO: 22, b) a Kozak sequence, c) a first nucleic acid sequence encoding: (i) a first engineered meganuclease comprising an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in any one of SEQ ID NOs: 43-51, wherein the engineered meganuclease binds and cleaves a recognition sequence comprising SEQ ID NO: 37 in a dystrophin gene; or (ii) a first engineered meganuclease comprising an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in any one of SEQ ID NOs: 52-59, wherein the engineered meganuclease binds and cleaves a recognition sequence comprising SEQ ID NO: 39 in a dystrophin gene; d) a 2A sequence, e) a second nucleic acid sequence encoding: (i) a second engineered meganuclease comprising an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in any one of SEQ ID NOs: 43-51, wherein the engineered meganuclease binds and cleaves a recognition sequence comprising SEQ ID NO: 37 in a dystrophin gene; or (ii) a second engineered meganuclease comprising an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in any one of SEQ ID NOs: 52-59, wherein the engineered meganuclease binds and cleaves a recognition sequence comprising SEQ ID NO: 39 in a dystrophin gene; and f) a WPRE sequence. In some embodiments, the first and the second engineered meganuclease are not identical.

In some embodiments, the first engineered meganuclease comprises an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 50. In some embodiments, the first engineered meganuclease comprises an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 58. In some embodiments, the second engineered meganuclease comprises an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 50. In some embodiments, the second engineered meganuclease comprising an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 58.

In some embodiments, the first engineered meganuclease comprises an amino acid sequence according to a sequence set forth in any one of SEQ ID NOs: 43-51 or SEQ ID NOs: 52-59. In some embodiments, the second engineered meganuclease comprises an amino acid sequence according to any one of SEQ ID NOs: 43-51 or SEQ ID NOs: 52-59.

In some embodiments, the first engineered meganuclease comprises an amino acid sequence according to a sequence set forth in SEQ ID NO: 50. In some embodiments, the first engineered meganuclease comprises an amino acid sequence according to a sequence identity to a sequence set forth in SEQ ID NO: 58. In some embodiments, the second engineered meganuclease comprises an amino acid sequence according to a sequence set forth in SEQ ID NO: 50. In some embodiments, the second engineered meganuclease comprises an amino acid sequence according to a sequence set forth in SEQ ID NO: 58.

In some embodiments, the first nucleic acid sequence and the second nucleic acid sequence has been modified to reduce CpG content. In some embodiments, the first nucleic acid sequence or the second nucleic acid sequence has been codon modified to reduce the percent sequence identity between the first nucleic acid sequence and the second nucleic acid sequence, wherein the codon modification does not alter the amino acid sequence of the first heterologous protein or the second heterologous protein. In some embodiments, the first nucleic acid sequence has no more than about 30% to about 90% sequence identity to the second nucleic acid sequence. In some embodiments, the first nucleic acid sequence has no more than about 40% to about 60% sequence identity to the second nucleic acid sequence. In some embodiments, the first nucleic acid sequence has no more than about 30%, about 35%, about 40%, about 45%, about 50%, about 55%, about 60%, about 65%, about 70%, about 75%, about 80%, about 85%, or about 90% sequence identity to the second nucleic acid sequence. In some embodiments, the first nucleic acid sequence has no more than about 40% sequence identity to the second nucleic acid sequence. In some embodiments, the first nucleic acid sequence has no more than about 50% sequence identity to the second nucleic acid sequence. In some embodiments, the first nucleic acid sequence has no more than about 60% sequence identity to the second nucleic acid sequence.

In some embodiments, the expression cassette comprises a nucleic acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in any one of SEQ ID NOs: 78-88. In some embodiments, the expression cassette comprises a nucleic acid sequence according to a sequence set forth in any one of SEQ ID NOs: 78-88.

In another aspect described herein is a muscle-specific expression cassette comprising a nucleic acid sequence encoding an engineered meganuclease operably linked to a muscle-specific promoter, wherein the expression cassette comprises from 5' to 3': a) a muscle-specific enhancer element according to SEQ ID NO: 1, b) a tMCK promoter according to SEQ ID NO: 22, c) a Kozak sequence, d) a first nucleic acid sequence encoding: (i) a first engineered meganuclease comprising an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100 sequence identity to a sequence set forth in any one of SEQ ID NOs: 43-51, wherein the engineered meganuclease binds and cleaves a recognition sequence comprising SEQ ID NO: 37 in a dystrophin gene; or (ii) a first engineered meganuclease comprising an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100 sequence identity to a sequence set forth in any one of SEQ ID NOs: 52-59, wherein the engineered meganuclease binds and cleaves a recognition sequence comprising SEQ ID NO: 39 in a dystrophin gene; e) a 2A sequence, f) a second nucleic acid sequence encoding: (i) a second engineered meganuclease comprising an amino acid sequence having at least 80% sequence identity to a sequence set forth in any one of SEQ ID NOs: 43-51, wherein the engineered meganuclease binds and cleaves a recognition sequence comprising SEQ ID NO: 37 in a dystrophin gene; or (ii) a second engineered meganuclease comprising an amino acid sequence having at least 80% sequence identity to a sequence set forth in any one of SEQ ID NOs: 52-59, wherein the engineered meganuclease binds and cleaves a recognition sequence comprising SEQ ID NO: 39 in a dystrophin gene; g) a WPRE sequence. In some embodiments, the first and second engineered meganuclease are not identical.

In some embodiments, the first engineered meganuclease comprises an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 50. In some embodiments, the first engineered meganuclease comprises an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 58. In some embodiments, the second engineered meganuclease comprises an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 50. In some embodiments, the second engineered meganuclease comprising an amino acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 58.

In some embodiments, the first engineered meganuclease comprises an amino acid sequence according to a sequence set forth in any one of SEQ ID NOs: 43-51 or SEQ ID NOs: 52-59. In some embodiments, the second engineered meganuclease comprises an amino acid sequence according to any one of SEQ ID NOs: 43-51 or SEQ ID NOs: 52-59.

In some embodiments, the first engineered meganuclease comprises an amino acid sequence according to a sequence set forth in SEQ ID NO: 50. In some embodiments, the first engineered meganuclease comprises an amino acid sequence according to a sequence identity to a sequence set forth in SEQ ID NO: 58. In some embodiments, the second engineered meganuclease comprises an amino acid sequence according to a sequence set forth in SEQ ID NO: 50. In some embodiments, the second engineered meganuclease comprises an amino acid sequence according to a sequence set forth in SEQ ID NO: 58.

In some embodiments, the first nucleic acid sequence and the second nucleic acid sequence has been modified to reduce CpG content. In some embodiments, the first nucleic acid sequence or the second nucleic acid sequence has been codon modified to reduce the percent sequence identity between the first nucleic acid sequence and the second nucleic acid sequence, wherein the codon modification does not alter the amino acid sequence of the first heterologous protein or the second heterologous protein. In some embodiments, the first nucleic acid sequence has no more than about 30% to about 90% sequence identity to the second nucleic acid sequence. In some embodiments, the first nucleic acid sequence has no more than about 40% to about 60% sequence identity to the second nucleic acid sequence. In some embodiments, the first nucleic acid sequence has no more than about 30%, about 35%, about 40%, about 45%, about 50%, about 55%, about 60%, about 65%, about 70%, about 75%, about 80%, about 85%, or about 90% sequence identity to the second nucleic acid sequence. In some embodiments, the first nucleic acid sequence has no more than about 40% sequence identity to the second nucleic acid sequence. In some embodiments, the first nucleic acid sequence has no more than about 50% sequence identity to the second nucleic acid sequence. In some embodiments, the first nucleic acid sequence has no more than about 60% sequence identity to the second nucleic acid sequence. In some embodiments, the expression cassette comprises a nucleic acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in any one of SEQ ID NOs: 78-88. In some embodiments, the expression cassette comprises a nucleic acid sequence according to a sequence set forth in any one of SEQ ID NOs: 78-88.

Another aspect described herein is a muscle-specific expression cassette comprising a nucleic acid sequence encoding an engineered meganuclease operably linked to a muscle-specific promoter, wherein the expression cassette comprises from 5' to 3': a) a muscle-specific enhancer element according to a sequence set forth in SEQ ID NO: 1, b) a tMCK promoter according to a sequence set forth in SEQ ID NO: 22, c) a Kozak sequence, d) a first nucleic acid sequence encoding: (i) a first engineered meganuclease comprising an amino acid sequence according to a sequence set forth in any one of SEQ ID NOs: 43-51, wherein the engineered meganuclease binds and cleaves a recognition sequence comprising SEQ ID NO: 37 in a dystrophin gene; or (ii) a first engineered meganuclease comprising an amino acid sequence according to a sequence set forth in any one of SEQ ID NOs: 52-59, wherein the engineered meganuclease binds and cleaves a recognition sequence comprising SEQ ID NO: 39 in a dystrophin gene; c) a 2A sequence, f) a second nucleic acid sequence encoding: (i) a second engineered meganuclease comprising an amino acid sequence according to a sequence set forth in any one of SEQ ID NOs: 43-51, wherein the engineered meganuclease binds and cleaves a recognition sequence comprising SEQ ID NO: 37 in a dystrophin gene; or (ii) a second engineered meganuclease comprising an amino acid sequence according to a sequence set forth in any one of SEQ ID NOs: 52-59, wherein the engineered meganuclease binds and cleaves a recognition sequence comprising SEQ ID NO: 39 in a dystrophin gene; and g) a WPRE sequence, wherein the first and the second engineered meganuclease are not identical.

In some embodiments, the first nucleic acid sequence and the second nucleic acid sequence has been modified to reduce CpG content. In some embodiments, the first nucleic acid sequence or the second nucleic acid sequence has been codon modified to reduce the percent sequence identity between the first nucleic acid sequence and the second nucleic acid sequence, wherein the codon modification does not alter the amino acid sequence of the first heterologous protein or the second heterologous protein. In some embodiments, the first nucleic acid sequence has no more than about 30% to about 90% sequence identity to the second nucleic acid sequence. In some embodiments, the first nucleic acid sequence has no more than about 40% to about 60% sequence identity to the second nucleic acid sequence. In some embodiments, the first nucleic acid sequence has no more than about 30%, about 35%, about 40%, about 45%, about 50%, about 55%, about 60%, about 65%, about 70%, about 75%, about 80%, about 85%, or about 90% sequence identity to the second nucleic acid sequence. In some embodiments, the first nucleic acid sequence has no more than about 40% sequence identity to the second nucleic acid sequence. In some embodiments, the first nucleic acid sequence has no more than about 50% sequence identity to the second nucleic acid sequence. In some embodiments, the first nucleic acid sequence has no more than about 60% sequence identity to the second nucleic acid sequence. In some embodiments, the expression cassette comprises a nucleic acid sequence having at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in any one of SEQ ID NOs: 78-88. In some embodiments, the expression cassette comprises a nucleic acid sequence according to a sequence set forth in any one of SEQ ID NOs: 78-88.

In another aspect described herein is a polynucleotide comprising any muscle-specific expression cassette described herein.

In another aspect described herein is a recombinant DNA construct comprising a polynucleotide comprising any muscle-specific expression cassette described herein. In some embodiments, the recombinant DNA construct described herein encodes any recombinant virus described herein. In some embodiments of the recombinant DNA construct described herein, the recombinant virus is a recombinant adenovirus, a recombinant lentivirus, a recombinant retrovirus, or a recombinant adeno-associated virus (AAV). In some embodiments of the recombinant DNA construct described herein, the recombinant virus is a recombinant AAV. In some embodiments of the recombinant DNA construct described herein, the recombinant AAV has an rh74 capsid or an AAV9 capsid. In some embodiments of the recombinant DNA construct described herein, the recombinant AAV has an AAV9 capsid. In some embodiments of the recombinant DNA construct described herein, the recombinant AAV comprises a 5' ITR comprising a first D-sequence and a 3' ITR comprising a second D-sequence.

In another aspect described herein is a recombinant virus comprising a polynucleotide comprising any muscle-specific expression cassette described herein. In some embodiments, the recombinant virus described herein is a recombinant adenovirus, a recombinant lentivirus, a recombinant retrovirus, or a recombinant AAV. In some embodiments, the recombinant virus described herein is a recombinant AAV. In some embodiments of the recombinant virus described herein, the recombinant AAV has an rh74 capsid or an AAV9 capsid. In some embodiments of the recombinant virus described herein, the recombinant AAV has an AAV9 capsid. In some embodiments of the recombinant virus described herein, the recombinant AAV comprises a 5' ITR comprising a first D-sequence and a 3' ITR comprising a second D-sequence.

In another aspect described herein is a pharmaceutical composition comprising a pharmaceutically acceptable carrier and any polynucleotide described herein.

In another aspect described herein is a pharmaceutical composition comprising a pharmaceutically acceptable carrier and any recombinant DNA construct described herein.

In another aspect described herein is a pharmaceutical composition comprising a pharmaceutically acceptable carrier and any recombinant virus described herein.

In another aspect described herein is a method for expressing a heterologous protein in a mammalian muscle cell, the method comprising introducing any muscle-specific expression cassette described herein to a mammalian cell composition comprising a mammalian muscle cell, wherein the heterologous protein is expressed in the mammalian muscle cell.

In some embodiments of the method, the muscle cell comprises a muscle precursor cell, a skeletal muscle cell, or a cardiac muscle cell. In some embodiments the mammalian muscle precursor cell comprises a muscle satellite cell that expresses the Pax7 protein. In some embodiments, the mammalian muscle cell is part of a skeletal muscle tissue or a cardiac muscle tissue. In some embodiments, the mammalian cell is a human cell. In some embodiments, the heterologous protein is expressed at a higher level in the mammalian muscle cell compared to a non-muscle cell. In some embodiments, the non-muscle cell comprises a non-muscle cell of the liver, a non-muscle cell of the brain, a germ line cell, or a non-muscle cell of the lung. In some embodiments, the heterologous protein is expressed by at least 15-fold to about 60-fold more in the muscle cell compared to a non-muscle cell. In some embodiments, the heterologous protein is expressed by at least 15-fold to about 60-fold more in the muscle cell compared to a non-muscle cell of the liver. In some embodiments, the heterologous protein is expressed by at least 15-fold to about 25-fold more in a skeletal muscle cell compared to a cardiac muscle cell.

In some embodiments, the muscle-specific expression cassette is introduced to the mammalian cell composition by any polynucleotide described herein. In some embodiments, the muscle-specific expression cassette is introduced to the mammalian cell composition by any recombinant DNA construct described herein. In some embodiments, the muscle-specific expression cassette is introduced to the mammalian cell composition by any recombinant virus described herein. In some embodiments, the muscle-specific expression cassette is introduced the mammalian cell composition by any pharmaceutical composition described herein. In some embodiments, the muscle-specific expression cassette is introduced to the mammalian cell composition in vitro. In some embodiments, the muscle-specific expression cassette is introduced to the mammalian cell composition in vivo. In some embodiments, the mammalian cell composition is a human cell composition.

In another aspect described herein is a method for enhancing expression of a heterologous protein in a mammalian skeletal muscle cell over a cardiac muscle cell, the method comprising introducing any muscle-specific expression cassette described herein to a mammalian cell composition comprising a mammalian skeletal muscle cell and a cardiac muscle cell, wherein the heterologous protein is expressed at higher levels in the mammalian skeletal muscle cell compared to the cardiac muscle cell.

In some embodiments of the method, the mammalian muscle cell is part of a skeletal muscle tissue or a cardiac muscle tissue. In some embodiments, the heterologous protein is expressed at a higher level in the mammalian muscle cell compared to a non-muscle cell. In some embodiments, the non-muscle cell comprises a non-muscle cell of the liver, a non-muscle cell of the brain, a germ line cell, or a non-muscle cell of the lung. In some embodiments, the heterologous protein is expressed by at least 15-fold to about 60-fold more in the muscle cell compared to a non-muscle cell. In some embodiments, the heterologous protein is expressed by at least 15-fold to about 60-fold more in the muscle cell compared to a non-muscle cell of the liver. In some embodiments, the heterologous protein is expressed by at least 15-fold to about 25-fold more in a skeletal muscle cell compared to a cardiac muscle cell.

In some embodiments, the muscle-specific expression cassette is introduced to the mammalian cell composition by any polynucleotide described herein. In some embodiments, the muscle-specific expression cassette is introduced to the mammalian cell composition by any recombinant DNA construct described herein. In some embodiments, the muscle-specific expression cassette is introduced to the mammalian cell composition by any recombinant virus described herein. In some embodiments, the muscle-specific expression cassette is introduced the mammalian cell composition by any pharmaceutical composition described herein. In some embodiments, the muscle-specific expression cassette is introduced to the mammalian cell composition in vitro. In some embodiments, the muscle-specific expression cassette is introduced to the mammalian cell composition in vivo. In some embodiments, the mammalian cell composition is a human cell composition.

In another aspect described herein is a method for expressing a heterologous protein in a mammalian muscle precursor cell, the method comprising introducing any muscle-specific expression cassette described herein to a mammalian cell composition comprising a mammalian muscle precursor cell, wherein the heterologous protein is expressed in the muscle precursor cell.

In some embodiments of the method, the muscle-specific expression cassette is any muscle-specific expression cassette described herein. In some embodiments, the mammalian muscle precursor cell is part of a skeletal muscle tissue or a cardiac muscle tissue. In some embodiments, the mammalian muscle precursor cell comprises a muscle satellite cell that expresses the Pax7 protein.

In some embodiments, the muscle-specific expression cassette is introduced to the mammalian cell composition by any polynucleotide described herein. In some embodiments, the muscle-specific expression cassette is introduced to the mammalian cell composition by any recombinant DNA construct described herein. In some embodiments, the muscle-specific expression cassette is introduced to the mammalian cell composition by any recombinant virus described herein. In some embodiments, the muscle-specific expression cassette is introduced the mammalian cell composition by any pharmaceutical composition described herein. In some embodiments, the muscle-specific expression cassette is introduced to the mammalian cell composition in vitro. In some embodiments, the muscle-specific expression cassette is introduced to the mammalian cell composition in vivo. In some embodiments, the mammalian cell composition is a human cell composition.

In another aspect described herein is a method for modifying a dystrophin gene selectively in a muscle cell in a subject, wherein the dystrophin gene is characterized by a mutation that alters the reading frame of the dystrophin gene from wild-type, the method comprising: delivering to the muscle cell any muscle-specific expression cassette described herein, wherein the heterologous protein is capable of modifying the dystrophin gene, wherein the heterologous protein is expressed in a muscle cell of the subject, thereby modifying the dystrophin gene in the muscle cell of the subject.

In some embodiments of the method, the heterologous protein is an engineered nuclease. In some embodiments, the expression cassette comprises a first nucleic acid sequence encoding a first heterologous protein and a second nucleic acid sequence encoding a second heterologous protein. In some embodiments, the first heterologous protein is a first engineered nuclease, the second heterologous protein is a second engineered nuclease.

In some embodiments of the method, a first engineered nuclease produces a first cleavage site in the dystrophin gene at a first recognition sequence located within the dystrophin gene, wherein a second engineered nuclease produces a second cleavage site in the dystrophin gene at a second recognition sequence located within the dystrophin gene wherein the first cleavage site and the second cleavage site have complementary 3' overhangs, wherein the intervening genomic DNA between the first cleavage site and the second cleavage site is excised from the dystrophin gene, wherein the dystrophin gene is annealed, and wherein a normal reading frame of the dystrophin gene is restored as compared to a full-length wild-type dystrophin gene. In some embodiments, the complementary 3' overhangs of the first cleavage site and the second cleavage site are directly re-ligated to one another. In some embodiments, the dystrophin gene comprises a nucleic acid sequence set forth in SEQ ID NO: 41. In some embodiments, the dystrophin gene encodes a modified dystrophin polypeptide lacking the amino acids encoded by exons 45-55 of a wild-type dystrophin gene. In some embodiments, the subject is converted to a Becker Muscular Dystrophy phenotype.

In some embodiments of the method, the muscle cell comprises a muscle precursor cell, a skeletal muscle cell, or a cardiac muscle cell. In some embodiments, the mammalian muscle precursor cell comprises a muscle satellite cell that expresses the Pax7 protein. In some embodiments, the muscle cell is part of a skeletal muscle tissue or a cardiac muscle tissue. In some embodiments, the heterologous protein is expressed at a higher level in the muscle cell compared to a non-muscle cell. In some embodiments, the non-muscle cell comprises a non-muscle cell of the liver, a non-muscle cell of the brain, a germ line cell, or a non-muscle cell of the lung. In some embodiments, the first engineered meganuclease and the second engineered meganuclease is expressed by at least 15-fold to about 60-fold more in the muscle cell compared to a non-muscle cell. In some embodiments, the first engineered meganuclease and the second engineered meganuclease is expressed by at least 15-fold to about 60-fold more in the muscle cell compared to a non-muscle cell of the liver. In some embodiments, the first engineered meganuclease and the second engineered meganuclease is expressed by at least 15-fold to about 25-fold more in a skeletal muscle cell compared to a cardiac muscle cell. In some embodiments, the muscle-specific expression cassette is delivered to the muscle cell by any polynucleotide described herein. In some embodiments, the muscle-specific expression cassette is delivered to the muscle cell by any recombinant DNA construct described herein. In some embodiments, the muscle-specific expression cassette is delivered to the muscle cell by any recombinant virus described herein. In some embodiments, the muscle-specific expression cassette is delivered to the muscle cell by any pharmaceutical composition described herein. In some embodiments, the subject is a human.

In another aspect described herein is a method for treating a muscle disorder in a subject having the muscle disorder, the method comprising administering any muscle-specific expression cassette described herein to the subject, wherein the heterologous protein is a therapeutic protein for treating the muscle disorder, wherein the therapeutic protein is expressed in a muscle cell of the subject, thereby treating the muscle disorder in the subject.

In some embodiments of the method, the muscle disorder comprises a muscular dystrophy. In some embodiments, the muscular dystrophy comprises DMD. In some embodiments, the therapeutic protein comprises a muscle transgene, a DNA binding regulatory protein, or an engineered nuclease. In some embodiments, the muscle transgene comprises a sarcoglycan or a dystrophin protein. In some embodiments, the dystrophin protein is a microdystrophin protein. In some embodiments, the therapeutic protein is an engineered nuclease.

In some embodiments of the method, the muscle disorder is DMD that is characterized by a mutation in a dystrophin gene that alters the reading frame of the dystrophin gene from wild-type. In some embodiments, the muscle-specific expression cassette comprises a first nucleic acid sequence encoding a first therapeutic protein and a second nucleic acid sequence encoding a second therapeutic protein. In some embodiments, the first therapeutic protein is a first engineered nuclease, the second therapeutic protein is a second engineered nuclease.

In some embodiments of the method, a first engineered nuclease produces a first cleavage site in the dystrophin gene at a first recognition sequence located within the dystrophin gene, wherein a second engineered nuclease produces a second cleavage site in the dystrophin gene at a second recognition sequence located within the dystrophin gene wherein the first cleavage site and the second cleavage site have complementary 3' overhangs, wherein the intervening genomic DNA between the first cleavage site and the second cleavage site is excised from the dystrophin gene, wherein the dystrophin gene is annealed, and wherein a normal reading frame of the dystrophin gene is restored as compared to a full-length wild-type dystrophin gene. In some embodiments, the complementary 3' overhangs of the first cleavage site and the second cleavage site are directly re-ligated to one another. In some embodiments, the dystrophin gene comprises a nucleic acid sequence set forth in SEQ ID NO: 41. In some embodiments, the dystrophin gene encodes a modified dystrophin polypeptide lacking the amino acids encoded by exons 45-55 of a wild-type dystrophin gene. In some embodiments, the subject is converted to a Becker Muscular Dystrophy phenotype.

In some embodiments of the method, the muscle cell comprises a muscle precursor cell, a skeletal muscle cell, or a cardiac muscle cell. In some embodiments, the muscle precursor cell comprises a muscle satellite cell that expresses the Pax7 protein. In some embodiments, the muscle cell is part of a skeletal muscle tissue or a cardiac muscle tissue. In some embodiments, the heterologous protein is expressed at a higher level in the muscle cell compared to a non-muscle cell. In some embodiments, the non-muscle cell comprises a non-muscle cell of the liver, a non-muscle cell of the brain, a germ line cell, or a non-muscle cell of the lung. In some embodiments, the heterologous protein is expressed by at least 15-fold to about 60-fold more in the muscle cell compared to a non-muscle cell. In some embodiments, the heterologous protein is expressed by at least 15-fold to about 60-fold more in the muscle cell compared to a non-muscle cell of the liver. In some embodiments, the heterologous protein is expressed by at least 15-fold to about 25-fold more in a skeletal muscle cell compared to a cardiac muscle cell. In some embodiments, the muscle-specific expression cassette is administered to the subject by administering any polynucleotide described herein. In some embodiments, the muscle-specific expression cassette is administered to the subject by administering any recombinant DNA construct described herein. In some embodiments, the muscle-specific expression cassette is administered to the subject by administering any recombinant virus described herein. In some embodiments, the muscle-specific expression cassette is administered to the subject by administering any pharmaceutical composition described herein. In some embodiments, the subject is a human.

In another aspect described herein is a method for expressing an engineered meganuclease in a mammalian muscle cell, the method comprising introducing any muscle-specific expression cassette described herein to a mammalian cell composition comprising a mammalian muscle cell, wherein the engineered meganuclease is expressed in the mammalian muscle cell.

In some embodiments of the method, the muscle cell comprises a muscle precursor cell, a skeletal muscle cell, or a cardiac muscle cell. In some embodiments the mammalian muscle precursor cell comprises a muscle satellite cell that expresses the Pax7 protein. In some embodiments, the mammalian muscle cell is part of a skeletal muscle tissue or a cardiac muscle tissue. In some embodiments, the mammalian cell is a human cell. In some embodiments, the engineered meganuclease is expressed at a higher level in the mammalian muscle cell compared to a non-muscle cell. In some embodiments, the non-muscle cell comprises a non-muscle cell of the liver, a non-muscle cell of the brain, a germ line cell, or a non-muscle cell of the lung. In some embodiments, the engineered meganuclease is expressed by at least 15-fold to about 60-fold more in the muscle cell compared to a non-muscle cell. In some embodiments, the engineered meganuclease is expressed by at least 15-fold to about 60-fold more in the muscle cell compared to a non-muscle cell of the liver. In some embodiments, the engineered meganuclease is expressed by at least 15-fold to about 25-fold more in a skeletal muscle cell compared to a cardiac muscle cell.

In some embodiments, the muscle-specific expression cassette is introduced to the mammalian cell composition by any polynucleotide described herein. In some embodiments, the muscle-specific expression cassette is introduced to the mammalian cell composition by any recombinant DNA construct described herein. In some embodiments, the muscle-specific expression cassette is introduced to the mammalian cell composition by any recombinant virus described herein. In some embodiments, the muscle-specific expression cassette is introduced the mammalian cell composition by any pharmaceutical composition described herein. In some embodiments, the muscle-specific expression cassette is introduced to the mammalian cell composition in vitro. In some embodiments, the muscle-specific expression cassette is introduced to the mammalian cell composition in vivo. In some embodiments, the mammalian cell composition is a human cell composition.

In another aspect described herein is a method for enhancing expression of an engineered meganuclease in a mammalian skeletal muscle cell over a cardiac muscle cell, the method comprising introducing any muscle-specific expression cassette described herein to a mammalian cell composition comprising a mammalian skeletal muscle cell and a cardiac muscle cell, wherein the engineered meganuclease is expressed at higher levels in the mammalian skeletal muscle cell compared to the cardiac muscle cell.

In some embodiments of the method, the mammalian muscle cell is part of a skeletal muscle tissue or a cardiac muscle tissue. In some embodiments, the engineered meganuclease is expressed at a higher level in the mammalian muscle cell compared to a non-muscle cell. In some embodiments, the non-muscle cell comprises a non-muscle cell of the liver, a non-muscle cell of the brain, a germ line cell, or a non-muscle cell of the lung. In some embodiments, the engineered meganuclease is expressed by at least 15-fold to about 60-fold more in the muscle cell compared to a non-muscle cell. In some embodiments, the engineered meganuclease is expressed by at least 15-fold to about 60-fold more in the muscle cell compared to a non-muscle cell of the liver. In some embodiments, the engineered meganuclease is expressed by at least 15-fold to about 25-fold more in a skeletal muscle cell compared to a cardiac muscle cell.

In some embodiments, the muscle-specific expression cassette is introduced to the mammalian cell composition by any polynucleotide described herein. In some embodiments, the muscle-specific expression cassette is introduced to the mammalian cell composition by any recombinant DNA construct described herein. In some embodiments, the muscle-specific expression cassette is introduced to the mammalian cell composition by any recombinant virus described herein. In some embodiments, the muscle-specific expression cassette is introduced the mammalian cell composition by any pharmaceutical composition described herein. In some embodiments, the muscle-specific expression cassette is introduced to the mammalian cell composition in vitro. In some embodiments, the muscle-specific expression cassette is introduced to the mammalian cell composition in vivo. In some embodiments, the mammalian cell composition is a human cell composition.

In another aspect described herein is a method for expressing an engineered meganuclease in a mammalian muscle precursor cell, the method comprising introducing any muscle-specific expression cassette described herein to a mammalian cell composition comprising a mammalian muscle precursor cell, wherein the engineered meganuclease is expressed in the muscle precursor cell.

In some embodiments of the method, the muscle-specific expression cassette is any muscle-specific expression cassette described herein. In some embodiments, the mammalian muscle precursor cell is part of a skeletal muscle tissue or a cardiac muscle tissue. In some embodiments, the mammalian muscle precursor cell comprises a muscle satellite cell that expresses the Pax7 protein.

In some embodiments, the muscle-specific expression cassette is introduced to the mammalian cell composition by any polynucleotide described herein. In some embodiments, the muscle-specific expression cassette is introduced to the mammalian cell composition by any recombinant DNA construct described herein. In some embodiments, the muscle-specific expression cassette is introduced to the mammalian cell composition by any recombinant virus described herein. In some embodiments, the muscle-specific expression cassette is introduced the mammalian cell composition by any pharmaceutical composition described herein. In some embodiments, the muscle-specific expression cassette is introduced to the mammalian cell composition in vitro. In some embodiments, the muscle-specific expression cassette is introduced to the mammalian cell composition in vivo. In some embodiments, the mammalian cell composition is a human cell composition.

In another aspect described herein is a method for modifying a dystrophin gene selectively in a muscle cell in a subject, wherein the dystrophin gene is characterized by a mutation that alters the reading frame of the dystrophin gene from wild-type, the method comprising: delivering to the muscle cell any muscle-specific expression cassette described herein, wherein the engineered meganuclease is capable of modifying the dystrophin gene, wherein the engineered meganuclease is expressed in a muscle cell of the subject, thereby modifying the dystrophin gene in the muscle cell of the subject.

In some embodiments, the expression cassette comprises a first nucleic acid sequence encoding a first engineered meganuclease and a second nucleic acid sequence encoding a second engineered meganuclease.

In some embodiments of the method, a first engineered meganuclease produces a first cleavage site in the dystrophin gene at a first recognition sequence located within the dystrophin gene, wherein a second engineered meganuclease produces a second cleavage site in the dystrophin gene at a second recognition sequence located within the dystrophin gene wherein the first cleavage site and the second cleavage site have complementary 3' overhangs, wherein the intervening genomic DNA between the first cleavage site and the second cleavage site is excised from the dystrophin gene, wherein the dystrophin gene is annealed, and wherein a normal reading frame of the dystrophin gene is restored as compared to a full-length wild-type dystrophin gene. In some embodiments, the complementary 3' overhangs of the first cleavage site and the second cleavage site are directly re-ligated to one another. In some embodiments, the dystrophin gene comprises a nucleic acid sequence set forth in SEQ ID NO: 41. In some embodiments, the dystrophin gene encodes a modified dystrophin polypeptide lacking the amino acids encoded by exons 45-55 of a wild-type dystrophin gene. In some embodiments, the subject is converted to a Becker Muscular Dystrophy phenotype.

In some embodiments of the method, the muscle cell comprises a muscle precursor cell, a skeletal muscle cell, or a cardiac muscle cell. In some embodiments, the mammalian muscle precursor cell comprises a muscle satellite cell that expresses the Pax7 protein. In some embodiments, the muscle cell is part of a skeletal muscle tissue or a cardiac muscle tissue. In some embodiments, the engineered meganuclease is expressed at a higher level in the muscle cell compared to a non-muscle cell. In some embodiments, the non-muscle cell comprises a non-muscle cell of the liver, a non-muscle cell of the brain, a germ line cell, or a non-muscle cell of the lung. In some embodiments, the first engineered meganuclease and the second engineered meganuclease is expressed by at least 15-fold to about 60-fold more in the muscle cell compared to a non-muscle cell. In some embodiments, the first engineered meganuclease and the second engineered meganuclease is expressed by at least 15-fold to about 60-fold more in the muscle cell compared to a non-muscle cell of the liver. In some embodiments, the first engineered meganuclease and the second engineered meganuclease is expressed by at least 15-fold to about 25-fold more in a skeletal muscle cell compared to a cardiac muscle cell. In some embodiments, the muscle-specific expression cassette is delivered to the muscle cell by any polynucleotide described herein. In some embodiments, the muscle-specific expression cassette is delivered to the muscle cell by any recombinant DNA construct described herein. In some embodiments, the muscle-specific expression cassette is delivered to the muscle cell by any recombinant virus described herein. In some embodiments, the muscle-specific expression cassette is delivered to the muscle cell by any pharmaceutical composition described herein. In some embodiments, the subject is a human.

In another aspect described herein is a method for treating a DMD in a subject having DMD, the method comprising administering any muscle-specific expression cassette described herein to the subject, wherein the engineered meganuclease is a therapeutic protein for treating the DMD, wherein the engineered meganuclease is expressed in a muscle cell of the subject, thereby treating the DMD in the subject.

In some embodiments of the method, the DMD is characterized by a mutation in a dystrophin gene that alters the reading frame of the dystrophin gene from wild-type. In some embodiments, the muscle-specific expression cassette comprises a first nucleic acid sequence encoding a first engineered meganuclease and a second nucleic acid sequence encoding a second engineered meganuclease.

In some embodiments of the method, a first engineered meganuclease produces a first cleavage site in the dystrophin gene at a first recognition sequence located within the dystrophin gene, wherein a second engineered meganuclease produces a second cleavage site in the dystrophin gene at a second recognition sequence located within the dystrophin gene wherein the first cleavage site and the second cleavage site have complementary 3' overhangs, wherein the intervening genomic DNA between the first cleavage site and the second cleavage site is excised from the dystrophin gene, wherein the dystrophin gene is annealed, and wherein a normal reading frame of the dystrophin gene is restored as compared to a full-length wild-type dystrophin gene. In some embodiments, the complementary 3' overhangs of the first cleavage site and the second cleavage site are directly re-ligated to one another. In some embodiments, the dystrophin gene comprises a nucleic acid sequence set forth in SEQ ID NO: 41. In some embodiments, the dystrophin gene encodes a modified dystrophin polypeptide lacking the amino acids encoded by exons 45-55 of a wild-type dystrophin gene. In some embodiments, the subject is converted to a Becker Muscular Dystrophy phenotype.

In some embodiments of the method, the muscle cell comprises a muscle precursor cell, a skeletal muscle cell, or a cardiac muscle cell. In some embodiments, the muscle precursor cell comprises a muscle satellite cell that expresses the Pax7 protein. In some embodiments, the muscle cell is part of a skeletal muscle tissue or a cardiac muscle tissue. In some embodiments, the engineered meganuclease is expressed at a higher level in the muscle cell compared to a non-muscle cell. In some embodiments, the non-muscle cell comprises a non-muscle cell of the liver, a non-muscle cell of the brain, a germ line cell, or a non-muscle cell of the lung. In some embodiments, the engineered meganuclease is expressed by at least 15-fold to about 60-fold more in the muscle cell compared to a non-muscle cell. In some embodiments, the engineered meganuclease is expressed by at least 15-fold to about 60-fold more in the muscle cell compared to a non-muscle cell of the liver. In some embodiments, the engineered meganuclease is expressed by at least 15-fold to about 25-fold more in a skeletal muscle cell compared to a cardiac muscle cell. In some embodiments, the muscle-specific expression cassette is administered to the subject by administering any polynucleotide described herein. In some embodiments, the muscle-specific expression cassette is administered to the subject by administering any recombinant DNA construct described herein. In some embodiments, the muscle-specific expression cassette is administered to the subject by administering any recombinant virus described herein. In some embodiments, the muscle-specific expression cassette is administered to the subject by administering any pharmaceutical composition described herein. In some embodiments, the subject is a human.

Figure 3A:
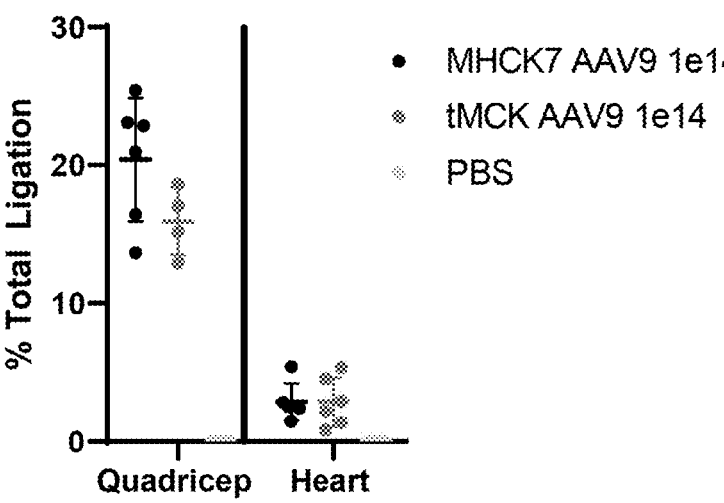
Figure 3B:
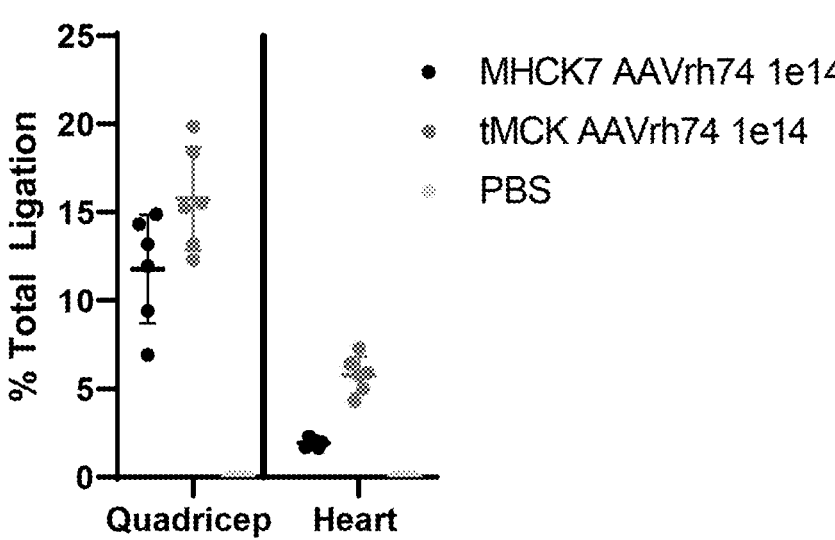

FIG. 3A and FIG. 3B provide bar graphs showing the percentage (%) of total ligation of genomic DNA adjacent to exons 45-55 following cleavage of the DMD 19-20 and DMD 35-36 recognition sequences by the DMD 19-20L.329 and DMD 35-36L.349 pair of meganucleases from both quadricep and heart tissue from hDMDdel52/mdx (hDMD) mice assessed by ddPCR assay. For each tissue in FIG. 3A, the left-hand dark dots indicate an expression construct utilizing the MHCK7 promoter and the middle light dots indicate an expression construct utilizing the tMCK promoter operably connected to the DMD 19-20L.329 and DMD 35-36L.349 pair of meganucleases delivered to mice via an AAV9 capsid. The right-hand dots indicate mice treated with PBS only. For each tissue in FIG. 3B, the left-hand dark dots indicate an expression construct utilizing the MHCK7 promoter and the middle light dots indicate an expression construct utilizing the tMCK promoter operably connected to the DMD 19-20L.329 and DMD 35-36L.349 pair of meganucleases delivered to mice via an AAVrh74 capsid. The right-hand dots indicate mice treated with PBS only.

Figure 4:
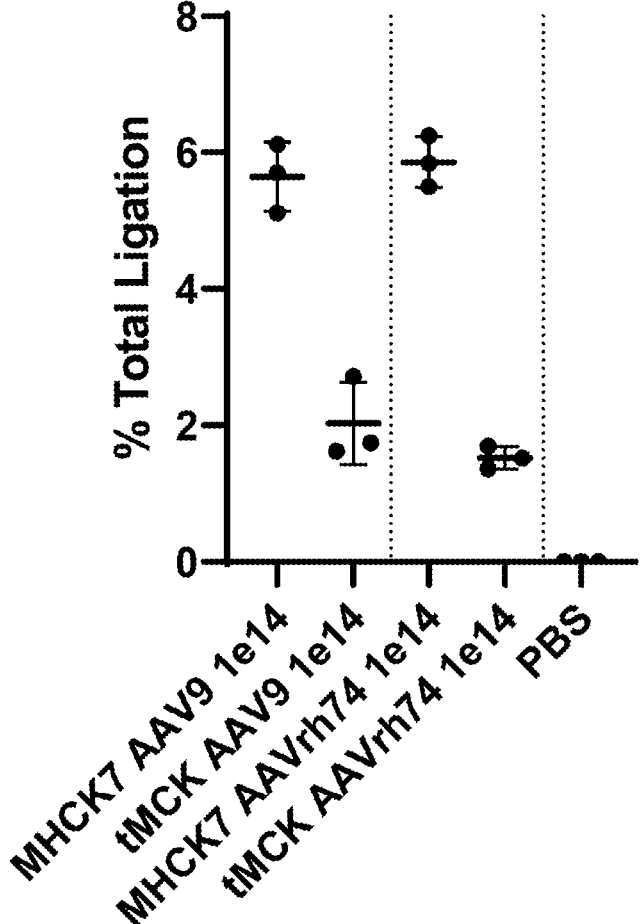

FIG. 4 provides a bar graph showing the percentage (%) of total ligation of genomic DNA adjacent to exons 45-55 following cleavage of the DMD 19-20 and DMD 35-36 recognition sequences by the DMD 19-20L.329 and DMD 35-36L.349 pair of meganucleases from liver tissue from hDMDdel52/mdx (hDMD) mice assessed by ddPCR assay for each of the indicated expression constructs.

Figure 5A:
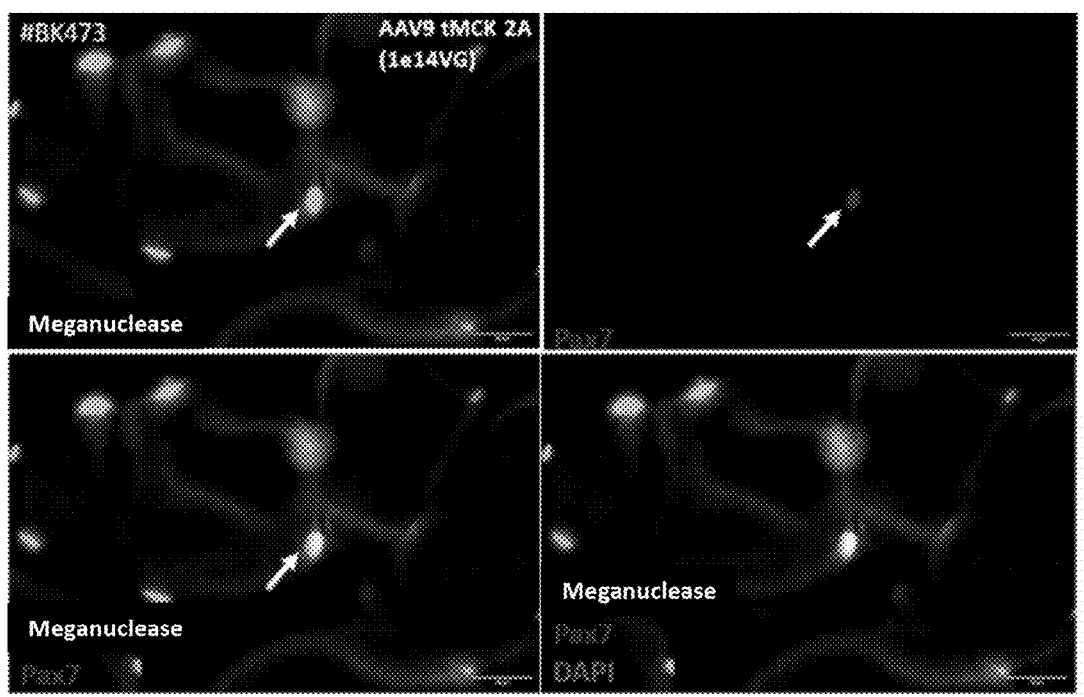
Figure 5B:
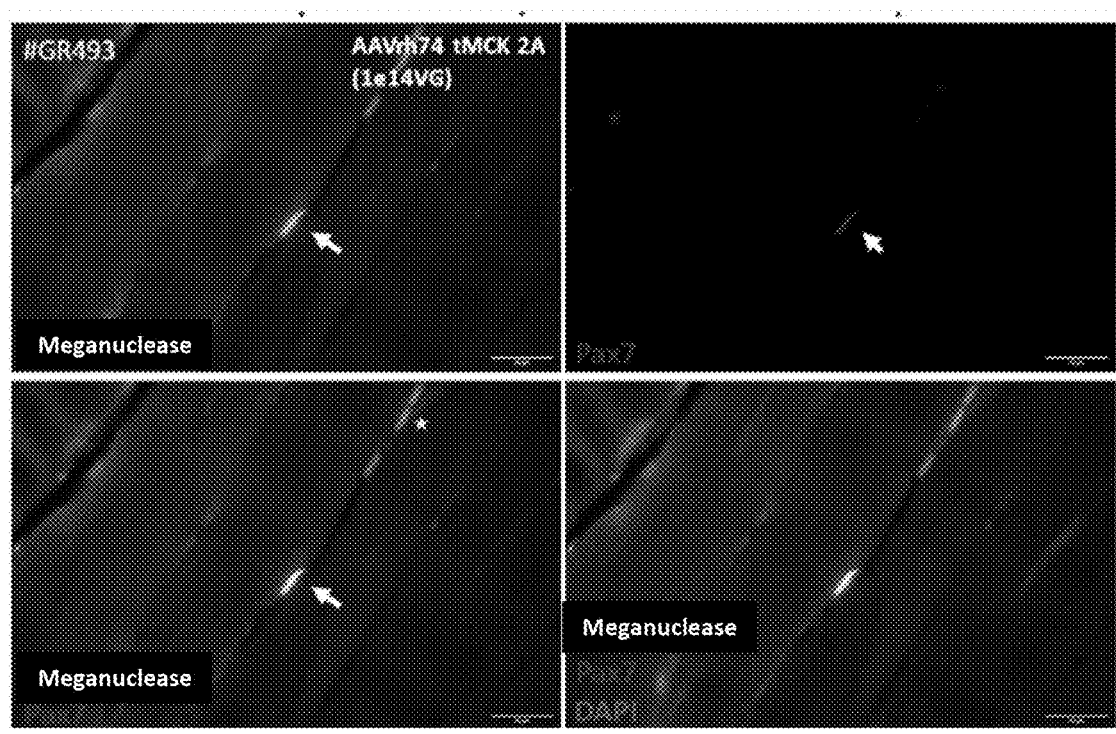
Figure 5C:
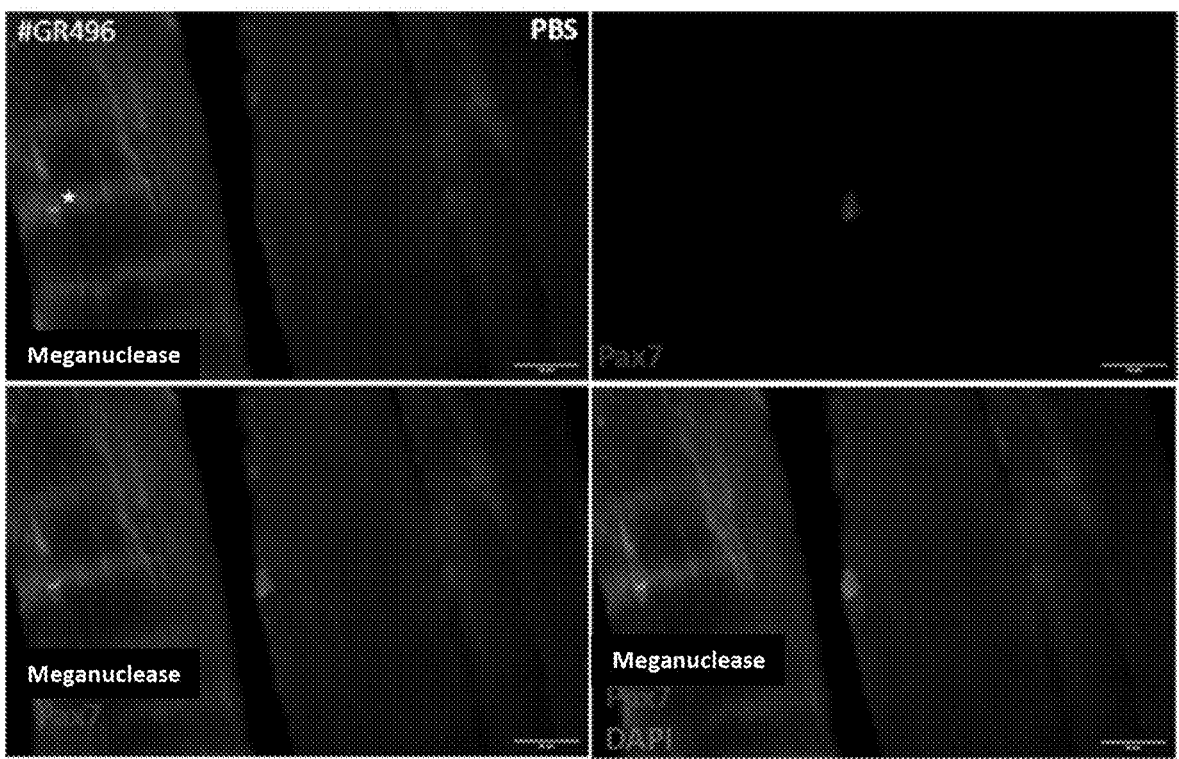

FIG. 5A-5C provides fluorescent immunohistochemistry imaging of murine quadricep tissue following treatment with either PBS or the DMD 19-20L.329 and DMD 35-36L.349 pair of meganucleases expressed from expression constructs utilizing the tMCK promoter delivered using either an AAVrH74 capsid or AAV9 capsid to hDMDdel52/mdx (hDMD) mice. In each figure of 5A-5C, the upper left panel is a control image that shows meganuclease expression detected by utilizing meganuclease specific antibodies. The upper right panel shows cells that express Pax7 indicated by the white arrowhead. The lower left panel shows both Pax7 (white arrowhead) and meganuclease expression in the same cell. The lower right panel shows Pax7, meganuclease expression and nuclear staining (DAPI). FIG. 5A provides imaging of meganuclease and Pax7 expression in quadricep tissue from meganuclease treated mice with an expression construct utilizing a tMCK promoter in an AAV9 capsid at a dosage of 1e14 VG/kg. FIG. 5B provides imaging of meganuclease and Pax7 expression in quadricep tissue from meganuclease treated mice with an expression construct utilizing a tMCK promoter in an rh74 AAV capsid at a dosage of 1e14 VG/kg. FIG. 5C provides imaging of meganuclease and Pax7 expression in quadricep tissue from meganuclease treated mice with PBS only; the star indicated in the upper left panel indicates non-specific background detection from the meganuclease specific antibodies.

Figure 6A:
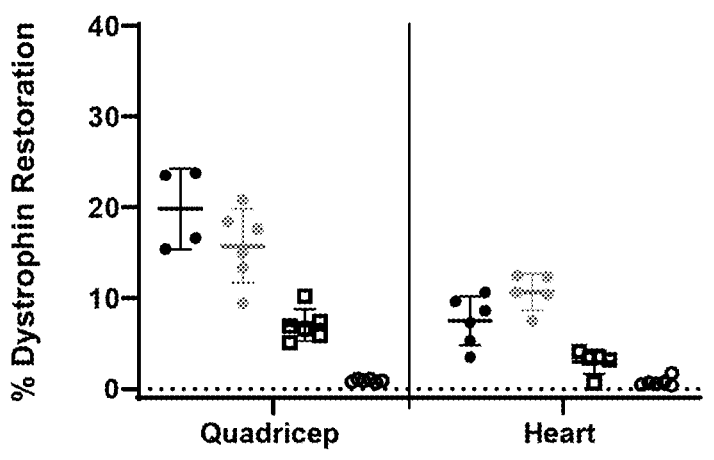
Figure 6B:
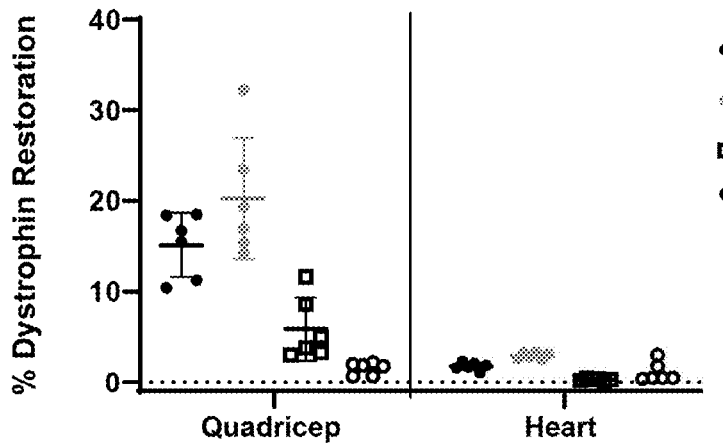

FIG. 6A and FIG. 6B provide bar graphs showing the shortened modified dystrophin protein levels by capillary Western immunoassay (WES) analysis normalized to the vinculin loading control for the DMD 19-20L.329 and DMD 35-36L.349 pair of meganucleases or PBS only from both quadricep and heart tissue. In FIG. 6A, mice were treated with an expression construct utilizing the tMCK promoter with a WPRE in an AAV9 capsid at the indicated dosages. In FIG. 6B, mice were treated with an expression construct utilizing the tMCK promoter without a WPRE in an AAV9 capsid at the indicated dosages.

FIG. 7 provides a table providing a list of heart lesions from each group of hDMDdel52/mdx (hDMD) mice treated with expression constructs that encoded the pair of DMD 19-20L.329 and DMD 35-36L.349 meganucleases. Group 1 indicates mice treated with an expression construct utilizing the MHCK7 promoter in an AAV9 capsid at a dosage of 1e14 VG/kg. Groups 2-4 indicates mice treated with an expression construct utilizing the MHCK7 promoter in an AAVrh74 capsid at a dosage of 1e14, 3e13, and 1e13 VG/kg, respectively. Groups 5-7 indicates mice treated with an expression construct utilizing the tMCK promoter in an AAV9 capsid at a dosage of 1e14, 3e13, and 1e13 VG/kg respectively. Groups 8-10 indicates mice treated with an expression construct utilizing the tMCK promoter in an rh74 capsid at a dosage of 1e14, 3e13, and 1e13 VG/kg respectively.

Figure 8A:
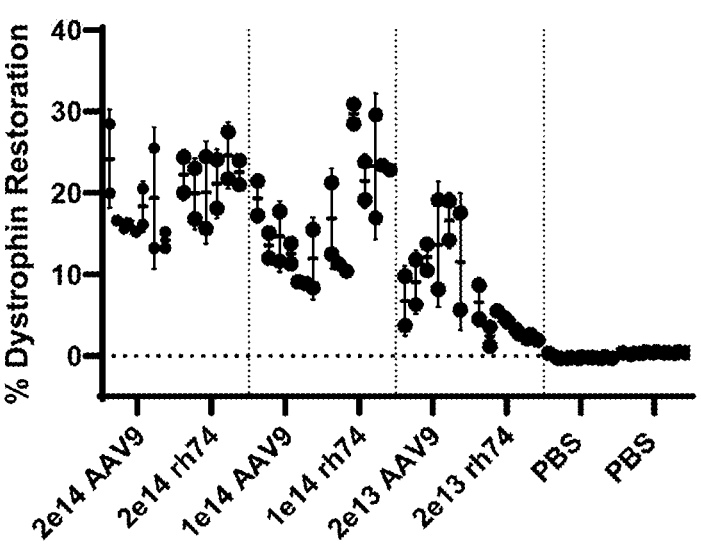
Figure 8B:
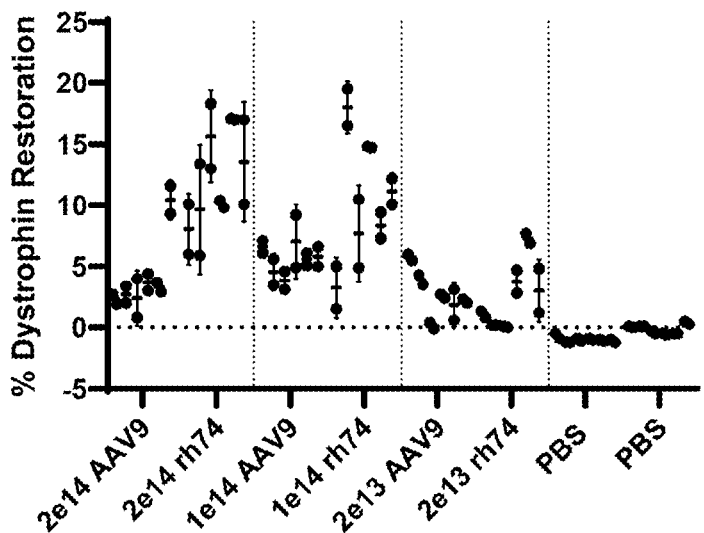
Figure 8C:
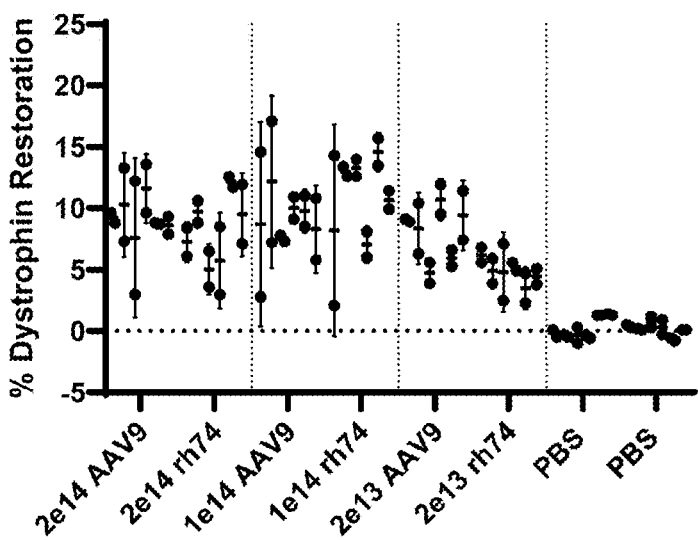
Figure 8D:
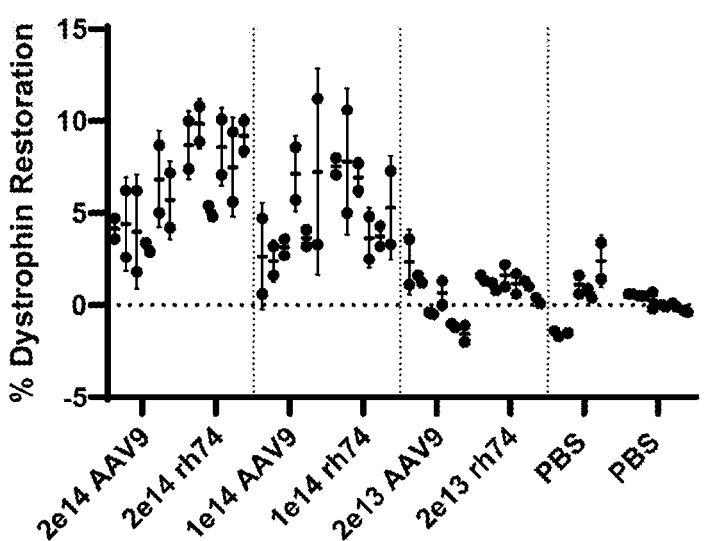
Figure 8E:
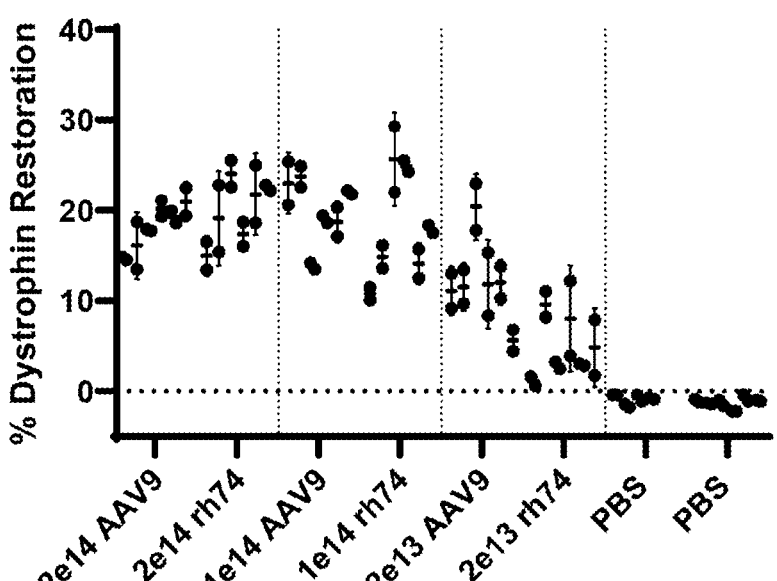

FIG. 8A-FIG. 8E provide charts showing the percentage of shortened modified dystrophin protein by WES analysis normalized to the vinculin loading control from various tissues from hDMDdel52/mdx (hDMD) mice treated with PBS or the DMD 19-20L.329 and DMD 35-36L.349 pair of meganucleases expressed from an expression construct utilizing the tMCK promoter in either an AAV9 or AAVrh74 capsid at the indicated dosages. FIG. 8A shows the percentage of shortened modified dystrophin restoration from quadricep tissue. FIG. 8B shows the percentage of shortened modified dystrophin restoration from tibialis anterior tissue. FIG. 8C shows the percentage of shortened modified dystrophin restoration from heart tissue. FIG. 8D shows the percentage of shortened modified dystrophin restoration from diaphragm tissue. FIG. 8E shows the percentage of shortened modified dystrophin restoration from gastrocnemius tissue.

Figure 9A:
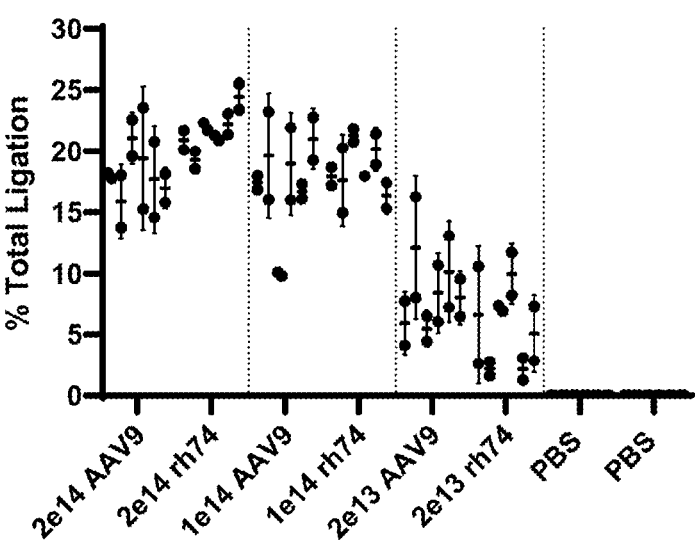
Figure 9B:
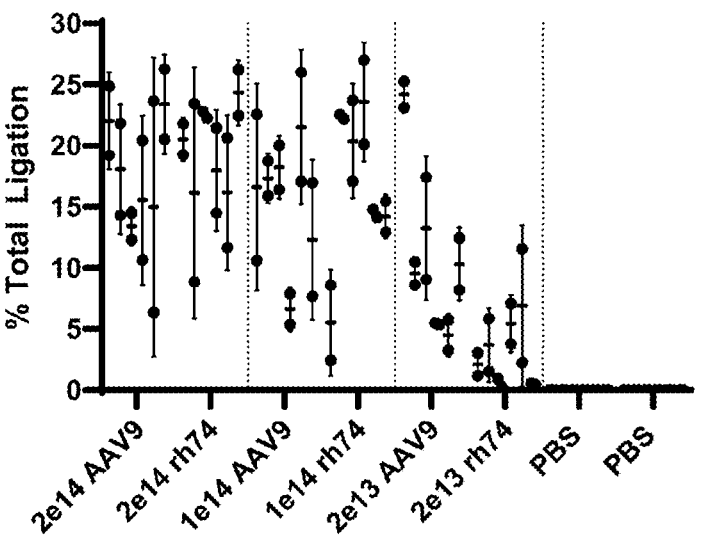
Figure 9C:
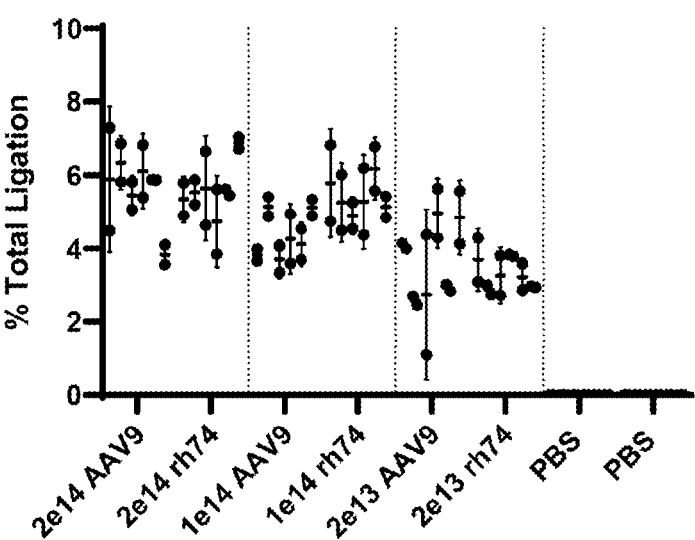
Figure 9D:
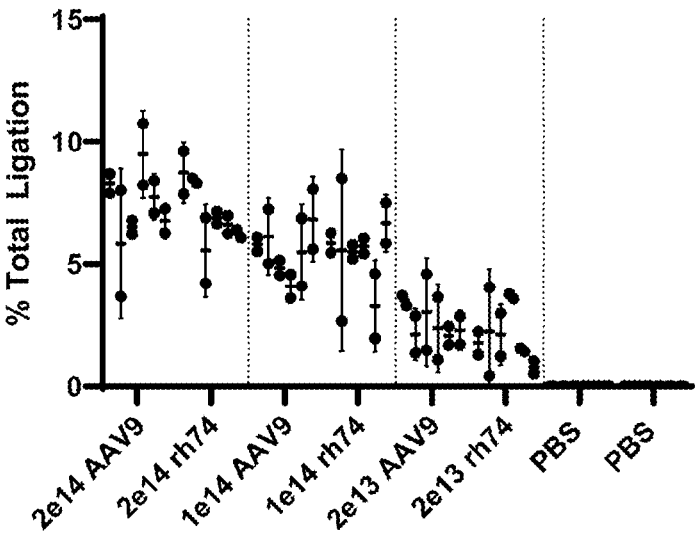
Figure 9E:
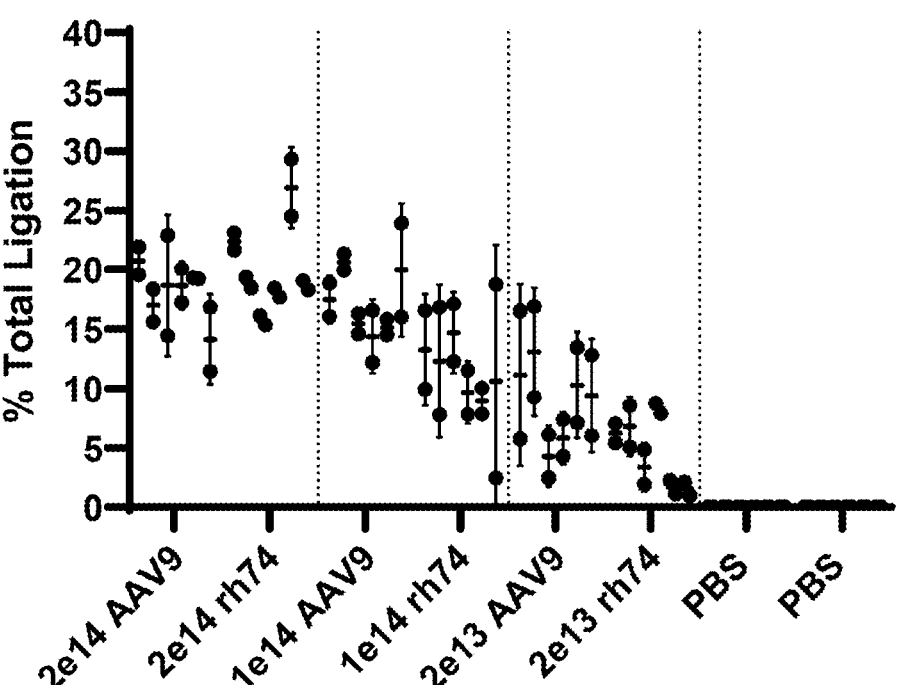

FIG. 9A-FIG. 9E provide charts showing the percentage (%) of total ligation of genomic DNA adjacent to exons 45-55 following cleavage of the DMD 19-20 and DMD 35-36 recognition sequences by the DMD 19-20L.329 and DMD 35-36L.349 pair of meganucleases in hDMDdel52/mdx (hDMD) mice treated with either PBS or the meganucleases. The meganucleases were expressed from an expression construct utilizing the tMCK promoter in either an AAV9 or AAVrh74 capsid at the indicated dosages. FIG. 9A shows the percentage of total ligation from quadricep tissue. FIG. 9B shows the percentage of total ligation from tibialis anterior tissue. FIG. 9C shows the percentage of total ligation from heart tissue. FIG. 9D shows the percentage of total ligation from diaphragm tissue. FIG. 9E shows the percentage of total ligation from gastrocnemius tissue.

Figure 10A:
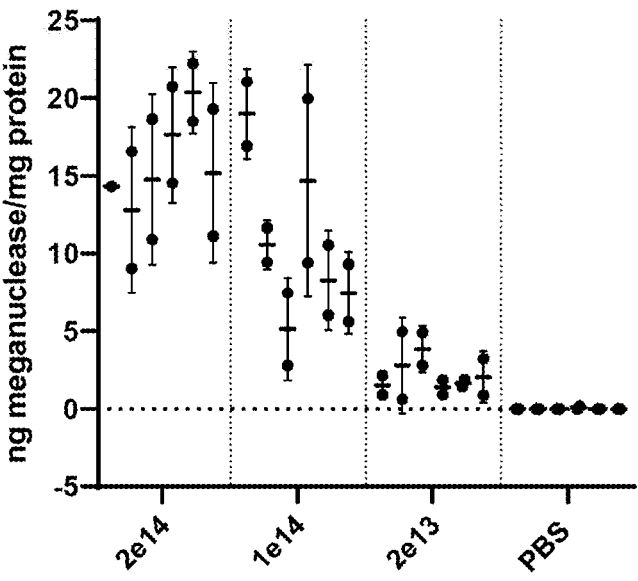
Figure 10B:
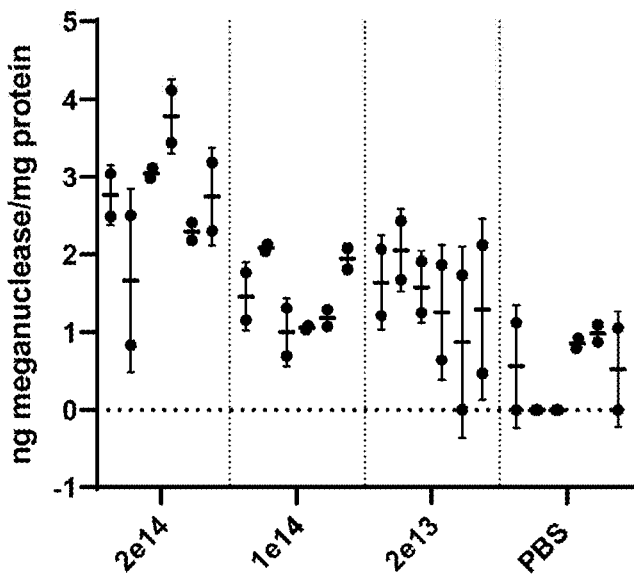
Figure 10C:
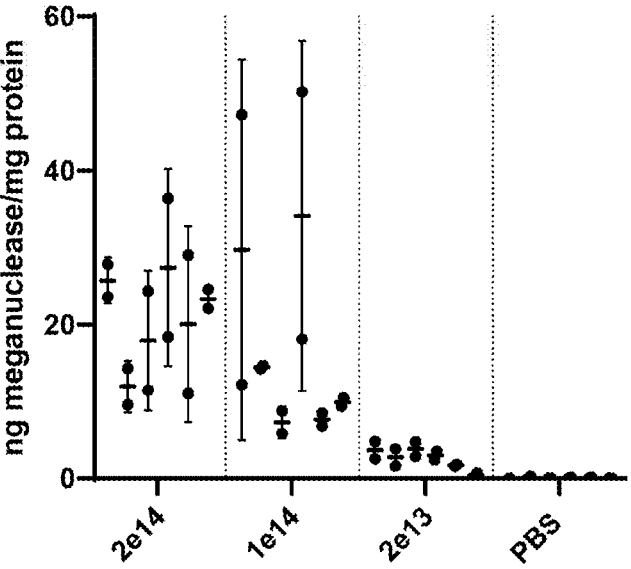
Figure 10D:
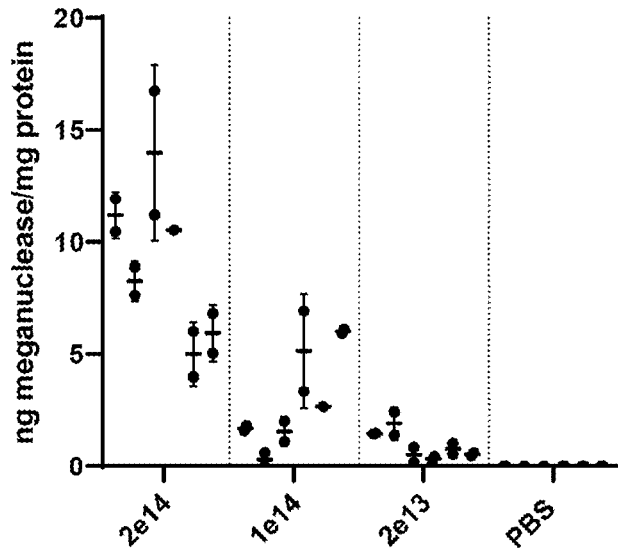
Figure 10E:
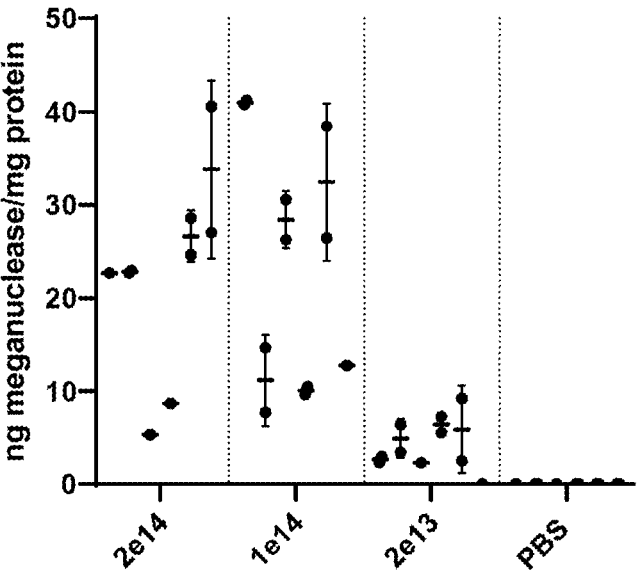
Figure 10F:
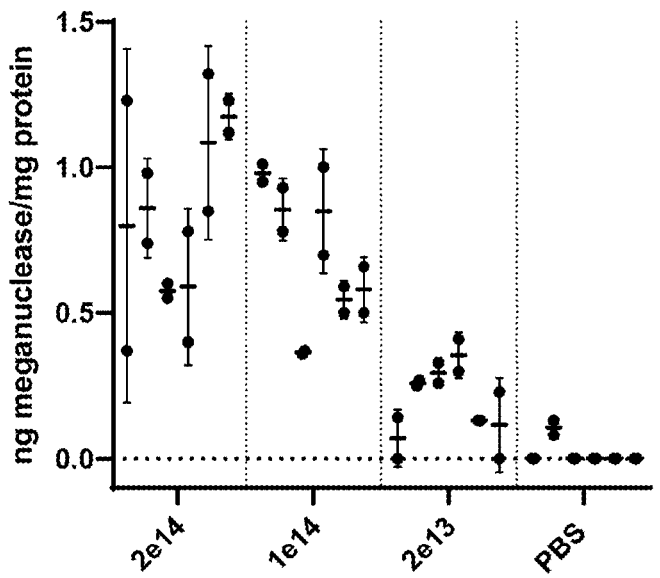

FIG. 10A-FIG. 10F provide charts of the meganuclease expression in ng of meganuclease/mg of total cellular protein from lysates from hDMDdel52/mdx (hDMD) mice treated with either PBS or the DMD 19-20L.329 and DMD 35-36L.349 pair of meganucleases at the indicated dosages. The meganucleases were expressed from an expression construct utilizing the tMCK promoter in an AAV9 capsid. FIG. 10A shows the meganuclease expression from quadricep tissue. FIG. 10B shows the meganuclease expression from heart tissue. FIG. 10C shows the meganuclease expression from gastrocnemius tissue. FIG. 10D shows the meganuclease expression from diaphragm tissue. FIG. 10E shows the meganuclease expression from tibialis anterior tissue. FIG. 10F shows the meganuclease expression from liver tissue.

Figure 11A:
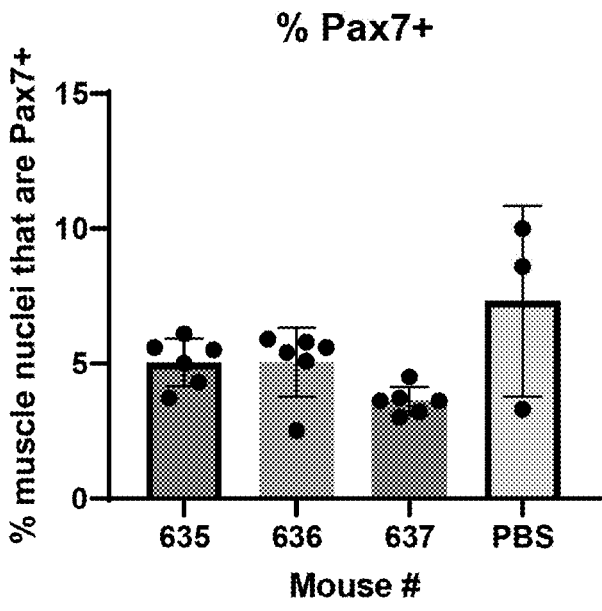
Figure 11B:
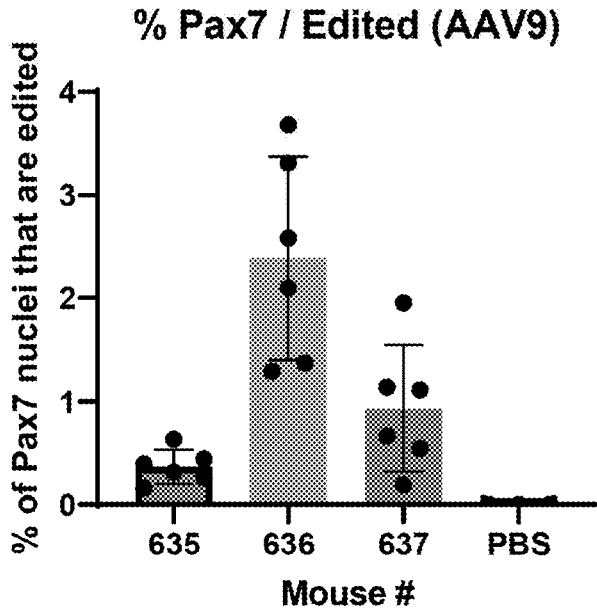

FIG. 11A and FIG. 11B. FIG. 11A provides a bar graph showing the percentage of Pax7 positive muscle satellite cells from quadricep muscle tissue from hDMDdel52/mdx (hDMD) mice treated with either PBS or an expression construct encoding the DMD 19-20L.329 and DMD 35-36L.349 pair of meganucleases in an AAV9 capsid. FIG. 11B provides the percentage of Pax7 positive cells in which exons 45-55 of the dystrophin gene were excised.

Figure 12A:
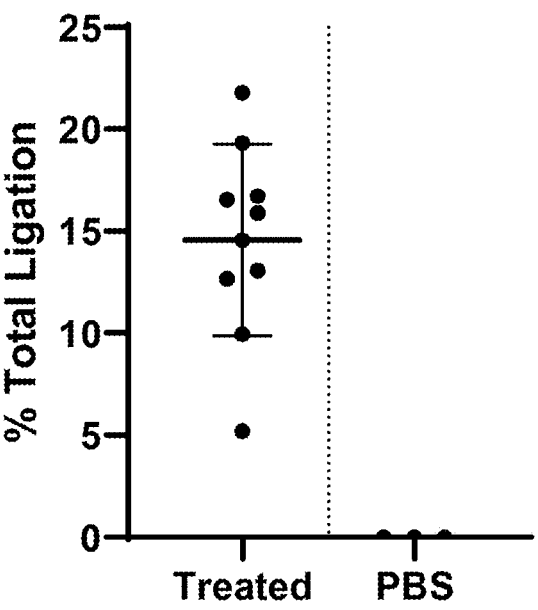
Figure 12B:
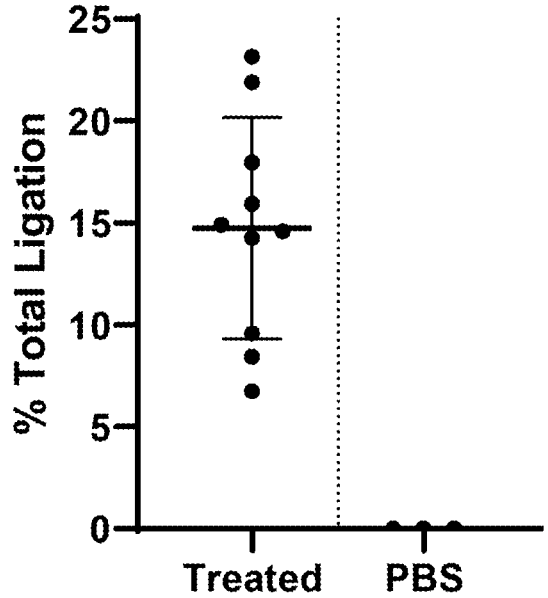
Figure 12C:
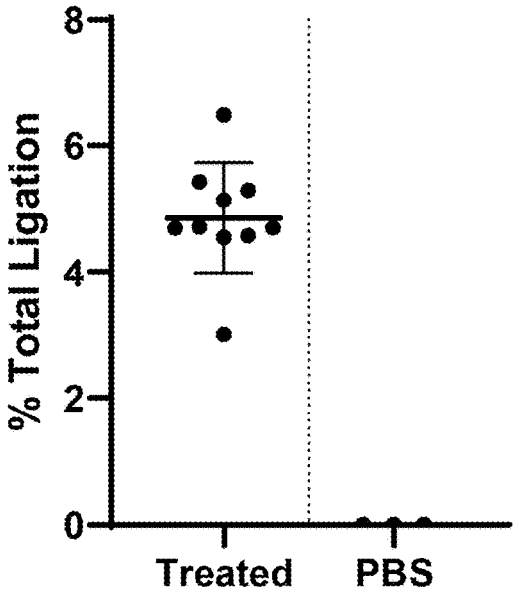
Figure 12D:
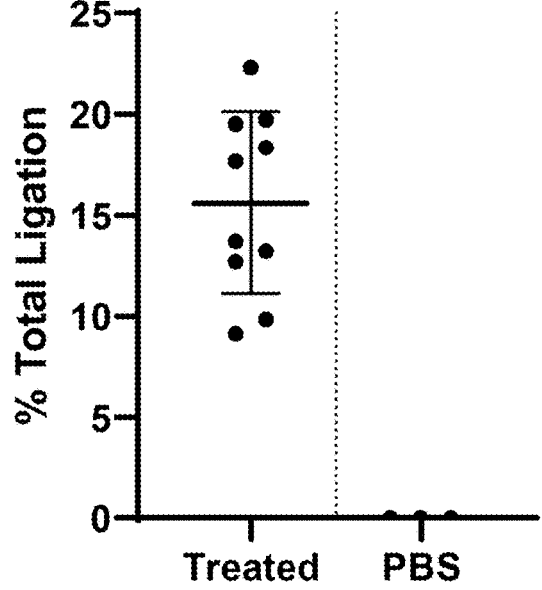
Figure 12E:
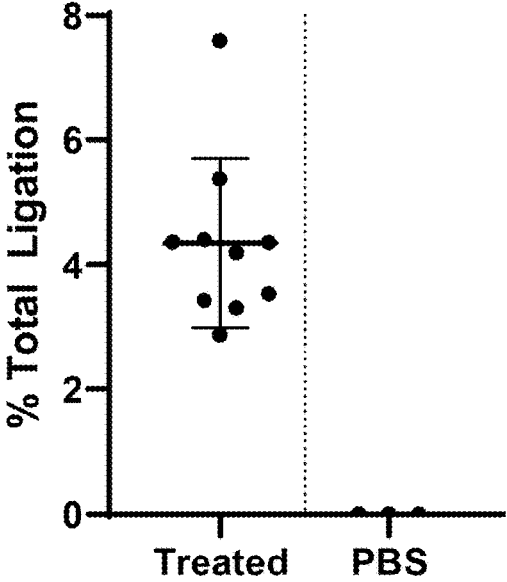
Figure 12F:
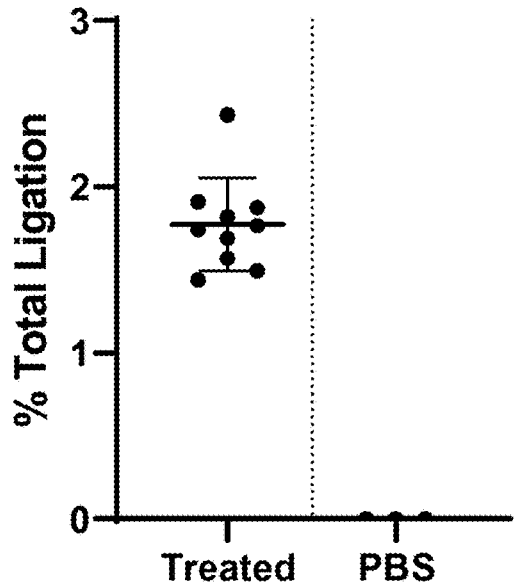

FIG. 12A-FIG. 12F provide charts showing the percentage (%) of total ligation of genomic DNA adjacent to exons 45-55 following cleavage of the DMD 19-20 and DMD 35-36 recognition sequences by the DMD 19-20L.329 and DMD 35-36L.349 pair of meganucleases in hDMDdel52/mdx (hDMD) mice treated with either PBS or the meganucleases. The meganucleases were expressed from an expression construct utilizing the tMCK promoter in an AAV9 capsid at a 1e14 VG/kg dosages. FIG. 12A shows the percentage of total ligation from quadricep tissue. FIG. 12B shows the percentage of total ligation from gastrocnemius tissue. FIG. 12C shows the percentage of total ligation from heart tissue. FIG. 12D shows the percentage of total ligation from tibialis anterior tissue. FIG. 12E shows the percentage of total ligation from diaphragm tissue. FIG. 12F shows the percentage of total ligation from liver tissue.

Figure 13A:
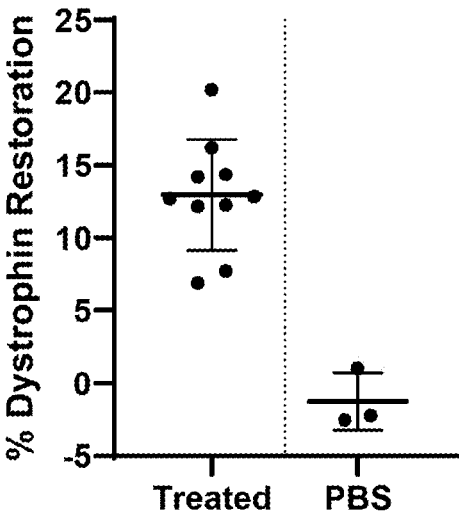
Figure 13B:
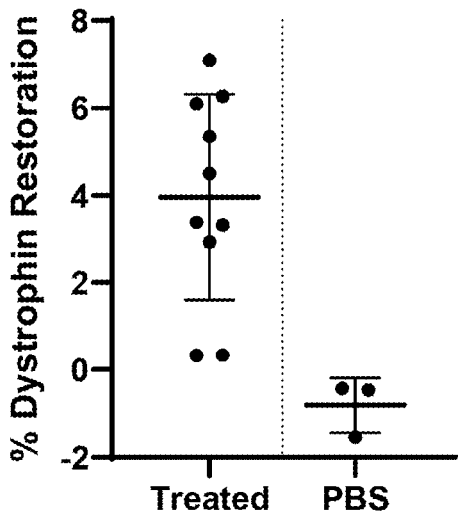
Figure 13C:
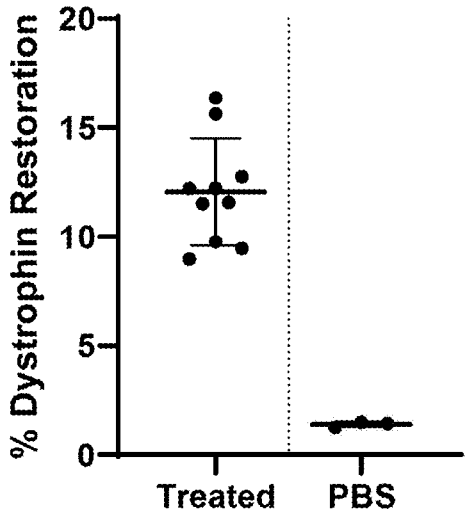
Figure 13D:
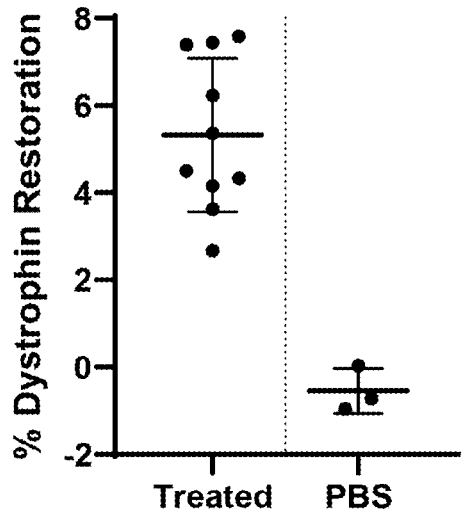
Figure 13E:
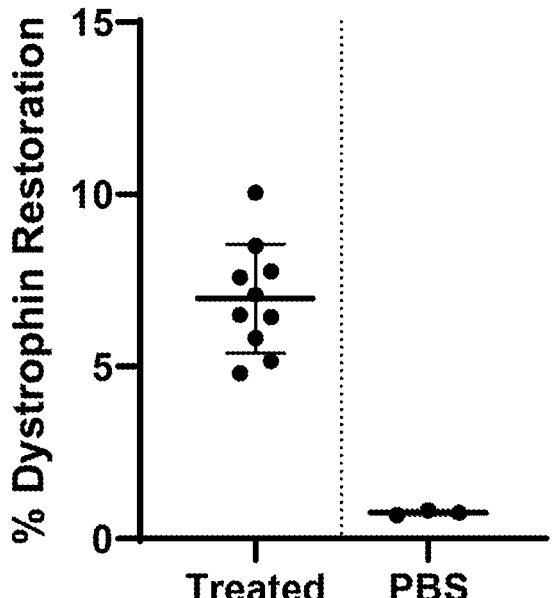

FIG. 13A-FIG. 13E provide charts showing the percentage of shortened modified dystrophin protein by WES analysis normalized to the vinculin loading control from various tissues from hDMDdel52/mdx (hDMD) mice treated with PBS or the DMD 19-20L.329 and DMD 35-36L.349 pair of meganucleases expressed from an expression construct utilizing the tMCK promoter in an AAV9 capsid at a 1e14 VG/kg dosages. FIG. 13A shows the percentage of shortened modified dystrophin restoration from quadricep tissue. FIG. 13B shows the percentage of shortened modified dystrophin restoration from gastrocnemius tissue. FIG. 13C shows the percentage of shortened modified dystrophin restoration from heart tissue. FIG. 13D shows the percentage of shortened modified dystrophin restoration from tibialis anterior tissue. FIG. 13E shows the percentage of shortened modified dystrophin restoration from diaphragm tissue.

Figure 14:
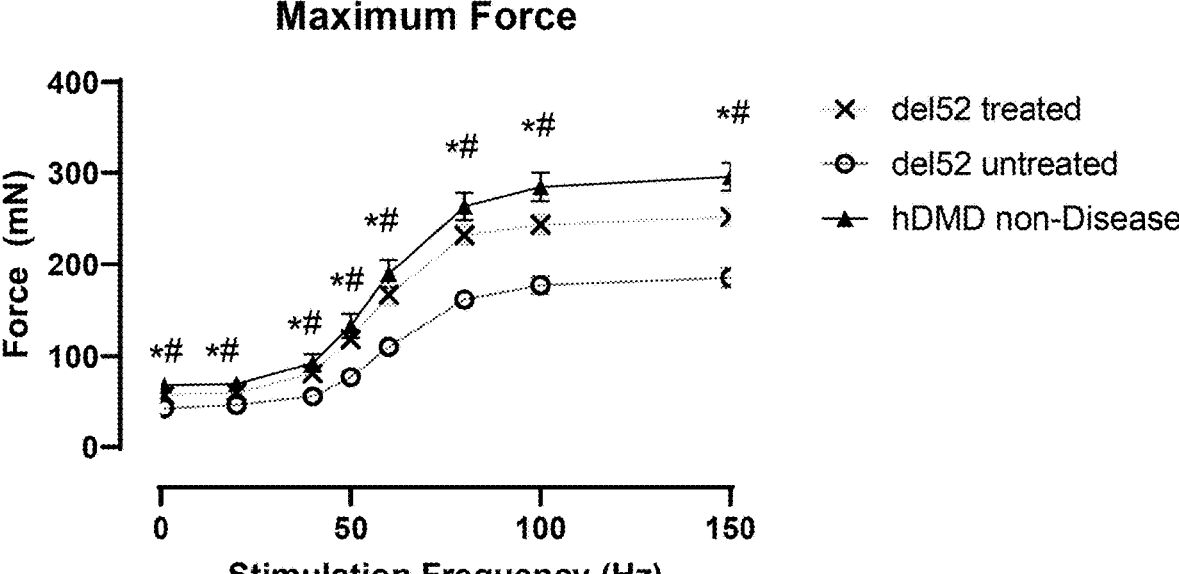

FIG. 14 provides a line graph showing the maximum force generation in hDMDdel52/mdx (hDMD) mice relative to non-diseased mice. The mice were treated with the DMD 19-20L.329 and DMD 35-36L.349 pair of meganucleases expressed from an expression construct utilizing the tMCK promoter in an AAV9 capsid at a 1e14 VG/kg dosages.

Figure 15A:
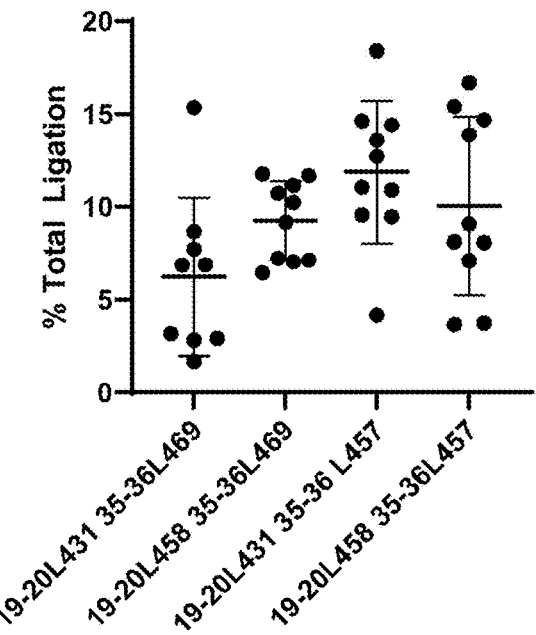
Figure 15B:
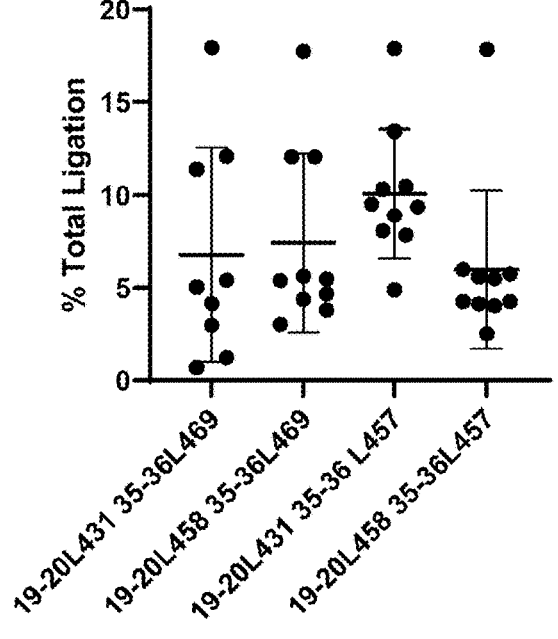
Figure 15C:
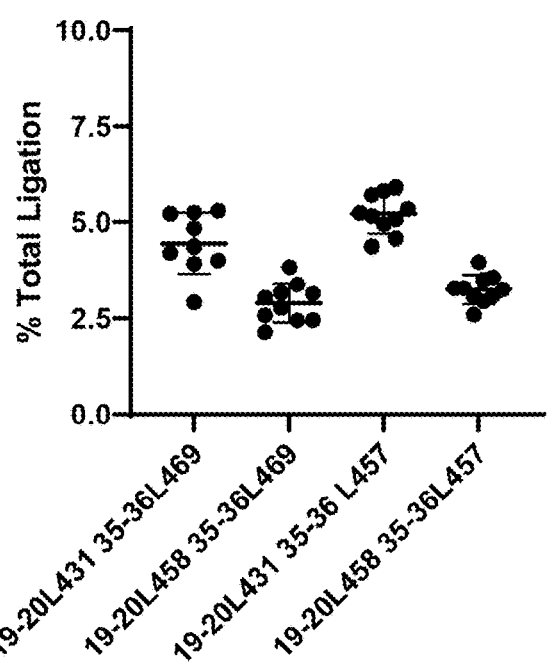
Figure 15D:
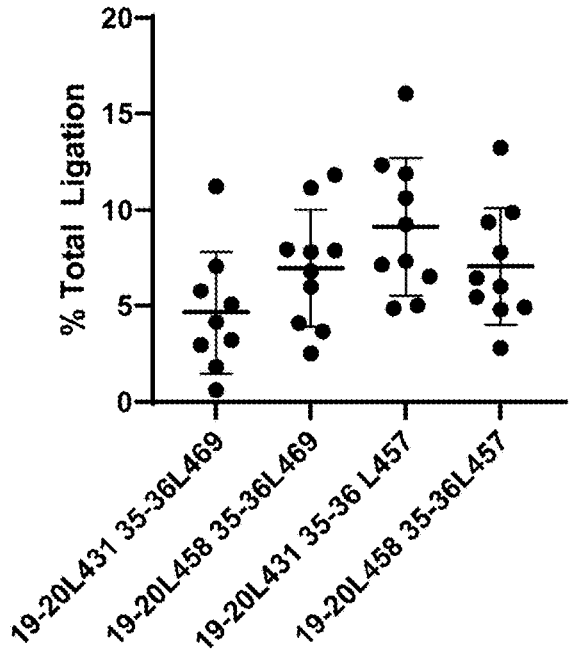
Figure 15E:
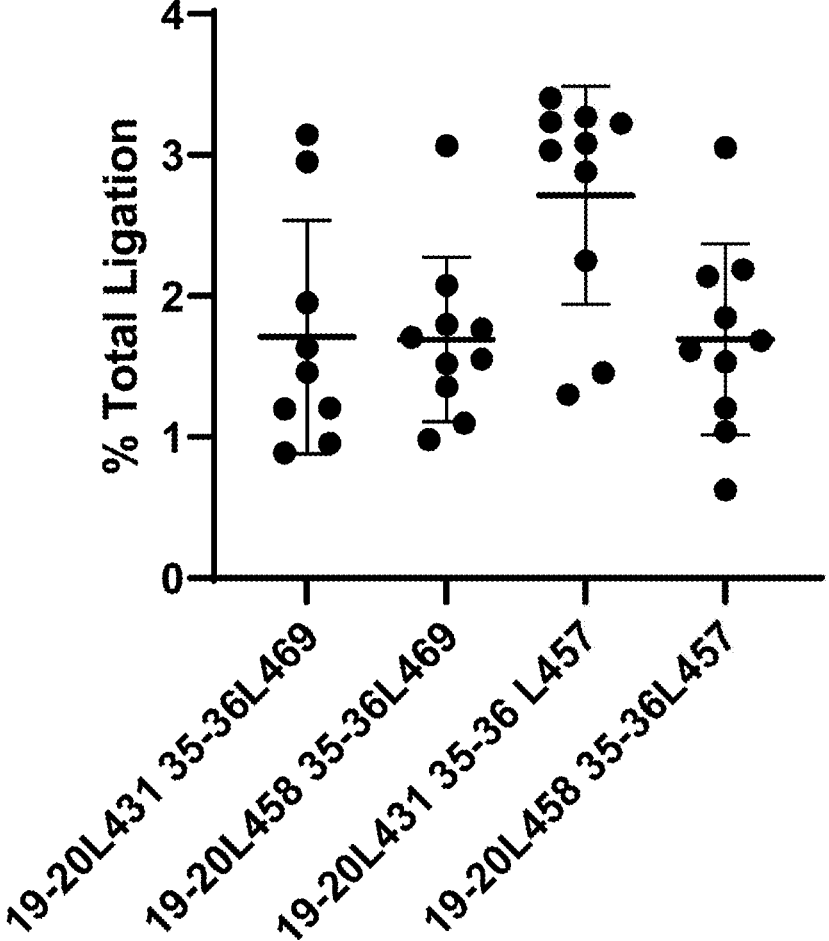

FIG. 15A-FIG. 15E provide charts showing the percentage (%) of total ligation of genomic DNA adjacent to exons 45-55 following cleavage of the DMD 19-20 and DMD 35-36 recognition sequences in hDMDdel52/mdx (hDMD) mice treated with either PBS or the indicated pairs of meganucleases. The meganucleases were expressed from an expression construct utilizing the tMCK promoter in an AAV9 capsid at a 3e13 VG/kg dosage. FIG. 15A shows the percentage of total ligation from quadricep tissue. FIG. 15B shows the percentage of total ligation from gastrocnemius tissue. FIG. 15C shows the percentage of total ligation from heart tissue. FIG. 15D shows the percentage of total ligation from tibialis anterior tissue. FIG. 15E shows the percentage of total ligation from diaphragm tissue.

Figure 16A:
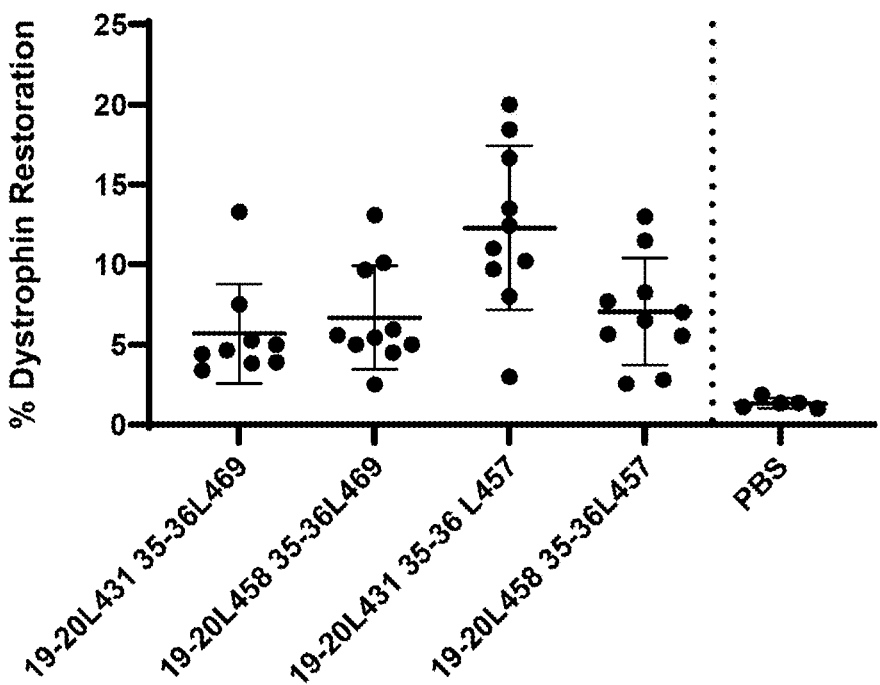
Figure 16B:
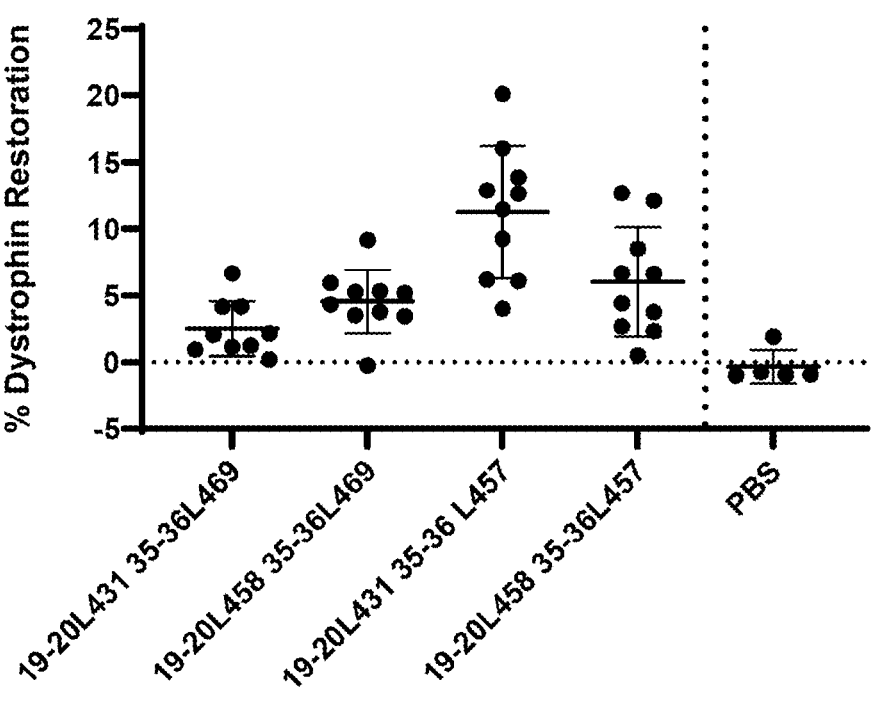
Figure 16C:
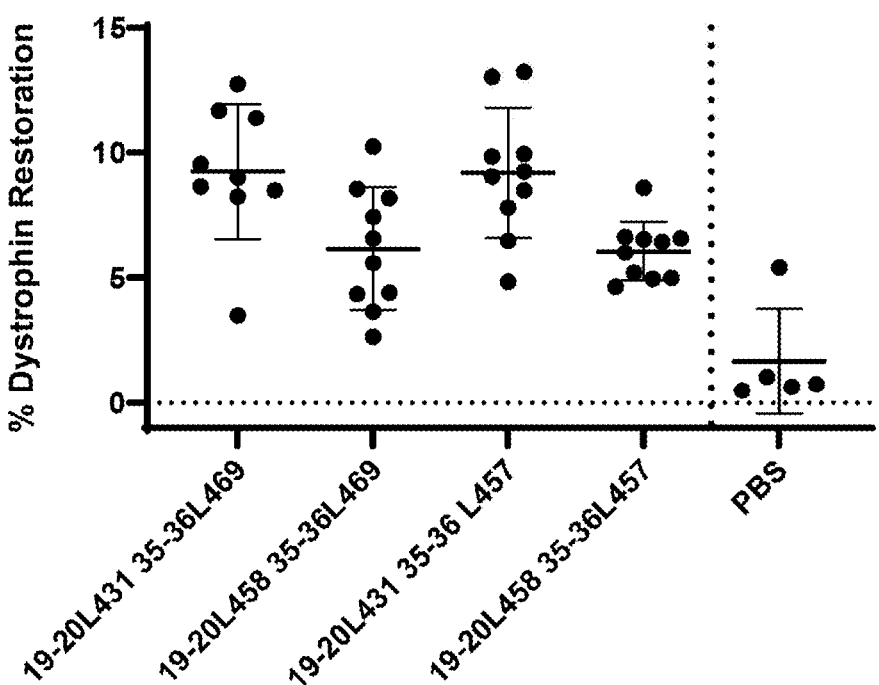
Figure 16D:
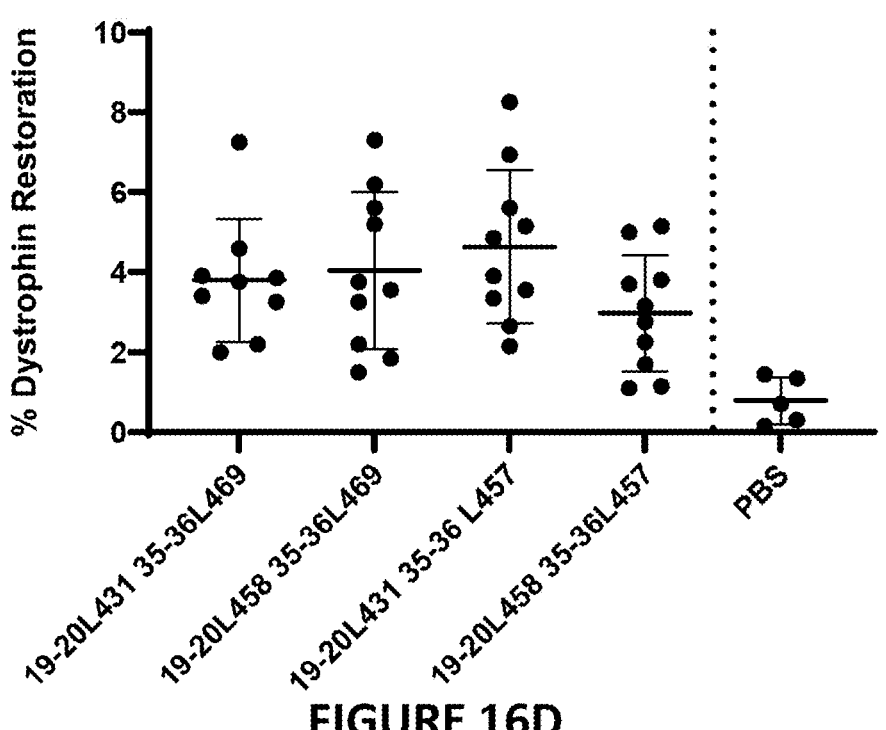
Figure 16E:
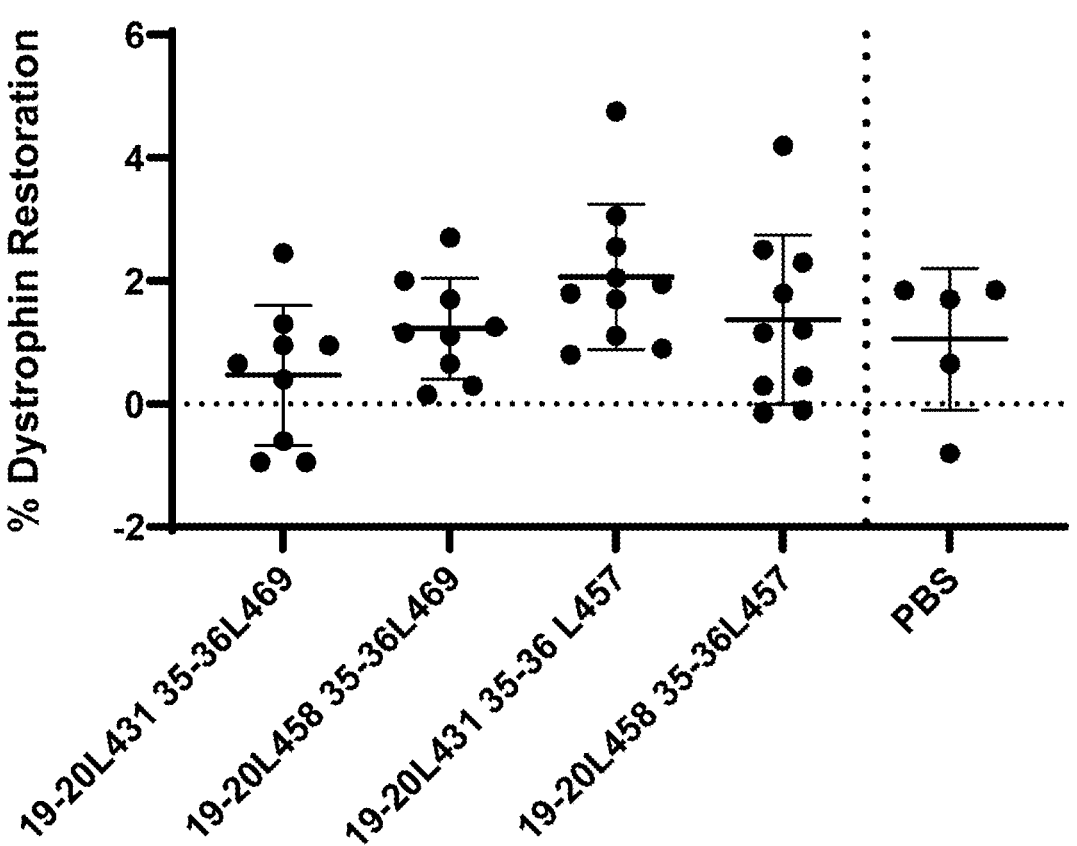

FIG. 16A-FIG. 16E provide charts showing the percentage of shortened modified dystrophin protein by WES analysis normalized to the vinculin loading control from various tissues from hDMDdel52/mdx (hDMD) mice treated with PBS or the indicated pairs of meganucleases expressed from an expression construct utilizing the tMCK promoter in an AAV9 capsid at a 3e13 VG/kg dosage. FIG. 16A shows the percentage of shortened modified dystrophin restoration from quadricep tissue. FIG. 16B shows the percentage of shortened modified dystrophin restoration from gastrocnemius tissue. FIG. 16C shows the percentage of shortened modified dystrophin restoration from heart tissue. FIG. 16D shows the percentage of shortened modified dystrophin restoration from tibialis anterior tissue. FIG. 16E shows the percentage of shortened modified dystrophin restoration from diaphragm tissue.

Figure 17:
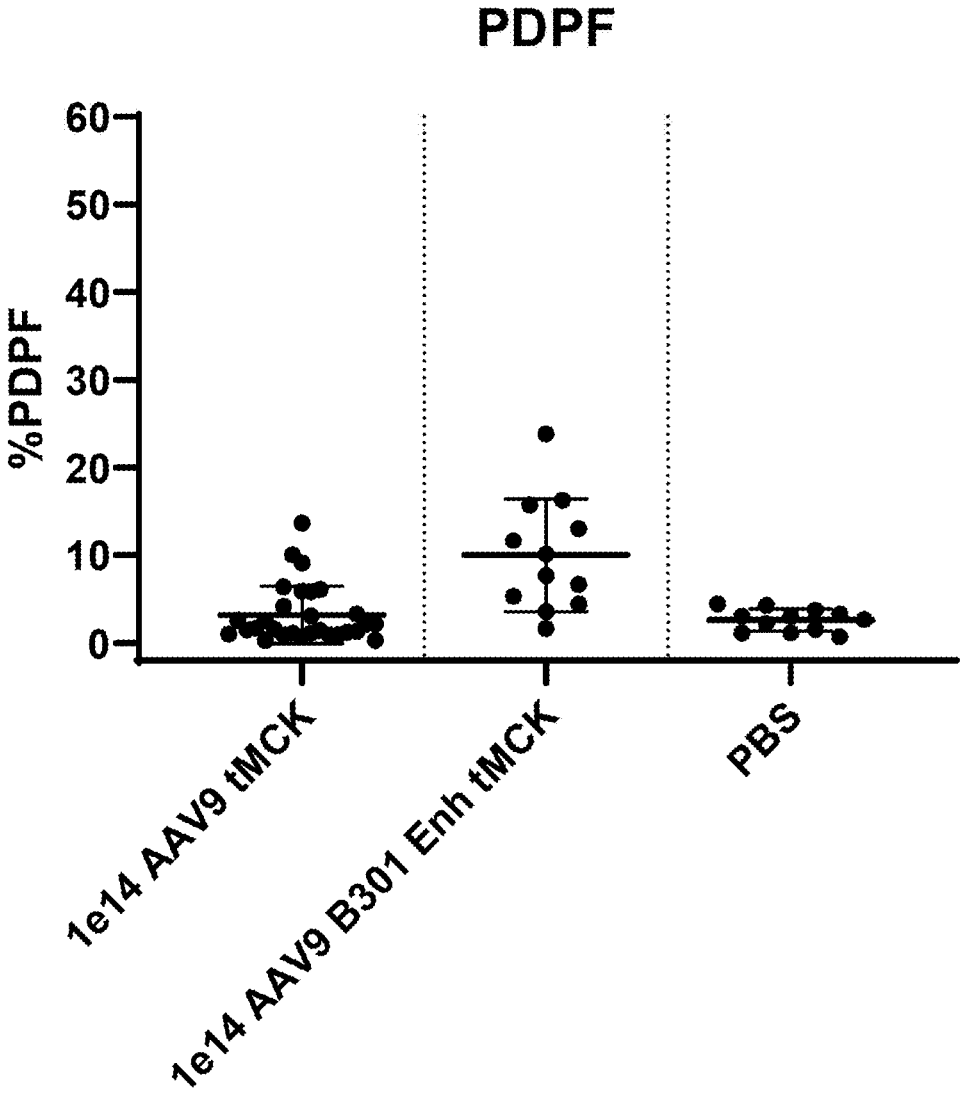

FIG. 17 provides a graph showing the percentage of dystrophin positive fibers in hDMDdel52/mdx (hDMD) mice that were treated with the DMD 19-20L.329 and DMD 35-36L.349 pair of meganucleases expressed from an expression construct having a B-301 enhancer element, a tMCK promoter in an AAV9 capsid at a 1e14 VG/kg dosage.

Figure 18A:
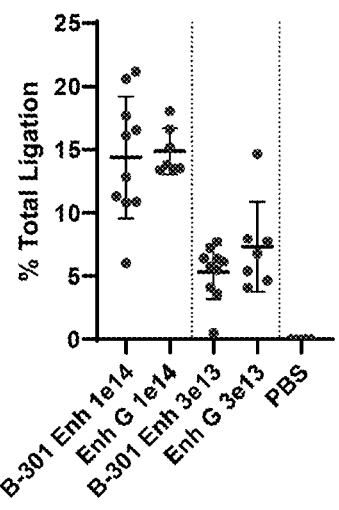

FIG. 18A-FIG. 18D provide charts showing the percentage (%) of total ligation of genomic DNA adjacent to exons 45-55 following cleavage of the DMD 19-20 and DMD 35-36 recognition sequences in hDMDdel52/mdx (hDMD) mice treated with either PBS or the indicated expression constructs. The meganucleases were expressed from an expression construct having either a B-301 enhancer element or an Enhancer G element with a tMCK promoter in an AAV9 capsid at either a 3e13 or 1e14 VG/kg dosage. FIG. 18A shows the percentage of total ligation from quadricep tissue.

Figure 18B:
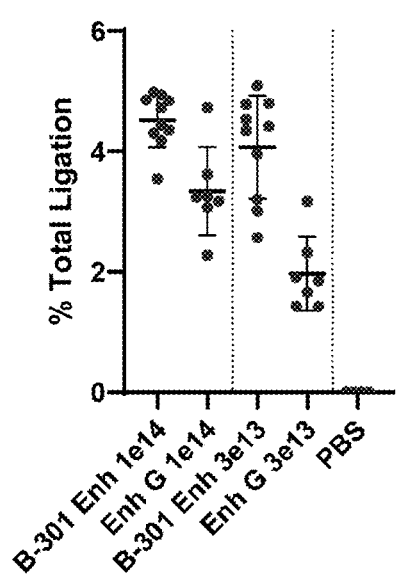
Figure 18C:
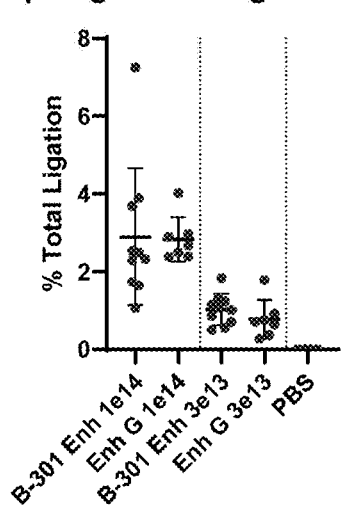
Figure 18D:
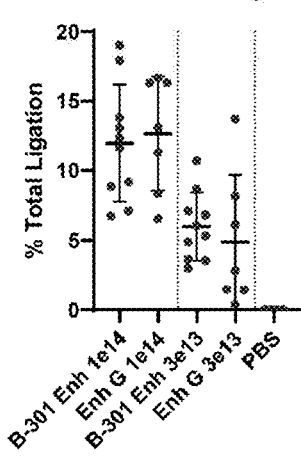

FIG. 18B shows the percentage of total ligation from heart tissue. FIG. 18C shows the percentage of total ligation from diaphragm tissue. FIG. 18D shows the percentage of total ligation from gastrocnemius tissue.

Figure 19A:
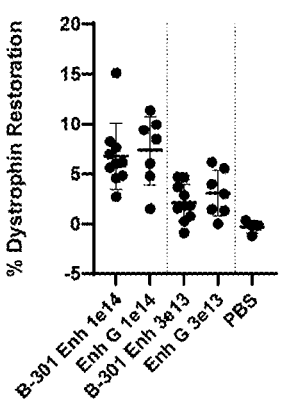
Figure 19B:
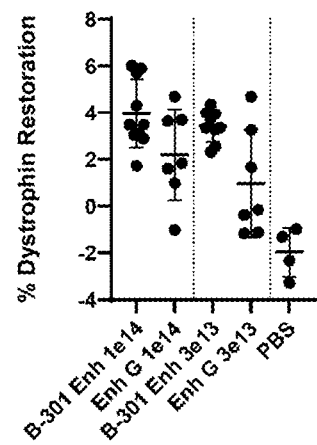
Figure 19C:
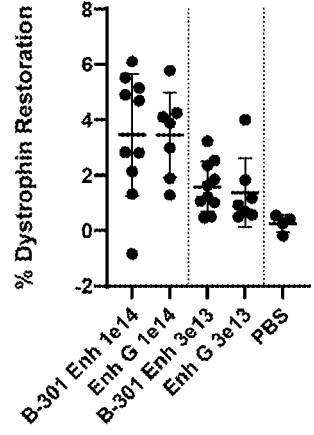
Figure 19D:
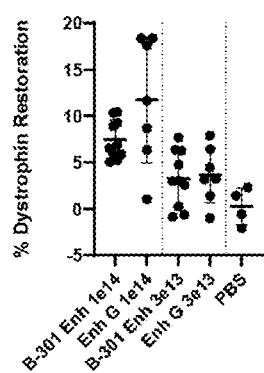

FIG. 19A-FIG. 19D provide charts showing the percentage of shortened modified dystrophin protein by WES analysis normalized to the vinculin loading control from various tissues from hDMDdel52/mdx (hDMD) mice treated with PBS or the indicated pairs expression constructs. The meganucleases were expressed from expression constructs having either a B-301 enhancer element or an Enhancer G element with a tMCK promoter in an AAV9 capsid at either a 3e13 or 1e14 VG/kg dosage. FIG. 19A shows the percentage of shortened modified dystrophin protein from quadricep tissue. FIG. 19B shows the percentage of shortened modified dystrophin protein from heart tissue. FIG. 19C shows the percentage of shortened modified dystrophin protein from diaphragm tissue. FIG. 19D shows the percentage of shortened modified dystrophin protein from gastrocnemius tissue.

Figure 20:
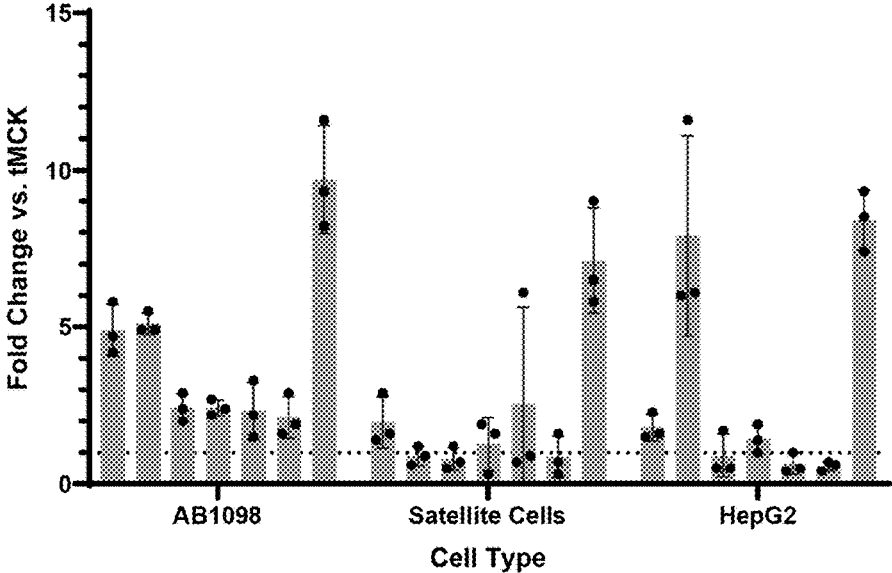

FIG. 20 provides a bar graph showing the expression of luciferin in AB1098, murine muscle satellite cells, or HepG2 immortalized liver cells utilizing the expression cassettes having the indicated muscle enhancers normalized to a muscle-specific expression cassette containing the tMCK promoter without any additional muscle-specific enhancer. Each bar for the treated cells (AB1098, satellite cells, and HepG2 cells) corresponds from left to right as constructs including the B-301 enhancer, the MTF1 enhancer, the SPDEF1 enhancer, Enhancer F, Enhancer G, Enhancer I, and the MHCK7 promoter alone. The first plasmid construct contained, from 5' to 3', the B301 enhancer, the muscle-specific promoter tMCK, Firefly Luciferase, a WPRE element, and an SV40 polyadenylation signal. The second plasmid construct contained, from 5' to 3', the MTF1 enhancer, the muscle-specific promoter tMCK, Firefly Luciferase, a WPRE element, and an SV40 polyadenylation signal. The third plasmid construct contained, from 5' to 3', the MTSPDEF1 enhancer, the muscle-specific promoter tMCK, Firefly Luciferase, a WPRE element, and an SV40 polyadenylation signal. The fourth plasmid construct contained, from 5' to 3', the enhancer F, the muscle-specific promoter tMCK, Firefly Luciferase, a WPRE element, and an SV40 polyadenylation signal. The fifth plasmid construct contained, from 5' to 3', the enhancer G, the muscle-specific promoter tMCK, Firefly Luciferase, a WPRE element, and an SV40 polyadenylation signal. The sixth plasmid construct contained, from 5' to 3', the enhancer I, the muscle-specific promoter tMCK, Firefly Luciferase, a WPRE element, and an SV40 polyadenylation signal. The seventh plasmid construct contained, from 5' to 3', the muscle-specific promoter MHCK7, Firefly Luciferase, a WPRE element, and an SV40 polyadenylation signal. The eighth plasmid construct contained, from 5' to 3', the muscle-specific promoter tMCK, Firefly Luciferase, a WPRE element, and an SV40 polyadenylation signal.

FIG. 21A-FIG. 21E provide charts showing the percentage (%) of total ligation of genomic DNA adjacent to exons 45-55 following cleavage of the DMD 19-20 and DMD 35-36 recognition sequences in various muscle tissues from hDMDdel52/mdx (hDMD) mice treated with 3e13 or 1e14 VG/kg of an AAV encoding the DMD 19-20L.431 and DMD35-36L.457 meganucleases, or PBS as a control. The figures illustrate the total ligation percentage observed in quadriceps (FIG. 21A), gastrocnemius (FIG. 21B), tibialis anterior (TA; FIG. 21C), heart (FIG. 21D), or diaphragm (FIG. 21E).

Figure 22A:
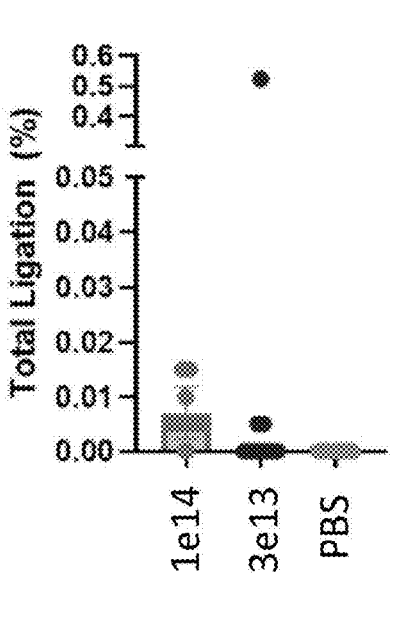
Figure 22B:
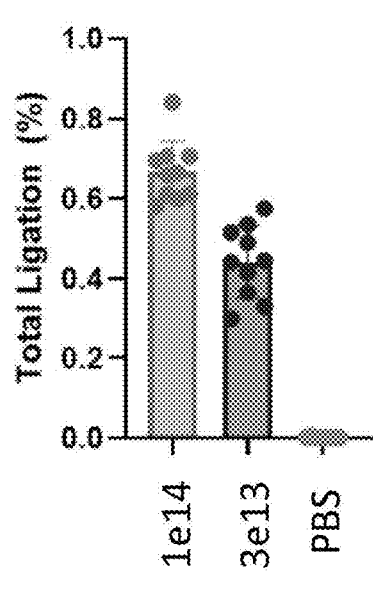
Figure 22C:
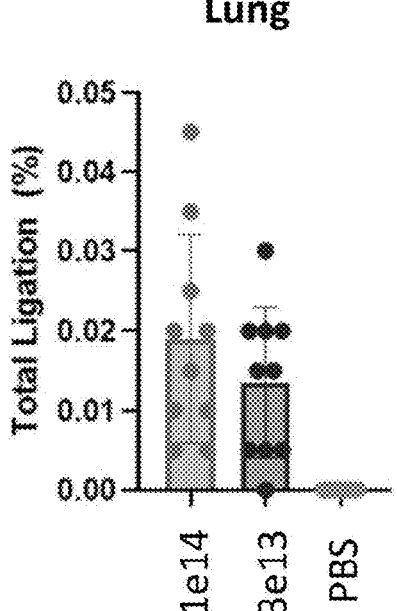

FIG. 22A-FIG. 22C provide charts showing the percentage (%) of total ligation of genomic DNA adjacent to exons 45-55 following cleavage of the DMD 19-20 and DMD 35-36 recognition sequences in various tissues from hDMDdel52/mdx (hDMD) mice treated with 3e13 or 1e14 VG/kg of an AAV encoding the DMD 19-20L.431 and DMD 35-36L.457 meganucleases, or PBS as a control. The figures illustrate the total ligation percentage observed in brain (FIG. 22A), liver (FIG. 22B), or lung (FIG. 22C).

BRIEF DESCRIPTION OF THE SEQUENCES

SEQ ID NO: 1 sets forth the nucleic acid sequence of the B-301 muscle-specific enhancer element.

SEQ ID NO: 2 sets forth the nucleic acid sequence of a MCK basal promoter region from position −358 to +7.

SEQ ID NO: 3 sets forth the nucleic acid sequence of a MCK basal promoter from position −80+7.

SEQ ID NO: 4 sets forth the nucleic acid sequence of a MCK-R control element.

SEQ ID NO: 5 sets forth the nucleic acid sequence of a MCK-R control element.

SEQ ID NO: 6 sets forth the nucleic acid sequence of a MCK-R control element.

SEQ ID NO: 7 sets forth the nucleic acid sequence of a MCK-R control element.

SEQ ID NO: 8 sets forth the nucleic acid sequence of a MCK-R control element.

SEQ ID NO: 9 sets forth the nucleic acid sequence of a MCK-R control element.

SEQ ID NO: 10 sets forth the nucleic acid sequence of a MCK-R control element.

SEQ ID NO: 11 sets forth the nucleic acid sequence of a MCK-R control element.

SEQ ID NO: 12 sets forth the nucleic acid sequence of a MCK-R control element.

SEQ ID NO: 13 sets forth the nucleic acid sequence of a MCK-R control element.

SEQ ID NO: 14 sets forth the nucleic acid sequence of a MCK-R control element.

SEQ ID NO: 15 sets forth the nucleic acid sequence of a MCK-R control element.

SEQ ID NO: 16 sets forth the nucleic acid sequence of a MCK-R control element.

SEQ ID NO: 17 sets forth the nucleic acid sequence of a MCK-R control element.

SEQ ID NO: 18 sets forth the nucleic acid sequence of a murine MCK promoter and enhancer.

SEQ ID NO: 19 sets forth the nucleic acid sequence of a human MCK promoter.

SEQ ID NO: 20 sets forth the nucleic acid sequence of a wild type murine MCK enhancer sequence.

SEQ ID NO: 21 sets forth the nucleic acid sequence of a modified murine MCK enhancer sequence.

SEQ ID NO: 22 sets forth the nucleic acid sequence of a tMCK promoter sequence.

SEQ ID NO: 23 sets forth the nucleic acid sequence of a MHCK7 promoter sequence.

SEQ ID NO: 24 sets forth the nucleic acid sequence of a WPRE sequence.

SEQ ID NO: 25 sets forth the amino acid sequence of a SV40 nuclear localization sequence. SEQ ID NO: 26 sets forth the amino acid sequence of a NLS5.

SEQ ID NO: 27 sets forth the amino acid sequence of a c-myc NLS.

SEQ ID NO: 28 sets forth the amino acid sequence of a SV40H2 NLS.

SEQ ID NO: 29 sets forth the nucleic acid sequence of a SV40 polyA signal.

SEQ ID NO: 30 sets forth the amino acid sequence of a rh.74 capsid sequence.

SEQ ID NO: 31 sets forth the amino acid sequence of a AAV9 capsid sequence.

SEQ ID NO: 32 sets forth the nucleic acid sequence of a Kozak sequence.

SEQ ID NO: 33 sets forth the amino acid sequence of the wild-type I-CreI meganuclease from *Chlamydomonas reinhardtii*.

SEQ ID NO: 34 sets forth the amino acid sequence of the LAGLIDADG motif.

SEQ ID NO: 35 sets forth the amino acid sequence of the wild-type dystrophin protein CCDS48091.1 (Gene ID 1756).

SEQ ID NO: 36 sets forth the amino acid sequence of the wild-type dystrophin protein CCDS48091.1 (Gene ID 1756) lacking amino acids encoded by exons 45-55.

SEQ ID NO: 37 sets forth the nucleic acid sequence of the sense strand of the DMD 19-20 recognition sequence.

SEQ ID NO: 38 sets forth the nucleic acid sequence of the antisense strand of the DMD 19-20 recognition sequence.

SEQ ID NO: 39 sets forth the nucleic acid sequence of the sense strand of the DMD 35-36 recognition sequence.

SEQ ID NO: 40 sets forth the nucleic acid sequence of the antisense strand of the DMD 35-36 recognition sequence.

SEQ ID NO: 41 sets forth the nucleic acid sequence of the ligated hybrid DMD 19-20/35-36 sense strands.

SEQ ID NO: 42 sets forth the nucleic acid sequence of the ligated hybrid DMD 19-20/35-36 antisense strands.

SEQ ID NO: 43 sets forth the amino acid sequence of the DMD 19-20x.13 engineered meganuclease.

SEQ ID NO: 44 sets forth the amino acid sequence of the DMD 19-20x.87 engineered meganuclease.

SEQ ID NO: 45 sets forth the amino acid sequence of the DMD 19-20L.249 engineered meganuclease.

SEQ ID NO: 46 sets forth the amino acid sequence of the DMD 19-20L.302 engineered meganuclease.

SEQ ID NO: 47 sets forth the amino acid sequence of the DMD 19-20L.329 engineered meganuclease.

SEQ ID NO: 48 sets forth the amino acid sequence of the DMD 19-20L.374 engineered meganuclease.

SEQ ID NO: 49 sets forth the amino acid sequence of the DMD 19-20L.375 engineered meganuclease.

SEQ ID NO: 50 sets forth the amino acid sequence of the DMD 19-20L.431 engineered meganuclease.

SEQ ID NO: 51 sets forth the amino acid sequence of the DMD 19-20L.458 engineered meganuclease.

SEQ ID NO: 52 sets forth the amino acid sequence of the DMD 35-36x.63 engineered meganuclease.

SEQ ID NO: 53 sets forth the amino acid sequence of the DMD 35-36x.81 engineered meganuclease.

SEQ ID NO: 54 sets forth the amino acid sequence of the DMD 35-36L.195 engineered meganuclease.

SEQ ID NO: 55 sets forth the amino acid sequence of the DMD 35-36L.282 engineered meganuclease.

SEQ ID NO: 56 sets forth the amino acid sequence of the DMD 35-36L.349 engineered meganuclease.

SEQ ID NO: 57 sets forth the amino acid sequence of the DMD 35-36L.376 engineered meganuclease.

SEQ ID NO: 58 sets forth the amino acid sequence of the DMD 35-36L.457 engineered meganuclease.

SEQ ID NO: 59 sets forth the amino acid sequence of the DMD 35-36L.469 engineered meganuclease.

SEQ ID NO: 60 sets forth a nucleic acid sequence of the DMD 19-20x.13 engineered meganuclease.

SEQ ID NO: 61 sets forth a nucleic acid sequence of the DMD 19-20x.87 engineered meganuclease.

SEQ ID NO: 62 sets forth a nucleic acid sequence of the DMD 19-20L.249 engineered meganuclease.

SEQ ID NO: 63 sets forth a nucleic acid sequence of the DMD 19-20L.302 engineered meganuclease.

SEQ ID NO: 64 sets forth a nucleic acid sequence of the DMD 19-20L.329 engineered meganuclease.

SEQ ID NO: 65 sets forth a nucleic acid sequence of the DMD 19-20L.374 engineered meganuclease.

SEQ ID NO: 66 sets forth a nucleic acid sequence of the DMD 19-20L.375 engineered meganuclease.

SEQ ID NO: 67 sets forth a nucleic acid sequence of the DMD 19-20L.431 engineered meganuclease.

SEQ ID NO: 68 sets forth a nucleic acid sequence of the DMD 19-20L.458 engineered meganuclease.

SEQ ID NO: 69 sets forth a nucleic acid sequence of the DMD 35-36x.63 engineered meganuclease.

SEQ ID NO: 70 sets forth a nucleic acid sequence of the DMD 35-36x.81 engineered meganuclease.

SEQ ID NO: 71 sets forth a nucleic acid sequence of the DMD 35-36L.195 engineered meganuclease.

SEQ ID NO: 72 sets forth a nucleic acid sequence of the DMD 35-36L.282 engineered meganuclease.

SEQ ID NO: 73 sets forth a nucleic acid sequence of the DMD 35-36L.349 engineered meganuclease.

SEQ ID NO: 74 sets forth a nucleic acid sequence of the DMD 35-36L.376 engineered meganuclease.

SEQ ID NO: 75 sets forth a nucleic acid sequence of the DMD 35-36L.457 engineered meganuclease.

SEQ ID NO: 76 sets forth a nucleic acid sequence of the DMD 35-36L.469 engineered meganuclease.

SEQ ID NO: 77 sets forth the amino acid sequence of a linker sequence.

SEQ ID NO: 78 sets forth the nucleic acid sequence of a muscle-specific expression cassette that comprises from 5' to 3', the muscle-specific promoter MHCK7, a coding sequence for the DMD 19-20L.329 meganuclease, a furin GSG P2A cleavage sequence, a coding sequence for the DMD 35-36L.349 meganuclease, a WPRE element, and an SV40 polyadenylation signal.

SEQ ID NO: 79 sets forth the nucleic acid sequence of a muscle-specific expression cassette that comprises from 5' to 3', the muscle-specific promoter tMCK, a coding sequence for the DMD 19-20L.329 nuclease, a furin GSG P2A cleavage sequence, a coding sequence for the DMD 35-36L.349 nuclease, a WPRE element, and an SV40 poly-adenylation signal.

SEQ ID NO: 80 sets forth the nucleic acid sequence of a muscle-specific expression cassette that comprises from 5' to 3', the muscle-specific promoter tMCK, a coding sequence for the DMD 19-20L.329 meganuclease, a furin GSG P2A cleavage sequence, a coding sequence for the DMD 35-36L.349 meganuclease, a WPRE element, and an SV40 polyadenylation signal.

SEQ ID NO: 81 sets forth the nucleic acid sequence of a muscle-specific expression cassette that comprises from 5' to 3', the muscle-specific promoter tMCK, a coding sequence for the DMD 19-20L.431 meganuclease, a furin GSG P2A cleavage sequence, a coding sequence for the DMD 35-36L.469 meganuclease, a WPRE element, and an SV40 polyadenylation signal.

SEQ ID NO: 82 sets forth the nucleic acid sequence of a muscle-specific expression cassette that comprises from 5' to 3', the muscle-specific promoter tMCK, a coding sequence for the DMD 19-20L.458 meganuclease, a furin GSG P2A cleavage sequence, a coding sequence for the DMD 35-36L.469 meganuclease, a WPRE element, and an SV40 polyadenylation signal.

SEQ ID NO: 83 sets forth the nucleic acid sequence of a muscle-specific expression cassette that comprises from 5' to 3', the muscle-specific promoter tMCK, a coding sequence for the DMD 19-20L.431 meganuclease, a furin GSG P2A cleavage sequence, a coding sequence for the DMD 35-36L.457 meganuclease, a WPRE element, and an SV40 polyadenylation signal.

SEQ ID NO: 84 sets forth the nucleic acid sequence of a muscle-specific expression cassette that comprises from 5' to 3', the muscle-specific promoter tMCK, a coding sequence for the DMD 19-20L.458 meganuclease, a furin GSG P2A cleavage sequence, a coding sequence for the DMD 35-36L.457 meganuclease, a WPRE element, and an SV40 polyadenylation signal.

SEQ ID NO: 85 sets forth the nucleic acid sequence of a muscle-specific expression cassette that comprises from 5' to 3', the B-301 enhancer, the muscle-specific promoter tMCK, a coding sequence for the DMD 19-20L.329 nuclease, a furin GSG P2A cleavage sequence, a coding sequence for the DMD 35-36L.349 nuclease, a WPRE element, and an SV40 polyadenylation signal.

SEQ ID NO: 86 sets forth the nucleic acid sequence of a muscle-specific expression cassette that comprises from 5' to 3', the B-301 enhancer, the muscle-specific promoter tMCK, a coding sequence for the DMD 19-20L.431 meganuclease, a furin GSG P2A cleavage sequence, a coding sequence for the DMD 35-36L.457 meganuclease, a WPRE element, and an SV40 polyadenylation signal, wherein elements of the cassette have been CpG reduced.

SEQ ID NO: 87 sets forth the nucleic acid sequence of a muscle-specific expression cassette that comprises from 5' to 3', the B-301 enhancer, the muscle-specific promoter tMCK, a coding sequence for the DMD 19-20L.431 meganuclease, a furin GSG P2A cleavage sequence, a coding sequence for the DMD 35-36L.457 meganuclease, a WPRE element, and an SV40 polyadenylation signal.

SEQ ID NO: 88 sets forth the nucleic acid sequence of a forward PCR primer used in a ddPCR assay for the DMD 19-20 to DMD 35-36 ligated recognition sequences.

SEQ ID NO: 89 sets forth the nucleic acid sequence of a reverse PCR primer used in a ddPCR assay for the DMD 19-20 to DMD 35-36 ligated recognition sequences.

SEQ ID NO: 90 sets forth the nucleic acid sequence of a probe used in a ddPCR assay for the DMD 19-20 to DMD 35-36 ligated recognition sequences.

SEQ ID NO: 91 sets forth the nucleic acid sequence of a primer for generating a reference amplicon used in a ddPCR assay.

SEQ ID NO: 92 sets forth the nucleic acid sequence of a primer for generating a reference amplicon used in a ddPCR assay.

SEQ ID NO: 93 sets forth the nucleic acid sequence of a primer for generating a reference amplicon used in a ddPCR assay.

SEQ ID NO: 94 sets forth the nucleic acid sequence of an AAV9 5' ITR D Sequence.

SEQ ID NO: 95 sets forth the nucleic acid sequence of an AAV9 3' ITR D sequence.

SEQ ID NO: 96 sets forth the nucleic acid sequence of the DMD 35-36L.349 engineered meganuclease, which has not been codon modified.

SEQ ID NO: 97 sets forth the nucleic acid sequence of the DMD 35-36L.457 engineered meganuclease, which has not been codon modified.

SEQ ID NO: 98 sets forth the nucleic acid sequence of the DMD 35-36L.469 engineered meganuclease, which has not been codon modified.

SEQ ID NO: 99 sets forth a nucleic acid sequence of the DMD 19-20L.431 engineered meganuclease comprised by the construct set forth in SEQ ID NO: 87.

SEQ ID NO: 100 sets forth a nucleic acid sequence of the DMD 35-36L.457 engineered meganuclease comprised by the construct set forth in SEQ ID NO: 87.

SEQ ID NO: 101 sets forth a CpG reduced nucleic acid sequence of the DMD 19-20L.431 engineered meganuclease comprised by the construct set forth in SEQ ID NO: 86.

SEQ ID NO: 102 sets forth a CpG reduced nucleic acid sequence of the DMD 35-36L.457 engineered meganuclease comprised by the construct set forth in SEQ ID NO: 86.

SEQ ID NO: 103 sets forth the amino acid sequence of a furin GSG P2A cleavage sequence.

SEQ ID NO: 104 sets forth a nucleic acid sequence of a furin GSG P2A cleavage sequence.

SEQ ID NO: 105 sets forth a CpG reduced nucleic acid sequence of a furin GSG P2A cleavage sequence.

SEQ ID NO: 106 sets forth a nucleic acid sequence of an SV40 nuclear localization sequence.

SEQ ID NO: 107 sets forth a CpG reduced nucleic acid sequence of an SV40 nuclear localization sequence.

SEQ ID NO: 108 sets forth a nucleic acid sequence of a c-myc nuclear localization sequence.

SEQ ID NO: 109 sets forth a CpG reduced nucleic acid sequence of a c-myc nuclear localization sequence.

SEQ ID NO: 110 sets forth a nucleic acid sequence of an SV40 nuclear localization sequence.

SEQ ID NO: 111 sets forth a CpG reduced nucleic acid sequence of an SV40 nuclear localization sequence.

SEQ ID NO: 112 sets forth a nucleic acid sequence of a c-myc nuclear localization sequence.

SEQ ID NO: 113 sets forth a CpG reduced nucleic acid sequence of a c-myc nuclear localization sequence.

SEQ ID NO: 114 sets forth a nucleic acid sequence of an SV40 polyA signal.

DETAILED DESCRIPTION

1.1 References and Definitions

The patent and scientific literature referred to herein establishes knowledge that is available to those of skill in the art. The issued US patents, allowed patent applications, published foreign patent applications, and references, including GenBank database sequences, which are cited herein are hereby incorporated by reference to the same extent as if each was specifically and individually indicated to be incorporated by reference.

The present disclosure can be embodied in different forms and should not be construed as limited to the embodiments set forth herein. Rather, these embodiments are provided so that this disclosure will be thorough and complete, and will fully convey the scope of the disclosure to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the present disclosure, which do not depart from therefrom.

Unless otherwise defined, all technical and scientific terms used herein have the same meaning as commonly understood by one of ordinary skill in the art to which this disclosure belongs. The terminology used in the disclosure is for the purpose of describing particular embodiments only and is not intended to be limiting thereto.

All publications, patent applications, patents, and other references mentioned herein are incorporated by reference herein in their entirety.

As used herein, "a," "an," or "the" can mean one or more than one. For example, "a" cell can mean a single cell or a multiplicity of cells.

As used herein, unless specifically indicated otherwise, the word "or" is used in the inclusive sense of "and/or" and not the exclusive sense of "either/or."

As used herein, all polynucleotide sequences written using the nucleic acid standard notation of the International Union of Pure and Applied Chemistry (IUPAC, Biochemistry (1970) Vol. 9:4022-4027); adenine (A), thymine (T), guanine (G), and cytosine (C) are equivalent to the corresponding RNA polynucleotide sequences. Therefore, "T" (Thymine) in all sequences is equivalent to "U" (uracil). For example, the sequence AATAAA in a DNA coding strand would also indicate the corresponding mRNA sequence AAUAAA.

As used herein the use of the term "codon modified" refers to a process in which a nucleotide sequence that encodes a heterologous protein (e.g., an engineered nuclease such as an engineered meganuclease) is modified so that the resulting nucleic acid coding sequence utilizes alternative three base codons without altering the originally encoded amino acid sequence. Modifying nucleic acid sequence codons relies upon the fact that in eukaryotic cells there are multiple three base codons that encode the same amino acid, wherein the third position in the codon can be selected from multiple nucleotides, i.e., can be "wobbled". As used herein, the use of the term "polynucleotide", "DNA", or "nucleic acid" is not intended to limit the disclosure to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides described herein also encompass all forms of sequences including, but not limited to, single-stranded forms, double-stranded forms, hairpins, stem-and-loop structures, and the like.

As used herein, the term "Kozak sequence" is a nucleic acid motif that functions as the protein translation initiation site in most eukaryotic mRNA transcripts. The vertebrate Kozak sequences have a consensus sequence of "gcc A/G ccATGG", wherein the upper case positions are more conserved than the lower case positions; wherein the ATG is the start codon. Therefore, Kozak sequence spans across 5' UTR and the coding sequence, wherein the portion within 5' UTR is UTR Kozak sequence. For example, a UTR Kozak sequence is the portion of the Kozak sequence from the first to the sixth base pair. In various embodiments, the first nucleotide of the Kozak sequence is A or G. In various embodiments, the second nucleotide of the Kozak sequence is C or T. In various embodiments, the third nucleotide of the Kozak sequence is A or C. In various embodiments, the fourth nucleotide of the Kozak sequence is A or G. In various embodiments, the fifth nucleotide of the Kozak sequence is A or C. In various embodiments, the sixth nucleotide of the Kozak sequence is A, C, or G. In specific embodiments, the Kozak sequence includes the sequence GCCACC that is part of a 5' UTR. In various embodiments, the seventh to tenth nucleotides of the Kozak sequence are ATGG. In specific embodiments, the Kozak sequence can include a portion of a NLS of the polynucleotide. Suitable Kozak sequences are described in PCT International Patent Application No. PCT/US2023/060258. For example, the Kozak sequence can include the sequence ATGGC that is part of the SV40 NLS. In various embodiments, a the Kozak sequence comprises SEQ ID NO 32.

As used herein, the term "muscle-specific enhancer" refers to a nucleotide element operably linked to a promoter (e.g., a muscle-specific promoter), which increases expression of a transgene within muscle cells. Muscle-specific enhancers described herein are less than 1 kb, 500 bp, 250 bp, and 150 bp. These muscle-specific enhancers include one or more transcription factor binding sites including E-box motifs, AP-1 binding motifs, and homing domain binding motifs. In some embodiments, such muscle-specific enhancers drive expression of a transgene in muscle precursor cells (e.g., Pax 7 positive muscle satellite cells). In some embodiments the muscle-specific enhancer comprises SEQ ID NO: 1.

As used herein, the term "MCK-R control element" refers to those control elements typically found in MCK promoter enhancer sequences with the consensus sequence AACAc/gc/gTGCa/t. In some embodiments, the MCK-R control elements comprise any one of SEQ ID NOs: 4-17.

As used herein, the term "basal promoter" refers to a portion of a promoter that interacts with regulatory elements and transcription factors responsible for the initiation of transcription of a gene or as in some embodiments described herein, an exogenous gene. Such basal promoters typically include a TATA box and or a downstream promoter element (DPE). In some embodiments, the basal promoter stems from a MCK promoter. In some embodiments, the basal promoter from the MCK promoter is from about 50 bp to about 1,000 bp in length. In some embodiments, the basal promoter from the MCK promoter is about 400 bp in length. In some embodiments, the basal promoter from the MCK promoter is about 90 bp in length. In some embodiments, the basal promoter comprises a nucleic acid sequence according to a sequence set forth in SEQ ID NO: 2. In some embodiments, the basal promoter comprises a nucleic acid sequence according to a sequence set forth in SEQ ID NO: 3.

As used herein, the term truncated MCK promoter (or tMCK) refers to an MCK promoter that has been shortened relative to the wild type MCK promoter. TMCK promoters useful as described herein can include a truncated version of the murine or huma MCK promoters. In some embodiments, a tMCK promoter includes a truncated promoter that includes a portion of the WT murine MCK promoter according to a sequence set forth in SEQ ID NO: 18. In some embodiments, a tMCK promoter includes a truncated promoter that includes a portion of the WT human MCK promoter according to a sequence set forth in SEQ ID NO: 19. Suitable tMCK promoters include at least one MCK enhancer element. In some embodiments the tMCK promoters described herein include three MCK enhancer elements described herein. In some embodiments described herein, the tMCK promoter comprises a nucleotide sequence according to a sequence set forth in SEQ ID NO: 22.

As used herein, the term MCK enhancer element refers to a portion of the MCK promoter, which enhances or increases expression of a gene that is operably connected to the MCK promoter. Such MCK enhancers include various transcription factor binding sites. In some embodiments, the MCK enhancer element refers to a sequence comprising one or more transcription factor binding motifs including the CArg, AP2, Trex, E-Box, NcoI or MEF2 motifs. In some embodiments, the MCK enhancer element comprises SEQ ID NO: 20 or 21.

As used herein, the term Post transcriptional regulatory element (PTRE) refers to a nucleotide sequence, which functions to increase the stability of mRNA and cytoplasmic transport of the mRNA. Stability is of an intron-less gene is typically increased by promoting mRNA exportation from the nucleus to the cytoplasm, enhancing 3' end processing and stability. Suitable PTRE(s) include PTREs derived from viruses including but not limited to the Hepatitis B virus (HPRE) and Woodchuck Hepatitis virus (WPRE). In some embodiments described herein, the PTRE is a WPRE. In some embodiments the WPRE comprises a nucleotide sequence according to a sequence set forth in SEQ ID NO: 24.

As used herein, the term "nucleoprotein" refers to any recombinant or naturally occurring protein that exhibits some biologic effect within the nucleus of a cell. In some embodiments described herein, nucleoproteins comprise DNA binding regulatory proteins and engineered nucleases. In specific embodiments, nucleoproteins described herein comprise engineered meganucleases.

As used herein, the term "DNA binding regulatory protein" refers to any protein that binds to DNA and regulates gene expression without directly editing the DNA. Such proteins typically function within the cellular nucleus. Gene expression regulation includes affecting transcription of an mRNA from the DNA. The mechanism by which DNA binding regulatory proteins affect mRNA transcription can include both epigenetic modifications (e.g., methylation, histone modification, and nucleosome positioning) and directly affecting the rate of transcription by functioning as a transcription factor (e.g., an artificial transcription factor having an activator or repressor domain). Such artificial transcription factors are well known; see, for example, PCT International Patent Application Publication No: WO/2003/066828.

As used herein, the terms "nuclease" and "endonuclease" are used interchangeably to refer to naturally occurring or engineered enzymes, which cleave a phosphodiester bond within a polynucleotide chain. Engineered nucleases can include, without limitation, engineered meganucleases, zinc finger nucleases, TALENs, compact TALENs, CRISPR system nucleases, and megaTALs. In addition, any engineered nuclease is envisioned that is capable of generating overhangs at its cleavage site.

As used herein, the term "compact TALEN" refers to an endonuclease comprising a DNA-binding domain with one or more TAL domain repeats fused in any orientation to any portion of the I-TevI homing endonuclease or any of the endonucleases listed in Table 2 in U.S. Patent Application Publication No. 2013/0117869, including but not limited to MmeI, EndA, End1, I-BasI, I-TevII, I-TevIII, I-TwoI, MspI, MvaI, NucA, and NucM. Compact TALENs do not require dimerization for DNA processing activity, alleviating the need for dual target sites with intervening DNA spacers. In some embodiments, the compact TALEN comprises 16-22 TAL domain repeats.

As used herein, the terms "CRISPR nuclease" or "CRISPR system nuclease" refers to a CRISPR (clustered regularly interspaced short palindromic repeats)-associated (Cas) endonuclease or a variant thereof, such as Cas9 or Cas12a, that associates with a guide RNA that directs nucleic acid cleavage by the associated endonuclease by hybridizing to a recognition site in a polynucleotide. In certain embodiments, the CRISPR nuclease is a class 2 CRISPR enzyme. In some of these embodiments, the CRISPR nuclease is a class 2, type II enzyme, such as Cas9. In other embodiments, the CRISPR nuclease is a class 2, type V enzyme, such as Cpf1. The guide RNA comprises a direct repeat and a guide sequence (often referred to as a spacer in the context of an endogenous CRISPR system), which is complementary to the target recognition site. In certain embodiments, the CRISPR system further comprises a tracrRNA (trans-activating CRISPR RNA) that is complementary (fully or partially) to the direct repeat sequence (sometimes referred to as a tracr-mate sequence) present on the guide RNA. In particular embodiments, the CRISPR nuclease can be mutated with respect to a corresponding wild-type enzyme such that the enzyme lacks the ability to cleave one strand of a target polynucleotide, functioning as a nickase, cleaving only a single strand of the target DNA. Non-limiting examples of CRISPR enzymes that function as a nickase include Cas9 enzymes with a D10A mutation within the RuvC I catalytic domain, or with a H840A, N854A, or N863A mutation. Given a predetermined DNA locus, recognition sequences can be identified using a number of programs known in the art (Labun et al. (2016). CHOPCHOP v2: a web tool for the next generation of CRISPR genome engineering. Nucleic Acids Research; doi: 10.1093/nar/gkw398; Montague et al. (2014). CHOPCHOP: a CRISPR/Cas9 and TALEN web tool for genome editing. Nucleic Acids Res. 42. W401-W407). Additional CRISPR system nucleases include CRISPR-based prime editor and base editor systems. CRISPR system nuclease can further include CRISPR-based epigenetic editing systems that modify the epigenome without modifying a gene sequence directly (Nakamura, M., Gao, Y., Dominguez, A. A. et al. CRISPR technologies for precise epigenome editing. Nat Cell Biol 23, 11-22 (2021)).

As used herein, a prime editor is a nuclease based on an enzyme that mediates insertions, deletions, and base conversions without generating a double strand break. Such prime editors include CRISPR/Cas9 prime editors, which are described in Anzalone et al. (2019) *Nature* 576(7785) 149-157. In this system, The pegRNA includes a single guide RNA that has a primer binding site and a reverse transcriptase template. When editing the genome, the DNA is nicked, and the primer binding site causes the nicked DNA strand to hybridize with the pegRNA and the template serves as a synthetic template for editing the gene. The presently disclosed compositions and methods utilizing a prime editing system may comprise a CRISPR nuclease (e.g., a Cas9 H840A nickase) and the pegRNA(s) or nucleic acids encoding the CRISPR nuclease and/or the pegRNA(s).

As used herein, a base editor is based on enzymes, which are capable of catalyzing cytosine/guanosine to thymidine/alanine conversions. On such base editor comprises the CRISPR/Cas9 enzyme fused to a cytidine deaminase enzyme, which does not induce a double strand break. The Cas9 enzyme is typically inactivated such that it can longer cleave DNA, but still functions to bind to the DNA in conjunction with a guide RNA. Mutations to inactivate the Cas9 enzyme include an Asp10Ala and a His840Ala mutation. These base editors effect a cytosine to thymidine or guanosine to adenosine substitution and are described in Komor et al. (2016) *Nature* 533(7603) 420-424. Another exemplary base editor includes CRISPR-free systems based on transcription activator-like effector (TALE) proteins fused to a double stranded DNA specific cytidine deaminase as described in Mok et al., (2022) *Nature Biotechnology* 40 1378-1387.

As used herein, the term "megaTAL" refers to a single-chain endonuclease comprising a TALE DNA binding domain with an engineered, sequence-specific homing endonuclease.

As used herein, the term "TALEN" refers to an endonuclease comprising a DNA-binding domain comprising a plurality of TAL domain repeats fused to a nuclease domain or an active portion thereof from an endonuclease or exonuclease, including but not limited to a restriction endonuclease, homing endonuclease, S1 nuclease, mung bean nuclease, pancreatic DNAse I, micrococcal nuclease, and yeast HO endonuclease. See, for example, Christian et al. (2010) Genetics 186:757-761, which is incorporated by reference in its entirety. Nuclease domains useful for the design of TALENs include those from a Type IIs restriction endonuclease, including but not limited to FokI, FoM, StsI, HhaI, HindIII, Nod, BbvCI, EcoRI, BglI, and AlwI. Additional Type IIs restriction endonucleases are described in International Publication No. WO 2007/014275, which is incorporated by reference in its entirety. In some embodiments, the nuclease domain of the TALEN is a FokI nuclease domain or an active portion thereof. TAL domain repeats can be derived from the TALE family of proteins used in the infection process by plant pathogens of the *Xanthomonas* genus. TAL domain repeats are 33-34 amino acid sequences with divergent 12th and 13th amino acids. These two positions, referred to as the repeat variable dipeptide (RVD), are highly variable and show a strong correlation with specific nucleotide recognition. Each base pair in the DNA target sequence is contacted by a single TAL repeat with the specificity resulting from the RVD. In some embodiments, the TALEN comprises 16-22 TAL domain repeats. DNA cleavage by a TALEN requires two DNA recognition regions (i.e., "half-sites") flanking a nonspecific central region (i.e., the "spacer"). The term "spacer" in reference to a TALEN refers to the nucleic acid sequence that separates the two nucleic acid sequences recognized and bound by each monomer constituting a TALEN. The TAL domain repeats can be native sequences from a naturally occurring TALE protein or can be redesigned through rational or experimental means to produce a protein that binds to a pre-determined DNA sequence (see, for example, Boch et al. (2009) Science 326(5959):1509-1512 and Moscou and Bogdanove (2009) Science 326(5959):1501, each of which is incorporated by reference in its entirety). See also, US Patent Application Publication No. 2011/0145940 and PCT International Patent Application Publication No. WO/2010/079430 for methods for engineering a TALEN to recognize and bind a specific sequence and examples of RVDs and their corresponding target nucleotides. In some embodiments, each nuclease (e.g., FokI) monomer can be fused to a TAL effector sequence that recognizes and binds a different DNA sequence, and only when the two recognition sites are in close proximity do the inactive monomers come together to create a functional enzyme. It is understood that the term "TALEN" can refer to a single TALEN protein or, alternatively, a pair of TALEN proteins (i.e., a left TALEN protein and a right TALEN protein) which bind to the upstream and downstream half-sites adjacent to the TALEN spacer sequence and work in concert to generate a cleavage site within the spacer sequence. Given a predetermined DNA locus or spacer sequence, upstream and downstream half-sites can be identified using a number of programs known in the art (Kornel Labun; Tessa G. Montague; James A. Gagnon; Summer B. Thyme; Eivind Valen. (2016). CHOPCHOP v2: a web tool for the next generation of CRISPR genome engineering. Nucleic Acids Research; doi: 10.1093/nar/gkw398; Tessa G. Montague; Jose M. Cruz; James A. Gagnon; George M. Church; Eivind Valen. (2014). CHOPCHOP: a CRISPR/Cas9 and TALEN web tool for genome editing. Nucleic Acids Res. 42. W401-W407). It is also understood that a TALEN recognition sequence can be defined as the DNA binding sequence (i.e., half-site) of a single TALEN protein or, alternatively, a DNA sequence comprising the upstream half-site, the spacer sequence, and the downstream half-site.

As used herein, the terms "zinc finger nuclease" or "ZFN" refers to a chimeric protein comprising a zinc finger DNA-binding domain fused to a nuclease domain from an endonuclease or exonuclease, including but not limited to a restriction endonuclease, homing endonuclease, S1 nuclease, mung bean nuclease, pancreatic DNAse I, micrococcal nuclease, and yeast HO endonuclease. Nuclease domains useful for the design of zinc finger nucleases include those from a Type IIs restriction endonuclease, including but not limited to FokI, FoM, and StsI restriction enzyme. Additional Type IIs restriction endonucleases are described in PCT International Patent Publication No. WO/2007/014275, which is incorporated by reference in its entirety. The structure of a zinc finger domain is stabilized through coordination of a zinc ion. DNA binding proteins comprising one or more zinc finger domains bind DNA in a sequence-specific manner. The zinc finger domain can be a native sequence or can be redesigned through rational or experimental means to produce a protein which binds to a pre-determined DNA sequence ~18 base pairs in length, comprising a pair of nine base pair half-sites separated by 2-10 base pairs. See, for example, U.S. Pat. Nos. 5,789,538, 5,925,523, 6,007,988, 6,013,453, 6,200,759, and PCT International Patent Application Publication Nos. WO 95/19431, WO 96/06166, WO 98/53057, WO 98/54311, WO 00/27878, WO 01/60970, WO 01/88197, and WO 02/099084, each of which is incorporated by reference in its entirety. By fusing this engineered protein domain to a nuclease domain, such as FokI nuclease, it is possible to target DNA breaks with genome-level specificity. The selection of target sites, zinc finger proteins and methods for design and construction of zinc finger nucleases are known to those of skill in the art and are described in detail in US Patent Application Publication Nos. 2003/0232410, 2005/0208489, 2005/064474, 2005/0026157, 2006/0188987 and PCT International Patent Application Publication No. WO 07/014275, each of which is incorporated by reference in its entirety. In the case of a zinc finger, the DNA binding domains typically recognize an 18-bp recognition sequence comprising a pair of nine base pair "half-sites" separated by a 2-10 base pair "spacer sequence", and cleavage by the nuclease creates a blunt end or a 5' overhang of variable length (frequently four base pairs). It is understood that the term "zinc finger nuclease" can refer to a single zinc finger protein or, alternatively, a pair of zinc finger proteins (i.e., a left ZFN protein and a right ZFN protein) that bind to the upstream and downstream half-sites adjacent to the zinc finger nuclease spacer sequence and work in concert to generate a cleavage site within the spacer sequence. Given a predetermined DNA locus or spacer sequence, upstream and downstream half-sites can be identified using a number of programs known in the art (Mandell and Barbas 3rd. Zinc Finger Tools: custom DNA-binding domains for transcription factors and nucleases. Nucleic Acids Res. 2006 Jul. 1; 34 (Web Server issue):W516-23). It is also understood that a zinc finger nuclease recognition sequence can be defined as the DNA binding sequence (i.e., half-site) of a single zinc finger nuclease protein or, alternatively, a DNA sequence comprising the upstream half-site, the spacer sequence, and the downstream half-site.

As used herein, the terms "cleave" or "cleavage" refer to the hydrolysis of phosphodiester bonds within the backbone of a recognition sequence within a target sequence that results in a double-stranded break within the target sequence, referred to herein as a "cleavage site".

As used herein, the term "meganuclease" refers to an endonuclease that binds double-stranded DNA at a recognition sequence that is greater than 12 base pairs. In some embodiments, the recognition sequence for a meganuclease of the present disclosure is 22 base pairs. A meganuclease can be an endonuclease that is derived from I-CreI (SEQ ID NO: 33), and can refer to an engineered variant of I-CreI that has been modified relative to natural I-CreI with respect to, for example, DNA-binding specificity, DNA cleavage activity, DNA-binding affinity, or dimerization properties. Methods for producing such modified variants of I-CreI are known in the art (e.g., PCT International Patent Application Publication No. WO/2007/047859, incorporated by reference in its entirety). A meganuclease as used herein binds to double-stranded DNA as a heterodimer. A meganuclease may also be a "single-chain meganuclease" in which a pair of DNA-binding domains is joined into a single polypeptide using a peptide linker. The term "homing endonuclease" is synonymous with the term "meganuclease." Meganucleases of the present disclosure are substantially non-toxic when expressed in the targeted cells as described herein such that cells can be transfected and maintained at 37° C. without observing deleterious effects on cell viability or significant reductions in meganuclease cleavage activity when measured using the methods described herein.

As used herein, the term "single-chain meganuclease" refers to a polypeptide comprising a pair of nuclease subunits joined by a linker. A single-chain meganuclease has the organization: N-terminal subunit-Linker-C-terminal subunit. The two meganuclease subunits will generally be non-identical in amino acid sequence and will bind non-identical DNA sequences. Thus, single-chain meganucleases typically cleave pseudo-palindromic or non-palindromic recognition sequences. A single-chain meganuclease may be referred to as a "single-chain heterodimer" or "single-chain heterodimeric meganuclease" although it is not, in fact, dimeric. For clarity, unless otherwise specified, the term "meganuclease" can refer to a dimeric or single-chain meganuclease.

As used herein, the term "linker" refers to an exogenous peptide sequence used to join two nuclease subunits into a single polypeptide. A linker may have a sequence that is found in natural proteins or may be an artificial sequence that is not found in any natural protein. A linker may be flexible and lacking in secondary structure or may have a propensity to form a specific three-dimensional structure under physiological conditions. A linker can include, without limitation, those encompassed by U.S. Pat. Nos. 8,445, 251, 9,340,777, 9,434,931, and 10,041,053. In some embodiments, a linker may have at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence set forth in SEQ ID NO: 77, which sets forth residues 154-195 of any one of SEQ ID NOs: 43-59.

As used herein, the term "nuclear localization sequence" or "NLS" refers to generally short peptides that act as a signal fragment that mediates the transport of proteins from the cytoplasm into the nucleus. Classical NLS encompasses two categories: monopartite (MP) and bipartite NLS. Monopartite NLSs have a single cluster composed of 4-8 basic amino acids, which generally contains 4 or more positively charged residues, that is, arginine (R) or lysine (K). The characteristic motif of MP NLS is usually defined as K (K/R) X (K/R), where X can be any residue. For example, the NLS of SV40 large T-antigen is 126PKKKRKV132, with 5 consecutive positively charged amino acids (KKKRK). Bipartite NLSs are characterized by two clusters of 2-3 positively charged amino acids that are separated by a 9-12 amino acid linker region, which contains several proline (P) residues. The consensus sequence can be expressed as R/K(X)10-12KRXK. Notably, in bipartite NLSs, the upstream and downstream clusters of amino acids are interdependent and indispensable, and jointly determine the localization of the protein in the cell. Non-classical nuclear localization sequences are neither similar to canonical signals nor rich in arginine or lysine residues. Among non-classical nuclear localization sequences, the "proline-tyrosine" category was studied in the most detail. PY-NLS is characterized by 20-30 amino acids that assume a disordered structure, consisting of N-terminal hydrophobic or basic motifs and C-terminal R/K/H(X) 2-5PY motifs (where X2-5 is any sequence of 2-5 residues). Two subclasses, hPY-NLS and bPY-NLS, were defined according to their N-terminal motifs. The hPY-NLS contains φG/A/Sφφ motifs (where φ is a hydrophobic residue), whereas bPY-NLS is enriched in basic residues. Collectively, the PY-NLS consensus corresponds to [basic/hydrophobic]-Xn-[R/H/K]-(X)2-5-PY, where X can be any residue. Human heterogeneous nuclear ribonucleoprotein A1 (hnRNP A1) is known as hPY-NLS due to its sequence 263FGNYNNQSSNFGPMKGGNFGGRSSGPY289, which includes a hydrophobic region (273FGPM276) required for its nuclear localization.

In some embodiments, an NLS comprises an SV40 NLS (SEQ ID NO: 25), an NLS5 (SEQ ID NO: 26), a c-myc NLS (SEQ ID NO: 27), or an SV40H2 NLS (SEQ ID NO: 28). In some embodiments, an NLS comprises an amino acid sequence having at least, 70%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more sequence identity to a sequence set forth in any one of SEQ ID NOs: 25-28. In some embodiments, an NLS comprises an amino acid sequence of any one of SEQ ID NOs: 25-28.

As used herein, the terms "recombinant" or "engineered," with respect to a protein, means having an altered amino acid sequence as a result of the application of genetic engineering techniques to nucleic acids that encode the protein and cells or organisms that express the protein. With respect to a nucleic acid, the term "recombinant" or "engineered" means having an altered nucleic acid sequence as a result of the application of genetic engineering techniques. Genetic engineering techniques include, but are not limited to, PCR and DNA cloning technologies; transfection, transformation, and other gene transfer technologies; homologous recombination; site-directed mutagenesis; and gene fusion. In accordance with this definition, a protein having an amino acid sequence identical to a naturally occurring protein but produced by cloning and expression in a heterologous host, is not considered recombinant or engineered.

As used herein, the term "wild-type" refers to the most common naturally occurring allele (i.e., polynucleotide sequence) in the allele population of the same type of gene, wherein a polypeptide encoded by the wild-type allele has its original functions. The term "wild-type" also refers to a polypeptide encoded by a wild-type allele. Wild-type alleles (i.e., polynucleotides) and polypeptides are distinguishable from mutant or variant alleles and polypeptides, which comprise one or more mutations and/or substitutions relative to the wild-type sequence(s). Whereas a wild-type allele or polypeptide can confer a normal phenotype in an organism, a mutant or variant allele or polypeptide can, in some instances, confer an altered phenotype. Wild-type nucleases are distinguishable from recombinant or non-naturally occurring nucleases. The term "wild-type" can also refer to a cell, an organism, and/or a subject which possesses a wild-type allele of a particular gene, or a cell, an organism, and/or a subject used for comparative purposes.

As used herein, the term "genetically modified" refers to a cell or organism in which, or in an ancestor of which, a genomic DNA sequence has been deliberately modified by recombinant technology. As used herein, the term "genetically modified" encompasses the term "transgenic."

As used herein, the term with respect to recombinant proteins, the term "modification" means any insertion, deletion, or substitution of an amino acid residue in the recombinant sequence relative to a reference sequence (e.g., a wild-type or a native sequence).

As used herein, the terms "recognition sequence" or "recognition site" refers to a DNA sequence that is bound and cleaved by a nuclease. In the case of a meganuclease, a recognition sequence comprises a pair of inverted, 9 base pair "half sites" which are separated by four base pairs. In the case of a single-chain meganuclease, the N-terminal domain of the protein contacts a first half-site and the C-terminal domain of the protein contacts a second half-site. Cleavage by a meganuclease produces four base pair 3' overhangs. "Overhangs," or "sticky ends" are short, single-stranded DNA segments that can be produced by endonu- clease cleavage of a double-stranded DNA sequence. In the case of meganucleases and single-chain meganucleases derived from I-CreI, the overhang comprises bases 10-13 of the 22 base pair recognition sequence. In the case of a compact TALEN, the recognition sequence comprises a first CNNNGN sequence that is recognized by the I-TevI domain, followed by a non-specific spacer 4-16 base pairs in length, followed by a second sequence 16-22 bp in length that is recognized by the TAL-effector domain (this sequence typically has a 5' T base). Cleavage by a compact TALEN produces two base pair 3' overhangs. In the case of a CRISPR nuclease, the recognition sequence is the sequence, typically 16-24 base pairs, to which the guide RNA binds to direct cleavage. Full complementarity between the guide sequence and the recognition sequence is not necessarily required to affect cleavage. Cleavage by a CRISPR nuclease can produce blunt ends (such as by a class 2, type II CRISPR nuclease) or overhanging ends (such as by a class 2, type V CRISPR nuclease), depending on the CRISPR nuclease. In those embodiments wherein a CpfI CRISPR nuclease is utilized, cleavage by the CRISPR complex comprising the same will result in 5' overhangs and in certain embodiments, 5 nucleotide 5' overhangs. Each CRISPR nuclease enzyme also requires the recognition of a PAM (protospacer adjacent motif) sequence that is near the recognition sequence complementary to the guide RNA. The precise sequence, length requirements for the PAM, and distance from the target sequence differ depending on the CRISPR nuclease enzyme, but PAMs are typically 2-5 base pair sequences adjacent to the target/recognition sequence. PAM sequences for particular CRISPR nuclease enzymes are known in the art (see, for example, U.S. Pat. No. 8,697,359 and US Patent Application Publication No. 2016/0208243) and PAM sequences for novel or engineered CRISPR nuclease enzymes can be identified using methods known in the art, such as a PAM depletion assay (see, for example, Karvelis et al. (2017) Methods 121-122:3-8). In the case of a zinc finger, the DNA binding domains typically recognize an 18-bp recognition sequence comprising a pair of nine base pair "half-sites" separated by 2-10 base pairs and cleavage by the nuclease creates a blunt end or a 5' overhang of variable length (frequently four base pairs).

As used herein, the terms "target site" or "target sequence" refers to a region of the chromosomal DNA of a cell comprising a recognition sequence for a nuclease.

As used herein, the terms "DNA-binding affinity" or "binding affinity" means the tendency of a nuclease to non-covalently associate with a reference DNA molecule (e.g., a recognition sequence or an arbitrary sequence). Binding affinity is measured by a dissociation constant, Kd. As used herein, a nuclease has "altered" binding affinity if the Kd of the nuclease for a reference recognition sequence is increased or decreased by a statistically significant percent change relative to a reference nuclease.

As used herein, the term "specificity" means the ability of a nuclease to bind and cleave double-stranded DNA mol- ecules only at a particular sequence of base pairs referred to as the recognition sequence, or only at a particular set of recognition sequences. The set of recognition sequences will share certain conserved positions or sequence motifs but may be degenerate at one or more positions. A highly specific nuclease is capable of cleaving only one or a very few recognition sequences. Specificity can be determined by any method known in the art.

As used herein, the term "dystrophin gene" refers to the gene associated with National Center for Biotechnology Information (NCBI) gene ID 1756, as well as naturally occurring variants thereof. The term "dystrophin" refers to a polypeptide encoded by the dystrophin gene. The dystrophin isoform expressed in muscle cells and muscle precursor cells is known as the Dp427m dystrophin variant. The amino acid sequence of a full-length, wild-type Dp427m dystrophin polypeptide is set forth in SEQ ID NO: 35. NCBI reference numbers NM_004006.3 and NP_003997.2 set forth the dystrophin Dp427m mRNA and polypeptide, respectively. In some embodiments described herein, the dystrophin gene is edited with a pair of engineered meganucleases, resulting in the excision of exons 45-55 and subsequent perfect ligation of the dystrophin gene. Removal of exons 45-55 from the wild-type dystrophin gene can result in a dystro- phin polypeptide comprising an amino acid sequence set forth in SEQ ID NO: 36.

As used herein, the terms "perfect ligation" or "perfectly ligate" refer to the ligation (i.e., annealing) of all four bases of a 3' overhang of a first cleavage site with all four bases of a complementary 3' overhang of a second cleavage site in a dystrophin gene following cleavage by a pair of engineered meganucleases described herein. The recognition sequences targeted by the disclosed engineered meganucleases have identical four base pair center sequences (e.g., GTAT), such that the first and second cleavage sites will have comple- mentary four base pair 3' overhangs. Accordingly, each base pair of the first 3' overhang pairs with its complement base pair on the second 3' overhang, and ligation occurs through a DNA ligase enzyme. Examples of sequences resulting from such perfect ligations are set forth in SEQ ID NO: 41 (i.e., perfect ligation of the DMD 19-20 and DMD 35-36 recognition sequences).

As used herein, the term "Becker Muscular Dystrophy phenotype" refers to a less severe form of muscular dystro- phy as compared to DMD. Individuals having Becker Mus- cular Dystrophy still comprise mutations within the dystro- phin gene but express more functional dystrophin protein in muscle cells (e.g., muscle precursor cells, skeletal muscle cells, and cardiac muscle cells) compared to individuals having DMD, generally leading to a better clinical progno- sis.

As used herein, the term "homologous recombination" or "HR" refers to the natural, cellular process in which a double-stranded DNA-break is repaired using a homologous DNA sequence as the repair template (see, e.g., Cahill et al. (2006) *Front. Biosci.* 11:1958-76). The homologous DNA sequence may be an endogenous chromosomal sequence or an exogenous nucleic acid that was delivered to the cell.

As used herein, the term "non-homologous end-joining" or "NHEJ" refers to the natural, cellular process in which a double-stranded DNA-break is repaired by the direct joining of two non-homologous DNA segments (see, e.g., Cahill et al. (2006)). DNA repair by non-homologous end-joining is error-prone and frequently results in the untemplated addi- tion or deletion of DNA sequences at the site of repair. In some instances, cleavage at a target recognition sequence results in NHEJ at a target recognition site. Nuclease- induced cleavage of a target site in the coding sequence of a gene followed by DNA repair by NHEJ, which can introduce mutations into the coding sequence, such as frameshift mutations, which disrupt gene function. Thus, engineered nucleases can be used to effectively knock-out a gene in a population of cells.

As used herein, the term "homology arms" or "sequences homologous to sequences flanking a nuclease cleavage site" refer to sequences flanking the 5' and 3' ends of a nucleic acid molecule, which promote insertion of the nucleic acid molecule into a cleavage site generated by a nuclease. In general, homology arms can have a length of at least 50 base pairs, preferably at least 100 base pairs, and up to 2000 base pairs or more, and can have at least 90%, preferably at least 95%, or more, sequence homology to their corresponding sequences in the genome. In some embodiments, the homology arms are about 500 base pairs.

As used herein, the term with respect to both amino acid sequences and nucleic acid sequences, the terms "percent identity," "sequence identity," "percentage similarity," "sequence similarity" and the like refer to a measure of the degree of similarity of two sequences based upon an alignment of the sequences that maximizes similarity between aligned amino acid residues or nucleotides, and which is a function of the number of identical or similar residues or nucleotides, the number of total residues or nucleotides, and the presence and length of gaps in the sequence alignment. A variety of algorithms and computer programs are available for determining sequence similarity using standard parameters. As used herein, sequence similarity is measured using the BLASTp program for amino acid sequences and the BLASTn program for nucleic acid sequences, both of which are available through the National Center for Biotechnology Information (www.ncbi.nlm.nih.gov/), and are described in, for example, Altschul et al. (1990) *J. Mol. Biol.* 215:403-10; Gish & States (1993) *Nature Genet.* 3:266-72; Madden et al. (1996) *Meth. Enzymol.* 266:131-41; Altschul et al. (1997) *Nucleic Acids Res.* 25:3389-3402; and Zhang et al. (2000) *J. Comput. Biol.* 7:203-14. As used herein, percent similarity of two amino acid sequences is the score based upon the following parameters for the BLASTp algorithm: word size=3; gap opening penalty=−11; gap extension penalty=−1; and scoring matrix=BLOSUM62. As used herein, percent similarity of two nucleic acid sequences is the score based upon the following parameters for the BLASTn algorithm: word size=11; gap opening penalty=−5; gap extension penalty=−2; match reward=1; and mismatch penalty=−3.

As used herein, the term "corresponding to" with respect to modifications of two proteins or amino acid sequences is used to indicate that a specified modification in the first protein is a substitution of the same amino acid residue as in the modification in the second protein, and that the amino acid position of the modification in the first protein corresponds to or aligns with the amino acid position of the modification in the second protein when the two proteins are subjected to standard sequence alignments (e.g., using the BLASTp program). Thus, the modification of residue "X" to amino acid "A" in the first protein will correspond to the modification of residue "Y" to amino acid "A" in the second protein if residues X and Y correspond to each other in a sequence alignment and despite the fact that X and Y may be different numbers.

As used herein, the term "recognition half-site," "recognition sequence half-site," or simply "half-site" means a nucleic acid sequence in a double-stranded DNA molecule that is recognized and bound by a monomer of a homodimeric or heterodimeric meganuclease or by one subunit of a single-chain meganuclease or by one subunit of a single-chain meganuclease.

As used herein, the term "hypervariable region" refers to a localized sequence within a meganuclease monomer or subunit that comprises amino acids with relatively high variability. A hypervariable region can comprise about 50-60 contiguous residues, about 53-57 contiguous residues, or preferably about 56 residues. In some embodiments, the residues of a hypervariable region may correspond to positions 24-79 or positions 215-270 of any one of SEQ ID NOs: 43-59. A hypervariable region can comprise one or more residues that contact DNA bases in a recognition sequence and can be modified to alter base preference of the monomer or subunit. A hypervariable region can also comprise one or more residues that bind to the DNA backbone when the meganuclease associates with a double-stranded DNA recognition sequence. Such residues can be modified to alter the binding affinity of the meganuclease for the DNA backbone and the target recognition sequence. In different embodiments, a hypervariable region may comprise between 1-20 residues that exhibit variability and can be modified to influence base preference and/or DNA-binding affinity. In particular embodiments, a hypervariable region comprises between about 15-20 residues that exhibit variability and can be modified to influence base preference and/or DNA-binding affinity. In some embodiments, variable residues within a hypervariable region correspond to one or more of positions 24, 26, 28, 30, 32, 33, 38, 40, 42, 44, 46, 68, 70, 75, and 77 of any one of SEQ ID NOs: 43-59. In certain embodiments, variable residues within a hypervariable region can further correspond to residues 48, 50, and 71-73 of any one of SEQ ID NOs: 43-59. In other embodiments, variable residues within a hypervariable region correspond to one or more of positions 215, 217, 219, 221, 223, 224, 229, 231, 233, 235, 237, 239, 241, 259, 261, 262, 263, 264, 266, and 268 of any one of SEQ ID NOs: 43-59. In certain embodiments, variable residues within a hypervariable region can further correspond to residues 239, 241, and 263-265 of any one of SEQ ID NOs: 43-59.

The terms "increase" in the context of dystrophin protein or mRNA levels refers to any increase in the levels of dystrophin protein or mRNA expression relative to a reference level including an increase of dystrophin protein or mRNA expression of at least 1%, 2%, 3%, 4%, 5%, 10%, 15%, 20%, 25%, 30%, 40%, 50%, 60%, 70%, 80%, 90%, 95%, 100%, or more, when compared to a reference level or control. In some embodiments, an increase in dystrophin protein or mRNA levels refers to an increase in a shortened dystrophin polypeptide or mRNA transcript, for example, missing a portion of the polypeptide encoded by at least one exon (e.g., a portion encoded by exons 45-55) or missing a portion of mRNA corresponding to exons 45-55 compared to the wild-type dystrophin polypeptide or gene.

As used herein, the term "reference level" in the context of dystrophin protein or mRNA levels refers to a level of dystrophin protein or mRNA as measured in, for example, a control cell, control cell population or a control subject, at a previous time point in the control cell, the control cell population or the subject undergoing treatment (e.g., a pre-dose baseline level obtained from the control cell, control cell population or subject), or a pre-defined threshold level of dystrophin protein or mRNA (e.g., a threshold level identified through previous experimentation).

As used herein, the term "a control" or "a control cell" refers to a cell that provides a reference point for measuring changes in genotype or phenotype of a genetically modified cell. A control cell may comprise, for example: (a) a wild-type cell, i.e., of the same genotype as the starting material for the genetic alteration which resulted in the genetically modified cell; (b) a cell of the same genotype as the genetically modified cell but which has been transformed with a null construct (i.e., with a construct which has no known effect on the trait of interest); or, (c) a cell genetically identical to the genetically modified cell but which is not exposed to conditions or stimuli or further genetic modifications that would induce expression of altered genotype or phenotype. A control subject may comprise, for example: a wild-type subject, i.e., of the same genotype as the starting subject for the genetic alteration which resulted in the genetically modified subject (e.g., a subject having the same mutation in a dystrophin gene), which is not exposed to conditions or stimuli or further genetic modifications that would induce expression of altered genotype or phenotype in the subject.

As used herein, the term "recombinant DNA construct," "recombinant construct," "expression cassette," "expression construct," "chimeric construct," "construct," and "recombinant DNA fragment" are used interchangeably herein and are single or double-stranded polynucleotides. A recombinant construct comprises an artificial combination of nucleic acid fragments, including, without limitation, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such a construct may be used by itself or may be used in conjunction with a vector.

As used herein, the term "vector" or "recombinant DNA vector" may be a construct that includes a replication system and sequences that are capable of transcription and translation of a polypeptide-encoding sequence in a given host cell. If a vector is used, then the choice of vector is dependent upon the method that will be used to transform host cells as is well known to those skilled in the art. Vectors can include, without limitation, plasmid vectors and recombinant AAV vectors, or any other vector known in the art suitable for delivering a gene to a target cell. The skilled artisan is well aware of the genetic elements that must be present on the vector in order to successfully transform, select and propagate host cells comprising any of the isolated nucleotides or nucleic acid sequences described herein. In some embodiments, a "vector" also refers to a viral vector. Viral vectors can include, without limitation, retroviral vectors, lentiviral vectors, adenoviral vectors, and AAV.

As used herein, the term "operably linked" is intended to mean a functional linkage between two or more elements. For example, an operable linkage between a nucleic acid sequence encoding a nuclease as disclosed herein and a regulatory sequence (e.g., a promoter) is a functional link that allows for expression of the nucleic acid sequence encoding the nuclease. Operably linked elements may be contiguous or non-contiguous. When used to refer to the joining of two protein coding regions, by operably linked is intended that the coding regions are in the same reading frame.

As used herein, the terms "treatment" or "treating a subject" refers to the administration of an engineered meganuclease described herein, or a polynucleotide encoding an engineered meganuclease described herein, or a pair of such engineered meganucleases or polynucleotides, to a subject having DMD for the purpose of increasing levels of a dystrophin protein in the subject. In some embodiments, expression of a shortened version (e.g., missing amino acids encoded by multiple exons) of the dystrophin protein is increased. In some embodiments, expression of a version of the dystrophin protein, lacking the amino acids encoded by exons 45-55, is increased. Such treatment, in some embodiments, transitions the DMD phenotype to a Becker Dystrophy phenotype.

As used herein, the term "gc/kg" or "gene copies/kilogram" refers to the number of copies of a nucleic acid sequence encoding an engineered meganuclease described herein per weight in kilograms of a subject that is administered a polynucleotide comprising the nucleic acid sequence.

As used herein, the term "effective amount" or "therapeutically effective amount" refers to an amount sufficient to effect beneficial or desirable biological and/or clinical results. The therapeutically effective amount will vary depending on the formulation or composition used, the disease and its severity and the age, weight, physical condition, and responsiveness of the subject to be treated. In specific embodiments, an effective amount of an engineered meganuclease or pair of engineered meganucleases described herein, or polynucleotide or pair of polynucleotides encoding the same, or pharmaceutical compositions disclosed herein, increases the level of expression of a dystrophin protein (e.g., a shortened dystrophin protein lacking the amino acids encoded by exons 45-55) and ameliorates at least one symptom associated with DMD.

As used herein, the recitation of a numerical range for a variable is intended to convey that the present disclosure may be practiced with the variable equal to any of the values within that range. Thus, for a variable which is inherently discrete, the variable can be equal to any integer value within the numerical range, including the end-points of the range. Similarly, for a variable that is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values $\geq 0$ and $\leq 2$ if the variable is inherently continuous.

2.1 Principle of the Disclosure

The present disclosure is based on the discovery of muscle-specific expression cassettes that function to better express a heterologous protein specifically in muscle tissue. In particular, these expression cassettes utilize muscle-specific promoters as part of a nucleic acid expression cassette that result in specific expression of a heterologous protein in skeletal and cardiac muscle tissues when delivered to a mammal in vivo utilizing AAV (e.g., AAV9 or AAVrh74). The expression cassettes described herein further demonstrate an ability to express a heterologous protein in muscle satellite cells (e.g., Pax7 positive muscle satellite cells).

In addition, it was further unexpectedly discovered that the muscle-specific expression cassettes described herein result in superior expression in skeletal muscle tissue compared to cardiac muscle tissue. These advantageous expression profiles allow for tuned expression of heterologous proteins in cardiac and muscle tissue to maximize the effectiveness of the delivered heterologous protein. As described herein, delivery of engineered nucleases (e.g., engineered meganucleases) in this manner provides increased efficacy in gene editing. The muscle-specific expression cassettes described herein are useful for the expression of heterologous proteins in muscle cells and tissues in vitro and in vivo. These muscle-specific expression cassettes are useful for the treatment of a muscle disorder where expression of a heterologous protein in an effected or diseased muscle cells is desired. In particular embodiments disclosed herein, the muscle-specific expression cassettes described herein are useful for the treatment of DMD utilizing site-specific nucleases.

2.2 Muscle-Specific Expression Cassettes for Expression of Heterologous Proteins in Cells Heterologous proteins (e.g., engineered nucleases) can be specifically expressed in muscle cells by the muscle-specific expression cassettes described herein. The muscle-specific expression cassettes described herein comprise a nucleic acid sequence, which comprises the heterologous protein. These muscle-specific expression cassettes are comprised by a larger delivery vehicle (e.g., as part of viral vector). According to the present disclosure, coding sequences of the heterologous proteins described herein are delivered to a muscle cell in a muscle-specific expression cassette that is in DNA form. As a part of the muscle-specific expression cassette, the heterologous protein should be operably linked to a promoter (i.e., a muscle-specific promoter) to facilitate transcription of the heterologous protein transgene.

Accordingly, a nucleic acid sequence encoding a heterologous protein described herein is operably linked to a muscle-specific promoter. In some particular embodiments, the promoter is capable of expressing an engineered meganuclease described herein in a muscle precursor cell (e.g., satellite cell or stem cell). Exemplary and non-limiting muscle promoters include C5-12 (Liu et al. (2004) *Hum Gene Ther.* 15:783-92), the muscle-specific creatine kinase (MCK) promoter (Yuasa et al. (2002) *Gene Ther.* 9:1576-88), or the smooth muscle 22 (SM22) promoter (Haase et al. (2013) *BMC Biotechnol.* 13:49-54).

In some embodiments, the muscle-specific promoter in the muscle-specific expression cassettes described herein is based on or comprises a portion of the MCK promoter. These promoters comprise a MCK enhancer element region and a MCK basal promoter region. In some embodiments, the MCK promoter is a tMCK promoter described herein. In some embodiments, the basal MCK promoter comprises a sequence from a WT human or murine MCK promoter sequence. In some embodiments, the basal MCK promoter is from about 50 bp to about 1,000 bp in length. In some embodiments, the basal MCK promoter is about 50 bp, about 55 bp, about 60 bp, about 65 bp, about 70 bp, about 75 bp, about 80 bp, about 85 bp, about 90 bp, about 95 bp, about 100 bp, about 150 bp, about 200 bp, about 250 bp, about 300 bp, about 350 bp, about 400 bp, about 450 bp, about 500 bp, about 600 bp, about 700 bp, about 800 bp, about 900 bp, or about 1000 bp in length. In some embodiments, the basal MCK promoter is about 350 bp in length. In some embodiments, the basal MCK promoter is about 90 bp in length.

In some embodiments, the basal MCK promoter comprises a nucleic acid sequence that is about 80%, 81%, 82%, 83%, 84%, 85%, 86%, 87%, 88%, 89%, 90%, 91%, 92%, 93%, 94%, 95%, 96%, 97%, 98%, 99% or 100% identical to SEQ ID NO: 2. In some embodiments, the basal MCK promoter comprises a nucleic acid sequence that is about 80%, 81%, 82%, 83%, 84%, 85%, 86%, 87%, 88%, 89%, 90%, 91%, 92%, 93%, 94%, 95%, 96%, 97%, 98%, 99% or 100% identical to SEQ ID NO: 3. In some embodiments, the basal MCK promoter comprises a nucleic acid sequence according to a sequence set forth in SEQ ID NO: 2. In some embodiments, the basal MCK promoter comprises a nucleic acid sequence according to a sequence set forth in SEQ ID NO: 3. In some embodiments, the MCK enhancer element comprises one or more MCK-R control element. In some embodiments, the MCK-R control element comprises a sequence according to a sequence set forth in any one of SEQ ID NOs: 4-17. In some embodiments, the MCK promoter comprises a sequence 80%, 81%, 82%, 83%, 84%, 85%, 86%, 87%, 88%, 89%, 90%, 91%, 92%, 93%, 94%, 95%, 96%, 97%, 98%, 99% or 100% identical to a murine MCK promoter comprising SEQ ID NO: 18. In some embodiments, the MCK promoter comprises a sequence 80%, 81%, 82%, 83%, 84%, 85%, 86%, 87%, 88%, 89%, 90%, 91%, 92%, 93%, 94%, 95%, 96%, 97%, 98%, 99% or 100% identical to a human MCK promoter comprising SEQ ID NO: 19.

In some embodiments, the MCK promoter comprises a MCK enhancer element sequence that is 80%, 81%, 82%, 83%, 84%, 85%, 86%, 87%, 88%, 89%, 90%, 91%, 92%, 93%, 94%, 95%, 96%, 97%, 98%, 99% or 100% identical to a MCK enhancer element sequence comprising SEQ ID NO: 20. In some embodiments, the MCK promoter comprises a modified MCK enhancer sequence that is 80%, 81%, 82%, 83%, 84%, 85%, 86%, 87%, 88%, 89%, 90%, 91%, 92%, 93%, 94%, 95%, 96%, 97%, 98%, 99% or 100% identical to a modified MCK enhancer comprising SEQ ID NO: 21.

In some embodiments, the MCK promoter is a tMCK promoter comprising a nucleic acid sequence that is about 80%, 81%, 82%, 83%, 84%, 85%, 86%, 87%, 88%, 89%, 90%, 91%, 92%, 93%, 94%, 95%, 96%, 97%, 98%, 99% or 100% identical to SEQ ID NO: 22. In some embodiments, the MCK promoter is a tMCK promoter comprising a nucleic acid sequence according to a sequence set forth in SEQ ID NO: 22.

In some embodiments, the muscle-specific expression cassette further comprises a post transcriptional regulatory element as described herein. In particular embodiments, the post transcriptional regulatory element is a WPRE described herein. In some embodiments, the WPRE comprises a nucleic acid sequence that is about 80%, 81%, 82%, 83%, 84%, 85%, 86%, 87%, 88%, 89%, 90%, 91%, 92%, 93%, 94%, 95%, 96%, 97%, 98%, 99% or 100% identical to SEQ ID NO: 24. In some embodiments, the WPRE comprises a nucleic acid sequence according to a sequence set forth in SEQ ID NO: 24.

In some embodiments, the muscle-specific expression cassette further comprises a poly A termination sequence. In particular embodiments, the poly A termination sequence is an SV40 poly A. In some embodiments, the poly A termination sequence comprises a nucleic acid sequence that is about 80%, 81%, 82%, 83%, 84%, 85%, 86%, 87%, 88%, 89%, 90%, 91%, 92%, 93%, 94%, 95%, 96%, 97%, 98%, 99% or 100% identical to SEQ ID NO: 29. In some embodiments, the poly A termination sequence comprises a nucleic acid sequence according to a sequence set forth in SEQ ID NO: 29.

In some embodiments, the muscle-specific promoter comprises a consensus Kozak sequence as described herein. Such Kozak sequences are known in the art and are generally suitable for the embodiments of the disclosure described herein. In some embodiments, the Kozak sequence comprises a sequence according to a sequence set forth in SEQ ID NO: 32.

In some embodiments, the muscle-specific expression cassettes comprise a muscle-specific enhancer located either 5' upstream or 3' downstream from the muscle-specific promoter. According to the disclosure, inclusion of a muscle-specific enhancer increases expression of a transgene in muscle tissues and muscle cell types without significantly increasing expression of the transgene in other tissue or cell types. In particular, it was discovered that the B-301 enhancer increases expression of a heterologous protein in Pax7 positive muscle satellite cells as well as differentiated muscle cells. According to some embodiments, the muscle-specific enhancer is located 5' upstream from the muscle-specific promoter described herein. In some embodiments, the muscle-specific enhancer comprises a B-301 enhancer sequence. In some embodiments, the B-301 enhancer sequence comprises a nucleic acid sequence that is about 80%, 81%, 82%, 83%, 84%, 85%, 86%, 87%, 88%, 89%, 90%, 91%, 92%, 93%, 94%, 95%, 96%, 97%, 98%, 99% or 100% identical to SEQ ID NO: 1. In some embodiments, the B-301 enhancer sequence comprises a nucleic acid sequence according to a sequence set forth in SEQ ID NO: 1.

In some embodiments, wherein a single polynucleotide comprises two separate nucleic acid sequences each encoding a heterologous protein (e.g., an engineered nuclease described herein, the heterologous protein transgenes are operably linked to two or more muscle-specific promoters described herein. These two or more muscle-specific promoters may be the same or different. In alternative embodiments, the two heterologous protein transgenes are operably linked to a single promoter, and in some examples can be separated by an internal-ribosome entry site (IRES) or a 2A peptide sequence (Szymczak & Vignali (2005) *Expert Opin Biol Ther.* 5:627-38). Such 2A peptide sequences can include, for example, a T2A, P2A, E2A, or F2A sequence. In some further embodiments, the 2A element comprises a furin cleavage motif. In some further embodiments, the 2A element comprises a furin cleavage motif with a GSG linker.

In embodiments of the methods and compositions described herein, the muscle-specific expression cassette results in an increased expression of a heterologous protein in a muscle cell compared to a non-muscle cell. The non-muscle cell may include any mammalian cell, which is not of muscle cell origin, for example a cell that is not differentiated from a Pax7+ muscle stem cell. In some embodiments, the non-muscle cell is a non-muscle cell of the liver, the brain, non-muscle cell of the kidney, non-muscle cell of the pancreas, non-muscle cell of the spleen, a germ cell, or non-muscle cell of the lung.

In some embodiments, the heterologous proteins described herein expressed from the muscle-specific expression cassettes described herein exhibit about a 1.5-fold to about a 2-fold, or about a 2-fold to about a 5-fold, or about a 5-fold to about a 10-fold, or about a 10-fold to about a 15-fold, or about a 15-fold to about a 20-fold, or about a 25-fold to about a 30-fold, or about a 30-fold to about a 40-fold, or about a 40-fold to about a 50-fold, or about a 50-fold to about a 60-fold, or about a 60-fold to about a 70-fold, or about a 70-fold to about a 80-fold, or about a 80-fold to about a 90-fold, or about a 90-fold to about a 100-fold increase in expression of a heterologous protein described herein in a muscle cell compared to a non-muscle cell described herein. In some embodiments, the heterologous proteins described herein expressed from the muscle-specific expression cassettes described herein exhibit about a 2-fold to about an 80-fold increase in expression of a heterologous protein described herein in a muscle cell compared to a non-muscle cell described herein. In some other embodiments, the heterologous proteins described herein expressed from the muscle-specific expression cassettes described herein exhibit about a 5-fold to about a 60-fold increase in expression of a heterologous protein described herein in a muscle cell compared to a non-muscle cell described herein. In some additional embodiments, the heterologous proteins described herein expressed from the muscle-specific expression cassettes described herein exhibit about a 15-fold to about a 60-fold increase in expression of a heterologous protein described herein in a muscle cell compared to a non-muscle cell described herein.

In embodiments of the methods and compositions described herein, the muscle-specific expression cassette results in an increased expression of a heterologous protein in a muscle cell compared to a cardiac muscle cell. In such embodiments, the heterologous protein is still expressed in a cardiac muscle cell but to a lesser extent when compared to a skeletal muscle cell.

In some embodiments, the heterologous proteins described herein expressed from the muscle-specific expression cassettes described herein exhibit about a 1.5-fold to about a 2-fold, or about a 2-fold to about a 5-fold, or about a 5-fold to about a 10-fold, or about a 10-fold to about a 15-fold, or about a 15-fold to about a 20-fold, or about a 25-fold to about a 30-fold, or about a 30-fold to about a 40-fold, or about a 40-fold to about a 50-fold, or about a 50-fold to about a 60-fold, or about a 60-fold to about a 70-fold, or about a 70-fold to about a 80-fold, or about a 80-fold to about a 90-fold, or about a 90-fold to about a 100-fold increase in expression of a heterologous protein described herein in a muscle cell compared to a cardiac muscle cell. In some embodiments, the heterologous proteins described herein expressed from the muscle-specific expression cassettes described herein exhibit about a 2-fold to about an 80-fold increase in expression of a heterologous protein described herein in a muscle cell compared to a cardiac muscle cell. In some other embodiments, the heterologous proteins described herein expressed from the muscle-specific expression cassettes described herein exhibit about a 5-fold to about a 60-fold increase in expression of a heterologous protein described herein in a muscle cell compared to a cardiac muscle cell. In some additional embodiments, the heterologous proteins described herein expressed from the muscle-specific expression cassettes described herein exhibit about a 15-fold to about a 60-fold increase in expression of a heterologous protein described herein in a muscle cell compared to a cardiac muscle cell.

2.3 Heterologous Proteins Encoded by Muscle-Specific Expression Cassettes

The muscle-specific expression cassettes described herein can encode any heterologous protein that is desired to be expressed in muscle cells. The heterologous protein may be a protein that is desired to study muscle cell function such as a fluorescently tagged (e.g., green fluorescent protein) version of a naturally occurring muscle protein. Alternatively, the heterologous protein may be a therapeutic protein that is a muscle protein for treating a muscular disorder described herein (e.g., DMD). Exemplary and non-limiting therapeutics include dystrophin proteins, such as microdystrophin 1 (MD1), follistatin (FST), sarcoglycan proteins, alpha-glucosidase, and myotubularin-1 (MTM-1).

In some embodiments, the heterologous protein is a nucleoprotein described herein. Such nucleoproteins exert their primary function in the cellular nucleus and may include proteins which regulate gene expression at the level of the DNA without editing the DNA. These proteins are referred to herein as DNA binding regulatory proteins. Such proteins include but are not limited to naturally occurring transcription factors, nuclease dead versions of engineered nucleases, and artificial transcription factors. An example of a nuclease dead versions of DNA binding regulator proteins include CRISPR-Cas proteins in which the CAS enzyme has been inactivated and linked to a gene activator domain or a gene repressor domain. In addition. a TALE, engineered ZFN, and engineered meganucleases in conjunction with gene repressor and activator domains can be utilized to modulate gene expression. Alternative nucleoproteins described herein directly edit genomic DNA and include engineered nucleases.

Accordingly, in some embodiments, the heterologous protein is an engineered nuclease. As described herein, the muscle-specific expression cassettes are suitable for expressing engineered nucleases for binding and cleaving recognition sequences within the genome of a mammalian muscle cell. In some embodiments, the methods described herein are useful for modifying a dystrophin gene utilizing the engineered nucleases described herein. In some other embodiments, the methods described herein are useful for treating DMD in a subject having DMD. Non-limiting examples of engineered nucleases useful in the present disclosure include, among others, engineered meganucleases, CRISPR system nucleases, ZFNs, TALENs, compact TALENs, megaTALs, base editors, and prime editors.

ZFNs can be engineered to recognize and cut pre-determined sites in a genome. ZFNs are chimeric proteins comprising a zinc finger DNA-binding domain fused to a nuclease domain from an endonuclease or exonuclease (e.g., Type IIs restriction endonuclease, such as the FokI restriction enzyme). The zinc finger domain can be a native sequence or can be redesigned through rational or experimental means to produce a protein which binds to a pre-determined DNA sequence ~18 base pairs in length. By fusing this engineered protein domain to the nuclease domain, it is possible to target DNA breaks with genome-level specificity. ZFNs have been used extensively to target gene addition, removal, and substitution in a wide range of eukaryotic organisms (reviewed in S. Durai et al., *Nucleic Acids Res* 33, 5978 (2005)).

Likewise, TALENs can be generated to cleave specific sites in genomic DNA. Like a ZFN, a TALEN comprises an engineered, site-specific DNA-binding domain fused to an endonuclease or exonuclease (e.g., Type I is restriction endonuclease, such as the FokI restriction enzyme) (reviewed in Mak, et al. (2013) *Curr Opin Struct Biol.* 23:93-9). In this case, however, the DNA binding domain comprises a tandem array of TAL-effector domains, each of which specifically recognizes a single DNA basepair.

Compact TALENs are an alternative endonuclease architecture that avoids the need for dimerization (Beurdeley, et al. (2013) *Nat Commun.* 4:1762). A Compact TALEN comprises an engineered, site-specific TAL-effector DNA-binding domain fused to the nuclease domain from the I-TevI homing endonuclease or any of the endonucleases listed in Table 2 in US Patent Application Publication No. 2013/0117869. Compact TALENs do not require dimerization for DNA processing activity, so a Compact TALEN is functional as a monomer.

Engineered endonucleases based on the CRISPR/Cas system are also known in the art (Ran, et al. (2013) *Nat Protoc.* 8:2281-2308; Mali et al. (2013) *Nat Methods.* 10:957-63). In those embodiments wherein a CRISPR system is used for insertion of a donor nucleic acid sequence into a heterologous polynucleotide or genomic locus, the CRISPR system comprises two components: (1) a CRISPR nuclease; and (2) a short "guide RNA" comprising a ~20 nucleotide targeting sequence that directs the nuclease to a location of interest in the genome or on a polynucleotide. The CRISPR system may also comprise a tracrRNA. By expressing multiple guide RNAs in the same cell, each having a different targeting sequence, it is possible to target DNA breaks simultaneously to multiple sites in the genome. The presently disclosed compositions and methods utilizing a CRISPR system may comprise a CRISPR nuclease and the guide RNA(s) or nucleic acids encoding the CRISPR nuclease and/or the guide RNA(s).

Nucleases referred to as megaTALs are single-chain endonucleases comprising a transcription activator-like effector (TALE) DNA binding domain with an engineered, sequence-specific homing endonuclease.

Exemplary and non-limiting prime editors consist of a fusion protein of a Cas9 H840A nickase fused to a reverse transcriptase and a prime editing guide RNA (pegRNA). Prime editors mediate insertions, deletions, and base conversions without generating a double strand break (Anzalone et al. (2019) *Nature* 576(7785) 149-157). The pegRNA includes a single guide RNA that has a primer binding site and a reverse transcriptase template. When editing the genome, the DNA is nicked, and the primer binding site causes the nicked DNA strand to hybridize with the pegRNA and the template serves as a synthetic template for editing the gene. The presently disclosed compositions and methods utilizing a prime editing system may comprise a CRISPR nuclease (e.g., a Cas9 H840A nickase) and the pegRNA(s) or nucleic acids encoding the CRISPR nuclease and/or the pegRNA(s).

Exemplary and non-limiting base editors are based on enzymes that are capable of catalyzing cytosine/guanosine to thymidine/alanine conversions. For example, a base editor that utilizes the CRISPR/CAS9 enzyme includes CRISPR/Cas9 enzyme fused to a cytidine deaminase enzyme, which does not induce a double strand break. The Cas9 enzyme is typically inactivated such that it can no longer cleave DNA, but still function to bind to the DNA in conjunction with a guide RNA. Mutations to inactivate the Cas9 enzyme include an Asp10Ala and a His840Ala mutation. These base editors effect a cytosine to thymidine or guanosine to adenosine substitution Komor et al. (2016) *Nature* 533 (7603) 420-424. Another exemplary and non-limiting base editor includes CRISPR-free systems based on transcription activator-like effector (TALE) proteins fused to a double stranded DNA specific cytidine deaminase as described in Mok et al., (2022) *Nature Biotechnology* 40 1378-1387.

The presently disclosed compositions and methods can utilize purified nuclease proteins, or nucleic acids encoding nucleases. These can be delivered into cells to cleave genomic DNA or a polynucleotide by a variety of different mechanisms known in the art, including those further detailed elsewhere herein. In some embodiments wherein a CRISPR system nuclease is utilized, a ribonucleoprotein complex comprising the CRISPR nuclease and guide RNA (s) can be introduced into a cell.

An engineered meganuclease can be, for example, an endonuclease that is derived from I-CreI and can refer to an engineered variant of I-CreI that has been modified relative to natural I-CreI with respect to, for example, DNA-binding specificity, DNA cleavage activity, DNA-binding affinity, or dimerization properties. Methods for producing such modified variants of I-CreI are known in the art (e.g., WO 2007/047859, incorporated by reference in its entirety). A meganuclease as used herein binds to double-stranded DNA as a heterodimer. A meganuclease may also be a "single-chain meganuclease" in which a pair of DNA-binding domains is joined into a single polypeptide using a peptide linker.

In particular embodiments, the meganucleases used to practice the embodiments of the present disclosure are single-chain meganucleases. A single-chain meganuclease comprises an N-terminal subunit and a C-terminal subunit joined by a linker peptide. Each of the two subunits recognizes and binds to half of the recognition sequence (i.e., a recognition half-site) and the site of DNA cleavage is at the middle of the recognition sequence near the interface of the two subunits. DNA strand breaks are offset by four base pairs such that DNA cleavage by a meganuclease generates a pair of four base pair, 3' single-strand overhangs. The first subunit of a single-chain meganuclease comprises a first hypervariable (HVR1) region, and the second subunit comprises a second hypervariable (HVR2) region. Further, the first subunit binds to a first recognition half-site in the recognition sequence, and the second subunit binds to a second recognition half-site in the recognition sequence.

In embodiments where the engineered meganuclease is a single-chain meganuclease, the first and second subunits can be oriented such that the first subunit, which comprises the HVR1 region and binds the first half-site, is positioned as the N-terminal subunit, and the second subunit, which comprises the HVR2 region and binds the second half-site, is positioned as the C-terminal subunit. In alternative embodiments, the first and second subunits can be oriented such that the first subunit, which comprises the HVR1 region and binds the first half-site, is positioned as the C-terminal subunit, and the second subunit, which comprises the HVR2 region and binds the second half-site, is positioned as the N-terminal subunit.

Recognition Sequences

It is known in the art that it is possible to use a site-specific nuclease to make a DNA break in the genome of a living cell, and that such a DNA break can result in permanent modification of the genome via mutagenic NHEJ repair or via homologous recombination with a transgenic DNA sequence. NHEJ can produce mutagenesis at the cleavage site, resulting in inactivation of the allele. NHEJ-associated mutagenesis may inactivate an allele via generation of early stop codons, frameshift mutations producing aberrant non-functional proteins, or could trigger mechanisms such as nonsense-mediated mRNA decay. The use of nucleases to induce mutagenesis via NHEJ can be used to target a specific mutation or a sequence present in a wild-type allele. Further, the use of nucleases to induce a double-strand break in a target locus is known to stimulate homologous recombination, particularly of transgenic DNA sequences flanked by sequences that are homologous to the genomic target. In this manner, exogenous polynucleotides can be inserted into a target locus. Such exogenous polynucleotides can encode any sequence or polypeptide of interest.

In particular embodiments, engineered meganucleases described herein have been designed to bind and cleave a DMD 19-20 recognition sequence (SEQ ID NO: 37) or a DMD 35-36 recognition sequence (SEQ ID NO: 39). Exemplary meganucleases that bind and cleave the DMD 19-20 recognition sequence are provided in SEQ ID NOs: 43-51. Exemplary meganucleases that bind and cleave the DMD 35-36 recognition sequence are provided in SEQ ID NOs: 52-59. The sequence of each recognition sequence, and the four base pair 3' overhang produced when cleaved by an engineered meganuclease described herein, is provided in Table 1 below.

TABLE 1

| Engineered Meganuclease Recognition Sequences | | |
|---|---|---|
| Recognition Sequence | SEQ ID NO: | 4 bp 3' Overhang |
| AAGGATTATGTATTACCTCCCG | 37 | GTAT |
| CTACATGGTGTATCTGACTAAG | 39 | GTAT |

In some embodiments to modify the dystrophin gene a pair of engineered meganucleases described herein are utilized together in the same cell. Such pairs of engineered meganucleases have been described in PCT International Patent Application Publication No: WO/2022/104062. These meganuclease were designed to generate a first cleavage site in an intron upstream of exon 45 and a second cleavage site in intron downstream of exon 55, allowing for removal of the 500,000 bp intervening genomic sequence. In some embodiments, meganuclease recognition sequences have complementary four base pair 3' overhangs following cleavage, which promotes repair of the dystrophin gene at high frequency by a perfect ligation of the 3' overhangs of the two cleavage sites. An example of a perfectly ligated recognition sequence after removal of exons 45-55 of the dystrophin gene is provided in SEQ ID NO: 41.

In some embodiments recognition sequences are further selected to be within intronic sequences that are normally spliced out during post transcriptional modification cellular processes. This reduces the likelihood of a mutation being introduced into the dystrophin gene and encoded polypeptide.

Exemplary Engineered Meganucleases

Engineered meganucleases described herein comprise a first subunit, comprising a HVR1 region, and a second subunit, comprising a HVR2 region. Further, the first subunit binds to a first recognition half-site in the recognition sequence (e.g., the DMD19 half-site), and the second subunit binds to a second recognition half-site in the recognition sequence (e.g., the DMD20 half-site).

In particular embodiments, the meganucleases are single-chain meganucleases. A single-chain meganuclease comprises an N-terminal subunit and a C-terminal subunit (i.e., the first and second subunits discussed above) joined by a linker peptide. Each of the two subunits recognizes and binds to a half-site of the recognition sequence and the site of DNA cleavage is at the middle of the recognition sequence near the interface of the two subunits. As discussed, DNA strand breaks are offset by four base pairs such that DNA cleavage by a meganuclease generates a pair of four base pair 3' single-strand overhangs.

In embodiments where the engineered meganuclease is a single-chain meganuclease, the first and second subunits can be oriented such that the first subunit, which comprises the HVR1 region and binds the first half-site, is positioned as the N-terminal subunit, and the second subunit, which comprises the HVR2 region and binds the second half-site, is positioned as the C-terminal subunit. In alternative embodiments, the first and second subunits can be oriented such that the first subunit, which comprises the HVR1 region and binds the first half-site, is positioned as the C-terminal subunit, and the second subunit, which comprises the HVR2 region and binds the second half-site, is positioned as the N-terminal subunit.

Exemplary DMD meganucleases of suitable for expression from the muscle-specific expression cassettes described herein and in the methods described herein are provided in SEQ ID NOs: 43-59. As described herein, combinations of meganucleases can be used to excise exons 45-55 from the dystrophin gene. Thus, in some embodiments, the first engineered meganuclease is an engineered meganuclease described herein that binds and cleaves a recognition sequence comprising SEQ ID NO: 37, and the second engineered meganuclease is an engineered meganuclease described herein that binds and cleaves a recognition sequence comprising SEQ ID NO: 39. In some embodiments, the first engineered meganuclease and the second engineered meganuclease encoded by the muscle-specific expression cassettes are selected from the combinations of meganucleases (and variants thereof described herein) provided in Table 2.

TABLE 2

| Combination | Recognition Sequence of SEQ ID NO: 37 | | Recognition Sequence of SEQ ID NO: 39 | |
|---|---|---|---|---|
| | First Meganuclease | SEQ ID NO: | Second Meganuclease | SEQ ID NO: |
| 1 | DMD 19-20x.13 | 43 | DMD 35-36x.63 | 52 |
| 2 | DMD 19-20x.87 | 44 | DMD 35-36x.63 | 52 |
| 3 | DMD 19-20L.249 | 45 | DMD 35-36x.63 | 52 |
| 4 | DMD 19-20L.302 | 46 | DMD 35-36x.63 | 52 |
| 5 | DMD 19-20L.329 | 47 | DMD 35-36x.63 | 52 |
| 6 | DMD 19-20L.374 | 48 | DMD 35-36x.63 | 52 |
| 7 | DMD 19-20L.375 | 49 | DMD 35-36x.63 | 52 |
| 8 | DMD 19-20L.431 | 50 | DMD 35-36x.63 | 52 |
| 9 | DMD 19-20L.458 | 51 | DMD 35-36x.63 | 52 |
| 10 | DMD 19-20x.13 | 43 | DMD 35-36x.81 | 53 |
| 11 | DMD 19-20x.87 | 44 | DMD 35-36x.81 | 53 |
| 12 | DMD 19-20L.249 | 45 | DMD 35-36x.81 | 53 |
| 13 | DMD 19-20L.302 | 46 | DMD 35-36x.81 | 53 |
| 14 | DMD 19-20L.329 | 47 | DMD 35-36x.81 | 53 |
| 15 | DMD 19-20L.374 | 48 | DMD 35-36x.81 | 53 |
| 16 | DMD 19-20L.375 | 49 | DMD 35-36x.81 | 53 |
| 17 | DMD 19-20L.431 | 50 | DMD 35-36x.81 | 53 |
| 18 | DMD 19-20L.458 | 51 | DMD 35-36x.81 | 53 |
| 19 | DMD 19-20x.13 | 43 | DMD 35-36L.195 | 54 |
| 20 | DMD 19-20x.87 | 44 | DMD 35-36L.195 | 54 |
| 21 | DMD 19-20L.249 | 45 | DMD 35-36L.195 | 54 |
| 22 | DMD 19-20L.302 | 46 | DMD 35-36L.195 | 54 |
| 23 | DMD 19-20L.329 | 47 | DMD 35-36L.195 | 54 |
| 24 | DMD 19-20L.374 | 48 | DMD 35-36L.195 | 54 |
| 25 | DMD 19-20L.375 | 49 | DMD 35-36L.195 | 54 |
| 26 | DMD 19-20L.431 | 50 | DMD 35-36L.195 | 54 |
| 27 | DMD 19-20L.458 | 51 | DMD 35-36L.195 | 54 |
| 28 | DMD 19-20x.13 | 43 | DMD 35-36L.282 | 55 |
| 29 | DMD 19-20x.87 | 44 | DMD 35-36L.282 | 55 |
| 30 | DMD 19-20L.249 | 45 | DMD 35-36L.282 | 55 |
| 31 | DMD 19-20L.302 | 46 | DMD 35-36L.282 | 55 |
| 32 | DMD 19-20L.329 | 47 | DMD 35-36L.282 | 55 |
| 33 | DMD 19-20L.374 | 48 | DMD 35-36L.282 | 55 |
| 34 | DMD 19-20L.375 | 49 | DMD 35-36L.282 | 55 |
| 35 | DMD 19-20L.431 | 50 | DMD 35-36L.282 | 55 |
| 36 | DMD 19-20L.458 | 51 | DMD 35-36L.282 | 55 |
| 37 | DMD 19-20x.13 | 43 | DMD 35-36L.349 | 56 |
| 38 | DMD 19-20x.87 | 44 | DMD 35-36L.349 | 56 |
| 39 | DMD 19-20L.249 | 45 | DMD 35-36L.349 | 56 |
| 40 | DMD 19-20L.302 | 46 | DMD 35-36L.349 | 56 |
| 41 | DMD 19-20L.329 | 47 | DMD 35-36L.349 | 56 |
| 42 | DMD 19-20L.374 | 48 | DMD 35-36L.349 | 56 |
| 43 | DMD 19-20L.375 | 49 | DMD 35-36L.349 | 56 |
| 44 | DMD 19-20L.431 | 50 | DMD 35-36L.349 | 56 |
| 45 | DMD 19-20L.458 | 51 | DMD 35-36L.349 | 56 |
| 46 | DMD 19-20x.13 | 43 | DMD 35-36L.376 | 57 |
| 47 | DMD 19-20x.87 | 44 | DMD 35-36L.376 | 57 |
| 48 | DMD 19-20L.249 | 45 | DMD 35-36L.376 | 57 |
| 49 | DMD 19-20L.302 | 46 | DMD 35-36L.376 | 57 |
| 50 | DMD 19-20L.329 | 47 | DMD 35-36L.376 | 57 |
| 51 | DMD 19-20L.374 | 48 | DMD 35-36L.376 | 57 |
| 52 | DMD 19-20L.375 | 49 | DMD 35-36L.376 | 57 |
| 53 | DMD 19-20L.431 | 50 | DMD 35-36L.376 | 57 |
| 54 | DMD 19-20L.458 | 51 | DMD 35-36L.376 | 57 |
| 55 | DMD 19-20x.13 | 43 | DMD 35-36L.457 | 58 |
| 56 | DMD 19-20x.87 | 44 | DMD 35-36L.457 | 58 |
| 57 | DMD 19-20L.249 | 45 | DMD 35-36L.457 | 58 |
| 58 | DMD 19-20L.302 | 46 | DMD 35-36L.457 | 58 |
| 59 | DMD 19-20L.329 | 47 | DMD 35-36L.457 | 58 |
| 60 | DMD 19-20L.374 | 48 | DMD 35-36L.457 | 58 |
| 61 | DMD 19-20L.375 | 49 | DMD 35-36L.457 | 58 |
| 62 | DMD 19-20L.431 | 50 | DMD 35-36L.457 | 58 |
| 63 | DMD 19-20L.458 | 51 | DMD 35-36L.457 | 58 |
| 64 | DMD 19-20x.13 | 43 | DMD 35-36L.469 | 59 |

TABLE 2-continued

| Combination | Recognition Sequence of SEQ ID NO: 37 | | Recognition Sequence of SEQ ID NO: 39 | |
| | First Meganuclease | SEQ ID NO: | Second Meganuclease | SEQ ID NO: |
| --- | --- | --- | --- | --- |
| 65 | DMD 19-20x.87 | 44 | DMD 35-36L.469 | 59 |
| 66 | DMD 19-20L.249 | 45 | DMD 35-36L.469 | 59 |
| 67 | DMD 19-20L.302 | 46 | DMD 35-36L.469 | 59 |
| 68 | DMD 19-20L.329 | 47 | DMD 35-36L.469 | 59 |
| 69 | DMD 19-20L.374 | 48 | DMD 35-36L.469 | 59 |
| 70 | DMD 19-20L.375 | 49 | DMD 35-36L.469 | 59 |
| 71 | DMD 19-20L.431 | 50 | DMD 35-36L.469 | 59 |
| 72 | DMD 19-20L.458 | 51 | DMD 35-36L.469 | 59 |

In different aspects, the disclosure provides engineered meganucleases described herein that are useful for binding and cleaving recognition sequences within a dystrophin gene of a cell (e.g., the human dystrophin gene). The disclosure also provides various methods for modifying a dystrophin gene in cells using engineered meganucleases described herein, methods for making genetically modified cells comprising a modified dystrophin gene, and methods of modifying a dystrophin gene in a target cell in a subject. In further aspects, the disclosure provides methods for treating DMD in a subject by administering the engineered meganucleases described herein, or polynucleotides encoding the same, to a subject, in some cases as part of a pharmaceutical composition.

Detection and Expression

Expression of a modified dystrophin (i.e., a gene lacking exons 45-55, or a protein lacking amino acids encoded by exons 45-55) in a genetically modified cell or subject can be detected using standard methods in the art. For example, levels of such modified dystrophin may be assessed based on the level of any variable associated with dystrophin gene expression, e.g., dystrophin mRNA levels or dystrophin protein levels. Increased levels or expression of such modified dystrophin may be assessed by an increase in an absolute or relative level of one or more of these variables compared with a reference level. Such modified dystrophin levels may be measured in a biological sample isolated from a subject, such as a tissue biopsy or a bodily fluid including blood, serum, plasma, cerebrospinal fluid, or urine. Optionally, such modified dystrophin levels are normalized to a standard protein or substance in the sample. Further, such modified dystrophin levels can be assessed any time before, during, or after treatment in accordance with the methods herein.

In various aspects, the methods described herein can increase protein levels of a modified dystrophin (i.e., lacking amino acids encoded by exons 45-55) in a genetically modified cell, target cell, or subject (e.g., as measured in a cell, a tissue, an organ, or a biological sample obtained from the subject), to at least 1%, 2%, 3%, 4%, 5%, 10%, 15%, 20%, 25%, 30%, 40%, 50%, 60%, 70%, 80%, 90%, 95%, 100%, or more, of a reference level (i.e., protein level of dystrophin in a wild-type cell or subject). In some embodiments, the methods herein are effective to increase the level of such modified dystrophin protein to about 10% to about 100% (e.g., 10%-20%, 20%-30%, 30%-40%, 40%-50%, 50%-60%, 60%-70%, 70%-80%, 80%-90%, 90%-100%, or more) of a reference level of dystrophin (i.e., protein level of dystrophin in a wild-type cell or subject).

2.4 Introduction of Muscle-Specific Expression Cassettes into Cells

Heterologous proteins disclosed herein (e.g., engineered nucleases) can be delivered into cells by a variety of different mechanisms known in the art, including those further detailed herein below. In specific embodiments, a muscle-specific expression cassette described herein is delivered on a recombinant DNA construct. For example, the recombinant DNA construct comprises the muscle-specific expression cassette described herein.

In another particular embodiment, a muscle-specific expression cassette described herein is introduced into the cell using a single-stranded DNA template. The single-stranded DNA can further comprise a 5' and/or a 3' AAV inverted terminal repeat (ITR) upstream and/or downstream of the sequence encoding the engineered nuclease. The single-stranded DNA can further comprise a 5' and/or a 3' homology arm upstream and/or downstream of the sequence encoding the engineered meganuclease.

In another particular embodiment, the muscle-specific expression cassettes described herein can be introduced into a cell using a linearized DNA template. Such linearized DNA templates can be produced by methods known in the art. For example, a plasmid DNA encoding a nuclease can be digested by one or more restriction enzymes such that the circular plasmid DNA is linearized prior to being introduced into a cell.

In some embodiments, the muscle-specific expression cassette described herein is coupled to a cell penetrating peptide or targeting ligand to facilitate cellular uptake. Examples of cell penetrating peptides known in the art include poly-arginine (Jearawiriyapaisarn et al. (2008) Mol Ther. 16:1624-29), TAT peptide from the HIV virus (Hudecz et al. (2005) Med. Res. Rev. 25:679-736), MPG (Simconi et al. (2003) Nucleic Acids Res. 31:2717-24), Pep-1 (Deshayes et al. (2004) Biochemistry 43:7698-7706, and HSV-1 VP-22 (Deshayes et al. (2005) Cell Mol Life Sci. 62:1839-49). In an alternative embodiment the muscle-specific expression cassettes described herein are coupled covalently or non-covalently to an antibody that recognizes a specific cell-surface receptor expressed on target cells such that the muscle-specific expression cassette binds to and is internalized by the target cells. Alternatively, the muscle-specific expression cassettes described herein can be coupled covalently or non-covalently to the natural ligand (or a portion of the natural ligand) for such a cell-surface receptor. (McCall et al. (2014) Tissue Barriers. 2(4):e944449; Dinda et al. (2013) Curr. Pharm. Biotechnol. 14:1264-74; Kang et al. (2014) Curr. Pharm. Biotechnol. 15:220-30; and Qian et al. (2014) Expert Opin. Drug Metab Toxicol. 10:1491-508).

In some embodiments, the muscle-specific expression cassettes described herein are encapsulated within biodegradable hydrogels for injection or implantation within the desired region of the liver (e.g., in proximity to hepatic sinusoidal endothelial cells or hematopoietic endothelial cells, or progenitor cells which differentiate into the same).

Hydrogels can provide sustained and tunable release of the therapeutic payload to the desired region of the target tissue without the need for frequent injections, and stimuli-responsive materials (e.g., temperature- and pH-responsive hydrogels) can be designed to release the payload in response to environmental or externally applied cues (Derwent et al. (2008) *Trans Am. Ophthalmol. Soc.* 106:206-14).

In some embodiments, the muscle-specific expression cassettes described herein are coupled covalently or, preferably, non-covalently to a nanoparticle or encapsulated within such a nanoparticle using methods known in the art (Sharma et al. (2014) *Biomed. Res. Int.* 2014:156010). A nanoparticle is a nanoscale delivery system whose length scale is <1 μm, preferably <100 nm. Such nanoparticles may be designed using a core composed of metal, lipid, polymer, or biological macromolecule, and multiple copies of the muscle-specific expression cassettes described herein can be attached to or encapsulated with the nanoparticle core. This increases the copy number of the DNA that is delivered to each cell and, so, increases the intracellular expression of each meganuclease to maximize the likelihood that the target recognition sequences will be cut. The surface of such nanoparticles may be further modified with polymers or lipids (e.g., chitosan, cationic polymers, or cationic lipids) to form a core-shell nanoparticle whose surface confers additional functionalities to enhance cellular delivery and uptake of the payload (Jian et al. (2012) *Biomaterials.* 33:7621-30). Nanoparticles may additionally be advantageously coupled to targeting molecules to direct the nanoparticle to the appropriate cell type and/or increase the likelihood of cellular uptake. Examples of such targeting molecules include antibodies specific for cell-surface receptors and the natural ligands (or portions of the natural ligands) for cell surface receptors.

In some embodiments, the muscle-specific expression cassettes described herein are encapsulated within liposomes or complexed using cationic lipids (see, e.g., LIPO-FECTAMINE™, Life Technologies Corp., Carlsbad, CA; Zuris et al. (2015) *Nat. Biotechnol.* 33:73-80; Mishra et al. (2011) *J. Drug Deliv.* 2011:863734). The liposome and lipoplex formulations can protect the payload from degradation, enhance accumulation and retention at the target site, and facilitate cellular uptake and delivery efficiency through fusion with and/or disruption of the cellular membranes of the target cells.

In some embodiments, the muscle-specific expression cassettes described herein are encapsulated within polymeric scaffolds (e.g., PLGA) or complexed using cationic polymers (e.g., PEI, PLL) (Tamboli et al. (2011) *Ther Deliv.* 2:523-36). Polymeric carriers can be designed to provide tunable drug release rates through control of polymer erosion and drug diffusion, and high drug encapsulation efficiencies can offer protection of the therapeutic payload until intracellular delivery to the desired target cell population.

In some embodiments, the muscle-specific expression cassettes described herein are combined with amphiphilic molecules that self-assemble into micelles (Tong et al. (2007) *J. Gene Med.* 9:956-66). Polymeric micelles may include a micellar shell formed with a hydrophilic polymer (e.g., polyethyleneglycol) that can prevent aggregation, mask charge interactions, and reduce non-specific interactions.

In some embodiments, the muscle-specific expression cassettes described herein are formulated into an emulsion or a nanoemulsion (i.e., having an average particle diameter of <1 nm) for administration and/or delivery to the target cell. The term "emulsion" refers to, without limitation, any oil-in-water, water-in-oil, water-in-oil-in-water, or oil-in-water-in-oil dispersions or droplets, including lipid structures that can form as a result of hydrophobic forces that drive apolar residues (e.g., long hydrocarbon chains) away from water and polar head groups toward water, when a water immiscible phase is mixed with an aqueous phase. These other lipid structures include, but are not limited to, unilamellar, paucilamellar, and multilamellar lipid vesicles, micelles, and lamellar phases. Emulsions are composed of an aqueous phase and a lipophilic phase (typically containing an oil and an organic solvent). Emulsions also frequently contain one or more surfactants. Nanoemulsion formulations are well known, for example, as described in U.S. Pat. Nos. 6,015,832, 6,506,803, 6,635,676, 6,559,189, and 7,767,216.

In some embodiments, the muscle-specific expression cassettes described herein are covalently attached to, or non-covalently associated with, multifunctional polymer conjugates, DNA dendrimers, and polymeric dendrimers (Mastorakos et al. (2015) *Nanoscale.* 7:3845-56; Cheng et al. (2008) *J. Pharm Sci.* 97:123-43). The dendrimer generation can control the payload capacity and size and can provide a high payload capacity. Moreover, display of multiple surface groups can be leveraged to improve stability, reduce nonspecific interactions, and enhance cell-specific targeting and drug release.

In some embodiments, the muscle-specific expression cassettes described herein are introduced into a cell using a recombinant virus (i.e., a recombinant viral vector). Such recombinant viruses are known in the art and include recombinant retroviruses, recombinant lentiviruses, recombinant adenoviruses, and recombinant AAVs (reviewed in Vannucci et al. (2013) *New Microbiol.* 36:1-22). Recombinant AAVs useful herein can have any serotype that allows for transduction of the virus into a target cell type and expression of the meganuclease gene in the target cell. For example, in some embodiments, recombinant AAVs have a serotype (i.e., a capsid) of AAV1, AAV2, AAV5 AAV6, AAV7, AAV8, AAV9, AAV12, or AAVrh.74. It is known in the art that different AAVs tend to localize to different tissues (Wang et al. (2014) *Expert Opin Drug Deliv* 11:345-34.). The AAVrh.74 serotype, which is closely related to AAV8, has further been described as targeting muscle tissue including skeletal muscle and cardiac muscle tissue (Mendell et al. (2020) *JAMA Neurol.* 77:1122-31). Accordingly, in some embodiments, the AAV serotype is AAV1. In some embodiments, the AAV serotype is AAV2. In some embodiments, the AAV serotype is AAV5. In some embodiments, the AAV serotype is AAV6. In some embodiments, the AAV serotype is AAV7. In some embodiments, the AAV serotype is AAV8. In some embodiments, the AAV serotype is AAV9. In some embodiments, the AAV serotype is AAV12. In some embodiments, the AAV serotype is AAVrh.74. AAVs can also be self-complementary such that they do not require second-strand DNA synthesis in the host cell (McCarty et al. (2001) *Gene Ther.* 8:1248-54). Polynucleotides delivered by recombinant AAVs can include left (5') and right (3') inverted terminal repeats as part of the viral genome. In some embodiments, the recombinant viruses are injected directly into target tissues. In alternative embodiments, the recombinant viruses are delivered systemically via the circulatory system.

In one embodiment, a recombinant virus used for meganuclease gene delivery is a self-limiting recombinant virus. A self-limiting virus can have limited persistence time in a cell or organism due to the presence of a recognition sequence for an engineered meganuclease within the viral genome. Thus, a self-limiting recombinant virus can be engineered to provide a coding sequence for a promoter, an engineered meganuclease described herein, and a meganuclease recognition site within the ITRs. The self-limiting recombinant virus delivers the meganuclease gene to a cell, tissue, or organism, such that the meganuclease is expressed and able to cut the genome of the cell at an endogenous recognition sequence within the genome. The delivered meganuclease will also find its target site within the self-limiting recombinant viral genome and cut the recombinant viral genome at this target site. Once cut, the 5' and 3' ends of the viral genome will be exposed and degraded by exonucleases, thus killing the virus, and ceasing production of the meganuclease.

Such polynucleotides comprising exogenous nucleic acids can be introduced into a cell and/or delivered to a target cell in a subject by any of the means previously discussed. In particular embodiments, such polynucleotides comprising exogenous nucleic acid molecules are introduced by way of a recombinant virus (i.e., a viral vector), such as a recombinant lentivirus, recombinant retrovirus, recombinant adenovirus, or a recombinant AAV. Recombinant AAVs useful for introducing a polynucleotide comprising an exogenous nucleic acid molecule can have any serotype (i.e., capsid) that allows for transduction of the virus into the cell and insertion of the exogenous nucleic acid molecule sequence into the cell genome. In some embodiments, recombinant AAVs have a serotype of AAV1, AAV2, AAV5 AAV6, AAV7, AAV8, AAV9, AAV12, or AAVrh.74. In some embodiments, the AAV serotype is AAV1. In some embodiments, the AAV serotype is AAV2. In some embodiments, the AAV serotype is AAV5. In some embodiments, the AAV serotype is AAV6. In some embodiments, the AAV serotype is AAV7. In some embodiments, the AAV serotype is AAV8. In some embodiments, the AAV serotype is AAV9. In some embodiments, the AAV serotype is AAV12. In some embodiments, the AAV serotype is AAVrh.74. The recombinant AAV can also be self-complementary such that it does not require second-strand DNA synthesis in the host cell. Exogenous nucleic acid molecules introduced using a recombinant AAV can be flanked by a 5' (left) and 3' (right) inverted terminal repeat in the viral genome.

In another particular embodiment, an exogenous nucleic acid molecule can be introduced into a cell using a single-stranded DNA template. The single-stranded DNA can comprise the exogenous nucleic acid molecule and, in particular embodiments, can comprise 5' and 3' homology arms to promote insertion of the nucleic acid sequence into the nuclease cleavage site by homologous recombination. The single-stranded DNA can further comprise a 5' AAV ITR sequence 5' upstream of the 5' homology arm, and a 3' AAV ITR sequence 3' downstream of the 3' homology arm.

In another particular embodiment, genes encoding a nuclease described herein and/or an exogenous nucleic acid molecule described herein can be introduced into a cell by transfection with a linearized DNA template. A plasmid DNA encoding an engineered nuclease and/or an exogenous nucleic acid molecule can, for example, be digested by one or more restriction enzymes such that the circular plasmid DNA is linearized prior to transfection into the cell.
Administration The target tissue(s) or target cell(s) include, without limitation, muscle cells, such as skeletal muscle cells, cardiac muscle cells, or muscle cells of the diaphragm. In some embodiments, the target cell is a muscle progenitor cell such as a skeletal muscle progenitor cell or a cardiac muscle progenitor cell. Such muscle progenitor cells have been described in the art and can either be present in a subject or derived from another stem cell population such as an induced pluripotent stem cell or an embryonic stem cell (Tey et al. (2019) *Front. Cell Dev. Biol.* 7:284 and Amini et al. (2017) *J. Cardiovasc. Thorac. Res.* 9:127-32).

In some embodiments, the muscle-specific expression cassettes described herein are delivered to a cell in vitro. In some embodiments, the muscle-specific expression cassettes described herein are delivered to a cell in a subject in vivo. In some embodiments, the muscle-specific expression cassettes described herein are supplied to target cells (e.g., a muscle cell or muscle progenitor cell) via injection directly to the target tissue. Alternatively, the muscle-specific expression cassettes described herein can be delivered systemically via the circulatory system.

In various embodiments of the methods, compositions described herein, such as the muscle-specific expression cassettes described herein, recombinant viruses comprising such polynucleotides, or lipid nanoparticles comprising such polynucleotides, can be administered via any suitable route of administration known in the art. Such routes of administration can include, for example, intravenous, intramuscular, intraperitoneal, subcutaneous, intrahepatic, transmucosal, transdermal, intraarterial, and sublingual. In some embodiments, the muscle-specific expression cassettes described herein, recombinant viruses comprising such polynucleotides, or lipid nanoparticles comprising such polynucleotides, are supplied to target cells (e.g., muscle cells or muscle precursor cells) via injection directly to the target tissue (e.g., muscle tissue). Other suitable routes of administration can be readily determined by the treating physician as necessary.

In some embodiments, a therapeutically effective amount of a therapeutic protein described herein (e.g., an engineered nuclease described herein) encoded by the muscle-specific expression cassettes described herein is administered to a subject in need thereof for the treatment of a disease. As appropriate, the dosage or dosing frequency of the muscle-specific expression cassettes described herein encoding a therapeutic protein described herein may be adjusted over the course of the treatment, based on the judgment of the administering physician. Appropriate doses will depend, among other factors, on the specifics of any AAV chosen (e.g., serotype, etc.), any lipid nanoparticle chosen, on the route of administration, on the subject being treated (i.e., age, weight, sex, and general condition of the subject), and the mode of administration. Thus, the appropriate dosage may vary from patient to patient. An appropriate effective amount can be readily determined by one of skill in the art or treating physician. Dosage treatment may be a single dose schedule or, if multiple doses are required, a multiple dose schedule. Moreover, the subject may be administered as many doses as appropriate. One of skill in the art can readily determine an appropriate number of doses. The dosage may need to be adjusted to take into consideration an alternative route of administration or balance the therapeutic benefit against any side effects.

In some embodiments, the methods further include administration of a polynucleotide comprising a nucleic acid sequence encoding a secretion-impaired hepatotoxin, or encoding tPA, which stimulates hepatocyte regeneration without acting as a hepatotoxin.

In some embodiments, a subject is administered a pharmaceutical composition comprising any muscle-specific expression cassette encoding a therapeutic protein described herein (e.g., an engineered nuclease), wherein the encoding muscle-specific expression cassette nucleic acid sequence is administered at a dose of about $1\times10^{10}$ gc/kg to about $1\times10^{14}$ gc/kg (e.g., about $1\times10^{10}$ gc/kg, about $1\times10^{11}$ gc/kg, about $1\times10^{12}$ gc/kg, about $1\times10^{13}$ gc/kg, or about $1\times10^{14}$ gc/kg). In some embodiments, a subject is administered a pharmaceutical composition comprising any muscle-specific expression cassette encoding a therapeutic protein described herein (e.g., an engineered nuclease), wherein the encoding muscle-specific expression cassette nucleic acid sequence is administered at a dose of about $1\times10^{10}$ gc/kg, about $1\times10^{11}$ gc/kg, about $1\times10^{12}$ gc/kg, about $1\times10^{13}$ gc/kg, or about $1\times10^{14}$ gc/kg. In some embodiments, a subject is administered a pharmaceutical composition comprising any muscle-specific expression cassette encoding a therapeutic protein described herein (e.g., an engineered nuclease), wherein the encoding muscle-specific expression cassette nucleic acid sequence is administered at a dose of about $1\times10^{10}$ gc/kg to about $1\times10^{11}$ gc/kg, about $1\times10^{11}$ gc/kg to about $1\times10^{12}$ gc/kg, about $1\times10^{12}$ gc/kg to about $1\times10^{13}$ gc/kg, or about $1\times10^{13}$ gc/kg to about $1\times10^{14}$ gc/kg. In some embodiments, a subject is administered a pharmaceutical composition comprising any muscle-specific expression cassette encoding a therapeutic protein described herein (e.g., an engineered nuclease), wherein the encoding muscle-specific expression cassette nucleic acid sequence is administered at a dose of about $1\times10^{13}$ gc/kg, $2\times10^{13}$ gc/kg, $3\times10^{13}$ gc/kg, $4\times10^{13}$ gc/kg, $5\times10^{13}$ gc/kg, $6\times10^{13}$ gc/kg, $7\times10^{13}$ gc/kg, $8\times10^{13}$ gc/kg, $9\times10^{13}$ gc/kg, $1\times10^{14}$ gc/kg, $2\times10^{14}$ gc/kg, $3\times10^{14}$ gc/kg, $4\times10^{14}$ gc/kg, $5\times10^{14}$ gc/kg, $6\times10^{14}$ gc/kg, $7\times10^{14}$ gc/kg, $8\times10^{14}$ gc/kg, $9\times10^{14}$ gc/kg, $1\times10^{15}$ gc/kg, $2\times10^{15}$ gc/kg, $3\times10^{15}$ gc/kg, $4\times10^{15}$ gc/kg, $5\times10^{15}$ gc/kg, $6\times10^{15}$ gc/kg, $7\times10^{15}$ gc/kg, $8\times10^{15}$ gc/kg, $9\times10^{15}$ gc/kg, $1\times10^{15}$ gc/kg, $2\times10^{15}$ gc/kg, $3\times10^{15}$ gc/kg, $4\times10^{15}$ gc/kg, $5\times10^{15}$ gc/kg, $6\times10^{15}$ gc/kg, $7\times10^{15}$ gc/kg, $8\times10^{15}$ gc/kg, or $9\times10^{15}$ gc/kg.

It should be understood that these doses can relate to the administration of a single polynucleotide comprising a single nucleic acid sequence encoding a single engineered meganuclease described herein or, alternatively, can relate to a single polynucleotide comprising a first nucleic acid sequence encoding a first engineered meganuclease described herein and a second nucleic acid sequence encoding a second engineered meganuclease described herein, wherein each of the two encoding nucleic acid

2.5 Pharmaceutical Compositions

The disclosure also provides a pharmaceutical composition comprising a pharmaceutically acceptable carrier and an engineered meganuclease described herein, or a pharmaceutically acceptable carrier and a polynucleotide described herein that comprises any muscle-specific expression cassette encoding a heterologous protein described herein (e.g., an engineered nuclease) In some such examples, the polynucleotide comprising any muscle-specific expression cassette described herein in the pharmaceutical composition can be comprised by a lipid nanoparticle or can be comprised by a recombinant virus (e.g., a recombinant AAV). In other embodiments, the disclosure provides a pharmaceutical composition comprising a pharmaceutically acceptable carrier and a genetically modified cell described herein, which can be delivered to a target tissue where the cell expresses the heterologous protein (e.g., an engineered nuclease) as disclosed herein. Such pharmaceutical compositions are formulated, for example, for systemic administration, or administration to target tissues.

In various embodiments, the pharmaceutical compositions can be useful for treating a muscle disorder and/or reducing the symptoms associated with a muscle disorder in a subject. Exemplary and non-limiting muscle disorders comprise neuromuscular disorders and heart diseases, such as Abetalipoproteinemia (Bassen Kornzwieg), Acetylcholine Receptor Deficiency (Congenital Myasthenic Syndrome), Charlevoix-Saguenay Syndrome/Disease, Benign Congenital Myopathy, Brody Disease, Centronuclear Myopathy (Myotubular Myopathy), Chondrodystrophic Myotonia (Schwartz-Jampel Syndrome), Chudley Syndrome, Fingerprint Myopathy, Hereditary Neuralgic Amyotrophy (Parsonage-Turner Syndrome), Inclusion Body Myopathy (e.g. Type 2 or Type 3), Inclusion Body Myositis, Isaac's Syndrome (Neuromyotonia), Kennedy's Disease (Spinal Bulbar (Muscular) Atrophy), Macrophagic Myofascitis, McAdle's Disease (Myophosphorylase Deficiency/Glycogen Storage Type V), Mononeuritis Multiplex, Muscle-Eye-Brain Disease, Nemaline Myopathy, Nonaka Myopathy, Rippling Muscle Disease, Tibial Muscular Dystrophy (Udd Distal Myopathy), Welender's Distal Myopathy, Acid Maltase Deficiency (Pompe's Disease/Glycogen Storage Disease Type II), Danon Disease (Gylcogen Storage Disease Type IIb/Vacuolar Myopathies), Debranching Enzyme Deficiency (Glycogen Storage Disease Type III/Forbe's Disease), Andersen Disease/Syndrome (Glycogen Storage Disease Type IV/Branching Enzyme Deficiency), Tauri's Disease (Glycogen Storage Disease Type VII/Phosphofructokinase Deficiency), Desmin Storage Myopathy (Myofibrillar Myopathy), Myodenylate Deaminase Deficiency, Adrenoleukodystrophy, Arthrogryposis Multiplex Congenita, Ataxia with Congenital Glaucoma, Ataxia with Vitamin E Deficiency, Barth Syndrome, Bethlem Myopathy, Carnitine Palmityl Transferase Deficiency, Carnitine Deficiency, Central Core Disease, Hereditary Motor and Sensory Neuropathy (e.g. Charcot-Maric-Tooth Diseases (CMT) such as CMT Type I, CMT Type II, CMT Type III (Dejerine-Sottas Disease), CMT Type IV (Refsum's Disease), CMT Type V; Peroneal Muscular Atrophy; Neuronal Type of Peroneal Muscular Atrophy), Hereditary Sensory and Autonomic Neuropathy (e.g. Type I, Type III (Familial Dysautonomia/Riley-Day Syndrome), Type IV (Congenital insensitivity to pain and anhidrosis), Congenital Fibre Type Disproportion Myopathy, Distal Spinal Muscular Atrophy, Familial Amyloid Neuropathy, Familial Dilated Cardiomyopathy with Muscular Dystrophy, Friedreich's Ataxia, Hyperkalemic Periodic Paralysis (Gamstorp Disease), Giant Axonal Neuropathy, Guillain-Barré Syndrome (Acute inflammatory Demyelinating/Polyradiculoneuropathy), Hyperthermia (Malignant Hyperthermia), Hypokalemic Periodic Paralysis, Iatrogenic Myopathy, Kearns-Sayre Syndrome, Kugelberg Welander Disease (Spinal Muscular Atrophy Type III), Laing Distal Myopathy, Lambert-Eaton (Myasthenic) Syndrome, Leigh's Syndrome, Minicore Myopathy/Multicore Myopathy, Mitochondrial Myopathy and/or Neuropathy, Mixed Connective Tissue Overlap Disease, Miyoshi Myopathy, Multifocal Motor Neuropathy with Conduction Block, Myasthenia Gravis, Myotonia Congenita (Thomsen's Disease), Myotonic Muscular Dystrophy (e.g. Type I (Steinert's Disease), Type II (Proximal Myotonic Myopathy)), Oculopharyngeal Muscular Dystrophy, Olivopontocerebellar Atrophy, Paramyotonia Congenita, Paraneoplastic neuropathy, Polymyopsitis, Reducing Body Myopathy, Scapuloperoneal Muscular Atrophy, Tubular Aggregate Myopathy, Walker-Warburg Syndrome, Werdnig-Hoffman Disease (Spinal Muscular Atrophy Type I), Zebra Body Myopathy, Nuclear Envelop Disease, muscular dystrophy, motor neuron diseases (MND), such as e.g. Charcot-Marie-Tooth Diseases (CMT) such as CMT Type I, CMT Type II, CMT Type III (Dejerine-Sottas Disease), CMT Type IV (Refsum's Disease), CMT Type V, spinal muscular atrophy (SMA), and amyotrophic lateral sclerosis (ALS), Emery-Dreifuss muscular dystrophy, facioscapulohumeral muscular dystrophy (FSHD), congenital muscular dystrophies, congenital myopathies, limb girdle muscular dystrophy, metabolic myopathies, muscle inflammatory diseases, myasthenia, mitochondrial myopathies, anomalies of ionic channels, nuclear envelop diseases, cardiomyopathies, cardiac hypertrophy, heart failure, and distal myopathies, cardiovascular diseases.

In various embodiments, the pharmaceutical compositions can be useful for treating DMD, converting a DMD disease phenotype to a Becker Muscular Dystrophy phenotype, and/or reducing the symptoms associated with DMD in a subject.

Such pharmaceutical compositions can be prepared in accordance with known techniques. See, e.g., Remington, The Science and Practice of Pharmacy (21st ed., Philadelphia, Lippincott, Williams & Wilkins, 2005). In the manufacture of a pharmaceutical formulation described herein, engineered meganucleases described herein, polynucleotides encoding the same, or cells expressing the same, are typically admixed with a pharmaceutically acceptable carrier and the resulting composition is administered to a subject. The carrier must be acceptable in the sense of being compatible with any other ingredients in the formulation and must not be deleterious to the subject. The carrier can be a solid or a liquid, or both, and can be formulated with the compound as a unit-dose formulation.

In some embodiments, pharmaceutical compositions described herein can further comprise one or more additional agents or biological molecules useful in the treatment of a disease in the subject. Likewise, the additional agent(s) and/or biological molecule(s) can be co-administered as a separate composition.

The pharmaceutical compositions described herein can include a therapeutically effective amount of any heterologous protein (e.g., an engineered nuclease disclosed herein), or any polynucleotide described herein comprising any muscle-specific expression cassette encoding any engineered meganuclease described herein. For example, in some embodiments, the pharmaceutical composition can include polynucleotides comprising any muscle-specific expression cassette described herein at any of the doses (e.g., gc/kg of an encoding nucleic acid sequence or mg/kg of mRNA) described herein.

In particular embodiments, the pharmaceutical compositions described herein can comprise one or more recombinant viruses (e.g., recombinant AAVs) described herein that comprise one or more polynucleotides described herein (i.e., packaged within the viral genome). In particular embodiments, the pharmaceutical composition comprises two or more recombinant viruses (e.g., recombinant AAVs) described herein, each comprising a polynucleotide comprising a muscle-specific expression cassette described herein encoding a different engineered meganuclease described herein. For example, a first recombinant virus (e.g., recombinant AAV) may comprise a first polynucleotide comprising a first muscle-specific expression cassette described herein encoding a first engineered meganuclease described herein having specificity for the DMD 19-20 recognition sequence, and a second recombinant virus (e.g., recombinant AAV) comprising a second polynucleotide comprising a second muscle-specific expression cassette described herein encoding a second engineered meganuclease described herein having specificity for the DMD 35-36 recognition sequence. The expression of such a pair of engineered meganucleases in the same cell (e.g., a muscle cell) would allow for the excision of exons 45-55 from the dystrophin gene according to certain embodiments described herein.

In other particular embodiments, the pharmaceutical compositions described herein can comprise a recombinant virus (e.g., recombinant AAV) described herein that comprises a polynucleotide (i.e., packaged within the viral genome) that comprises a muscle-specific expression cassette described herein encoding two separate engineered meganucleases described herein. For example, the recombinant virus (e.g., recombinant AAV) can comprise a polynucleotide comprising a muscle-specific expression cassette described herein that comprises a first nucleic acid sequence encoding a first engineered meganuclease described herein having specificity for the DMD 19-20 recognition sequence, and a second nucleic acid sequence encoding a second engineered meganuclease described herein having specificity for the DMD 35-36 recognition sequence. The expression of such a pair of engineered meganucleases would allow for the excision of exons 45-55 from the dystrophin gene.

In some embodiments, pharmaceutical compositions described herein can further comprise one or more additional agents useful in the treatment of DMD in the subject.

The present disclosure also provides muscle-specific expression cassettes encoding a heterologous protein described herein (e.g., an engineered nuclease), or cells described herein comprising the muscle-specific expression cassettes described herein, wherein the heterologous protein is expressed from the muscle-specific expression cassette in a muscle cell or muscle tissue for use as a medicament. The disclosure further provides the use of the muscle-specific expression cassettes described herein encoding a heterologous protein described herein (e.g., an engineered nuclease) expressing the heterologous protein (e.g., an engineered nuclease) described herein in the manufacture of a medicament for treating DMD, for increasing levels of a modified dystrophin protein (i.e., lacking the amino acids encoded by exons 45-55 of the dystrophin gene), or reducing the symptoms associated with DMD.

2.6 Methods for Producing Recombinant Viruses

The disclosure also provides recombinant viruses, such as recombinant AAVs, for use in the methods described herein. Recombinant AAVs are typically produced in mammalian cell lines such as HEK-293. Because the viral cap and rep genes are removed from the recombinant virus to prevent its self-replication to make room for the therapeutic gene(s) to be delivered (e.g., the meganuclease gene), it is necessary to provide these in trans in the packaging cell line. In addition, it is necessary to provide the "helper" (e.g., adenoviral) components necessary to support replication (Cots et al. (2013) *Curr. Gene Ther.* 13:370-81). Frequently, recombinant AAVs are produced using a triple-transfection in which a cell line is transfected with a first plasmid encoding the "helper" components, a second plasmid comprising the cap and rep genes, and a third plasmid comprising the viral ITRs containing the intervening DNA sequence to be packaged into the virus. The third plasmid may contain an ITR with one or more D sequences. Alternatively, the third plasmid may contain an ITR with one D sequence and a second ITR without a D sequence. Lastly, the third plasmid may contain a first ITR with one D sequence and a second ITR with one D sequence. AAV D sequences are typically 20 nucleotides in length and do not contribute to the formation of hairpin structures. Instead, they play a role as a viral packaging signal. In some embodiments, the D sequence comprises a sequence according to a sequence set forth in SEQ ID NOs: 94-95. Viral particles comprising a genome (ITRs and intervening gene(s) of interest) encased in a capsid are then isolated from cells by freeze-thaw cycles, sonication, detergent, or other means known in the art. Particles are then purified using cesium-chloride density gradient centrifugation or affinity chromatography and subsequently delivered to the gene(s) of interest to cells, tissues, or an organism such as a human patient.

Because recombinant AAV particles are typically produced (manufactured) in cells, precautions must be taken herein to ensure that in certain embodiments disclosed herein, the engineered nuclease is not expressed in the packaging cells. Because the recombinant viral genomes described herein may comprise a recognition sequence for the nuclease, any nuclease expressed in the packaging cell line may be capable of cleaving the viral genome before it can be packaged into viral particles. This will result in reduced packaging efficiency and/or the packaging of fragmented genomes. Several approaches can be used to prevent nuclease expression in the packaging cells.

As described herein the nuclease is encoded by a muscle-specific expression cassette, which includes a muscle-specific promoter (e.g., the MCK promoter) operable linked to the nucleic acid sequence encoding the engineered nuclease. This muscle-specific promoter is not active in the packaging cells, and therefore, any expression in the packaging cells is greatly reduced or completely eliminated.

In addition, the recombinant virus can be packaged in cells from a different species in which the nuclease is not likely to be expressed. For example, viral particles can be produced in microbial, insect, or plant cells using mammalian promoters, such as the well-known cytomegalovirus- or SV40 virus-early promoters, which are not active in the non-mammalian packaging cells. In a particular embodiment, viral particles are produced in insect cells using the baculovirus system as described by Gao et al. (2007) *J. Biotechnol.* 131:138-43. A nuclease under the control of a mammalian promoter is unlikely to be expressed in these cells (Airenne et al. (2013) *Mol. Ther.* 21:739-49). Moreover, insect cells utilize different mRNA splicing motifs than mammalian cells. Thus, it is possible to incorporate a mammalian intron, such as the human growth hormone (HGH) intron or the SV40 large T antigen intron, into the coding sequence of a nuclease. Because these introns are not spliced efficiently from pre-mRNA transcripts in insect cells, insect cells will not express a functional nuclease and will package the full-length genome. In contrast, mammalian cells to which the resulting recombinant AAV particles are delivered will properly splice the pre-mRNA and will express functional nuclease protein. Chen has reported using HGH and SV40 large T antigen introns to attenuate expression of the toxic proteins barnase and diphtheria toxin fragment A in insect packaging cells, enabling the production of recombinant AAV vectors carrying these toxin genes (Chen (2012) *Mol. Ther. Nucleic Acids.* 1: e57).

Furthermore, the engineered nuclease gene can be operably linked to an inducible promoter element such that a small-molecule inducer is required for nuclease expression. Examples of inducible promoters include the Tet-On system (Clontech; Chen et al. (2015) *BMC Biotechnol.* 15:4) and the RheoSwitch system (Intrexon; Sowa i (2011) *Spine* 36:E623-8). Both systems, as well as similar systems known in the art, rely on ligand-inducible transcription factors (variants of the Tet Repressor and Ecdysone receptor, respectively) that activate transcription in response to a small-molecule activator (Doxycycline or Ecdysone, respectively). Such a method of using such ligand-inducible transcription activators includes: 1) placing the engineered nuclease gene under the control of a promoter that responds to the corresponding transcription factor, the nuclease gene having (a) binding site(s) for the transcription factor; and 2) including the gene encoding the transcription factor in the packaged viral genome. The latter step is necessary because the engineered nuclease will not be expressed in the target cells or tissues following recombinant AAV delivery if the transcription activator is not also provided to the same cells. The transcription activator then induces meganuclease gene expression only in cells or tissues that are treated with the cognate small-molecule activator. This approach is advantageous because it enables nuclease gene expression to be regulated in a spatio-temporal manner by selecting when and to which tissues the small-molecule inducer is delivered. However, the requirement to include the inducer in the viral genome, which has significantly limited carrying capacity, creates a drawback to this approach.

In another particular embodiment, recombinant AAV particles are produced in a mammalian cell line that expresses a transcription repressor that prevents expression of the nuclease. Transcription repressors are known in the art and include the Tet-Repressor, the Lac-Repressor, the Cro repressor, and the Lambda-repressor. Many nuclear hormone receptors such as the ecdysone receptor also act as transcription repressors in the absence of their cognate hormone ligand. Accordingly, packaging cells are transfected/transduced with a vector encoding a transcription repressor and the nuclease gene in the viral genome (packaging vector) is operably linked to a muscle-specific promoter that is modified to comprise binding sites for the repressor such that the repressor silences the promoter. The gene encoding the transcription repressor can be placed in a variety of positions. It can be encoded on a separate vector; it can be incorporated into the packaging vector outside of the ITR sequences; it can be incorporated into the cap/rep vector or the adenoviral helper vector; or it can be stably integrated into the genome of the packaging cell such that it is expressed constitutively. Methods to modify common mammalian promoters to incorporate transcription repressor sites are known in the art. For example, Chang & Roninson modified the strong, constitutive CMV and RSV promoters to comprise operators for the Lac repressor and showed that gene expression from the modified promoters was greatly attenuated in cells expressing the repressor (Chang & Roninson (1996) Gene 183:137-42). The use of a non-human transcription repressor ensures that transcription of the meganuclease gene will be repressed only in the packaging cells expressing the repressor and not in target cells or tissues transduced with the resulting recombinant AAV.

EXAMPLES

The disclosure is further supplemented by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

Example 1

Comparison of Meganuclease Expression and Editing of Dystrophin Gene In Vivo in hDMD Mouse Study

1. Methods

An in vivo study in hDMDdel52/mdx (hDMD) mice was conducted to investigate in vivo editing and shortened modified human dystrophin protein restoration induced by delivery of the DMD 19-20L.329 and DMD 35-36L.349 pair of meganucleases utilizing different muscle-specific promoters and AAV capsid types. Mice were injected by retro orbital systemic injection with four different constructs encapsulated with either AAV9 or AAVrh74 (1e14 VG/kg). The first AAV9-encapsulated product comprised a viral genome, comprising SEQ ID NO: 78, that includes, from 5' to 3', the muscle-specific promoter MHCK7, a first SV40 nuclear localization sequence (NLS) coding sequence, a coding sequence for the DMD 19-20L.329 meganuclease, a first c-myc NLS coding sequence, a furin GSG P2A cleavage sequence, a second SV40 NLS coding sequence, a coding sequence for the DMD 35-36L.349 meganuclease, a second c-myc NLS coding sequence, a WPRE element, and an SV40 polyadenylation signal. The second AAV9-encapsulated product comprised a viral genome, comprising SEQ ID NO: 79, that includes, from 5' to 3', the muscle-specific promoter tMCK, a first SV40 NLS coding sequence, a coding sequence for the DMD 19-20L.329 nuclease, a first c-myc NLS coding sequence, a furin GSG P2A cleavage sequence, a second SV40 NLS coding sequence, a coding sequence for the DMD 35-36L.349 nuclease, a second c-myc NLS coding sequence, a WPRE element, and an SV40 polyadenylation signal. The first AAVrh74-encapsulated product comprised a viral genome, comprising SEQ ID NO: 78, that includes, from 5' to 3', the muscle-specific promoter MHCK7, a first SV40 NLS coding sequence, a coding sequence for the DMD 19-20L.329 meganuclease, a first c-myc NLS coding sequence, a furin GSG P2A cleavage sequence, a second SV40 NLS coding sequence, a coding sequence for the DMD 35-36L.349 meganuclease, a second c-myc NLS coding sequence, a WPRE element, and an SV40 polyadenylation signal. The second AAVrh74-encapsulated product comprised a viral genome, comprising SEQ ID NO: 79, that includes, from 5' to 3', the muscle-specific promoter tMCK, a first SV40 NLS coding sequence, a coding sequence for the DMD 19-20L.329 meganuclease, a first c-myc NLS coding sequence, a furin GSG P2A cleavage sequence, a second SV40 NLS coding sequence, a coding sequence for the DMD 35-36L.349 meganuclease, a second c-myc NLS coding sequence, a WPRE element, and an SV40 polyadenylation signal. The nucleic acid coding sequence of the DMD 35-36L.349 engineered meganuclease was codon modified to reduce the percent identity between nucleic acid sequences common to both meganucleases without modifying the encoded amino acid sequence. The unmodified nucleic acid coding sequence of the DMD 35-36L.349 engineered meganuclease is provided as SEQ ID NO: 96 herein. This engineered meganuclease was codon modified such that approximately 40% of the nucleotides were changed in the DMD 35-36L.349 engineered meganuclease. Accordingly, the codon modified DMD 35-36L.349 meganuclease had less than about 60% nucleotide sequence identity to the DMD 19-20L.329 engineered meganuclease. At 28 days post-injection, mice were sacrificed and tissue sections from skeletal muscle (quadricep), heart, and liver were collected for molecular, protein, and histological analysis.

Meganuclease protein expression at day 28 was measured with the Meso Scale Discovery (MSD) system, which is an electrochemiluminescence assay used for high sensitivity meganuclease protein expression quantitation. Briefly, standard 96-well plates were coated with an anti-meganuclease R54 rabbit antibody (made in-house by Precision BioSciences) and left overnight at 4° C. Cell lysates were combined with the MSD lysis buffer and incubated for 15 minutes at room temperature, centrifuged at 10,000 g for 30 minutes, and the supernatant collected. Protein concentration was determined using BCA and diluted to 1 mg/ml with MSD Diluent 100. The plate was removed from 4° C. and allowed to come to room temperature for 30 minutes, blotted to remove any excess R54 antibody and MSD blocker added for 1 hour. Meganuclease standards were prepared by serial dilution of 1 mg/ml stock to produce 7 standards. The plate was then washed, excess liquid removed, and standards and samples were added to the plate, which was then incubated for 90 minutes at room temperature. Following incubation, the plate was washed 4 times with MSD buffer and the MSD sulfo-tagged V34 antibody added to each well and incubated for 1 hour at room temperature. After this final incubation, the plate was washed 4 times in MSD buffer and tapped to remove excess liquid. MSD Gold Read buffer was added, the plate sealed and analyzed on the MSD instrument. When electricity is applied to the plate, light emissions from the sulfo-tags are measured to quantitate meganuclease levels.

Samples were analyzed on the WES™ system (Protein Simple) for dystrophin protein identification and quantitation. Briefly, lysates prepared from tissue samples using the RIPA protein lysis and diluted in sample buffer to a concentration of 500 ng/µl, and 4 µl of diluted sample was transferred to a PCR tube. The lysates were mixed with fluorescent master mix (Protein Simple) and denatured. The detection reagents, including the primary antibodies (anti-dystrophin MANDYS106 [Sigma, MABT827], anti-vinculin [Abcam, ab129002), and secondary antibodies (Wes 20× rabbit, Wes 1× mouse, and goat anti-rabbit [Abcam, AB6702]) antibodies and the samples were transferred to a 66 to 440 kilodalton (kDa) cassette and run according to the standard manufacturer's protocol on the Wes system. After the run, peak analysis was performed by assigning a peak to dystrophin with a size of 285 kDa and 125 kDa for vinculin. To determine dystrophin restoration, standard curves for vinculin and dystrophin were prepared from lysates of the corresponding tissues from hDMD mice and included in each run; there is currently no purified dystrophin protein available due to its large size and instability. The formulae for the trendline were used to then calculate the relative load of each sample based on vinculin and dystrophin signal. The signal was corrected for variation in sample load (using the relative load from the vinculin calculation) and this load was divided by the total load of 500 ng to determine percent dystrophin restoration.

Digital droplet PCR was utilized to determine the frequency of ligation (i.e., % total ligation) between the cleaved DMD 19-20 and DMD 35-36 target sites, utilizing primer pairs and probes that span the junction of the 19-20 target site and the corresponding 35-36 target site. This ddPCR assay used a forward primer 5' of the 19-20 binding site (primer 143) and a reverse primer 3' to the 35-36 site (primer 145) and a probe specific to the sequence 51 base pairs 5' to the ligated 19-20/35-36 site (primer 134). A reference amplicon assay was included using primers 66, 68, and 69 to generate a reference amplicon. Amplifications were multiplexed in a 20 uL reaction containing 1×ddPCR Supermix for Probes (no dUTP, BioRad), 250 nM of each probe, 900 nM of each primer, 5 U of HindIII-HF, and about 50 ng cellular gDNA. Droplets were generated using a QX100 droplet generator (BioRad). Cycling conditions were as follows: 1 cycle of 95° C. (2° C./s ramp) for 10 minutes, 44 cycles of 95° C. (1° C./s ramp) for 30 seconds, 59° C. (1° C./s ramp) for 45 seconds (see annealing temperature below per target site), 72° C. (0.2° C./s ramp) for 2 minutes, 1 cycle of 98° C. for 10 minutes, 4° C. hold. Droplets were analyzed using a QX200 droplet reader (BioRad) and QuantaSoft analysis software (BioRad) was used to acquire and analyze data. Indel frequencies were calculated by dividing the number of positive copies for the binding site probe by the number of positive copies for the reference probe and comparing loss of FAM+ copies in nuclease-treated cells to mock-transfected cells.

TABLE 3

Primers used in ddPCR assay for total ligation determination.

| Primer Name | Primer Sequence | SEQ ID NO. |
|---|---|---|
| 143 DMDligfor4 | GGGTGGGTTGCTTTACCTCTC TAG | 88 |
| 145 DMD1936REv | TCACATCATGAGATTTAGTCA CTTCC | 89 |
| 134 DMDimpLIG | TTGCTACTTCACAGTAACCAC ATG | 90 |
| 68 DMD ref rev | TATGATCGCCTGTTCCTCCA | 91 |
| 69 DMD REF | TAAGACCCAGCTTCACGGAG | 92 |
| 66 DMD ref3 63.6 | AGGACAAAAGAGGACGGTCTG CCCTGG | 93 |

Quadricep tissue sections from the nuclease-treated mice were also subjected to IHC analyses to visualize meganuclease protein expression and Pax7 a marker for muscle satellite cells. Briefly, quadricep tissues were dewaxed and treated with HIER (Heat-Induced Epitope Retrieval) with ER1 for 40 min on the BOND RX. Slides were blocked in 10% NGS PBST (PBS with 0.1% Tween20) with MoM (Mouse on Mouse Blocking reagent, VECTOR) blocking reagent for 1 h at room temp then incubated with Rabbit monoclonal anti-meganuclease antibody (PBI, Rab54) at a dilution of 1:1500 and Mouse Monoclonal anti-Pax7 antibody (DSHB, Supernatant, 1:5) in PBST with 2% NGS at 4 C overnight in a humid chamber. The next day samples were incubated with Secondary antibodies (Goat-anti-mouse IgG1 Alexa647 (Invitrogen), goat-anti-rabbit Alexa555 (Invitrogen), 1:500) for 1 hr at room temperature followed by DAPI nuclear counterstained for 5 min. Excess BOND RX wash buffer was removed, and coverslips were mounted using VectaShield Vibrance Antifade Mounting Medium. Imaging was performed on Zeiss Apotome 2.0

Tissue samples were prepped for histopathology using H&E staining and sent to a CRO for histopathology analysis. Tissue sections were mounted on microscope slides and deparaffinized and rehydrated (3 times with xylene, 3 times with 100% ethanol, 1 time each with 95% and 80% ethanol, 1 time with deionized water). Next, the slide was immersed in hematoxylin stain for 3 minutes, rinsed with deionized water and put in tap water for 5 minutes to allow the stain to develop. The slide was dipped ~10 times rapidly in acid ethanol to destain and rinsed for 2 minutes in deionized water. The slide was stained with eosin for ~30 seconds, rinsed 3 times with 95% ethanol then 100% ethanol (5 minutes/rinse) and rinsed 3 times with xylene (15 minutes/rinse). A coverslip was then placed on the slide using Permount™ and left to dry overnight. After staining, slides were visualized under light microscopy by the Study Pathologist. Severity scores for histopathologic findings were minimal, mild, moderate, and marked.

2. Results

Figure 1A:
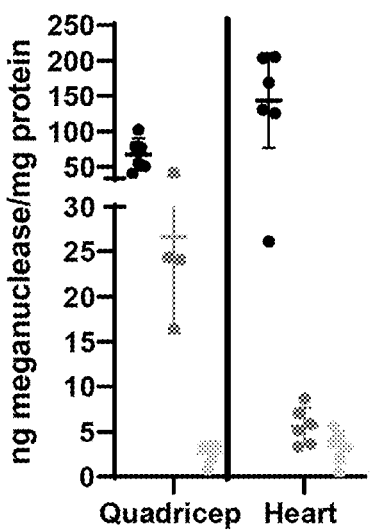
FIG. 1A-FIG. 1B provide charts of the meganuclease expression in ng of meganuclease/mg of total cellular protein from lysates from hDMDdel52/mdx (hDMD) mice from both quadricep and heart tissue. For each tissue in FIG. 1A, the left-hand dark dots indicate an expression construct utilizing the MHCK7 promoter and the middle light dots indicate an expression construct utilizing the tMCK promoter operably connected to the DMD 19-20L.329 and DMD 35-36L.349 pair of meganucleases delivered to mice via an AAV9 capsid. The right-hand dots indicate mice treated with PBS only. For each tissue in FIG. 1B, the left-hand dark dots indicate an expression construct utilizing the MHCK7 promoter and the middle light dots indicate an expression construct utilizing the tMCK promoter operably connected to the DMD 19-20L.329 and DMD 35-36L.349 pair of meganucleases delivered to mice via an AAVrh74 capsid. The right-hand dots indicate mice treated with PBS only.
Figure 1B:
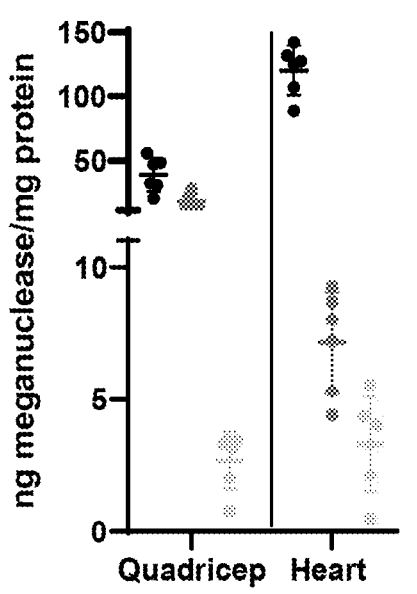

To determine differences between muscle-specific promoters in driving meganuclease protein expression, meganuclease levels were measured using MSD. Meganuclease expression was measured in mice treated with meganucleases injected with either AAV9 or AAVrh74 in the heart and the quadriceps using MSD as described above. Meganuclease protein measured in the quadricep ranged from approximately 40 to 102 (MHCK7 promoter) and 16 to 42 (tMCK promoter) ng of meganuclease per mg of total protein with AAV transgene delivered by AAV9. Meganuclease protein measured in the heart ranged from approximately 26 to 206 (MHCK7 promoter) and 3 to 9 (tMCK promoter) ng of meganuclease per mg of total protein with AAV transgene delivered by AAV9 (FIG. 1A). Meganuclease protein measured in the quadricep ranged from approximately 20 to 56 (MHCK7 promoter) and 12 to 28 (tMCK promoter) ng of meganuclease per mg of total protein with AAV transgene delivered by AAVrh74. Meganuclease protein measured in the heart ranged from approximately 88 to 142 ng (MHCK7 promoter) and 5 to 9.5 (tMCK promoter) ng of meganuclease per mg of total protein with AAV transgene delivered by AAVrh74 (FIG. 1B).

Figure 2A:
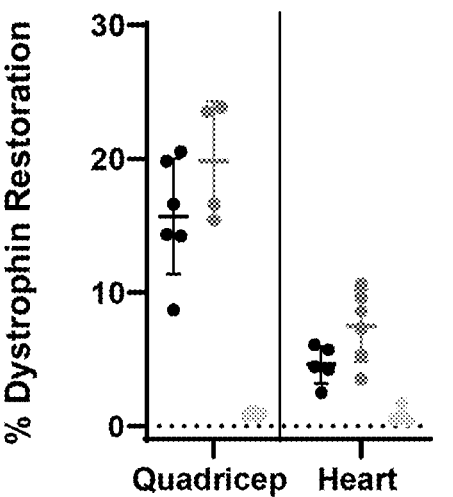
FIG. 2A and FIG. 2B provide bar graphs showing the shortened modified dystrophin protein levels by WES analysis normalized to the vinculin loading control for the DMD 19-20L.329 and DMD 35-36L.349 pair of meganucleases from both quadricep and heart tissue from hDMDdel52/mdx (hDMD) mice. For each tissue in FIG. 2A, the left-hand dark dots indicate an expression construct utilizing the MHCK7 promoter and the middle light dots indicate an expression construct utilizing the tMCK promoter operably connected to the DMD 19-20L.329 and DMD 35-36L.349 pair of meganucleases delivered to mice via an AAV9 capsid. The right-hand dots indicate mice treated with PBS only. For each tissue in FIG. 2B, the left-hand dark dots indicate an expression construct utilizing the MHCK7 promoter and the middle light dots indicate an expression construct utilizing the tMCK promoter operably connected to the DMD 19-20L.329 and DMD 35-36L.349 pair of meganucleases delivered to mice via an AAVrh74 capsid. The right-hand dots indicate mice treated with PBS only.
Figure 2B:
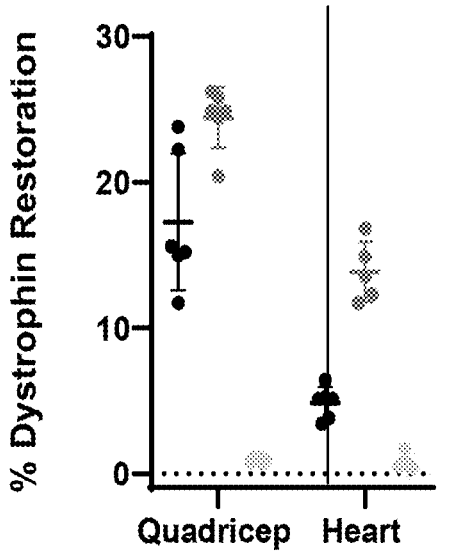

To determine differences between muscle-specific promoters in restoring dystrophin protein expression dystrophin protein levels were measured in heart and quadricep tissue using WES. Dystrophin restoration was quantified by comparing dystrophin protein from the corresponding tissues in hDMD mice from a protein standard by a standard curve from WES protein analysis. Based on the standard curve, AAV9 MHCK7-treated mice were found to average 4.4% dystrophin in the heart and 15% dystrophin in the quadricep. AAV9 tMCK-treated mice were found to average 7% dystrophin in the heart and 20% dystrophin in the quadricep (FIG. 2A). AAVrh74 MHCK7-treated mice were found to average 5% dystrophin in the heart and 17% dystrophin in the quadricep. AAVrh74 tMCK-treated mice were found to average 13% dystrophin in the heart and 22% dystrophin in the quadricep (FIG. 2B).

To determine differences between muscle-specific promoters in large excision of exons 45-55 total ligation was measured in heart and quadricep tissue by ddPCR. Total ligation events in AAV9 MHCK7 mice averaged 20% in the quadricep and 2.4% in the heart. Total ligation events in AAV9 tMCK mice averaged 16% in the quadricep and 2.8% in the heart (FIG. 3A). Total ligation events in AAVrh74 MHCK7 mice averaged 12% in the quadricep and 2% in the heart. Total ligation events in AAVrh74 tMCK mice averaged 15.5% in the quadricep and 5.8% in the heart (FIG. 3B). Total ligation events in AAV9 and AAVrh74 MHCK7 mice averaged 6% in the liver and total ligation events in AAV9 and AAVrh74 tMCK mice averaged approximately 2% in the liver (FIG. 4).

Immunofluorescence staining of quadricep tissue sections in nuclease-treated animals, showed co-staining of a population of Pax7 positive cells indicating expression of the nuclease in muscle satellite cells (FIG. 5A and FIG. 5B). Immunofluorescence staining of quadricep tissue sections show minimal background staining (green) for nuclease in PBS treated animals and clear Pax7 staining of satellite cells (red) (FIG. 5C).

To determine the role of the WPRE element in restoring dystrophin protein expression, dystrophin protein levels were measured in heart and quadricep tissue using WES. Dystrophin restoration was quantified by comparing dystrophin protein from the corresponding tissues in hDMD mice from a protein standard by a standard curve from WES protein analysis. Based on the standard curve, AAV9 tMCK WPRE-treated mice were found to average 7-10% (at 1e14 and 3e14 VG/Kg dose levels) and 2% (1e13 VG/Kg dose level) dystrophin in the heart and 20% (at 1e14 dose level) and 15% (3e14 VG/Kg dose level) and 6.6% (1e13 VG/Kg dose level) dystrophin in the quadricep (FIG. 6A). AAV9 tMCK with no WPRE-treated mice were found to average 2% (at 1e14 and 3e14 VG/Kg dose levels) and 0.5% (1e13 VG/Kg dose level) dystrophin in the heart and 15% (at 1e14 dose level) and 20% (3e14 VG/Kg dose level) and 5% (1e13 VG/Kg dose level) dystrophin in the quadricep (FIG. 6B).

As shown in FIG. 1, there was substantially more meganuclease expression in the heart for expression constructs utilizing the MHCK7 promoter compared to the tMCK promoter. Therefore, heart histological analysis was completed to investigate any potential adverse effects of the higher meganuclease expression in the heart. As shown in FIG. 7, the MHCK7 promoter had higher grades of necrosis, vacuolation, inflammatory cell infiltration and atrial thrombosis. These higher grades of heart lesions were significantly less in mice treated with an expression construct utilizing the tMCK promoter with either AAV9 or rh74 AAV capsids compared to mice treated with MHCK7 containing expression cassettes.

3. Conclusions

Meganuclease expression in the quadricep was highest with AAV9 compared to AAVrh74 with transgenes containing the MHCK7 promoter. Meganuclease expression was significantly lower in both serotype groups with transgenes containing the tMCK promoter. Significantly, there was a greater than 10-fold increase in meganuclease expression in the heart with expression cassettes utilizing the MHCK7 promoter. These high levels of expression were associated with increased cardiac lesions. Despite having less overall meganuclease expression, constructs utilizing the tMCK promoter yielded higher levels of dystrophin restoration in the heart concomitantly with significantly fewer heart lesions. Similarly, but to a lesser extent, there was more average dystrophin restoration in the quadricep with the tMCK promoter compared to the MHCK7 promoter despite again having lower meganuclease expression levels with the tMCK promoter. Dystrophin editing (excision of exons 45-55) detected by total ligation ddPCR assay across serotypes and promoters were measured with in a similar range again inconsistent with the large differences seen in meganuclease expression in the same tissues, which was particularly evident in the heart. These data suggest that the overexpression of the meganuclease driven by the MHCK7 promoter are in significant excess in the heart leading less meganuclease activity and increased cardiac complications. Furthermore, off tissue editing in the liver was significantly reduced independent of serotype with AAV transgenes that contained the tMCK promoter compared to those utilizing the MHCK7 promoter.

There was additional evidence of muscle satellite cell transduction shown by IHC with nuclei being positive for markers of Pax7 and meganuclease expression. Lastly, removal of the WPRE from the expression cassette had a minimal effect on dystrophin restoration in the quadricep compared to the significant reduction in dystrophin restoration measured in the heart suggesting that a post transcriptional regulatory element such as a WPRE is necessary in cardiac muscle tissues.

Thus, these data overall suggest a significant advantage of using the tMCK promoter with a posttranscriptional regulatory element (e.g., a WPRE) for the selective editing of a dystrophin gene in the skeletal and cardiac muscle tissues independent of AAV serotype.

Example 2

Dose Dependent Editing of Dystrophin Gene In Vivo in hDMD Mouse Study

1. Methods

An in vivo study in hDMDdel52/mdx (hDMD) mice was conducted to investigate potential dose response editing and shortened modified human dystrophin protein restoration induced by delivery of the DMD 19-20L.329 and DMD 35-36L.349 pair of meganucleases. Mice were injected by retro orbital systemic injection with one construct encapsulated with AAV9 (2e14 VG/kg, 1e14 VG/kg, and 2e 13 VG/kg) and another construct encapsulated with AAVrh74 (2014 VG/kg, 1e14 VG/kg, and 2e13 VG/kg). The AAV9-encapsulated product comprised a viral genome, comprising SEQ ID NO: 79, that includes, from 5' to 3', the muscle-specific promoter tMCK, a first SV40 NLS coding sequence, a coding sequence for the DMD 19-20L.329 meganuclease, a first c-myc NLS coding sequence, a furin GSG P2A cleavage sequence, a second SV40 NLS coding sequence, a coding sequence for the DMD 35-36L.349 meganuclease, a second c-myc NLS coding sequence, a WPRE element, and an SV40 polyadenylation signal. The AAVrh74-encapsulated product comprised a viral genome, comprising SEQ ID NO: 79, that includes, from 5' to 3', the muscle-specific promoter tMCK, a first SV40 NLS coding sequence, a coding sequence for the DMD 19-20L.329 meganuclease, a first c-myc NLS coding sequence, a furin GSG P2A cleavage sequence, a second SV40 NLS coding sequence, a coding sequence for the DMD 35-36L.349 meganuclease, a second c-myc NLS coding sequence, a WPRE element, and an SV40 polyadenylation signal. The nucleic acid sequence of the DMD 35-36L.349 meganuclease was codon modified as described in Example 1. At 28 days post-injection, mice were sacrificed and tissue sections from skeletal muscle (quadricep), heart, diaphragm, gastrocnemius, tibialis anterior (TA) and liver were collected for molecular, protein, and histological analysis. As in Example 1, digital droplet PCR was utilized to determine the frequency of large deletions (indel %) utilizing primer pairs and probes that span the junction of the 19-20 target site and the corresponding DMD nuclease for 35-36. In addition, samples were analyzed on the WES™ system (Protein Simple) for dystrophin protein identification and quantitation following the same method outlined in Example 1. Furthermore, AAV9-treated samples were analyzed for meganuclease protein expression via the MSD platform referencing the method highlighted in Example 1.

Satellite Cell Editing was Measured Using a Basescope Method.

Slides with the target quadricep tissue were baked for 1 hour at 60° C. and dewaxed using washes of xylene and alcohol (100%). The tissues were then covered with RNA-scope® hydrogen peroxide solution for 10 minutes at room temperature (RT). Target retrieval was performed by placing slides in RNAscope® 1× Target Retrieval Reagent (ACD/322000) filled container in a steamer for 15 minutes at 95° C. Tissue sections were covered with RNAscope® Protease IV and incubated in the HybEZ™ oven (ACD/321711) for 30 minutes at 40° C. Probes for edited DMD44-56 (ACD/1064961-C2) and mPax7 (ACD/1070841-C1) were mixed, then added to sections and incubated in the HybEZ™ oven at 40° C. for 2 hours. The tissue sections were washed with RNAScope wash buffer twice, then stored in 5× saline-sodium citrate (SSC) overnight. Following the overnight incubation, the slides were washed with wash buffer twice and incubated with a series of Hybridize BaseScope™ Duplex AMP reagents (ACD/323810) (reagents 1-8) in HybEZ™ at 40° C. and washed twice with wash buffer in between each reagent. The mixed Duplex Fast Red-B and Duplex Fast Red-A solution was added to the slides for 10 minutes at RT. Once the red signal was observed with an upright microscope (Fisherbrand™ Research Grade Upright Microscope), the slides were washed twice with wash buffer and then with Hybridize BaseScope™ Duplex AMP reagents 9-12 in HybEZ™ at 40° C. and washed twice with wash buffer in between the addition of each AMP reagent. The mixed Duplex Green-B to Duplex Green-A solution was added to the slides and the slides were incubated for 10 minutes at RT. Once the green signal was observed with an upright microscope (Fisherbrand™ Research Grade Upright Microscope) the slides were washed twice with wash buffer, counterstained with Gills Hematoxylin and bluing reagents were used to visualize nuclei. The slides were dried in the oven (Manufacturer/model) at 60° C. for 15 minutes. Slides were then mounted on HistoCore SPECTRA Workstation with HistoCore SPECTRA CV X1 mounting medium (3801733, Leica) and the whole tissue scanned with a Leica GT 450. The images captured with the Leica GT 450 microscope were analyzed using the HALO software (ISH IHC V 3. 1. 4). Once an image with a positive signal was opened in the main viewing window, under the analysis tab the ISH-IHC module was selected, the working magnification selected and the dye parameters were set for edited DMD44-56, mPax7 probes, and hematoxylin. Optimization detection of the edited DMD44-56, mPax7 and hematoxylin (nuclear) detection was performed in the Real-time Tuning window and advanced analysis options were set. The region of interest was selected by drawing around it, the layers saved for analysis and the program run. Following the analysis, the results were verified manually by visual inspection, and the data exported as CSV files to GraphPad prism.

2. Results

To determine if there was a dose response in shortened modified dystrophin restoration at different meganuclease doses in two different AAV capsids (AAV9 and AAVrh74), dystrophin protein levels were measured using WES. Results for dystrophin restoration in the quadricep, tibialis anterior, heart, diaphragm, and gastrocnemius tissues are provided in FIGS. 8A-8E, respectively. Dystrophin restoration was quantified by comparing dystrophin protein from the corresponding tissues in hDMD mice from a protein standard by a standard curve from WES protein analysis. In quadricep tissue, responses were similar between AAV9 and rh74 at the 2e14 VG/kg and 1e14 VG/kg doses; however, at a low dose of 2e13 VG/kg AAV9 resulted in a higher percentage of dystrophin restoration (FIG. 8A). In the tibialis anterior tissue, there was a more pronounced dose response for meganucleases delivered via AAVrh74 than AAV9 with generally higher percentages of dystrophin restoration with AAVrh74 in this tissue. At the 2e14 dose, there was an unexpected decrease in dystrophin restoration percentage with the AAV9 treatment group that was not observed with AAVRH74 (FIG. 8B). In the heart tissue dystrophin restoration was similar across all doses tested. At a dose of 2e13 VG/kg, there was slightly less dystrophin restoration with AAVrh74 when compared to AAV9 (FIG. 8C). In the diaphragm, there was little to no dystrophin restoration with either AAV at the low 2e13 VG/kg dose. At the higher doses, dystrophin restoration was slightly higher in the 2e14 dose compared to the 1e14 dose with the AAVrh74 tending to yield slightly higher levels of dystrophin restoration (FIG. 8D). In the gastrocnemius tissue, there was increased dystrophin restoration at the 1e14 VG/kg and the 2014 VG/kg doses, with restoration levels at these higher doses being similar in both AAV9 and AAVrh74 capsids (FIG. 8E).

The total ligation assay was utilized to determine if there was a dose response in editing, measured by total ligation of the dystrophin gene at different meganuclease doses in two different AAV capsids (AAV9 and AAVrh74). Results for the percentage of total ligation of the dystrophin gene in the quadricep, tibialis anterior, heart, diaphragm, and gastrocnemius tissues are provided in FIGS. 9A-9E, respectively. In the quadricep tissue, an increasing response in total ligation percentage to meganuclease dose was observed in both AAV9 and AAVrh74 delivered meganucleases with each of the AAV9 and AAVrh74 capsids generating about the same level of total ligation percentage (FIG. 9A). In the tibialis anterior tissue, responses were more varied between individually treated mice. However, there was a discernable increase in total ligation from the 1e14 VG/kg dose in both AAV treatment groups with the higher 1e14 and 2e14 doses (FIG. 9B). In the heart tissue total ligation percentage was slightly elevated compared to the 2e 13vg/KG dose in both AAV groups at the 2014 vg/KG and 1e14 vg/KG doses. The level of total ligation percentage was similar at these higher doses (FIG. 9C). In the diaphragm, there was a nearly linearly increasing dose response of total ligation observed across the administered doses. In this tissue, AAV9 tended to yield slightly higher levels of total ligation when compared to AAV rh.74 (FIG. 9D). In the gastrocnemius tissue, there was a similar linearly increasing dose response for total ligation for both AAV9 and AAVrh74 treatment groups, which were similar (FIG. 9E).

Meganuclease expression levels were measured to determine if increasing doses of the transgene encoding the meganucleases in the AAV9 capsid resulted in higher meganuclease protein levels. Results for meganuclease protein expression restoration in the quadricep, heart, gastrocnemius, diaphragm, tibialis anterior, and liver tissues is provided in FIGS. 10A-10F, respectively. In the quadricep, gastrocnemius, and diaphragm tissues, there was an increase in meganuclease protein levels from the 2e13 to the 2e14 VG/kg dosage (FIG. 10A, FIG. 10C, and FIG. 10D). In the heart tissue, there were similar levels of meganuclease protein levels at the 2e13 and 1e14 VG/kg dosage and about a 2-fold increase in meganuclease protein at the 2014 VG/kg dosage (FIG. 10B). In the tibialis anterior tissue, meganuclease expression levels were more varied but tended to show the same increase in protein levels from the 2e13 to 2e14 VG/kg dosage as observed in the quadricep, gastrocnemius, and diaphragm tissues (FIG. 10E). In the liver, there was very little off tissue meganuclease protein expression observed. For example, at the 2e 14 VG/kg dosage, there was 10 to 40-fold less meganuclease protein in the liver compared to the gastrocnemius tissue. The amount of meganuclease expression also increased in a linear fashion with dose (FIG. 10F).

Next the amount of Pax7+ muscle satellite cells that were edited from select treated mice was calculated using the BaseScope assay described above. As shown in FIG. 11A, the amount of muscle nuclei that were Pax7+ in the quadricep tissue sample was about 5% to about 7% in meganuclease treated as well as PBS control treated animals. Then taking these cells, the percentage of Pax7+ cells that were edited in the sample tissue ranged from about 0.5% to about 2.5% in meganuclease treated animals without any editing observed in the PBS control treated animals (FIG. 11B).

3. Conclusions

Most of the muscle tissues examined in this study demonstrated a dose dependent increase in dystrophin restoration and total ligation of the dystrophin gene with the muscle-specific expression cassettes encoding the meganucleases in both an AAV9 and an AAVrh74 capsid. Similarly, meganuclease protein levels also generally increased in the tissues at a higher dosage of AAV. Notably the heart tissue only exhibited minor increases in total ligation and dystrophin restoration at a dose that is an order of magnitude higher than the lowest dose tested. This is despite the fact that the amount of meganuclease expression showed a significant 2 to 3-fold increase in meganuclease protein levels from the 2e13 to 2014 VG/kg dose. This indicates that in some tissues, such as the heart, the lowest tested dosage may be close to the maximum effective dose. In addition, there were low levels of total ligation and meganuclease expression concomitant with low dystrophin restoration in the non-muscle liver tissue. This result was despite the fact that most AAVs predominantly go to the liver even given any other particular tissue tropism of the AAV. This indicates that the muscle-specific expression cassette utilizing the tMCK minimized non-muscle cell expression in vivo.

It was also shown in this study that in quadricep muscle tissue, meganucleases delivered via AAV9 in a muscle-specific expression cassette could edit Pax7+ muscle satellite cells.

Example 3

Editing of Dystrophin Gene In Vivo in hDMD Mouse Study

1. Methods

An in vivo study in hDMDdel52/mdx (hDMD) and hDMD/mdx mice was conducted to investigate in vivo editing and shortened modified human dystrophin protein restoration induced by delivery of the DMD 19-20L.329 and DMD 35-36L.349 pair of meganucleases. This study was also conducted to further investigate functional muscle recovery in the hDMD mouse model through a maximum force recovery assay. Mice were injected by retro orbital systemic injection with one construct encapsulated with AAV9 (1e14 VG/kg). The AAV9-encapsulated product comprised a viral genome, comprising SEQ ID NO: 80, that includes, from 5' to 3', the muscle-specific promoter tMCK, a first SV40 NLS coding sequence, a coding sequence for the DMD 19-20L.329 meganuclease, a first c-myc NLS coding sequence, a furin GSG P2A cleavage sequence, a second SV40 NLS coding sequence, a coding sequence for the DMD 35-36L.349 meganuclease, a second c-myc NLS coding sequence, a WPRE element, and an SV40 polyadenylation signal. This AAV9 product contained a D-sequence in each of the 5' and 3' ITR sequences to improve packaging efficiency. The nucleic acid sequence of the DMD 35-36L.349 meganuclease was codon modified as described in Example 1. Thirty mice were provided to Myologica (Baltimore, MD) and were either treated with engineered meganucleases (n=10/group) or a vehicle. Twenty hDMD-del52/mdx (hDMD) male mice were either treated with the AAV9 product (n=10/group) or a vehicle (PBS pH 7.4+ 0.001% P188). An additional ten hDMD/mdx mice were injected with the vehicle (PBS pH 7.4+0.001% P188). Mice were injected with test article or vehicle via retro orbital injection at 6 weeks of age. One week after treatment, mice were shipped to the University of Maryland Veterinary Resources and kept until successfully passed quarantine. Once released from quarantine, at approximately 10 to 12 weeks of age, all mice underwent hindlimb muscle function and susceptibility to injury testing, then euthanized and tissues collected. Eleven mice underwent hindlimb muscle function and susceptibility to injury testing in a blinded fashion, so that the tester did not know which group each animal was in. After hindlimb muscle function testing the mice were euthanized and tissues collected. Muscle performance was measured in vivo with a 305 C muscle lever system (Aurora Scientific Inc., Aurora, CAN). Anesthesia in the mouse was accomplished via inhalation (~5% isoflurane, or to effect), placed on a thermostatically controlled table where anesthesia maintenance was used via nose-cone (~2-3% isoflurane, or to effect). The right knee was isolated using a pin pressed against the tibial head and the foot firmly fixed to a footplate on the motor shaft. For the plantarflexor muscle group, contractions are elicited by percutaneous electrical stimulation of the sciatic nerve. Optimal isometric twitch torque is determined by increasing the current with a minimum of 30 s between each contraction to avoid fatigue. Force Frequency was measured using a series of stimulations are then performed at increasing frequency of stimulation (0.2 ms pulse, 500 ms train duration): 1, 20, 40, 50, 60, 80, 100, 150 Hz and maximal peak isometric force will be plotted.

2. Results

The total ligation percentage of mice treated with the DMD 19-20L.329 and DMD 35-36L.349 pair of meganucleases is shown in FIG. 12A-FIG. 12F for the quadricep, gastrocnemius, heart, tibialis anterior, and diaphragm muscle tissues and the liver, respectively. Treatment with this pair of meganucleases resulted in positive total ligation percentages in the quadricep, gastrocnemius, heart, tibialis anterior, and diaphragm muscle tissues that was similar to Example 1 and Example 2 (FIG. 12A-12E). As previously reported in the prior Example 1 and Example 2, off-tissue editing in the liver was lower than in any of the muscle tissues (FIG. 12F).

The percentage shortened modified dystrophin restoration of mice treated with the DMD 19-20L.329 and DMD 35-36L.349 pair of meganucleases is shown in FIG. 13A-FIG. 13E for the quadricep, gastrocnemius, heart, tibialis anterior, and diaphragm muscle tissues, respectively. Treatment with this pair of meganucleases resulted in a percentage restoration of the shortened dystrophin protein in the quadricep, gastrocnemius, heart, tibialis anterior, and diaphragm muscle tissues that was similar to what was observed in Example 1 and Example 2 (FIG. 13A-13E).

The maximum force recovery assay for functional restoration of muscle function in the hDMDdel52/mdx (hDMD) mouse model is provided in FIG. 14. The triangle-shaped data points represent a non-diseased control hDMD mouse and an upper baseline for maximum muscle force generation. The square data points provide the force in mN for the hDMDdel52/mdx (hDMD) that were untreated and represents the lower baseline for muscle force generation. The circular data points provide the force in mN for the hDMDdel52/mdx (hDMD) mice that were treated with the DMD 19-20L.329 and DMD 35-36L.349 pair of meganucleases expressed from the muscle-specific expression cassette described above in an AAV9 capsid. The meganuclease-treated mice had a statistically significant restoration of muscular maximum force generation when compared to the non-treated mice at all muscle stimulation frequencies. This muscle function restoration of maximum force generation was nearly the same as the non-diseased mice at lower stimulation frequencies.

3. Conclusions

These data demonstrate that mice treated with an AAV9 vector encapsulating the muscle-specific expression cassette described above encoding the DMD 19-20L.329 and DMD 35-36L.349 pair of meganucleases can result in editing of the dystrophin locus and restoration of a shortened modified dystrophin protein, consistent with Example 1 and Example 2. This study further demonstrates a significant finding in that restoring a shortened modified dystrophin protein through treatment with engineered meganucleases expressed from a muscle-specific expression cassette results in a functional recovery of muscle function in an hDMDdel52/mdx (hDMD) diseased mouse model.

Example 4

Editing of Dystrophin Gene In Vivo in hDMD Mouse Study

1. Methods

An in vivo study in hDMDdel52/mdx (hDMD) mice was conducted to investigate in vivo editing and shortened modified human dystrophin protein restoration induced by delivery of the different DMD meganuclease pairs which include DMD 19-20L.431 in combination with DMD 35-36L.469, DMD 19-20L.458 in combination with DMD 35-36L.469, DMD 19-20L.431 in combination with DMD 35-36L.457, and DMD 19-20L.458 in combination with DMD 35-36L.457. Mice were injected by retro orbital systemic injection with four constructs encapsulated with AAV9 (3e13 VG/kg).

The first AAV9-encapsulated product comprised a viral genome, comprising SEQ ID NO: 81, that includes, from 5' to 3', the muscle-specific promoter tMCK, a first SV40 NLS coding sequence, a coding sequence for the DMD 19-20L.431 meganuclease, a first c-myc NLS coding sequence, a furin GSG P2A cleavage sequence, a second SV40 NLS coding sequence, a coding sequence for the DMD 35-36L.469 meganuclease, a second c-myc NLS coding sequence, a WPRE element, and an SV40 polyadenylation signal. The second AAV9-encapsulated product comprised a viral genome, comprising SEQ ID NO: 82, that includes, from 5' to 3', the muscle-specific promoter tMCK, a first sv40 NLS coding sequence, a coding sequence for the DMD 19-20L.458 meganuclease, a first c-myc NLS coding sequence, a furin GSG P2A cleavage sequence, a second SV40 NLS coding sequence, a coding sequence for the DMD 35-36L.469 meganuclease, a second c-myc NLS coding sequence, a WPRE element, and an SV40 polyadenylation signal. The third AAV9-encapsulated product comprised a viral genome, comprising SEQ ID NO: 83, that includes, from 5' to 3', the muscle-specific promoter tMCK, a first SV40 NLS coding sequence, a coding sequence for the DMD 19-20L.431 meganuclease, a first c-myc NLS coding sequence, a furin GSG P2A cleavage sequence, a second SV40 NLS coding sequence, a coding sequence for the DMD 35-36L.457 meganuclease, a second c-myc NLS coding sequence, a WPRE element, and an SV40 polyadenylation signal. The fourth AAV9-encapsulated product comprised a viral genome, comprising SEQ ID NO: 84, that includes, from 5' to 3', the muscle-specific promoter tMCK, a first SV40 NLS coding sequence, a coding sequence for the DMD 19-20L.458 meganuclease, a first c-myc NLS coding sequence, a furin GSG P2A cleavage sequence, a second SV40 NLS coding sequence, a coding sequence for the DMD 35-36L.457 meganuclease, a second c-myc NLS coding sequence, a WPRE element, and an SV40 polyadenylation signal. The nucleic acid coding sequence of the DMD 35-36L.457 and DMD 35-36L.469 engineered meganucleases were codon modified to reduce the percent identity between nucleic acid sequences common to paired DMD 19-20 meganucleases without modifying the encoded amino acid sequence. The unmodified nucleic acid coding sequence of the DMD 35-36L.457 and DMD 35-36L.469 engineered meganucleases are provided as SEQ ID NO: 97 and 98, respectively herein. These engineered meganucleases were codon modified such that approximately 40% of the nucleotides were changed in the DMD 35-36L.457 and DMD 35-36L.469 engineered meganucleases. Accordingly, the codon modified DMD 35-36L.457 meganuclease had less than about 60% nucleotide sequence identity to the DMD 19-20L.431 or DMD 19-20L.458 engineered meganucleases. The codon-modified DMD 35-36L.469 also had less than about 60% nucleotide sequence identity with the DMD 19-20L.431 and DMD 19-20L.458 engineered meganucleases. At 28 days post-injection, mice were sacrificed and tissue sections from skeletal muscle (quadricep), heart, diaphragm, gastrocnemius, tibialis anterior (TA) and liver were collected for molecular, protein, and histological analysis. As in Example 1, digital droplet PCR was utilized to determine the frequency of large deletions (indel %) utilizing primer pairs and probes that span the junction of the 19-20 target site and the corresponding DMD nuclease for 35-36. In addition, samples were analyzed on the WES™ system (Protein Simple) for dystrophin protein identification and quantitation following the same method outlined in Example 1.

2. Results

The total ligation percentage of mice treated with the indicated pairs of meganucleases is shown in FIG. 15A-FIG. 15E for the quadricep, gastrocnemius, heart, tibialis anterior, and diaphragm muscle tissues, respectively. Treatment with these pairs of meganucleases at a dosage level of 3e13 VG/kg resulted in positive total ligation percentages in the quadricep, gastrocnemius, heart, tibialis anterior, and diaphragm muscle tissues that were similar to the low meganuclease dosage of 2e13 VG/kg of Example 2 (FIG. 15A-15E). For each muscle tissue type sampled, the DMD 19-20L.431 and DMD 35-36L.457 pair of meganucleases demonstrated the highest levels of editing assessed by total ligation assay of all of the tested meganucleases.

The percentage dystrophin restoration of mice treated with the indicated pairs of meganucleases is shown in FIG. 16A-FIG. 16E for the quadricep, gastrocnemius, heart, tibialis anterior, and diaphragm muscle tissues, respectively. These data show that treatment with these pairs of meganucleases resulted in a percentage restoration of the shortened dystrophin protein in the quadricep, gastrocnemius, heart, tibialis anterior, and diaphragm muscle tissues that was again similar to what was observed in Example 2 (FIG. 16A-16E). Consistent with the total ligation data of FIG. 15, the data of FIG. 16 also show that for the quadricep, gastrocnemius, tibialis anterior, and diaphragm muscle tissues, the DMD 19-20L.431 and DMD 35-36L.457 pair of meganucleases demonstrated the highest levels of shortened dystrophin protein restoration. In the heart, however, the DMD 19-20L.431 and DMD 35-36L.469 pair of meganucleases led to a similar percentage of dystrophin restoration that was measured with the DMD 19-20L.431 and DMD 35-36L.457 pair of meganucleases.

3. Conclusions

These data demonstrate that treatment with additional pairings of meganucleases expressed from the muscle-specific expression cassettes described above in an AAV9 vector results in similar levels of editing and shortened dystrophin protein restoration. In most tissues, the pairing of the DMD 19-20L.431 and DMD 35-36L.457 meganucleases resulted in the highest levels of editing of the dystrophin gene assessed by total ligation concomitant with the highest levels of shortened dystrophin protein restoration. These data indicate both that the muscle-specific expression cassettes tested are suitable for expression of different pairings of meganucleases and that these meganucleases are functionally active in restoring dystrophin protein levels through the gene editing approach described herein.

Example 5

Editing of Dystrophin Gene In Vivo in hDMD Mouse Study

1. Methods

An in vivo study in hDMDdel52/mdx (hDMD) mice was conducted to investigate in vivo editing and shortened modified human dystrophin protein restoration induced by delivery of the DMD 19-20L.329 and DMD 35-36L.349 pair of meganucleases. In particular, this study assessed the percentage of dystrophin-positive muscle fibers in mice treated with the pairs of meganucleases. In order to further potentially enhance in vivo expression and editing of the meganucleases from the muscle-specific expression cassette, a B-301 muscle-specific enhancer was incorporated 5' of the tMCK promoter as described below. Mice were injected by retro orbital systemic injection with two different constructs encapsulated with AAV9 (1e14 VG/kg and 3e13 VG/kg). A first AAV9-encapsulated product comprised a viral genome, comprising SEQ ID NO: 80, that includes, from 5' to 3', the muscle-specific promoter tMCK, a first SV40 NLS coding sequence, a coding sequence for the DMD 19-20L.329 meganuclease, a first c-myc NLS coding sequence, a furin GSG P2A cleavage sequence, second SV40 NLS coding sequence, a coding sequence for the DMD 35-36L.349 meganuclease, a second c-myc NLS coding sequence, a WPRE element, and an SV40 polyadenylation signal. A second AAV9-encapsulated product comprised a viral genome, comprising SEQ ID NO: 85, that includes, from 5' to 3', the B-301 enhancer, the muscle-specific promoter tMCK, a first SV40 NLS coding sequence, a coding sequence for the DMD 19-20L.329 nuclease, a first c-myc NLS coding sequence, a furin GSG P2A cleavage sequence, a second SV40 NLS coding sequence, a coding sequence for the DMD 35-36L.349 nuclease, a second c-myc NLS coding sequence, a WPRE element, and an SV40 polyadenylation signal. Both of these AAV9 products contained a D-sequence in each of the 5' and 3' ITR sequences to improve packaging efficiency. The nucleic acid sequence of the DMD 35-36L.349 meganuclease was codon modified as described in Example 1. At 28 days post-injection, mice were sacrificed and tissue sections from skeletal muscle (quadricep) were collected for histological analysis. The presence of dystrophin-positive muscle cells in the quadricep were measured by fluorescence microscopy. Skeletal muscle fibers were analyzed for dystrophin-positive fibers using a dual stain of laminin and dystrophin and quantified with the HALO software. Tissue sections of meganuclease treated or PBS treated quadricep were mounted on microscope slides and prepared for immunohistochemical staining (deparaffinized, blocked for endogenous peroxidase activity, and antigen retrieval performed). Slides were incubated in a humid slide chamber with primary antibodies (anti-Laminin [Sigma-Aldrich, L9393] and anti-human dystrophin [Millipore, MABT827]) in 2% normal goat serum (NGS) in 0.1% Tween20 in PBS (PBST) overnight at 4° C. Slides were moved to the Leica BOND/RX Autostainer for secondary antibody incubation (goat-anti-rabbit Alexa 555 and goat-anti-mouse Alexa 647) in 2% NGS in PBST for 1 hour at room temperature. Slides were rinsed with BOND Wash Solution for 3 min. DAPI staining reagent (0.5 ug/ml; Chemometec, 910-3012) in PBS was applied for nuclear counterstain for 5 minutes. Final rinse with BOND Wash Solution 5 times (3 minutes each). Slides were mounted with VECTASHIELD Vibrance® Antifade mounting medium (Vector Labs, H-1700-10). 20× images were scanned and tiled by Zeiss ZEN workstation. Acquired images were analyzed and quantitated by Muscle Fiber FL Module HALO (Indica Labs).

2. Results

FIG. 17 provides the results of the histological analysis of dystrophin-positive fibers after treatment of hDMDdel52/mdx (hDMD) mice with the DMD 19-20L.329 and DMD 35-36L.349 pair of meganucleases. This pair of meganucleases expressed from a muscle-specific expression cassette described above yielded less than 5% dystrophin positive fibers. However, inclusion of the B-301 muscle enhancer element to the muscle-specific expression cassette increased the percentage of dystrophin positive fibers to around 10%.

3. Conclusions

This study demonstrated that treatment of hDMDdel52/mdx (hDMD) mice resulted in detectable dystrophin within muscle fibers of these mice that normally lack dystrophin. In addition, it was demonstrated that the inclusion of the B-301 muscle enhancer element further increased this effect by around 2-fold. Therefore, inclusion of this additional muscle enhancer represents a means for increasing dystrophin expression in muscle fibers.

Example 6

Editing of Dystrophin Gene In Vivo in hDMD Mouse Study

1. Methods

An in vivo study in hDMDdel52/mdx (hDMD) mice was conducted to investigate in vivo editing and shortened modified human dystrophin protein restoration induced by delivery of the DMD meganuclease pair DMD 19-20L.431 in combination with DMD 35-36L.457. Mice were injected by retro orbital systemic injection with two constructs encapsulated with AAV9 at two different doses (1e14 VG/kg and 3e13 VG/kg). Because there was an improvement of dystrophin expression in muscle fibers as shown in Example 5, an additional muscle enhancer from the myosin light chain, phosphorylatable, fast skeletal muscle (MYLFP) gene (referred to herein as enhancer G) was tested in conjunction with the tMCK promoter. The first AAV9-encapsulated product comprised a viral genome, comprising SEQ ID NO: 86, that includes, from 5' to 3', the B-301 enhancer, the muscle-specific promoter tMCK, a first SV40 NLS coding sequence, a coding sequence for the DMD 19-20L.431 meganuclease, a first c-myc NLS coding sequence, a furin GSG P2A cleavage sequence, a second SV40 NLS coding sequence, a coding sequence for the DMD 35-36L.457 meganuclease, a second c-myc NLS coding sequence, a WPRE element, and an SV40 polyadenylation signal. The second AAV9-encapsulated product comprised the same components, with the exception that the B-301 enhancer sequence (SEQ ID NO: 1) was replaced by the enhancer G sequence. Certain elements in each of these products were CpG-reduced, including the NLS sequences, the furin GSG P2A cleavage sequence, and the sequences encoding each of the meganucleases. In addition, these AAV9 products contained a D-sequence in each of the 5' and 3' ITR sequences to improve packaging efficiency.

At 28 days post-injection, mice were sacrificed and tissue sections from skeletal muscle (quadricep), heart, diaphragm, and gastrocnemius were collected for molecular and protein analysis. The nucleic acid sequence of the DMD 35-36L.457 meganuclease was codon modified as described in Example 1. As in Example 1, digital droplet PCR was utilized to determine the frequency of large deletions (indel %) utilizing primer pairs and probes that span the junction of the 19-20 target site and the corresponding DMD nuclease for 35-36. In addition, samples were analyzed on the WES™ system (Protein Simple) for dystrophin protein identification and quantitation following the same method outlined in Example 1.

2. Results

The total ligation percentage of the dystrophin gene in mice treated with the DMD 19-20L.431 and DMD 35-36L.457 pair of meganucleases is shown in FIG. 18A-FIG. 18D for the quadricep, heart, diaphragm, and gastrocnemius muscle tissues, respectively. Treatment with this pair of meganucleases at either a 3e13 or 1e14 VG/kg dosage level resulted in positive total ligation percentages in the quadricep, heart, diaphragm, and gastrocnemius muscle tissues. Although independent experiments cannot be directly compared, the total ligation results from this study were lower but in a similar range of the study of Example 4 at the 3e 13 VG/kg dosage. In the quadricep tissue, total ligation between the B-301 enhancer and enhancer G were nearly the same with a small increase in total ligation observed with enhancer G at both doses (FIG. 18A). In the heart tissue, total ligation obtained with the B-301 enhancer was notably higher than that observed with enhancer G at both doses (FIG. 18B). In the diaphragm and gastrocnemius tissues, there was little difference in percentage of total ligation observed between the B-301 and enhancer G elements (FIG. 18C and FIG. 18D).

The percentage dystrophin restoration of mice treated with the indicated pairs of meganucleases is shown in FIG. 19A-FIG. 19D for the quadricep, heart, diaphragm, and gastrocnemius muscle tissues, respectively. These data show that treatment with these pairs of meganucleases resulted in a percentage restoration of the shortened dystrophin protein in the quadricep, heart, diaphragm, and gastrocnemius muscle tissues that were in a similar range of the study of Example 4 at the 3e13 VG/kg dosage. These data are also consistent with total ligation results of FIG. 18. For each muscle tissue, the percentage of total ligation and dystrophin restoration followed the same trend. Accordingly, in the quadricep tissue, the percentage of dystrophin restoration between the B-301 enhancer and enhancer G were nearly the same with a small increase in total ligation observed with enhancer G at both doses (FIG. 19A). In the heart tissue, and consistent with the total ligation data, the dystrophin restoration percentage obtained with the B-301 enhancer was notably higher than that observed with enhancer G at both doses (FIG. 19B). In the diaphragm tissue, there was little difference in percentage of total ligation observed between the B-301 and enhancer G elements (FIG. 19C). In the gastrocnemius tissue there was little difference between the B-301 and enhancer G element at the 3e13 VG/kg dose; however, at the higher 1e14 VG/kg dose that was a more noted increase in dystrophin restoration for the enhancer G element compared to the B-301 element (FIG. 19D).

3. Conclusions

These data demonstrate that the use of two distinct muscle enhancer elements in conjunction with the tMCK promoter result in positive total ligation of the dystrophin gene and a concomitant increase in shortened modified dystrophin protein. Overall, the two enhancers performed similarly across the quadricep, diaphragm, and gastrocnemius tissues. However, in the heart, there was a more notable increase in total ligation percentage of the dystrophin gene and percentage of shortened dystrophin protein in expression cassettes utilizing the B-301 enhancer. Thus, the inclusion of the B-301 enhancer in conjunction with the tMCK promoter could provide an important and clinically relevant muscle-specific expression cassette design for improved dystrophin restoration in cardiac tissue for the treatment of DMD.

Example 7

In Vitro Screen to Identify Suitable Muscle-Specific Enhancer Elements

1. Methods

An in vitro study was conducted using AB1098, an immortalized cell line consisting of human DMD patient cell line, mouse satellite cells derived from hDMDdel52/mdx (hDMD) mice, and HepG2, an immortalized cell line consisting of human liver carcinoma cells, to investigate the effect of various additional muscle enhancers on the tMCK promoter ability to express a transgene specifically in muscle or muscle satellite cells. Eight plasmid constructs were utilized for this evaluation including two controls with the promoters, tMCK and MHCK7. The first plasmid construct contained, from 5' to 3', the B301 enhancer, the muscle-specific promoter tMCK, Firefly Luciferase, a WPRE element, and an SV40 polyadenylation signal. The second plasmid construct contained, from 5' to 3', the MTF1 enhancer, the muscle-specific promoter tMCK, Firefly Luciferase, a WPRE element, and an SV40 polyadenylation signal. The third plasmid construct contained, from 5' to 3', the MTSPDEF1 enhancer, the muscle-specific promoter tMCK, Firefly Luciferase, a WPRE element, and an SV40 polyadenylation signal. The fourth plasmid construct contained, from 5' to 3', the enhancer F (a first enhancer from the MYLPF gene), the muscle-specific promoter tMCK, Firefly Luciferase, a WPRE element, and an SV40 polyadenylation signal. The fifth plasmid construct contained, from 5' to 3', the enhancer G (a second enhancer from the MYLPF gene), the muscle-specific promoter tMCK, Firefly Luciferase, a WPRE element, and an SV40 polyadenylation signal. The sixth plasmid construct contained, from 5' to 3', the enhancer I (third enhancer from the MYLPF gene), the muscle-specific promoter tMCK, Firefly Luciferase, a WPRE element, and an SV40 polyadenylation signal. The seventh plasmid construct contained, from 5' to 3', the muscle-specific promoter MHCK7, Firefly Luciferase, a WPRE element, and an SV40 polyadenylation signal. The eighth plasmid construct contained, from 5' to 3', the muscle-specific promoter tMCK, Firefly Luciferase, a WPRE element, and an SV40 polyadenylation signal.

Mouse satellite cells were extracted using the satellite cell isolation kit, mouse from Miltenyi Biotec according to manufacturer's instructions. In addition, there was an inclusion of the anti-integrin α-7 microbeads for the isolation of integrin α-7 positive cells. 500 mg-1 g of quadricep and lower leg tissue was extracted from hDMDdel52/mdx (hDMD). Tissues were diced and shredded using razor blades in an effort to homogenize the tissue for processing. Gentlemacs dissociator, also from Miltenyi Biotec, was used for further processing of the tissues according to manufacturer's instructions. The previous day a 96 well cell culture plate was coated with 100 µL per well of Stemcell MyoCult-SF Attachment Substrate at a 1:50 dilution with PBS with Ca and Mg then sealed with parafilm and placed at 4° C. Isolated mouse satellite cells were cultured in the media of DMEM-F-12 with 15 mM HEPES (STEMCELL), Myocult Expansion 10× supplement at a 1× dilution (STEMCELL), and Primocin (Invitrogen) at a 1:500 dilution. Once cells were isolated, they were pooled and resuspended in 8.5 mL of media where 100 µL of suspension was transferred to the empty 96 well culture plate (previously coated with Stemcell MyoCult-SF attachment substrate) across 10 columns. After 3 days of incubation at 37 C in a 5% CO2 incubator the cells had a media swap of 100 µL before being transfected with Lipofectamine 3000 at a dose of 0.014 pmol of DNA per well according to manufacturer's instructions (0.3 µL Lipofectamine 3000 with 0.2 µL P3000). To evaluate expression in vitro, a luciferase assay was conducted using the Luciferase Assay System (Promega, E1500) according to manufacturer's instructions. The RLUs (Relative Light Units) for each transfected construct were compared against the tMCK promoter alone (the eighth plasmid) and the data was viewed as a fold change versus this construct.

2. Results

The results of the screening of additional muscle enhancers in vitro are provided in FIG. 20. In the human AB 1098 muscle cell line, all of the tested enhancers provided a significant increase in protein expression versus the tMCK promoter alone. The B-301 and MTF1 enhancers performed the best of the tested enhancers with nearly a 5-fold increase in protein expression in these muscle cells. In Pax7+ murine muscle satellite cells, the B-301 and enhancer G muscle enhancers performed the best out of the tested group at about a two-fold increase in transgene expression in muscle satellite cells over the tMCK promoter alone. Given that the enhancer G treated cells had one significantly high outlier data point, it is likely that the B-301 enhancer yielded the best transgene expression in these cells. Lastly, in liver cells, each of the enhancers F, G, I, and SPDEF1 had about the same or slightly less transgene expression compared to the tMCK promoter alone. The B-301 enhancer yielded modestly elevated transgene expression in liver cells compared to tMCK promoter alone. In contrast, the MTF1 enhancer yielded about an 8-fold increase and the MHCK7 promoter yielded about a 9-fold increase in transgene expression in liver cells compared to the tMCK promoter alone.

3. Conclusions

The results of this study indicate that certain muscle enhancers are better at promoting muscle-specific expression in muscle cells than others. Overall, the data suggests that the B-301 enhancer provided the strongest transgene expression in human muscle cells and in murine muscle satellite cells with low expression in non-muscle liver cells. The MTF1 enhancer provided equally strong transgene expression in AB1098 human muscle cells compared to the B-301 enhancer; however, it demonstrated a significantly higher non-muscle cell expression profile in the liver. Similarly, the MHCK7 promoter provided the strongest transgene expression in the AB1098 human muscle cells and the murine satellite cells; however, that expression was also seen at significantly higher levels in liver cells compared to the other enhancer elements. This result with the MHCK7 promoter is consistent with what was observed with total ligation percentage in vivo in Example 1 (FIG. 4).

Overall, these data suggest that the B-301 enhancer element provides a better balance of transgene expression in muscle tissue with low non-muscle cell expression when directly compared to other muscle enhancer elements or the MHCK7 promoter alone.

Example 8

Editing of Dystrophin Gene In Vivo in hDMD Mouse Study

1. Methods

An in vivo study in hDMDdel52/mdx (hDMD) mice was conducted to investigate in vivo editing of the dystrophin gene induced by delivery of the DMD meganuclease pair DMD 19-20L.431 in combination with DMD 35-36L.457. Mice were injected by retro orbital systemic injection with a construct encapsulated with AAV9 at two different doses (1e14 VG/kg and 3e13 VG/kg). The AAV9-encapsulated product comprised a viral genome, comprising SEQ ID NO:

87, that includes, from 5' to 3', the B-301 enhancer, the muscle-specific promoter tMCK, a first SV40 NLS coding sequence, a coding sequence for the DMD 19-20L.431 meganuclease, a first c-myc NLS coding sequence, a furin GSG P2A cleavage sequence, a second SV40 NLS coding sequence, a coding sequence for the DMD 35-36L.457 meganuclease, a second c-myc NLS coding sequence, a WPRE element, and an SV40 polyadenylation signal. This AAV9 product contained a D-sequence in each of the 5' and 3' ITR sequences to improve packaging efficiency. In contrast to the product evaluated in Example 6 (set forth in SEQ ID NO: 86), elements in this product were not CpG-reduced.

At 28 days post-injection, mice were sacrificed and tissue sections from skeletal muscle (quadricep), gastrocnemius, tibialis anterior (TA), heart, and diaphragm were collected for molecular analysis. Tissue sections were also collected from brain, lung, and liver. The nucleic acid sequence of the DMD 35-36L.457 meganuclease was codon modified as described in Example 1. Additionally, in contrast to Example 6, the nucleic acid sequences of the DMD 19-20L.431 and DMD 35-36L.457 nucleases were not CpG-depleted for this study.

As in Example 1, digital droplet PCR was utilized to determine the frequency of total ligation of the DMD 19-20 and DMD 35-36 cleavage sites in the genome of each collected muscle and tissue type, utilizing primer pairs and probes that span the junction of the 19-20 target site and the corresponding 35-36 target site.

2. Results

The total ligation percentage of the dystrophin gene in mice treated with the DMD 19-20L.431 and DMD 35-36L.457 pair of meganucleases is shown in FIGS. 21A-21E for the quadricep, gastrocnemius, TA, heart, and diaphragm, respectively. The total ligation percentage of the dystrophin gene in the collected brain, liver, and lung tissues is shown in FIG. 22A-22C, respectively. As shown, treatment with this pair of meganucleases at dosage levels of 3e13 or 1e14 VG/kg resulted in dose-dependent total ligation percentages in each of the collected muscle tissues. Total ligation percentages averaged between ~14%-15% in the quadricep and gastrocnemius muscle, approximately 7% in the TA, ~5% in the heart, and ~3% in the diaphragm at the high AAV dose. Total ligation percentages averaged between ~5%-6% in the quadricep and gastrocnemius, between ~4%-5% in the TA and heart, and ~1.5% in the diaphragm at the low AAV dose. By contrast, total ligation percentages observed in non-muscle tissues were substantially lower even at the high AAV dose, with percentages of approximately 0.7% in liver, 0.2% in lung, and less than 0.01% in the brain.

3. Conclusions

Although independent experiments cannot be directly compared, the total ligation results from this study at the 1e14 dose were similar to those observed in Example 6, the difference being that the nucleic acid sequences encoding the two meganucleases were not CpG depleted in these experiments. Accordingly, these experiments demonstrate that this pair of meganucleases, in this particular construct design and without CpG depletion, were capable of effectively excising exons 45-55 of the dystrophin gene and ligating the two cleaved ends in the genomes of various muscle tissues.

```
                          Sequence Listing

SEQ ID NO: 1
CTGTCTGAAAGGGAAGATATGAAAGGAATTTGTCGGTAAGTTTCTTATGATTGACTCACA

TGACGTGCTTTGTTTAACTCAGTGGAATCACGCTCATAAACCAAATATGTGCATGTGATC

SEQ ID NO: 2
AATCAAGGCTGTGGGGGACTGAGGGCAGGCTGTAACAGGCTTGGGGGCCAGGGCTTATA

CGTGCCTGGGACTCCCAAAGTATTACTGTTCCATGTTCCCGGCGAAGGGCCAGCTGTCCCC

CGCCAGCTAGACTCAGCACTTAGTTTAGGAACCAGTGAGCAAGTCAGCCCTTGGGGCAGC

CCATACAAGGCCATGGGGCTGGGCAAGCTGCACGCCTGGGTCCGGGGTGGGCACGGTGC

CCGGGCAACGAGCTGAAAGCTCATCTGCTCTCAGGGGCCCCTCCCTGGGGACAGCCCCTC

CTGGCTAGTCACACCCTGTAGGCTCCTCTATATAACCCAGGGGCACAGGGGCTGCCCCCG

GGTCAC

SEQ ID NO: 3
CCTCCCTGGGGACAGCCCCTCCTGGCTAGTCACACCCTGTAGGCTCCTCTATATAACCCAG

GGGCACAGGGGCTGCCCCCGGGTCAC

SEQ ID NO: 4
AACACCTGCTGC

SEQ ID NO: 5
AACAGGTGCT

SEQ ID NO: 6
AACACGTGCT

SEQ ID NO: 7
AACAGCTGCT
```

-continued

| Sequence Listing |
| --- |

SEQ ID NO: 8
AACACCTGCA

SEQ ID NO: 9
AACAGGTGCA

SEQ ID NO: 10
AACACGTGCA

SEQ ID NO: 11
AACAGCTGCA

SEQ ID NO: 12
AACAGGTGCTGC

SEQ ID NO: 13
AACACGTGCTGC

SEQ ID NO: 14
AACAGCTGCTGC

SEQ ID NO: 15
AACACCTGCAGC

SEQ ID NO: 16
AACAGGTGCAGC

SEQ ID NO: 17
AACACGTGCAGC

SEQ ID NO: 18
CCATCCTGGTCTATAGAGAGAGTTCCAGAACAGCCAGGGCTACAGATAAACCCATCTGGA

AAAACAAAGTTGAATGACCCAAGAGGGGTTCTCAGAGGGTGGCGTGTGCTCCCTGGCAA

GCCTATGACATGGCCGGGGCCTGCCTCTCTCTGCCTCTGACCCTCAGTGGCTCCCATGAAC

TCCTTGCCCAATGGCATCTTTTTCCTGCGCTCCTTGGGTTATTCCAGTCTCCCCTCAGCATT

CCTTCCTCAGGGCCTCGCTCTTCTCTCTGCTCCCTCCTTGCACAGCTGGCTCTGTCCACCTC

AGATGTCACAGTGCTCTCTCAGAGGAGGAAGGCACCATGTACCCTCTGTTTCCCAGGTAA

GGGTTCAATTTTTAAAAATGGTTTTTTGTTTGTTTGTTTGTTTGTTTGTTTGTTTTTCA

AGACAGGGCTCCTCTGTGTAGTCCTAACTGTCTTGAAACTCCCTCTGTAGACCAGGTCGAC

CTCGAACTCTTGAAACCTGCCACGGACCACCCAGTCAGGTATGGAGGTCCCTGGAATGAG

CGTCCTCGAAGCTAGGTGGGTAAGGGTTCGGCGGTGACAAACAGAAACAAACACAGAGG

CAGTTTGAATCTGAGTGTATTTTGCAGCTCTCAAGCAGGGGATTTTATACATAAAAAAAA

AAAAAAAAAAAAAACCAAACATTACATCTCTTAGAAACTATATCCAATGAAACAATCAC

AGATACCAACCAAAACCATTGGGCAGAGTAAAGCACAAAAATCATCCAAGCATTACAAC

TCTGAAACCATGTATTCAGTGAATCACAAACAGAACAGGTAACATCATTATTAATATAAA

TCACCAAAATATAACAATTCTAAAAGGATGTATCCAGTGGGGGCTGTCGTCCAAGGCTAG

TGGCAGATTTCCAGGAGCAGGTTAGTAAATCTTAACCACTGAACTAACTCTCCAGCCCCA

TGGTCAATTATTATTTAGCATCTAGTGCCTAATTTTTTTTTATAAATCTTCACTATGTAATT

TAAAACTATTTTAATTCTTCCTAATTAAGGCTTTCTTTACCATATACCAAAATTCACCTCCA

ATGACACACGCGTAGCCATATGAAATTTTATTGTTGGGAAAATTTGTACCTATCATAATAG

TTTTGTAAATGATTTAAAAAGCAAAGTGTTAGCCGGGCGTGGTGGCACACGCCTTTAATC

CCTGCACTCGGGAGGCAGGGGCAGGAGGATTTCTGAGTTTGAGGCCAGCCTGGTCTACAG

AGTGAGTTCCAGGACAGCCAGGGCTACACAGAGAAACCCTGTCTCGAACCCCCCACCCCC

CAAAAAAAGCAAAGTGTTGGTTTCCTTGGGGATAAAGTCATGTTAGTGGCCCATCTCTAG

Sequence Listing

GCCCATCTCACCCATTATTCTCGCTTAAGATCTTGGCCTAGGCTACCAGGAACATGTAAAT

AAGAAAAGGAATAAGAGAAAACAAAACAGAGAGATTGCCATGAGAACTACGGCTCAATA

TTTTTTCTCTCCGGCGAAGAGTTCCACAACCATCTCCAGGAGGCCTCCACGTTTTGAGGTC

AATGGCCTCAGTCTGTGGAACTTGTCACACAGATCTTACTGGAGGTGGTGTGGCAGAAAC

CCATTCCTTTTAGTGTCTTGGGCTAAAAGTAAAAGGCCCAGAGGAGGCCTTTGCTCATCTG

ACCATGCTGACAAGGAACACGGGTGCCAGGACAGAGGCTGGACCCCAGGAACACCTTAA

ACACTTCTTCCCTTCTCCGCCCCCTAGAGCAGGCTCCCCTCACCAGCCTGGGCAGAAATGG

GGGAAGATGGAGTGAAGCCATACTGGCTACTCCAGAATCAACAGAGGGAGCCGGGGGCA

ATACTGGAGAAGCTGGTCTCCCCCCAGGGGCAATCCTGGCACCTCCCAGGCAGAAGAGGA

AACTTCCACAGTGCATCTCACTTCCATGAATCCCCTCCTCGGACTCTGAGGTCCTTGGTCA

CAGCTGAGGTGCAAAAGGCTCCTGTCATATTGTGTCCTGCTCTGGTCTGCCTTCCACAGCT

TGGGGGCCACCTAGCCCACCTCTCCCTAGGGATGAGAGCAGCCACTACGGGTCTAGGCTG

CCCATGTAAGGAGGCAAGGCCTGGGGACACCCGAGATGCCTGGTTATAATTAACCCAGAC

ATGTGGCTGCCCCCCCCCCCCCAACACCTGCTGCCTGAGCCTCACCCCCACCCCGGTGCCT

GGGTCTTAGGCTCTGTACACCATGGAGGAGAAGCTCGCTCTAAAAATAACCCTGTCCCTG

GTGGATCCAGGGTGAGGGGCAGGCTGAGGGCGGCCACTTCCCTCAGCCGCAGGTTTGTTT

TCCCAAGAATGGTTTTTCTGCTTCTGTAGCTTTTCCTGTCAATTCTGCCATGGTGGAGCAGC

CTGCACTGGGCTTCTGGGAGAAACCAAACCGGGTTCTAACCTTTCAGCTACAGTTATTGCC

TTTCCTGTAGATGGGCGACTACAGCCCCACCCCCACCCCCGTCTCCTGTATCCTTCCTGGG

CCTGGGGATCCTAGGCTTTCACTGGAAATTTCCCCCCAGGTGCTGTAGGCTAGAGTCACG

GCTCCCAAGAACAGTGCTTGCCTGGCATGCATGGTTCTGAACCTCCAACTGCAAAAAATG

ACACATACCTTGACCCTTGGAAGGCTGAGGCAGGGGGATTGCCATGAGTGCAAAGCCAG

ACTGGGTGGCATAGTTAGACCCTGTCTCAAAAAACCAAAAACAATTAAATAACTAAAGTC

AGGCAAGTAATCCTACTCGGGAGACTGAGGCAGAGGGATTGTTACATGTCTGAGGCCAGC

CTGGACTACATAGGGTTTCAGGCTAGCCCTGTCTACAGAGTAAGGCCCTATTTCAAAAAC

ACAAACAAAATGGTTCTCCCAGCTGCTAATGCTCACCAGGCAATGAAGCCTGGTGAGCAT

TAGCAATGAAGGCAATGAAGGAGGGTGCTGGCTACAATCAAGGCTGTGGGGGACTGAGG

GCAGGCTGTAACAGGCTTGGGGGCCAGGGCTTATACGTGCCTGGGACTCCCAAAGTATTA

CTGTTCCATGTTCCCGGCGAAGGGCCAGCTGTCCCCCGCCAGCTAGACTCAGCACTTAGTT

TAGGAACCAGTGAGCAAGTCAGCCCTTGGGGCAGCCCATACAAGGCCATGGGGCTGGGC

AAGCTGCACGCCTGGGTCCGGGGTGGGCACGGTGCCCGGGCAACGAGCTGAAAGCTCAT

CTGCTCTCAGGGGCCCCTCCCTGGGGACAGCCCCTCCTGGCTAGTCACACCCTGTAGGCTC

CTCTATATAACCCAGGGGCACAGGGGCTGCCCCCGGGTCAC

SEQ ID NO: 19
CCTGAGTTTGAATCTCTCCAACTCAGCCAGCCTCAGTTTCCCCTCCACTCAGTCCCTAGGA

GGAAGGGGCGCCCAAGCGGGTTTCTGGGGTTAGACTGCCCTCCATTGCAATTGGTCCTTCT

CCCGGCCTCTGCTTCCTCCAGCTCACAGGGTATCTGCTCCTCCTGGAGCCACACCTTGGTT

CCCCGAGGTGCCGCTGGGACTCGGGTAGGGGTGAGGGCCCAGGGGCGACAGGGGGAGCC

GAGGGCCACAGGAAGGGCTGGTGGCTGAAGGAGACTCAGGGGCCAGGGGACGGTGGCTT

-continued

Sequence Listing

CTACGTGCTTGGGACGTTCCCAGCCACCGTCCCATGTTCCCGGCGGGGGCCAGCTGTCCCC

ACCGCCAGCCCAACTCAGCACTTGGTTAGGGTATCAGCTTGGTGGGGCGTGAGCCCAGC

CCTGGGGCGCTCAGCCCATACAAGGCCATGGGGCTGGGCGCAAAGCATGCCTGGGTTCAG

GGTGGGTATGGTGCCGGAGCAGGGAGGTGAGAGGCTCAGCTGCCCTCCAGAACTCCTCCC

TGGGGACAACCCCTCCCAGCCAATAGCACAGCCTAGGTCCCCCTATATAAGGCCACGGCT

GCTGGCCCTTCCTTTGGGTCAGTGTCACCTCCAGGATACAGACAGCCCCCCTT

SEQ ID NO: 20
CCACTACGGGTCTAGGCTGCCCATGTAAGGAGGCAAGGCCTGGGGACACCCGAGATGCCT

GGTTATAATTAACCCAGACATGTGGCTGCCCCCCCCCCCCCCAACACCTGCTGCCTGAGCCT

CACCCCCACCCCGGTGCCTGGGTCTTAGGCTCTGTACACCATGGAGGAGAAGCTCGCTCT

AAAAATAACCCTGTCCCTGGTGGAT

SEQ ID NO: 21
CCACTACGGGTCTAGGCTGCCCATGTAAGGAGGCAAGGCCTGGGGACACCCGAGATGCCT

GGTTATAATTAACCCCAACACCTGCTGCCCCCCCCCCCCCCAACACCTGCTGCCTGAGCCTG

AGCGGTTACCCCACCCCGGTGCCTGGGTCTTAGGCTCTGTACACCATGGAGGAGAAGCTC

GCTCTAAAAATAACCCTGTCCCTGGTGGAT

SEQ ID NO: 22
CCACTACGGGTCTAGGCTGCCCATGTAAGGAGGCAAGGCCTGGGGACACCCGAGATGCCT

GGTTATAATTAACCCCAACACCTGCTGCCCCCCCCCCCCCCAACACCTGCTGCCTGAGCCTG

AGCGGTTACCCCACCCCGGTGCCTGGGTCTTAGGCTCTGTACACCATGGAGGAGAAGCTC

GCTCTAAAAATAACCCTGTCCCTGGTGGATCCACTACGGGTCTAGGCTGCCCATGTAAGG

AGGCAAGGCCTGGGGACACCCGAGATGCCTGGTTATAATTAACCCCAACACCTGCTGCCC

CCCCCCCCCAACACCTGCTGCCTGAGCCTGAGCGGTTACCCCACCCCGGTGCCTGGGTCT

TAGGCTCTGTACACCATGGAGGAGAAGCTCGCTCTAAAAATAACCCTGTCCCTGGTGGAT

CCACTACGGGTCTAGGCTGCCCATGTAAGGAGGCAAGGCCTGGGGACACCCGAGATGCCT

GGTTATAATTAACCCCAACACCTGCTGCCCCCCCCCCCCCCAACACCTGCTGCCTGAGCCTG

AGCGGTTACCCCACCCCGGTGCCTGGGTCTTAGGCTCTGTACACCATGGAGGAGAAGCTC

GCTCTAAAAATAACCCTGTCCCTGGTGGATCCTCCCTGGGGACAGCCCCTCCTGGCTAGTC

ACACCCTGTAGGCTCCTCTATATAACCCAGGGGCACAGGGGCTGCCCCCGGGTCAC

SEQ ID NO: 23
AAGCTTGCATGTCTAAGCTAGACCCTTCAGATTAAAAATAACTGAGGTAAGGGCCTGGGT

AGGGGAGGTGGTGTGAGACGCTCCTGTCTCTCCTCTATCTGCCCATCGGCCCTTTGGGGAG

GAGGAATGTGCCCAAGGACTAAAAAAAGGCCATGGAGCCAGAGGGGCGAGGGCAACAG

ACCTTTCATGGGCAAACCTTGGGGCCCTGCTGTCTAGCATGCCCCACTACGGGTCTAGGCT

GCCCATGTAAGGAGGCAAGGCCTGGGGACACCCGAGATGCCTGGTTATAATTAACCCAGA

CATGTGGCTGCCCCCCCCCCCCCCAACACCTGCTGCCTCTAAAAATAACCCTGTCCCTGGTG

GATCCCCTGCATGCGAAGATCTTCGAACAAGGCTGTGGGGGACTGAGGGCAGGCTGTAAC

AGGCTTGGGGGCCAGGGCTTATACGTGCCTGGGACTCCCAAAGTATTACTGTTCCATGTTC

CCGGCGAAGGGCCAGCTGTCCCCCGCCAGCTAGACTCAGCACTTAGTTTAGGAACCAGTG

AGCAAGTCAGCCCTTGGGGCAGCCCATACAAGGCCATGGGGCTGGGCAAGCTGCACGCCT

GGGTCCGGGGTGGGCACGGTGCCCGGGCAACGAGCTGAAAGCTCATCTGCTCTCAGGGGC

-continued

---
Sequence Listing
---

CCCTCCCTGGGGACAGCCCCTCCTGGCTAGTCACACCCTGTAGGCTCCTCTATATAACCCA

GGGGCACAGGGGCTGCCCTCATTCTACCACCACCTCCACAGCACAGACAGACACTCAGGA

GCAGCCAGC

SEQ ID NO: 24
ATCAACCTCTGGATTACAAAATTTGTGAAAGATTGACTGATATTCTTAACTATGTTGCTCC

TTTTACGCTGTGTGGATATGCTGCTTTAATGCCTCTGTATCATGCTATTGCTTCCCGTACGG

CTTTCGTTTTCTCCTCCTTGTATAAATCCTGGTTGCTGTCTCTTTATGAGGAGTTGTGGCCC

GTTGTCCGTCAACGTGGCGTGGTGTGCTCTGTGTTTGCTGACGCAACCCCCACTGGCTGGG

GCATTGCCACCACCTGTCAACTCCTTTCTGGGACTTTCGCTTTCCCCCTCCCGATCGCCACG

GCAGAACTCATCGCCGCCTGCCTTGCCCGCTGCTGGACAGGGGCTAGGTTGCTGGGCACT

GATAATTCCGTGGTGTTGTCGGGGAAGCTGACGTCCTTTCCAGGGCTGCTCGCCTGTGTTG

CCAACTGGATCCTGCGCGGGACGTCCTTCTGCTACGTCCCTTCGGCTCTCAATCCAGCGGA

CCTCCCTTCCCGAGGCCTTCTGCCGGTTCTGCGGCCTCTCCCGCGTCTTCGCTTTCGGCCTC

CGACGAGTCGGATCTCCCTTTGGGCCGCCTCCCCGCCTG

SEQ ID NO: 25
MAPKKKRKVH

SEQ ID NO: 26
RAAKRPRTT

SEQ ID NO: 27
PAAKRVKLD

SEQ ID NO: 28
HHPKKKRKV

SEQ ID NO: 29
GATCCAGACATGATAAGATACATTGATGAGTTTGGACAAACCACAACTAGAATGCAGTGA

AAAAAATGCTTTATTTGTGAAATTTGTGATGCTATTGCTTTATTTGTAACCATTATAAGCT

GCAATAAACAAGTT

SEQ ID NO: 30
MAADGYLPDWLEDNLSEGIREWWDLKPGAPKPKANQQKQDNGRGLVLPGYKYLGPFNGLD

KGEPVNAADAAALEHDKAYDQQLQAGDNPYLRYNHADAEFQERLQEDTSFGGNLGRAVFQ

AKKRVLEPLGLVESPVKTAPGKKRPVEPSPQRSPDSSTGIGKKGQQPAKKRLNFGQTGDSESV

PDPQPIGEPPAGPSGLGSGTMAAGGGAPMADNNEGADGVGSSSGNWHCDSTWLGDRVITTST

RTWALPTYNNHLYKQISNGTSGGSTNDNTYFGYSTPWGYFDFNRFHCHFSPRDWQRLINNN

WGFRPKRLNFKLFNIQVKEVTQNEGTKTIANNLTSTIQVFTDSEYQLPYVLGSAHQGCLPPFPA

DVFMIPQYGYLTLNNGSQAVGRSSFYCLEYFPSQMLRTGNNFEFSYNFEDVPFHSSYAHSQSL

DRLMNPLIDQYLYYLSRTQSTGGTAGTQQLLFSQAGPNNMSAQAKNWLPGPCYRQQRVSTT

LSQNNNSNFAWTGATKYHLNGRDSLVNPGVAMATHKDDEERFFPSSGVLMFGKQGAGKDN

VDYSSVMLTSEEEIKTTNPVATEQYGVVADNLQQQNAAPIVGAVNSQGALPGMVWQNRDVY

LQGPIWAKIPHTDGNFHPSPLMGGFGLKHPPPQILIKNTPVPADPPTTFNQAKLASFITQYSTGQ

VSVEIEWELQKENSKRWNPEIQYTSNYYKSTNVDFAVNTEGTYSEPRPIGTRYLTRNL

SEQ ID NO: 31
MAADGYLPDWLEDNLSEGIREWWALKPGAPQPKANQQHQDNARGLVLPGYKYLGPGNGLD

KGEPVNAADAAALEHDKAYDQQLKAGDNPYLKYNHADAEFQERLKEDTSFGGNLGRAVFQ

-continued

---

Sequence Listing

---

AKKRLLEPLGLVEEAAKTAPGKKRPVEQSPQEPDSSAGIGKSGAQPAKKRLNFGQTGDTESVP

DPQPIGEPPAAPSGVGSLTMASGGGAPVADNNEGADGVGSSSGNWHCDSQWLGDRVITTSTR

TWALPTYNNHLYKQISNSTSGGSSNDNAYFGYSTPWGYFDFNRFHCHFSPRDWQRLINNNWG

FRPKRLNFKLFNIQVKEVTDNNGVKTIANNLTSTVQVFTDSDYQLPYVLGSAHEGCLPPFPAD

VFMIPQYGYLTLNDGSQAVGRSSFYCLEYFPSQMLRTGNNFQFSYEFENVPFHSSYAHSQSLD

RLMNPLIDQYLYYLSKTINGSGQNQQTLKFSVAGPSNMAVQGRNYIPGPSYRQQRVSTTVTQ

NNNSEFAWPGASSWALNGRNSLMNPGPAMASHKEGEDRFFPLSGSLIFGKQGTGRDNVDAD

KVMITNEEEIKTTNPVATESYGQVATNHQSAQAQAQTGWVQNQGILPGMVWQDRDVYLQG

PIWAKIPHTDGNFHPSPLMGGFGMKHPPPQILIKNTPVPADPPTAFNKDKLNSFITQYSTGQVS

VEIEWELQKENSKRWNPEIQYTSNYYKSNNVEFAVNTEGVYSEPRPIGTRYLTRNL

SEQ ID NO: 32
GCCACCATGG

SEQ ID NO: 33
MNTKYNKEFLLYLAGFVDGDGSIIAQIKPNQSYKFKHQLSLAFQVTQKTQRRWFLDKLVDEIG

VGYVRDRGSVSDYILSEIKPLHNFLTQLQPFLKLKQKQANLVLKIIWRLPSAKESPDKFLEVCT

WVDQIAALNDSKTRKTTSETVRAVLDSLSEKKKSSP

SEQ ID NO: 34
LAGLIDADG

SEQ ID NO: 35
MLWWEEVEDCYEREDVQKKTFTKWVNAQFSKFGKQHIENLFSDLQDGRRLLDLLEGLTGQK

LPKEKGSTRVHALNNVNKALRVLQNNNVDLVNIGSTDIVDGNHKLTLGLIWNIILHWQVKNV

MKNIMAGLQQTNSEKILLSWVRQSTRNYPQVNVINFTTSWSDGLALNALIHSHRPDLFDWNS

VVCQQSATQRLEHAFNIARYQLGIEKLLDPEDVDTTYPDKKSILMYITSLFQVLPQQVSIEAIQE

VEMLPRPPKVTKEEHFQLHHQMHYSQQITVSLAQGYERTSSPKPRFKSYAYTQAAYVTTSDPT

RSPFPSQHLEAPEDKSFGSSLMESEVNLDRYQTALEEVLSWLLSAEDTLQAQGEISNDVEVVK

DQFHTHEGYMMDLTAHQGRVGNILQLGSKLIGTGKLSEDEETEVQEQMNLLNSRWECLRVA

SMEKQSNLHRVLMDLQNQKLKELNDWLTKTEERTRKMEEEPLGPDLEDLKRQVQQHKVLQ

EDLEQEQVRVNSLTHMVVVVDESSGDHATAALEEQLKVLGDRWANICRWTEDRWVLLQDIL

LKWQRLTEEQCLFSAWLSEKEDAVNKIHTTGFKDQNEMLSSLQKLAVLKADLEKKKQSMGK

LYSLKQDLLSTLKNKSVTQKTEAWLDNFARCWDNLVQKLEKSTAQISQAVTTTQPSLTQTTV

METVTTVTTREQILVKHAQEELPPPPPQKKRQITVDSEIRKRLDVDITELHSWITRSEAVLQSPE

FAIFRKEGNFSDLKEKVNAIEREKAEKFRKLQDASRSAQALVEQMVNEGVNADSIKQASEQL

NSRWIEFCQLLSERLNWLEYQNNIIAFYNQLQQLEQMTTTAENWLKIQPTTPSEPTAIKSQLKI

CKDEVNRLSDLQPQIERLKIQSIALKEKGQGPMFLDADFVAFTNHFKQVFSDVQAREKELQTIF

DTLPPMRYQETMSAIRTWVQQSETKLSIPQLSVTDYEIMEQRLGELQALQSSLQEQQSGLYYL

STTVKEMSKKAPSEISRKYQSEFEEIEGRWKKLSSQLVEHCQKLEEQMNKLRKIQNHIQTLKK

WMAEVDVFLKEEWPALGDSEILKKQLKQCRLLVSDIQTIQPSLNSVNEGGQKIKNEAEPEFAS

RLETELKELNTQWDHMCQQVYARKEALKGGLEKTVSLQKDLSEMHEWMTQAEEEYLERDF

EYKTPDELQKAVEEMKRAKEEAQQKEAKVKLLTESVNSVIAQAPPVAQEALKKELETLTTNY

QWLCTRLNGKCKTLEEVWACWHELLSYLEKANKWLNEVEFKLKTTENIPGGAEEISEVLDSL

ENLMRHSEDNPNQIRILAQTLTDGGVMDELINEELETFNSRWRELHEEAVRRQKLLEQSIQSA

-continued

Sequence Listing

QETEKSLHLIQESLTFIDKQLAAYIADKVDAAQMPQEAQKIQSDLTSHEISLEEMKKHNQGKE

AAQRVLSQIDVAQKKLQDVSMKFRLFQKPANFEQRLQESKMILDEVKMHLPALETKSVEQEV

VQSQLNHCVNLYKSLSEVKSEVEMVIKTGRQIVQKKQTENPKELDERVTALKLHYNELGAKV

TERKQQLEKCLKLSRKMRKEMNVLTEWLAATDMELTKRSAVEGMPSNLDSEVAWGKATQK

EIEKQKVHLKSITEVGEALKTVLGKKETLVEDKLSLLNSNWIAVTSRAEEWLNLLLEYQKHM

ETFDQNVDHITKWIIQADTLLDESEKKKPQQKEDVLKRLKAELNDIRPKVDSTRDQAANLMA

NRGDHCRKLVEPQISELNHRFAAISHRIKTGKASIPLKELEQFNSDIQKLLEPLEAEIQQGVNLK

EEDFNKDMNEDNEGTVKELLQRGDNLQQRITDERKREEIKIKQQLLQTKHNALKDLRSQRRK

KALEISHQWYQYKRQADDLLKCLDDIEKKLASLPEPRDERKIKEIDRELQKKKEELNAVRRQA

EGLSEDGAAMAVEPTQIQLSKRWREIESKFAQFRRLNFAQIHTVREETMMVMTEDMPLEISYV

PSTYLTEITHVSQALLEVEQLLNAPDLCAKDFEDLFKQEESLKNIKDSLQQSSGRIDIIHSKKTA

ALQSATPVERVKLQEALSQLDFQWEKVNKMYKDRQGRFDRSVEKWRRFHYDIKIFNQWLTE

AEQFLRKTQIPENWEHAKYKWYLKELQDGIGQRQTVVRTLNATGEEIIQQSSKTDASILQEKL

GSLNLRWQEVCKQLSDRKKRLEEQKNILSEFQRDLNEFVLWLEEADNIASIPLEPGKEQQLKE

KLEQVKLLVEELPLRQGILKQLNETGGPVLVSAPISPEEQDKLENKLKQTNLQWIKVSRALPEK

QGEIEAQIKDLGQLEKKLEDLEEQLNHLLLWLSPIRNQLEIYNQPNQEGPFDVKETEIAVQAKQ

PDVEEILSKGQHLYKEKPATQPVKRKLEDLSSEWKAVNRLLQELRAKQPDLAPGLTTIGASPT

QTVTLVTQPVVTKETAISKLEMPSSLMLEVPALADFNRAWTELTDWLSLLDQVIKSQRVMVG

DLEDINEMIIKQKATMQDLEQRRPQLEELITAAQNLKNKTSNQEARTIITDRIERIQNQWDEVQ

EHLQNRRQQLNEMLKDSTQWLEAKEEAEQVLGQARAKLESWKEGPYTVDAIQKKITETKQL

AKDLRQWQTNVDVANDLALKLLRDYSADDTRKVHMITENINASWRSIHKRVSEREAALEET

HRLLQQFPLDLEKFLAWLTEAETTANVLQDATRKERLLEDSKGVKELMKQWQDLQGEIEAH

TDVYHNLDENSQKILRSLEGSDDAVLLQRRLDNMNFKWSELRKKSLNIRSHLEASSDQWKRL

HLSLQELLVWLQLKDDELSRQAPIGGDFPAVQKQNDVHRAFKRELKTKEPVIMSTLETVRIFL

TEQPLEGLEKLYQEPRELPPEERAQNVTRLLRKQAEEVNTEWEKLNLHSADWQRKIDETLERL

RELQEATDELDLKLRQAEVIKGSWQPVGDLLIDSLQDHLEKVKALRGEIAPLKENVSHVNDL

ARQLTTLGIQLSPYNLSTLEDLNTRWKLLQVAVEDRVRQLHEAHRDFGPASQHELSTSVQGP

WERAISPNKVPYYINHETQTTCWDHPKMTELYQSLADLNNVRFSAYRTAMKLRRLQKALCL

DLLSLSAACDALDQHNLKQNDQPMDILQIINCLTTIYDRLEQEHNNLVNVPLCVDMCLNWLL

NVYDTGRTGRIRVLSFKTGIISLCKAHLEDKYRYLFKQVASSTGFCDQRRLGLLLHDSIQIPRQ

LGEVASFGGSNIEPSVRSCFQFANNKPEIEAALFLDWMRLEPQSMVWLPVLHRVAAAETAKH

QAKCNICKECPIIGFRYRSLKHFNYDICQSCFFSGRVAKGHKMHYPMVEYCTPTTSGEDVRDF

AKVLKNKFRTKRYFAKHPRMGYLPVQTVLEGDNMETPVTLINFWPVDSAPASSPQLSHDDTH

SRIEHYASRLAEMENSNGSYLNDSISPNESIDDEHLLIQHYCQSLNQDSPLSQPRSPAQILISLES

EERGELERILADLEEENRNLQAEYDRLKQQHEHKGLSPLPSPPEMMPTSPQSPRDAELIAEAKL

LRQHKGRLEARMQILEDHNKQLESQLHRLRQLLEQPQAEAKVNGTTVSSPSTSLQRSDSSQPM

LLRVVGSQTSDSMGEEDLLSPPQDTSTGLEEVMEQLNNSFPSSRGRNTPGKPMREDTM

-continued

Sequence Listing

SEQ ID NO: 36

MLWWEEVEDCYEREDVQKKTFTKWVNAQFSKFGKQHIENLFSDLQDGRRLLDLLEGLTGQK

LPKEKGSTRVHALNNVNKALRVLQNNNVDLVNIGSTDIVDGNHKLTLGLIWNIILHWQVKNV

MKNIMAGLQQTNSEKILLSWVRQSTRNYPQVNVINFTTSWSDGLALNALIHSHRPDLFDWNS

VVCQQSATQRLEHAFNIARYQLGIEKLLDPEDVDTTYPDKKSILMYITSLFQVLPQQVSIEAIQE

VEMLPRPPKVTKEEHFQLHHQMHYSQQITVSLAQGYERTSSPKPRFKSYAYTQAAYVTTSDPT

RSPFPSQHLEAPEDKSFGSSLMESEVNLDRYQTALEEVLSWLLSAEDTLQAQGEISNDVEVVK

DQFHTHEGYMMDLTAHQGRVGNILQLGSKLIGTGKLSEDEETEVQEQMNLLNSRWECLRVA

SMEKQSNLHRVLMDLQNQKLKELNDWLTKTEERTRKMEEEPLGPDLEDLKRQVQQHKVLQ

EDLEQEQVRVNSLTHMVVVVDESSGDHATAALEEQLKVLGDRWANICRWTEDRWVLLQDIL

LKWQRLTEEQCLFSAWLSEKEDAVNKIHTTGFKDQNEMLSSLQKLAVLKADLEKKKQSMGK

LYSLKQDLLSTLKNKSVTQKTEAWLDNFARCWDNLVQKLEKSTAQISQAVTTTQPSLTQTTV

METVTTVTTREQILVKHAQEELPPPPPQKKRQITVDSEIRKRLDVDITELHSWITRSEAVLQSPE

FAIFRKEGNFSDLKEKVNAIEREKAEKFRKLQDASRSAQALVEQMVNEGVNADSIKQASEQL

NSRWIEFCQLLSERLNWLEYQNNIIAFYNQLQQLEQMTTTAENWLKIQPTTPSEPTAIKSQLKI

CKDEVNRLSDLQPQIERLKIQSIALKEKGQGPMFLDADFVAFTNHFKQVFSDVQAREKELQTIF

DTLPPMRYQETMSAIRTWVQQSETKLSIPQLSVTDYEIMEQRLGELQALQSSLQEQQSGLYYL

STTVKEMSKKAPSEISRKYQSEFEEIEGRWKKLSSQLVEHCQKLEEQMNKLRKIQNHIQTLKK

WMAEVDVFLKEEWPALGDSEILKKQLKQCRLLVSDIQTIQPSLNSVNEGGQKIKNEAEPEFAS

RLETELKELNTQWDHMCQQVYARKEALKGGLEKTVSLQKDLSEMHEWMTQAEEEYLERDF

EYKTPDELQKAVEEMKRAKEEAQQKEAKVKLLTESVNSVIAQAPPVAQEALKKELETLTTNY

QWLCTRLNGKCKTLEEVWACWHELLSYLEKANKWLNEVEFKLKTTENIPGGAEEISEVLDSL

ENLMRHSEDNPNQIRILAQTLTDGGVMDELINEELETFNSRWRELHEEAVRRQKLLEQSIQSA

QETEKSLHLIQESLTFIDKQLAAYIADKVDAAQMPQEAQKIQSDLTSHEISLEEMKKHNQGKE

AAQRVLSQIDVAQKKLQDVSMKFRLFQKPANFEQRLQESKMILDEVKMHLPALETKSVEQEV

VQSQLNHCVNLYKSLSEVKSEVEMVIKTGRQIVQKKQTENPKELDERVTALKLHYNELGAKV

TERKQQLEKCLKLSRKMRKEMNVLTEWLAATDMELTKRSAVEGMPSNLDSEVAWGKATQK

EIEKQKVHLKSITEVGEALKTVLGKKETLVEDKLSLLNSNWIAVTSRAEEWLNLLLEYQKHM

ETFDQNVDHITKWIIQADTLLDESEKKKPQQKEDVLKRLKAELNDIRPKVDSTRDQAANLMA

NRGDHCRKLVEPQISELNHRFAAISHRIKTGKASIPLKELEQFNSDIQKLLEPLEAEIQQGVNLK

EEDFNKDMNEDNEGTVKELLQRGDNLQQRITDERKREEIKIKQQLLQTKHNALKDLRSQRRK

KALEISHQWYQYKRQADDLLKCLDDIEKKLASLPEPRDERKIKEIDRELQKKKEELNAVRRQA

EGLSEDGAAMAVEPTQIQLSKRWREIESKFAQFRRLNFAQIHTVREETMMVMTEDMPLEISYV

PSTYLTEITHVSQALLEVEQLLNAPDLCAKDFEDLFKQEESLKNIKDSLQQSSGRIDIIHSKKTA

ALQSATPVERVKLQEALSQLDFQWEKVNKMYKDRQGRFDRSVEKWRRFHYDIKIFNQWLTE

AEQFLRKTQIPENWEHAKYKWYLKDLQGEIEAHTDVYHNLDENSQKILRSLEGSDDAVLLQR

RLDNMNFKWSELRKKSLNIRSHLEASSDQWKRLHLSLQELLVWLQLKDDELSRQAPIGGDFP

AVQKQNDVHRAFKRELKTKEPVIMSTLETVRIFLTEQPLEGLEKLYQEPRELPPEERAQNVTRL

-continued

---

Sequence Listing

---

LRKQAEEVNTEWEKLNLHSADWQRKIDETLERLRELQEATDELDLKLRQAEVIKGSWQPVG

DLLIDSLQDHLEKVKALRGEIAPLKENVSHVNDLARQLTTLGIQLSPYNLSTLEDLNTRWKLL

QVAVEDRVRQLHEAHRDFGPASQHELSTSVQGPWERAISPNKVPYYINHETQTTCWDHPKMT

ELYQSLADLNNVRFSAYRTAMKLRRLQKALCLDLLSLSAACDALDQHNLKQNDQPMDILQII

NCLTTIYDRLEQEHNNLVNVPLCVDMCLNWLLNVYDTGRTGRIRVLSFKTGIISLCKAHLEDK

YRYLFKQVASSTGFCDQRRLGLLLHDSIQIPRQLGEVASFGGSNIEPSVRSCFQFANNKPEIEAA

LFLDWMRLEPQSMVWLPVLHRVAAAETAKHQAKCNICKECPIIGFRYRSLKHFNYDICQSCFF

SGRVAKGHKMHYPMVEYCTPTTSGEDVRDFAKVLKNKFRTKRYFAKHPRMGYLPVQTVLE

GDNMETPVTLINFWPVDSAPASSPQLSHDDTHSRIEHYASRLAEMENSNGSYLNDSISPNESID

DEHLLIQHYCQSLNQDSPLSQPRSPAQILISLESEERGELERILADLEEENRNLQAEYDRLKQQH

EHKGLSPLPSPPEMMPTSPQSPRDAELIAEAKLLRQHKGRLEARMQILEDHNKQLESQLHRLR

QLLEQPQAEAKVNGTTVSSPSTSLQRSDSSQPMLLRVVGSQTSDSMGEEDLLSPPQDTSTGLEE

VMEQLNNSFPSSRGRNTPGKPMREDTM

SEQ ID NO: 37
AAGGATTATGTATTACCTCCCG

SEQ ID NO: 38
TTCCTAATACATAATGGAGGGC

SEQ ID NO: 39
CTACATGGTGTATCTGACTAAG

SEQ ID NO: 40
GATGTACCACATAGACTGATTC

SEQ ID NO: 41
AAGGATTATGTATCTGACTAAG

SEQ ID NO: 42
TTCCTAATACATAGACTGATTC

SEQ ID NO: 43
MNTKYNKEFLLYLAGFVDSDGSIYATIRPVQSTKFKHTLRLWFAVTQKTQRRWFLDKLVDEI

GVGYVYDNGSVSWYYLSEIKPLHNFLTQLQPFLKLKQKQANLVLKIIEQLPSAKESPDKFLEV

CTWVDQIAALNDSKTRKTTSETVRAVLDSLPGSVGGLSPSQASSAASSASSSPGSGISEALRAG

AGSGTGYNKEFLLYLAGFVDGDGSICACIVPRQDRKFKHQLRLFFEVGQKTKRRWFLDKLVD

EIGVGYVEDTGRASRYRLSQIKPLHNFLTQLQPFLKLKQKQANLVLKIIEQLPSAKESPDKFLE

VCTWVDQIAALNDSRTRKTTSETVRAVLDSLSEKKKSSP

SEQ ID NO: 44
MNTKYNKEFLLYLAGFVDSDGSIFAVIEPVQSAKFKHRLKLSFVVTQKTQRRWFLDKLVDEIG

VGYVYDQGSVSFYRLSEIKPLHNFLTQLQPFLKLKQKQANLVLKIIEQLPSAKESPDKFLEVCT

WVDQIAALNDSKTRKTTSETVRAVLDSLPGSVGGLSPSQASSAASSASSSPGSGISEALRAGAG

SGTGYNKEFLLYLAGFVDGDGSICACIVPRQDRKFKHQLRLFFEVGQTTRRRWFLDKLVDEIG

VGYVFDKGSASMYRLSEIKPLHNFLTQLQPFLKLKQKQANLVLKIIEQLPSAKESPDKFLEVCT

WVDQIAALNDSRTRKTTSETVRAVLDSLSEKKKSSP

SEQ ID NO: 45
MNTKYNKEFLLYLAGFVDSDGSIYASIMPIQTAKFKHRLKLQFAVAQKTQRRWFLDKLVDEI

GVGYVYDFGSVSYYRLSQIKPLHNFLTQLQPFLKLKQKQANLVLKIIEQLPSAKESPDKFLEVC

TWVDQIAALNDSKTRKTTSETVRAVLDSLPGSVGGLSPSQASSAASSASSSPGSGISEALRAGA

-continued

Sequence Listing

GSGTGYNKEFLLYLAGFVDGDGSICACIVPRQDRKFKHQLRLFFEVGQKTQRRWFLDKLVDEI

GVGYVRDLGSASTYRLSEIKPLHNFLTQLQPFLKLKQKQANLVLKIIEQLPSAKESPDKFLEVC

TWVDQIAALNDSRTRKTTSETVRAVLDSLSEKKKSSP

```
                                                           SEQ ID NO: 46
MNTKYNKEFLLYLAGFVDSDGSIIAFIMPSQTAKFKHRLKLQFAVAQKTQRRWFLDKLVDEIG

VGYVYDFGSVSYYRLSQIKPLHNFLTQLQPFLKLKQKQANLVLKIIEQLPSAKESPDKFLEVCT

WVDQIAALNDSKTRKTTSETVRAVLDSLPGSVGGLSPSQASSAASSASSSPGSGISEALRAGAG

SGTGYNKEFLLYLAGFVDGDGSICACIVPRQDRKFKHQLRLFFEIGQKTQRRWFLDKLVDEIG

VGYVRDLGSASTYRLSQIKPLHNFLTQLQPFLKLKQKQANLVLKIIEQLPSAKESPDKFLEVCT

WVDQIAALNDSKTRKTTSETVRAVLDSLSEKKKSSP
```

```
                                                           SEQ ID NO: 47
MNTKYNKEFLLYLAGFVDSDGSIMAFIMPTQTAKFKHRLKLQFAVAQKTQRRWFLDKLVDEI

GVGYVYDFGSVSYYRLSEIKPLHNFLTQLQPFLKLKQKQANLVLKIIEQLPSAKESPDKFLEVC

TWVDQIAALNDSKTRKTTSETVRAVLDSLPGSVGGLSPSQASSAASSASSSPGSGISEALRAGA

GSGTGYNKEFLLYLAGFVDGDGSICACIVPRQDRKFKHQLRLFFEVGQKTQRRWFLDKLVDEI

GVGYVRDLGSASTYRLSQIKPLHNFLTQLQPFLKLKQKQANLVLKIIEQLPSAKESPDKFLEVC

TWVDQIAALNDSRTRKTTSETVRAVLDSLSEKKKSSP
```

```
                                                           SEQ ID NO: 48
MNTKYNKEFLLYLAGFVDSDGSIMAFILPEQHMKFKHRLRLQFAVAQKTQRRWFLDKLVDEI

GVGYVYDFGSVSYYRLSEIKPLHNFLTQLQPFLKLKQKQANLVLKIIEQLPSAKESPDKFLEVC

TWVDQIAALNDSKTRKTTSETVRAVLDSLPGSVGGLSPSQASSAASSASSSPGSGISEALRAGA

GSGTGYNKEFLLYLAGFVDGDGSICACIVPRQDRKFKHQLRLFFEVGQKTQRRWFLDKLVDEI

GVGYVRDLGSASTYRLSEIKPLHNFLTQLQPFLKLKQKQANLVLKIIEQLPSAKESPDKFLEVC

TWVDQIAALNDSRTRKTTSETVRAVLDSLSEKKKSSP
```

```
                                                           SEQ ID NO: 49
MNTKYNKEFLLYLAGFVDSDGSIMAFILPEQHLKFKHRLRLQFAVAQKTQRRWFLDKLVDEI

GVGYVYDFGSVSYYRLSEIKPLHNFLTQLQPFLKLKQKQANLVLKIIEQLPSAKESPDKFLEVC

TWVDQIAALNDSKTRKTTSETVRAVLDSLPGSVGGLSPSQASSAASSASSSPGSGISEALRAGA

GSGTGYNKEFLLYLAGFVDGDGSICACIVPRQDRKFKHQLRLFFEVGQKTQRRWFLDKLVDEI

GVGYVRDLGSASTYRLSEIKPLHNFLTQLQPFLKLKQKQANLVLKIIEQLPSAKESPDKFLEVC

TWVDQIAALNDSRTRKTTSETVRAVLDSLSEKKSSP
```

```
                                                           SEQ ID NO: 50
MNTKYNKEFLLYLAGFVDSDGSIMAFILPEQGLKFKHRLRLQFAVAQKTQRRWFLDKLVDEI

GVGYVYDFGSVSYYRLSQIKPLHNFLTQLQPFLKLKQKQANLVLKIIEQLPSAKESPDKFLEVC

TWVDQIAALNDSKTRKTTSETVRAVLDSLPGSVGGLSPSQASSAASSASSSPGSGISEALRAGA

GSGTGYNKEFLLYLAGFVDGDGSICACIVPRQDRKFKHQLRLFFEVGQKTQRRWFLDKLVDEI

GVGYVRDLGSASTYRLSQIKPLHNFLTQLQPFLKLKQKQANLVLKIIEQLPSAKESPDKFLEVC

TWVDQIAALNDSRTRKTTSETVRAVLDSLSEKKKSSP
```

```
                                                           SEQ ID NO: 51
MNTKYNKEFLLYLAGFVDSDGSIMAFIMPDQAPKFKHRLRLQFAVAQKTQRRWFLDKLVDEI

GVGYVYDFGSVSYYRLSEIKPLHNFLTQLQPFLKLKQKQANLVLKIIEQLPSAKESPDKFLEVC

TWVDQIAALNDSKTRKTTSETVRAVLDSLPGSVGGLSPSQASSAASSASSSPGSGISEALRAGA
```

-continued

Sequence Listing

GSGTGYNKEFLLYLAGFVDGDGSICACIVPRQDRKFKHQLRLFFEVGQKTQRRWFLDKLVDEI

GVGYVRDLGSASTYRLSQIKPLHNFLTQLQPFLKLKQKQANLVLKIIEQLPSAKESPDKFLEVC

TWVDQIAALNDSRTRKTTSETVRAVLDSLSEKKKSSP

SEQ ID NO: 52
MNTKYNKEFLLYLAGFVDADGSIYACIKPHQQLKFKHQLLLYFEVYQKTQRRWFLDKLVDEI

GVGYVADRGSVSEYRLSQIKPLHNFLTQLQPFLKLKQKQANLVLKIIEQLPSAKESPDKFLEVC

TWVDQIAALNDSKTRKTTSETVRAVLDSLPGSVGGLSPSQASSAASSASSSPGSGISEALRAGA

GSGTGYNKEFLLYLAGFVDGDGSIFASIMPTQWTKFKHSLLLRFRVTQSTRRRWFLDKLMDEI

GVGYVSDQGRASYYTLSEIKPLHNFLTQLQPFLKLKQKQANLVLKIIEQLPSAKESPDKFLEVC

TWVDQIAALNDSRTRKTTSETVRAVLDSLSEKKKSSP

SEQ ID NO: 53
MNTKYNKEFLLYLAGFVDADGSIYACIKPHQQLKFKHQLLLYFEVYQKTQRRWFLDKLVDEI

GVGYVIDSGSVSTYRLSQIKPLHNFLTQLQPFLKLKQKQANLVLKIIEQLPSAKESPDKFLEVCT

WVDQIAALNDSKTRKTTSETVRAVLDSLPGSVGGLSPSQASSAASSASSSPGSGISEALRAGAG

SGTGYNKEFLLYLAGFVDGDGSIFASIIPSQLVKFKHTLLLRFRVTQATRRRWFLDKLVDEIGV

GYVTDNGRASYYTLSEIKPLHNFLTQLQPFLKLKQKQANLVLKIIEQLPSAKESPDKFLEVCTW

VDQIAALNDSRTRKTTSETVRAVLDSLSEKKKSSP

SEQ ID NO: 54
MNTKYNKEFLLYLAGFVDADGSIYACIKPHQQLKFKHQLLLYFEVYQKTQRRWFLDKLVDEI

GVGYVADRGSVSEYRLSQIKPLHNFLTQLQPFLKLKQKQANLVLKIIEQLPSAKESPDKFLEVC

TWVDQIAALNDSKTRKTTSETVRAVLDSLPGSVGGLSPSQASSAASSASSSPGSGISEALRAGA

GSGTGYNKEFLLYLAGFVDGDGSIFASIIPSQLVKFKHTLLLRFRVCQATKRRWFLDKLVDEIG

VGYVSDQGSASYYTLSEIKPLHNFLTQLQPFLKLKQKQANLVLKIIEQLPSAKESPDKFLEVCT

WVDQIAALNDSRTRKTTSETVRAVLDSLSEKKKSSP

SEQ ID NO: 55
MNTKYNKEFLLYLAGFVDSDGSIYACIKPHQQLKFKHQLLLYFEVYQKTQRRWFLDKLVDEI

GVGYVADRGSVSEYRLSQIKPLHNFLTQLQPFLKLKQKQANLVLKIIEQLPSAKESPDKFLEVC

TWVDQIAALNDSKTRKTTSETVRAVLDSLPGSVGGLSPSQASSAASSASSSPGSGISEALRAGA

GSGTGYNKEFLLYLAGFVDGDGSIFASIIPSQEVKFKHTLLLRFRVCQATKRRWFLDKLVDEIG

VGYVSDQGSASYYTLSEIKPLHNFLTQLQPFLKLKQKQANLVLKIIEQLPSAKESPDKFLEVCT

WVDQIAALNDSRTRKTTSETVRAVLDSLSEKKKSSP

SEQ ID NO: 56
MNTKYNKEFLLYLAGFVDADGSIYACIKPHQQLKFKHQLLLYFEVYQKTQRRWFLDKLVDEI

GVGYVADRGSVSEYRLSQIKPLHNFLTQLQPFLKLKQKQANLVLKIIEQLPSAKESPDKFLEVC

TWVDQIAALNDSKTRKTTSETVRAVLDSLPGSVGGLSPSQASSAASSASSSPGSGISEALRAGA

GSGTGYNKEFLLYLAGFVDGDGSIFASIIPSQEVKFKHTLLLRFRVCQATKRRWFLDKLVDEIG

VGYVSDQGSASYYTLSEIKPLHNFLTQLQPFLKLKQKQANLVLKIIEQLPSAKESPDKFLEVCT

WVDQIAALNDSRTRKTTSETVRAVLDSLSEKKKSSP

SEQ ID NO: 57
MNTKYNKEFLLYLAGFVDADGSIYACIKPHQQLKFKHQLLLYFEVYQKTQRRWFLDKLVDEI

GVGYVADRGSVSEYRLSQIKPLHNFLTQLQPFLKLKQKQANLVLKIIEQLPSAKESPDKFLEVC

| Sequence Listing |
| --- |

TWVDQIAALNDSKTRKTTSETVRAVLDSLPGSVGGLSPSQASSAASSASSSPGSGISEALRAGA

GSGTGYNKEFLLYLAGFVDGDGSIFASIIPSQEVKFKHTLLLRFRVTQATKRRWFLDKLVDEIG

VGYVSDVGSASYYTLSEIKPLHNFLTQLQPFLKLKQKQANLVLKIIEQLPSAKESPDKFLEVCT

WVDQIAALNDSRTRKTTSETVRAVLDSLSEKKKSSP

SEQ ID NO: 58
MNTKYNKEFLLYLAGFVDSDGSIYACIKPHQQLKFKHQLLLYFEVYQKTQRRWFLDKLVDEI

GVGYVADRGSVSEYRLSQIKPLHNFLTQLQPFLKLKQKQANLVLKIIEQLPSAKESPDKFLEVC

TWVDQIAALNDSKTRKTTSETVRAVLDSLPGSVGGLSPSQASSAASSASSSPGSGISEALRAGA

GSGTGYNKEFLLYLAGFVDGDGSIFASIIPSQEVKFKHTLLLRFRVCQATKRRWFLDKLVDEIG

VGYVSDRGSASYYTLSEIKPLHNFLTQLQPFLKLKQKQANLVLKIIEQLPSAKESPDKFLEVCT

WVDQIAALNDSRTRKTTSETVRAVLDSLSEKKKSSP

SEQ ID NO: 59
MNTKYNKEFLLYLAGFVDADGSIYACIKPHQELKFKHQLLLYFEVYQKTQRRWFLDKLVDEI

GVGYVADRGSVSEYRLSEIKPLHNFLTQLQPFLKLKQKQANLVLKIIEQLPSAKESPDKFLEVC

TWVDQIAALNDSKTRKTTSETVRAVLDSLPGSVGGLSPSQASSAASSASSSPGSGISEALRAGA

GSGTGYNKEFLLYLAGFVDGDGSIFASIIPSQEVKFKHTLLLRFRVCQATKRRWFLDKLVDEIG

VGYVSDQGSASYYTLSQIKPLHNFLTQLQPFLKLKQKQANLVLKIIEQLPSAKESPDKFLEVCT

WVDQIAALNDSRTRKTTSETVRAVLDSLSEKKKSSP

SEQ ID NO: 60
ATGAATACAAAATATAATAAAGAGTTCTTACTCTACTTAGCAGGGTTTGTAGACTCTGAC

GGTTCCATCTATGCCACGATCCGGCCTGTTCAAAGTACTAAGTTCAAGCACACTCTGCGGC

TCTGGTTCGCGGTCACGCAGAAGACACAGCGCCGTTGGTTCCTCGACAAGCTGGTGGACG

AGATCGGTGTGGGTTACGTGTATGACAATGGCAGCGTCTCCTGGTACTATCTGTCCGAGAT

CAAGCCTTTGCATAATTTTTTAACACAACTACAACCTTTTCTAAAACTAAAACAAAAACAA

GCAAATTTAGTTTTAAAAATTATTGAACAACTTCCGTCAGCAAAAGAATCCCCGGACAAA

TTCTTAGAAGTTTGTACATGGGTGGATCAAATTGCAGCTCTGAATGATTCGAAGACGCGT

AAAACAACTTCTGAAACCGTTCGTGCTGTGCTAGACAGTTTACCAGGATCCGTGGGAGGT

CTATCGCCATCTCAGGCATCCAGCGCCGCATCCTCGGCTTCCTCAAGCCCGGGTTCAGGGA

TCTCCGAAGCACTCAGAGCTGGAGCAGGTTCCGGCACTGGATACAACAAGGAATTCCTGC

TCTACCTGGCGGGCTTCGTCGACGGGGACGGCTCCATCTGTGCCTGTATCGTGCCTCGTCA

AGATCGGAAGTTCAAGCACCAGCTGCGGCTCTTTTTCGAGGTCGGTCAGAAGACAAAGCG

CCGTTGGTTCCTCGACAAGCTGGTGGACGAGATCGGTGTGGGTTACGTGGAGGACACGGG

CAGGGCGAGCAGGTACCGGCTGTCCCAGATCAAGCCTCTGCACAACTTCCTGACCCAGCT

CCAGCCCTTCCTGAAGCTCAAGCAGAAGCAGGCCAACCTCGTGCTGAAGATCATCGAGCA

GCTGCCCTCCGCCAAGGAATCCCCGGACAAGTTCCTGGAGGTGTGCACCTGGGTGGACCA

GATCGCCGCTCTGAACGACTCCAGGACCCGCAAGACCACTTCCGAAACCGTCCGCGCCGT

TCTAGACAGTCTCTCCGAGAAGAAGAAGTCGTCCCCC

SEQ ID NO: 61
ATGAATACAAAATATAATAAAGAGTTCTTACTCTACTTAGCAGGGTTTGTAGACTCTGAC

GGTTCCATCTTTGCCGTTATCGAGCCTGTTCAAAGTGCTAAGTTCAAGCACCGGCTGAAGC

TCTCGTTCGTTGTCACTCAGAAGACACAGCGCCGTTGGTTCCTCGACAAGCTGGTGGACG

-continued

Sequence Listing

AGATCGGTGTGGGTTACGTGTATGACCAGGGCAGCGTCTCCTTTTACAGGCTGTCCGAGA

TCAAGCCTTTGCATAATTTTTTAACACAACTACAACCTTTTCTAAAACTAAAACAAAAACA

AGCAAATTTAGTTTTAAAAATTATTGAACAACTTCCGTCAGCAAAAGAATCCCCGGACAA

ATTCTTAGAAGTTTGTACATGGGTGGATCAAATTGCAGCTCTGAATGATTCGAAGACGCG

TAAAACAACTTCTGAAACCGTTCGTGCTGTGCTAGACAGTTTACCAGGATCCGTGGGAGG

TCTATCGCCATCTCAGGCATCCAGCGCCGCATCCTCGGCTTCCTCAAGCCCGGGTTCAGGG

ATCTCCGAAGCACTCAGAGCTGGAGCAGGTTCCGGCACTGGATACAACAAGGAATTCCTG

CTCTACCTGGCGGGCTTCGTCGACGGGGACGGCTCCATCTGTGCCTGTATCGTGCCTCGTC

AAGATCGGAAGTTCAAGCACCAGCTGCGGCTCTTTTTCGAGGTCGGGCAGACGACAAGGC

GCCGTTGGTTCCTCGACAAGCTGGTGGACGAGATCGGTGTGGGTTACGTGTTTGACAAGG

GCAGCGCGAGCATGTACCGGCTGTCCGAGATCAAGCCTCTGCACAACTTCCTGACCCAGC

TCCAGCCCTTCCTGAAGCTCAAGCAGAAGCAGGCCAACCTCGTGCTGAAGATCATCGAGC

AGCTGCCCTCCGCCAAGGAATCCCCGGACAAGTTCCTGGAGGTGTGCACCTGGGTGGACC

AGATCGCCGCTCTGAACGACTCCAGGACCCGCAAGACCACTTCCGAAACCGTCCGCGCCG

TTCTAGACAGTCTCTCCGAGAAGAAGAAGTCGTCCCCC

SEQ ID NO: 62

ATGAATACAAAATATAATAAAGAGTTCTTACTCTACTTAGCAGGGTTTGTAGACTCTGAC

GGTTCCATCTATGCCAGTATCATGCCTATTCAAACGGCTAAGTTCAAGCACCGTCTGAAGC

TCCAGTTCGCGGTCGCTCAGAAGACACAGCGCCGTTGGTTCCTCGACAAGCTGGTGGACG

AGATCGGTGTGGGTTACGTGTATGACTTTGGCAGCGTCTCCTATTACAGGCTGTCCCAGAT

CAAGCCTTTGCATAATTTTTTAACACAACTACAACCTTTTCTAAAACTAAAACAAAAACAA

GCAAATTTAGTTTTAAAAATTATTGAACAACTTCCGTCAGCAAAAGAATCCCCGGACAAA

TTCTTAGAAGTTTGTACATGGGTGGATCAAATTGCAGCTCTGAATGATTCGAAGACGCGT

AAAACAACTTCTGAAACCGTTCGTGCTGTGCTAGACAGTTTACCAGGATCCGTGGGAGGT

CTATCGCCATCTCAGGCATCCAGCGCCGCATCCTCGGCTTCCTCAAGCCCGGGTTCAGGGA

TCTCCGAAGCACTCAGAGCTGGAGCAGGTTCCGGCACTGGATACAACAAGGAATTCCTGC

TCTACCTGGCGGGCTTCGTCGACGGGGACGGCTCCATCTGTGCCTGTATCGTGCCTCGTCA

AGATCGGAAGTTCAAGCACCAGCTGCGGCTCTTTTTCGAGGTCGGTCAGAAGACACAGCG

CCGTTGGTTCCTCGACAAGCTGGTGGACGAGATCGGTGTGGGTTACGTGAGGGACCTTGG

CAGCGCGAGCACTTACCGTCTGTCCGAGATCAAGCCTCTGCACAACTTCCTGACCCAGCTC

CAGCCCTTCCTGAAGCTCAAGCAGAAGCAGGCCAACCTCGTGCTGAAGATCATCGAGCAG

CTGCCCTCCGCCAAGGAATCCCCGGACAAGTTCCTGGAGGTGTGCACCTGGGTGGACCAG

ATCGCCGCTCTGAACGACTCCAGGACCCGCAAGACCACTTCCGAAACCGTCCGCGCCGTT

CTAGACAGTCTCTCCGAGAAGAAGAAGTCGTCCCCC

SEQ ID NO: 63

ATGAATACAAAATATAATAAAGAGTTCTTACTCTACTTAGCAGGGTTTGTAGACTCTGAC

GGTTCCATCATTGCCTTTATCATGCCTAGTCAGACGGCTAAGTTCAAGCACCGTCTGAAGC

TCCAGTTCGCGGTCGCTCAGAAGACACAGCGCCGTTGGTTCCTCGACAAGCTGGTGGACG

AGATCGGTGTGGGTTACGTGTATGACTTTGGCAGCGTCTCCTATTACAGGCTGTCCCAGAT

-continued

---

Sequence Listing

---

CAAGCCTTTGCATAATTTTTTAACACAACTACAACCTTTTCTAAAACTAAAACAAAAACAA

GCAAATTTAGTTTTAAAAATTATTGAACAACTTCCGTCAGCAAAAGAATCCCCGGACAAA

TTCTTAGAAGTTTGTACATGGGTGGATCAAATTGCAGCTCTGAATGATTCGAAGACGCGT

AAAACAACTTCTGAAACCGTTCGTGCTGTGCTAGACAGTTTACCAGGATCCGTGGGAGGT

CTATCGCCATCTCAGGCATCCAGCGCCGCATCCTCGGCTTCCTCAAGCCCGGGTTCAGGGA

TCTCCGAAGCACTCAGAGCTGGAGCAGGTTCCGGCACTGGATACAACAAGGAATTCCTGC

TCTACCTGGCGGGCTTCGTCGACGGGGACGGCTCCATCTGTGCCTGTATCGTGCCTCGTCA

AGATCGGAAGTTCAAGCACCAGCTGCGGCTCTTTTTCGAGATCGGTCAGAAGACACAGCG

CCGTTGGTTCCTCGACAAGCTGGTGGACGAGATCGGTGTGGGTTACGTGAGGGACCTTGG

CAGCGCGAGCACTTACCGTCTGTCCCAGATCAAGCCTCTGCACAACTTCCTGACCCAGCTC

CAGCCCTTCCTGAAGCTCAAGCAGAAGCAGGCCAACCTCGTGCTGAAGATCATCGAGCAG

CTGCCCTCCGCCAAGGAATCCCCGGACAAGTTCCTGGAGGTGTGCACCTGGGTGGACCAG

ATCGCCGCTCTGAACGACTCCAAGACCCGCAAGACCACTTCCGAAACCGTCCGCGCCGTT

CTAGACAGTCTCTCCGAGAAGAAGAAGTCGTCCCCC

SEQ ID NO: 64
ATGAATACAAAATATAATAAAGAGTTCTTACTCTACTTAGCAGGGTTTGTAGACTCTGAC

GGTTCCATCATGGCCTTTATCATGCCTACTCAGACGGCTAAGTTCAAGCACCGTCTGAAGC

TCCAGTTCGCGGTCGCTCAGAAGACACAGCGCCGTTGGTTCCTCGACAAGCTGGTGGACG

AGATCGGTGTGGGTTACGTGTATGACTTTGGCAGCGTCTCCTATTACAGGCTGTCCGAGAT

CAAGCCTTTGCATAATTTTTTAACACAACTACAACCTTTTCTAAAACTAAAACAAAAACAA

GCAAATTTAGTTTTAAAAATTATTGAACAACTTCCGTCAGCAAAAGAATCCCCGGACAAA

TTCTTAGAAGTTTGTACATGGGTGGATCAAATTGCAGCTCTGAATGATTCGAAGACGCGT

AAAACAACTTCTGAAACCGTTCGTGCTGTGCTAGACAGTTTACCAGGATCCGTGGGAGGT

CTATCGCCATCTCAGGCATCCAGCGCCGCATCCTCGGCTTCCTCAAGCCCGGGTTCAGGGA

TCTCCGAAGCACTCAGAGCTGGAGCAGGTTCCGGCACTGGATACAACAAGGAATTCCTGC

TCTACCTGGCGGGCTTCGTCGACGGGGACGGCTCCATCTGTGCCTGTATCGTGCCTCGTCA

AGATCGGAAGTTCAAGCACCAGCTGCGGCTCTTTTTCGAGGTCGGTCAGAAGACACAGCG

CCGTTGGTTCCTCGACAAGCTGGTGGACGAGATCGGTGTGGGTTACGTGAGGGACCTTGG

CAGCGCGAGCACTTACCGTCTGTCCCAGATCAAGCCTCTGCACAACTTCCTGACCCAGCTC

CAGCCCTTCCTGAAGCTCAAGCAGAAGCAGGCCAACCTCGTGCTGAAGATCATCGAGCAG

CTGCCCTCCGCCAAGGAATCCCCGGACAAGTTCCTGGAGGTGTGCACCTGGGTGGACCAG

ATCGCCGCTCTGAACGACTCCAGGACCCGCAAGACCACTTCCGAAACCGTCCGCGCCGTT

CTAGACAGTCTCTCCGAGAAGAAGAAGTCGTCCCCC

SEQ ID NO: 65
ATGAATACAAAATATAATAAAGAGTTCTTACTCTACTTAGCAGGGTTTGTAGACTCTGAC

GGTTCCATCATGGCCTTTATCTTGCCTGAGCAGCATATGAAGTTCAAGCACCGTCTGAGGC

TCCAGTTCGCGGTCGCTCAGAAGACACAGCGCCGTTGGTTCCTCGACAAGCTGGTGGACG

AGATCGGTGTGGGTTACGTGTATGACTTTGGCAGCGTCTCCTATTACAGGCTGTCCGAGAT

CAAGCCTTTGCATAATTTTTTAACACAACTACAACCTTTTCTAAAACTAAAACAAAAACAA

GCAAATTTAGTTTTAAAAATTATTGAACAACTTCCGTCAGCAAAAGAATCCCCGGACAAA

Sequence Listing

```
TTCTTAGAAGTTTGTACATGGGTGGATCAAATTGCAGCTCTGAATGATTCGAAGACGCGT

AAAACAACTTCTGAAACCGTTCGTGCTGTGCTAGACAGTTTACCAGGATCCGTGGGAGGT

CTATCGCCATCTCAGGCATCCAGCGCCGCATCCTCGGCTTCCTCAAGCCCGGGTTCAGGGA

TCTCCGAAGCACTCAGAGCTGGAGCAGGTTCCGGCACTGGATACAACAAGGAATTCCTGC

TCTACCTGGCGGGCTTCGTCGACGGGGACGGCTCCATCTGTGCCTGTATCGTGCCTCGTCA

AGATCGGAAGTTCAAGCACCAGCTGCGGCTCTTTTTCGAGGTCGGTCAGAAGACACAGCG

CCGTTGGTTCCTCGACAAGCTGGTGGACGAGATCGGTGTGGGTTACGTGAGGGACCTTGG

CAGCGCGAGCACTTACCGTCTGTCCGAGATCAAGCCTCTGCACAACTTCCTGACCCAGCTC

CAGCCCTTCCTGAAGCTCAAGCAGAAGCAGGCCAACCTCGTGCTGAAGATCATCGAGCAG

CTGCCCTCCGCCAAGGAATCCCCGGACAAGTTCCTGGAGGTGTGCACCTGGGTGGACCAG

ATCGCCGCTCTGAACGACTCCAGGACCCGCAAGACCACTTCCGAAACCGTCCGCGCCGTT

CTAGACAGTCTCTCCGAGAAGAAGAAGTCGTCCCCC
```
                                              SEQ ID NO: 66
```
ATGAATACAAAATATAATAAAGAGTTCTTACTCTACTTAGCAGGGTTTGTAGACTCTGAC

GGTTCCATCATGGCCTTTATCTTGCCTGAGCAGCATCTTAAGTTCAAGCACCGTCTGAGGC

TCCAGTTCGCGGTCGCTCAGAAGACACAGCGCCGTTGGTTCCTCGACAAGCTGGTGGACG

AGATCGGTGTGGGTTACGTGTATGACTTTGGCAGCGTCTCCTATTACAGGCTGTCCGAGAT

CAAGCCTTTGCATAATTTTTTAACACAACTACAACCTTTTCTAAAACTAAAACAAAAACAA

GCAAATTTAGTTTTAAAAATTATTGAACAACTTCCGTCAGCAAAAGAATCCCCGGACAAA

TTCTTAGAAGTTTGTACATGGGTGGATCAAATTGCAGCTCTGAATGATTCGAAGACGCGT

AAAACAACTTCTGAAACCGTTCGTGCTGTGCTAGACAGTTTACCAGGATCCGTGGGAGGT

CTATCGCCATCTCAGGCATCCAGCGCCGCATCCTCGGCTTCCTCAAGCCCGGGTTCAGGGA

TCTCCGAAGCACTCAGAGCTGGAGCAGGTTCCGGCACTGGATACAACAAGGAATTCCTGC

TCTACCTGGCGGGCTTCGTCGACGGGGACGGCTCCATCTGTGCCTGTATCGTGCCTCGTCA

AGATCGGAAGTTCAAGCACCAGCTGCGGCTCTTTTTCGAGGTCGGTCAGAAGACACAGCG

CCGATGGTTCCTCGACAAGCTGGTGGACGAGATCGGTGTGGGTTACGTGAGGGACCTTGG

CAGCGCGAGCACTTACCGTCTGTCCGAGATCAAGCCTCTGCACAACTTCCTGACCCAGCTC

CAGCCCTTCCTGAAGCTCAAGCAGAAGCAGGCCAACCTCGTGCTGAAGATCATCGAGCAG

CTGCCCTCCGCCAAGGAATCCCCGGACAAGTTCCTGGAGGTGTGCACCTGGGTGGACCAG

ATCGCCGCTCTGAACGACTCCAGGACCCGCAAGACCACTTCCGAAACCGTCCGCGCCGTT

CTAGACAGTCTCTCCGAGAAGAAGAAGTCGTCCCCC
```
                                              SEQ ID NO: 67
```
ATGAATACAAAATATAATAAAGAGTTCTTACTCTACTTAGCAGGGTTTGTAGACTCTGAC

GGTTCCATCATGGCCTTTATCTTGCCTGAGCAGGGTCTGAAGTTCAAGCACCGTCTGAGGC

TCCAGTTCGCGGTCGCTCAGAAGACACAGCGCCGTTGGTTCCTCGACAAGCTGGTGGACG

AGATCGGTGTGGGTTACGTGTATGACTTTGGCAGCGTCTCCTATTACAGGCTGTCCCAGAT

CAAGCCTTTGCATAATTTTTTAACACAACTACAACCTTTTCTAAAACTAAAACAAAAACAA

GCAAATTTAGTTTTAAAAATTATTGAACAACTTCCGTCAGCAAAAGAATCCCCGGACAAA

TTCTTAGAAGTTTGTACATGGGTGGATCAAATTGCAGCTCTGAATGATTCGAAGACGCGT
```

-continued

---

Sequence Listing

---

AAAACAACTTCTGAAACCGTTCGTGCTGTGCTAGACAGTTTACCAGGATCCGTGGGAGGT

CTATCGCCATCTCAGGCATCCAGCGCCGCATCCTCGGCTTCCTCAAGCCCGGGTTCAGGGA

TCTCCGAAGCACTCAGAGCTGGAGCAGGTTCCGGCACCGGATACAACAAGGAATTCCTGC

TCTACCTGGCGGGCTTCGTCGACGGGGACGGCTCCATCTGTGCCTGTATCGTGCCTCGTCA

AGATCGGAAGTTCAAGCACCAGCTGCGGCTCTTTTTCGAGGTCGGTCAGAAGACACAGCG

CCGTTGGTTCCTCGACAAGCTGGTGGACGAGATCGGTGTGGGTTACGTGAGGGACCTTGG

CAGCGCGAGCACTTACCGTCTGTCCCAGATCAAGCCTCTGCACAACTTCCTGACCCAGCTC

CAGCCCTTCCTGAAGCTCAAGCAGAAGCAGGCCAACCTCGTGCTGAAGATCATCGAGCAG

CTGCCCTCCGCCAAGGAATCCCCGGACAAGTTCCTGGAGGTGTGCACCTGGGTGGACCAG

ATCGCCGCTCTGAACGACTCCAGGACCCGCAAGACCACTTCCGAAACCGTCCGCGCCGTT

CTAGACAGTCTCTCCGAGAAGAAGAAGTCGTCCCCC

SEQ ID NO: 68

ATGAATACAAAATATAATAAAGAGTTCTTACTCTACTTAGCAGGGTTTGTAGACTCTGAC

GGTTCCATCATGGCCTTTATCATGCCTGATCAGGCGCCTAAGTTCAAGCACCGTCTGAGGC

TCCAGTTCGCGGTCGCTCAGAAGACACAGCGCCGTTGGTTCCTCGACAAGCTGGTGGACG

AGATCGGTGTGGGTTACGTGTATGACTTTGGCAGCGTCTCCTATTACAGGCTGTCCGAGAT

CAAGCCTTTGCATAATTTTTTAACACAACTACAACCTTTTCTAAAACTAAAACAAAAACAA

GCAAATTTAGTTTTAAAAATTATTGAACAACTTCCGTCAGCAAAAGAATCCCCGGACAAA

TTCTTAGAAGTTTGTACATGGGTGGATCAAATTGCAGCTCTGAATGATTCGAAGACGCGT

AAAACAACTTCTGAAACCGTTCGTGCTGTGCTAGACAGTTTACCAGGATCCGTGGGAGGT

CTATCGCCATCTCAGGCATCCAGCGCCGCATCCTCGGCTTCCTCAAGCCCGGGTTCAGGGA

TCTCCGAAGCACTCAGAGCTGGAGCAGGTTCCGGCACTGGATACAACAAGGAATTCCTGC

TCTACCTGGCGGGCTTCGTCGACGGGGACGGCTCCATCTGTGCCTGTATCGTGCCTCGTCA

AGATCGGAAGTTCAAGCACCAGCTGCGGCTCTTTTTCGAGGTCGGTCAGAAGACACAGCG

CCGTTGGTTCCTCGACAAGCTGGTGGACGAGATCGGTGTGGGTTACGTGAGGGACCTTGG

CAGCGCGAGCACTTACCGTCTGTCCCAGATCAAGCCTCTGCACAACTTCCTGACCCAGCTC

CAGCCCTTCCTGAAGCTCAAGCAGAAGCAGGCCAACCTCGTGCTGAAGATCATCGAGCAG

CTGCCCTCCGCCAAGGAATCCCCGGACAAGTTCCTGGAGGTGTGCACCTGGGTGGACCAG

ATCGCCGCTCTGAACGACTCCAGGACCCGCAAGACCACTTCCGAAACCGTCCGCGCCGTT

CTAGACAGTCTCTCCGAGAAGAAGAAGTCGTCCCCC

SEQ ID NO: 69

ATGAATACAAAATATAATAAAGAGTTCTTACTCTACTTAGCAGGGTTTGTAGACGCTGAC

GGTTCCATCTATGCCTGTATCAAGCCTCATCAACAGCTTAAGTTCAAGCACCAGCTGTTGC

TCTATTTCGAGGTCTATCAGAAGACACAGCGCCGTTGGTTCCTCGACAAGCTGGTGGACG

AGATCGGTGTGGGTTACGTGGCTGACCGTGGCAGCGTCTCCGAGTACCGTCTGTCCCAGA

TCAAGCCTTTGCATAATTTTTTTAACACAACTACAACCTTTTCTAAAACTAAAACAAAAACA

AGCAAATTTAGTTTTAAAAATTATTGAACAACTTCCGTCAGCAAAAGAATCCCCGGACAA

ATTCTTAGAAGTTTGTACATGGGTGGATCAAATTGCAGCTCTGAATGATTCGAAGACGCG

TAAAACAACTTCTGAAACCGTTCGTGCTGTGCTAGACAGTTTACCAGGATCCGTGGGAGG

TCTATCGCCATCTCAGGCATCCAGCGCCGCATCCTCGGCTTCCTCAAGCCCGGGTTCAGGG

-continued

Sequence Listing

```
ATCTCCGAAGCACTCAGAGCTGGAGCAGGTTCCGGCACTGGATACAACAAGGAATTCCTG

CTCTACCTGGCGGGCTTCGTCGACGGGGACGGCTCCATCTTTGCCTCTATCATGCCGACGC

AGTGGACGAAGTTCAAGCACTCGCTGTTGCTCCGGTTCCGGGTCACCCAGTCGACAAGGC

GCCGTTGGTTCCTCGACAAGCTGATGGACGAGATTGGTGTGGGTTACGTGTCTGACCAGG

GCAGGGCGAGCTACTACACCCTGTCCGAGATCAAGCCTCTGCACAACTTCCTGACCCAGC

TCCAGCCCTTCCTGAAGCTCAAGCAGAAGCAGGCCAACCTCGTGCTGAAGATCATCGAGC

AGCTGCCCTCCGCCAAGGAATCCCCGGACAAGTTCCTGGAGGTGTGCACCTGGGTGGACC

AGATCGCCGCTCTGAACGACTCCAGGACCCGCAAGACCACTTCCGAAACCGTCCGCGCCG

TTCTAGACAGTCTCTCCGAGAAGAAGAAGTCGTCCCCC
```

SEQ ID NO: 70
```
ATGAATACAAAATATAATAAAGAGTTCTTACTCTACTTAGCAGGGTTTGTAGACGCTGAC

GGTTCCATCTATGCCTGTATCAAGCCTCATCAACAGCTTAAGTTCAAGCACCAGCTGTTGC

TCTATTTCGAGGTCTATCAGAAGACACAGCGCCGTTGGTTCCTCGACAAGCTGGTGGACG

AGATCGGTGTGGGTTACGTGATTGACTCGGGCAGCGTCTCCACGTACCGGCTGTCCCAGA

TCAAGCCTTTGCATAATTTTTTAACACAACTACAACCTTTTCTAAAACTAAAACAAAAACA

AGCAAATTTAGTTTTAAAAATTATTGAACAACTTCCGTCAGCAAAAGAATCCCCGGACAA

ATTCTTAGAAGTTTGTACATGGGTGGATCAAATTGCAGCTCTGAATGATTCGAAGACGCG

TAAAACAACTTCTGAAACCGTTCGTGCTGTGCTAGACAGTTTACCAGGATCCGTGGGAGG

TCTATCGCCATCTCAGGCATCTAGCGCCGCATCCTCGGCTTCCTCAAGCCCGGGTTCAGGG

ATCTCCGAAGCACTCAGAGCTGGAGCAGGTTCCGGCACTGGATACAACAAGGAATTCCTG

CTCTACCTGGCGGGCTTCGTCGACGGGGACGGCTCCATCTTTGCCTCTATCATTCCGTCGC

AGCTGGTTAAGTTCAAGCACACTCTGCTGCTCCGTTTCCGGGTCACCCAGGCGACAAGGC

GCCGTTGGTTCCTCGACAAGCTGGTGGACGAGATCGGTGTGGGTTACGTGACGGACAACG

GCAGGGCGAGCTACTACACCCTGTCCGAGATCAAGCCTCTGCACAACTTCCTGACCCAGC

TCCAGCCCTTCCTGAAGCTCAAGCAGAAGCAGGCCAACCTCGTGCTGAAGATCATCGAGC

AGCTGCCCTCCGCCAAGGAATCCCCGGACAAGTTCCTGGAGGTGTGCACCTGGGTGGACC

AGATCGCCGCTCTGAACGACTCCAGGACCCGCAAGACCACTTCCGAAACCGTCCGCGCCG

TTCTAGACAGTCTCTCCGAGAAGAAGAAGTCGTCCCCC
```

SEQ ID NO: 71
```
ATGAATACAAAATATAATAAAGAGTTCTTACTCTACTTAGCAGGGTTTGTAGACGCTGAC

GGTTCCATCTATGCCTGTATCAAGCCTCATCAACAGCTTAAGTTCAAGCACCAGCTGTTGC

TCTATTTCGAGGTCTATCAGAAGACACAGCGCCGTTGGTTCCTCGACAAGCTGGTGGACG

AGATCGGTGTGGGTTACGTGGCTGACCGTGGCAGCGTCTCCGAGTACCGTCTGTCCCAGA

TCAAGCCTTTGCATAATTTTTTAACACAACTACAACCTTTTCTAAAACTAAAACAAAAACA

AGCAAATTTAGTTTTAAAAATTATTGAACAACTTCCGTCAGCAAAAGAATCCCCGGACAA

ATTCTTAGAAGTTTGTACATGGGTGGATCAAATTGCAGCTCTGAATGATTCGAAGACGCG

TAAAACAACTTCTGAAACCGTTCGTGCTGTGCTAGACAGTTTACCAGGATCCGTGGGAGG

TCTATCGCCATCTCAGGCATCCAGCGCCGCATCCTCGGCTTCCTCAAGCCCGGGTTCAGGG

ATCTCCGAAGCACTCAGAGCTGGAGCAGGTTCCGGCACTGGATACAACAAGGAATTCCTG
```

-continued

Sequence Listing

CTCTACCTGGCGGGCTTCGTCGACGGGGACGGCTCCATCTTTGCCTCTATCATTCCGTCGC

AGCTGGTTAAGTTCAAGCACACTCTGCTGCTCCGTTTCCGGGTCTGCCAGGCGACAAAGC

GCCGTTGGTTCCTCGACAAGCTGGTGGACGAGATTGGTGTGGGTTACGTGTCTGACCAGG

GCAGCGCGAGCTACTACACCCTGTCCGAGATCAAGCCTCTGCACAACTTCCTGACCCAGC

TCCAGCCCTTCCTGAAGCTCAAGCAGAAGCAGGCCAACCTCGTGCTGAAGATCATCGAGC

AGCTGCCCTCCGCCAAGGAATCCCCGGACAAGTTCCTGGAGGTGTGCACCTGGGTGGACC

AGATCGCCGCTCTGAACGACTCCAGGACCCGCAAGACCACTTCCGAAACCGTCCGCGCCG

TTCTAGACAGTCTCTCCGAGAAGAAGAAGTCGTCCCCC

SEQ ID NO: 72
ATGAATACAAAATATAATAAAGAGTTCTTACTCTACTTAGCAGGGTTTGTAGACTCTGAC

GGTTCCATCTATGCCTGTATCAAGCCTCATCAACAGCTTAAGTTCAAGCACCAGCTGTTGC

TCTATTTCGAGGTCTATCAGAAGACACAGCGCCGTTGGTTCCTCGACAAGCTGGTGGACG

AGATCGGTGTGGGTTACGTGGCTGACCGTGGCAGCGTCTCCGAGTACCGTCTGTCCCAGA

TCAAGCCTTTGCATAATTTTTTAACACAACTACAACCTTTTCTAAAACTAAAACAAAAACA

AGCAAATTTAGTTTTAAAAATTATTGAACAACTTCCGTCAGCAAAAGAATCCCCGGACAA

ATTCTTAGAAGTTTGTACATGGGTGGATCAAATTGCAGCTCTGAATGATTCGAAGACGCG

TAAAACAACTTCTGAAACCGTTCGTGCTGTGCTAGACAGTTTACCAGGATCCGTGGGAGG

TCTATCGCCATCTCAGGCATCCAGCGCCGCATCCTCGGCTTCCTCAAGCCCGGGTTCAGGG

ATCTCCGAAGCACTCAGAGCTGGAGCAGGTTCCGGCACTGGATACAACAAGGAATTCCTG

CTCTACCTGGCGGGCTTCGTCGACGGGGACGGCTCCATCTTTGCCTCTATCATTCCGTCGC

AGGAGGTTAAGTTCAAGCACACTCTGCTGCTCCGTTTCCGGGTCTGCCAGGCGACAAAGC

GCCGTTGGTTCCTCGACAAGCTGGTGGACGAGATTGGTGTGGGTTACGTGTCTGACCAGG

GCAGCGCGAGCTACTACACCCTGTCCGAGATCAAGCCTCTGCACAACTTCCTGACCCAGC

TCCAGCCCTTCCTGAAGCTCAAGCAGAAGCAGGCCAACCTCGTGCTGAAGATCATCGAGC

AGCTGCCCTCCGCCAAGGAATCCCCGGACAAGTTCCTGGAGGTGTGCACCTGGGTGGACC

AGATCGCCGCTCTGAACGACTCCAGGACCCGCAAGACCACTTCCGAAACCGTCCGCGCCG

TTCTAGACAGTCTCTCCGAGAAGAAGAAGTCGTCCCCC

SEQ ID NO: 73
ATGAATACAAAATATAATAAAGAGTTCTTACTCTACTTAGCAGGGTTTGTAGACGCTGAC

GGTTCCATCTATGCCTGTATCAAGCCTCATCAACAGCTTAAGTTCAAGCACCAGCTGTTGC

TCTATTTCGAGGTCTATCAGAAGACACAGCGCCGTTGGTTCCTCGACAAGCTGGTGGACG

AGATCGGTGTGGGTTACGTGGCTGACCGTGGCAGCGTCTCCGAGTACCGTCTGTCCCAGA

TCAAGCCTTTGCATAATTTTTTAACACAACTACAACCTTTTCTAAAACTAAAACAAAAACA

AGCAAATTTAGTTTTAAAAATTATTGAACAACTTCCGTCAGCAAAAGAATCCCCGGACAA

ATTCTTAGAAGTTTGTACATGGGTGGATCAAATTGCAGCTCTGAATGATTCGAAGACGCG

TAAAACAACTTCTGAAACCGTTCGTGCTGTGCTAGACAGTTTACCAGGATCCGTGGGAGG

TCTATCGCCATCTCAGGCATCCAGCGCCGCATCCTCGGCTTCCTCAAGCCCGGGTTCAGGG

ATCTCCGAAGCACTCAGAGCTGGAGCAGGTTCCGGCACTGGATACAACAAGGAATTCCTG

CTCTACCTGGCGGGCTTCGTCGACGGGGACGGCTCCATCTTTGCCTCTATCATTCCGTCGC

AGGAGGTTAAGTTCAAGCACACTCTGCTGCTCCGTTTCCGGGTCTGCCAGGCGACAAAGC

-continued

Sequence Listing

GCCGTTGGTTCCTCGACAAGCTGGTGGACGAGATTGGTGTGGGTTACGTGTCTGACCAGG

GCAGCGCGAGCTACTACACCCTGTCCGAGATCAAGCCTCTGCACAACTTCCTGACCCAGC

TCCAGCCCTTCCTGAAGCTCAAGCAGAAGCAGGCCAACCTCGTGCTGAAGATCATCGAGC

AGCTGCCCTCCGCCAAGGAATCCCCGGACAAGTTCCTGGAGGTGTGCACCTGGGTGGACC

AGATCGCCGCTCTGAACGACTCCAGGACCCGCAAGACCACTTCCGAAACCGTCCGCGCCG

TTCTAGACAGTCTCTCCGAGAAGAAGAAGTCGTCCCCC

SEQ ID NO: 74
ATGAATACAAAATATAATAAAGAGTTCTTACTCTACTTAGCAGGGTTTGTAGACGCTGAC

GGTTCCATCTATGCCTGTATCAAGCCTCATCAACAGCTTAAGTTCAAGCACCAGCTGTTGC

TCTATTTCGAGGTCTATCAGAAGACACAGCGCCGTTGGTTCCTCGACAAGCTGGTGGACG

AGATCGGTGTGGGTTACGTGGCTGACCGTGGCAGCGTCTCCGAGTACCGTCTGTCCCAGA

TCAAGCCTTTGCATAATTTTTTAACACAACTACAACCTTTTCTAAAACTAAAACAAAAACA

AGCAAATTTAGTTTTAAAAATTATTGAACAACTTCCGTCAGCAAAAGAATCCCCGGACAA

ATTCTTAGAAGTTTGTACATGGGTGGATCAAATTGCAGCTCTGAATGATTCGAAGACGCG

TAAAACAACTTCTGAAACCGTTCGTGCTGTGCTAGACAGTTTACCAGGATCCGTGGGAGG

TCTATCGCCATCTCAGGCATCCAGCGCCGCATCCTCGGCTTCCTCAAGCCCGGGTTCAGGG

ATCTCCGAAGCACTCAGAGCTGGAGCAGGTTCCGGCACTGGATACAACAAGGAATTCCTG

CTCTACCTGGCGGGCTTCGTCGACGGGGACGGCTCCATCTTTGCCTCTATCATTCCGTCGC

AGGAGGTTAAGTTCAAGCACACTCTGCTGCTCCGTTTCAGGGTCACTCAGGCGACAAAGC

GCCGTTGGTTCCTCGACAAGCTGGTGGACGAGATTGGTGTGGGTTACGTGTCTGACGTTG

GCAGCGCGAGCTATTACACCCTGTCCGAGATCAAGCCTCTGCACAACTTCCTGACCCAGC

TCCAGCCCTTCCTGAAGCTCAAGCAGAAGCAGGCCAACCTCGTGCTGAAGATCATCGAGC

AGCTGCCCTCCGCCAAGGAATCCCCGGACAAGTTCCTGGAGGTGTGCACCTGGGTGGACC

AGATCGCCGCTCTGAACGACTCCAGGACCCGCAAGACCACTTCCGAAACCGTCCGCGCCG

TTCTAGACAGTCTCTCCGAGAAGAAGAAGTCGTCCCCC

SEQ ID NO: 75
ATGAATACAAAATATAATAAAGAGTTCTTACTCTACTTAGCAGGGTTTGTAGACTCTGAC

GGTTCCATCTATGCCTGTATCAAGCCTCATCAACAGCTTAAGTTCAAGCACCAGCTGTTGC

TCTATTTCGAGGTCTATCAGAAGACACAGCGCCGTTGGTTCCTCGACAAGCTGGTGGACG

AGATCGGTGTGGGTTACGTGGCTGACCGTGGCAGCGTCTCCGAGTACCGTCTGTCCCAGA

TCAAGCCTTTGCATAATTTTTTAACACAACTACAACCTTTTCTAAAACTAAAACAAAAACA

AGCAAATTTAGTTTTAAAAATTATTGAACAACTTCCGTCAGCAAAAGAATCCCCGGACAA

ATTCTTAGAAGTTTGTACATGGGTGGATCAAATTGCAGCTCTGAATGATTCGAAGACGCG

TAAAACAACTTCTGAAACCGTTCGTGCTGTGCTAGACAGTTTACCAGGATCCGTGGGAGG

TCTATCGCCATCTCAGGCATCCAGCGCCGCATCCTCGGCTTCCTCAAGCCCGGGTTCAGGG

ATCTCCGAAGCACTCAGAGCTGGAGCAGGTTCCGGCACTGGATACAACAAGGAATTCCTG

CTCTACCTGGCGGGCTTCGTCGACGGGGACGGCTCCATCTTTGCCTCTATCATTCCGTCGC

AGGAGGTTAAGTTCAAGCACACTCTGCTGCTCCGTTTCCGGGTCTGCCAGGCGACAAAGC

GCCGTTGGTTCCTCGACAAGCTGGTGGACGAGATTGGTGTGGGTTACGTGTCTGACCGTG

-continued

Sequence Listing

```
GCAGCGCGAGCTATTACACCCTGTCCGAGATCAAGCCTCTGCACAACTTCCTGACCCAGC

TCCAGCCCTTCCTGAAGCTCAAGCAGAAGCAGGCCAACCTCGTGCTGAAGATCATCGAGC

AGCTGCCCTCCGCCAAGGAATCCCCGGACAAGTTCCTGGAGGTGTGCACCTGGGTGGACC

AGATCGCCGCTCTGAACGACTCCAGGACCCGCAAGACCACTTCCGAAACCGTCCGCGCCG

TTCTAGACAGTCTCTCCGAGAAGAAGAAGTCGTCCCCC
```

SEQ ID NO: 76
```
ATGAATACAAAATATAATAAAGAGTTCTTACTCTACTTAGCAGGGTTTGTAGACGCTGAC

GGTTCCATCTATGCCTGTATCAAGCCTCATCAAGAGCTTAAGTTCAAGCACCAGCTGTTGC

TCTATTTCGAGGTCTATCAGAAGACACAGCGCCGTTGGTTCCTCGACAAGCTGGTGGACG

AGATCGGTGTGGGTTACGTGGCTGACCGTGGCAGCGTCTCCGAGTACCGTCGTCCGAGA

TCAAGCCTTTGCATAATTTTTTAACACAACTACAACCTTTTCTAAAACTAAAACAAAAACA

AGCAAATTTAGTTTTAAAAATTATTGAACAACTTCCGTCAGCAAAAGAATCCCCGGACAA

ATTCTTAGAAGTTTGTACATGGGTGGATCAAATTGCAGCTCTGAATGATTCGAAGACGCG

TAAAACAACTTCTGAAACCGTTCGTGCTGTGCTAGACAGTTTACCAGGATCCGTGGGAGG

TCTATCGCCATCTCAGGCATCCAGCGCCGCATCCTCGGCTTCCTCAAGCCCGGGTTCAGGG

ATCTCCGAAGCACTCAGAGCTGGAGCAGGTTCCGGCACTGGATACAACAAGGAATTCCTG

CTCTACCTGGCGGGCTTCGTCGACGGGGACGGCTCCATCTTTGCCTCTATCATTCCGTCGC

AGGAGGTTAAGTTCAAGCACACTCTGCTGCTCCGTTTCCGGGTCTGCCAGGCGACAAAGC

GCCGTTGGTTCCTCGACAAGCTGGTGGACGAGATTGGTGTGGGTTACGTGTCTGACCAGG

GCAGCGCGAGCTACTACACCCTGTCCCAGATCAAGCCTCTGCACAACTTCCTGACCCAGC

TCCAGCCCTTCCTGAAGCTCAAGCAGAAGCAGGCCAACCTCGTGCTGAAGATCATCGAGC

AGCTGCCCTCCGCCAAGGAATCCCCGGACAAGTTCCTGGAGGTGTGCACCTGGGTGGACC

AGATCGCCGCTCTGAACGACTCCAGGACCCGCAAGACCACTTCCGAAACCGTCCGCGCCG

TTCTAGACAGTCTCTCCGAGAAGAAGAAGTCGTCCCCC
```

SEQ ID NO: 77
```
SLPGSVGGLSPSQASSAASSASSSPGSGISEALRAGAGSGTG
```

SEQ ID NO: 78
```
AAGCTTGCATGTCTAAGCTAGACCCTTCAGATTAAAAATAACTGAGGTAAGGGCCTGGGT

AGGGGAGGTGGTGTGAGACGCTCCTGTCTCTCCTCTATCTGCCCATCGGCCCTTTGGGGAG

GAGGAATGTGCCCAAGGACTAAAAAAAGGCCATGGAGCCAGAGGGGCGAGGGCAACAG

ACCTTTCATGGGCAAACCTTGGGGCCCTGCTGTCTAGCATGCCCCACTACGGGTCTAGGCT

GCCCATGTAAGGAGGCAAGGCCTGGGGACACCCGAGATGCCTGGTTATAATTAACCCAGA

CATGTGGCTGCCCCCCCCCCCCCAACACCTGCTGCCTCTAAAAATAACCCTGTCCCTGGTG

GATCCCCTGCATGCGAAGATCTTCGAACAAGGCTGTGGGGGACTGAGGGCAGGCTGTAAC

AGGCTTGGGGGCCAGGGCTTATACGTGCCTGGGACTCCCAAAGTATTACTGTTCCATGTTC

CCGGCGAAGGGCCAGCTGTCCCCCGCCAGCTAGACTCAGCACTTAGTTTAGGAACCAGTG

AGCAAGTCAGCCCTTGGGGCAGCCCATACAAGGCCATGGGGCTGGGCAAGCTGCACGCCT

GGGTCCGGGGTGGGCACGGTGCCCGGGCAACGAGCTGAAAGCTCATCTGCTCTCAGGGGC

CCCTCCCTGGGGACAGCCCCTCCTGGCTAGTCACACCCTGTAGGCTCCTCTATATAACCCA

GGGGCACAGGGGCTGCCCTCATTCTACCACCACCTCCACAGCACAGACAGACACTCAGGA
```

-continued

Sequence Listing

```
GCAGCCAGCGCCACCATGGCACCGAAGAAGAAGCGCAAGGTGCATATGAATACAAAATA

TAATAAAGAGTTCTTACTCTACTTAGCAGGGTTTGTAGACTCTGACGGTTCCATCATGGCC

TTCATCATGCCTACTCAAACCGCAAAGTTCAAGCACCGTCTGAAGCTCCAGTTCGCGGTCG

CACAGAAGACACAGCGCCGTTGGTTCCTCGACAAGCTGGTGGACGAGATCGGTGTGGGTT

ACGTGTATGACTTCGGCAGCGTCTCCTACTACCGTCTGTCCGAGATCAAGCCTTTGCATAA

TTTTTTAACACAACTACAACCTTTTCTAAAACTAAAACAAAAACAAGCAAATTTAGTTTTA

AAAATTATTGAACAACTTCCGTCAGCAAAAGAATCCCCGGACAAATTCTTAGAAGTTTGT

ACATGGGTGGATCAAATTGCAGCTCTGAATGATTCGAAGACGCGTAAAACAACTTCTGAA

ACCGTTCGTGCTGTGCTAGACAGTTTACCAGGCTCCGTGGGAGGTCTATCGCCATCTCAGG

CATCCAGCGCCGCATCCTCGGCTTCCTCAAGCCCGGGTTCAGGGATCTCCGAAGCACTCA

GAGCTGGAGCAGGTTCCGGCACTGGATACAACAAGGAATTCCTGCTCTACCTGGCGGGCT

TCGTAGACGGGGACGGCTCCATCTGTGCCTGTATCGTGCCTCGTCAAGATCGGAAGTTCA

AGCACCAGCTGCGGCTCTTTTTCGAGGTCGGTCAGAAGACACAGCGCCGTTGGTTCCTCG

ACAAGCTGGTGGACGAGATCGGTGTGGGTTACGTGCGTGACCTGGGCTCCGCGAGCACGT

ACCGGCTGTCCCAGATCAAGCCTCTGCACAACTTCCTGACCCAGCTCCAGCCCTTCCTGAA

GCTCAAGCAGAAGCAGGCCAACCTCGTGCTGAAGATCATCGAGCAGCTGCCCTCCGCCAA

GGAATCCCCGGACAAGTTCCTGGAGGTGTGCACCTGGGTGGACCAGATCGCCGCTCTGAA

CGACTCCAGGACCCGCAAGACCACTTCCGAAACCGTCCGCGCCGTTCTAGACAGTCTCTC

CGAGAAGAAGAAGTCGTCCCCTTCGCCGGCCGCTAAGCGCGTGAAGCTGGACGGTAGAG

CCAAGAGATCTGGAAGCGGCGCCACAAATTTCTCACTGCTGAAACAGGCCGGCGACGTGG

AAGAGAACCCTGGACCTGCTAGCGGAATGGCACCGAAAAAAAAGCGCAAAGTACATATG

AACACCAAGTACAACAAGGAATTTCTCTTGTATCTCGCCGGCTTCGTCGATGCCGATGGG

AGTATATACGCGTGCATAAAGCCCCACCAACAGTTGAAATTTAAACATCAGTTACTCTTGT

ACTTTGAGGTGTACCAAAAAAACCCAAAGGAGGTGGTTTTTGGATAAGCTGGTCGATGAGA

TAGGAGTCGGGTATGTCGCCGATCGCGGGTCGGTGAGTGAGTATCGTTTAAGTCAAATAA

AACCGCTCCACAACTTCCTCACCCAGTTGCAGCCGTTCTTGAAGTTGAAGCAGAAGCAGG

CCAACCTCGTGCTCAAGATAATAGAGCAGTTGCCCAGCGCCAAGGAGAGTCCCGATAAGT

TTCTGGAGGTGTGTACCTGGGTGGACCAGATAGCCGCGTTAAACGACAGCAAAACCAGGA

AAACCACGAGCGAGACGGTGAGAGCGGTCTTGGATTCGCTCCCTGGCAGTGTCGGCGGAT

TGAGCCCAAGCCAAGCCAGTTCGGCAGCCAGTAGCGCGAGTAGCTCGCCAGGAAGCGGC

ATAAGTGAGGCTTTGAGAGCTGGAGCTGGAAGTGGTACCGGTTACAACAAGGAGTTCTTA

CTGTACTTAGCCGGGTTCGTGGATGGCGATGGGAGTATATTCGCGTCCATAATCCCCAGCC

AAGAGGTGAAATTTAAACATACCTTACTCTTGCGATTTCGCGTGTGCCAAGCAACCAAAA

GGAGGTGGTTTTTGGATAAGCTGGTCGATGAGATAGGAGTCGGGTATGTCTCCGATCAGG

GGTCGGCCTCGTACTATACCTTAAGTGAGATAAAACCGTTACATAACTTCTTAACGCAATT

GCAACCGTTTCTGAAACTGAAGCAGAAGCAAGCGAATCTGGTCCTGAAGATCATCGAACA

ACTGCCGAGTGCGAAGGAGTCCCCCGATAAGTTCCTCGAGGTCTGCACGTGGGTCGATCA

AATAGCGGCGTTAAATGATAGTAGGACGAGGAAAACGACGAGTGAGACGGTGAGGGCGG

TGTTGGATTCGTTGAGTGAAAAGAAAAAGAGCAGTCCTTCGCCGGCAGCGAAGAGGGTTA
```

-continued

---
Sequence Listing

---

AGCTCGACTAGTAAGCTTATCAACCTCTGGATTACAAAATTTGTGAAAGATTGACTGATAT

TCTTAACTATGTTGCTCCTTTTACGCTGTGTGGATATGCTGCTTTAATGCCTCTGTATCATG

CTATTGCTTCCCGTACGGCTTTCGTTTTCTCCTCCTTGTATAAATCCTGGTTGCTGTCTCTTT

ATGAGGAGTTGTGGCCCGTTGTCCGTCAACGTGGCGTGGTGTGCTCTGTGTTTGCTGACGC

AACCCCCACTGGCTGGGGCATTGCCACCACCTGTCAACTCCTTTCTGGGACTTTCGCTTTC

CCCCTCCCGATCGCCACGGCAGAACTCATCGCCGCCTGCCTTGCCCGCTGCTGGACAGGG

GCTAGGTTGCTGGGCACTGATAATTCCGTGGTGTTGTCGGGGAAGCTGACGTCCTTTCCAG

GGCTGCTCGCCTGTGTTGCCAACTGGATCCTGCGCGGGACGTCCTTCTGCTACGTCCCTTC

GGCTCTCAATCCAGCGGACCTCCCTTCCCGAGGCCTTCTGCCGGTTCTGCGGCCTCTCCCG

CGTCTTCGCTTTCGGCCTCCGACGAGTCGGATCTCCCTTTGGGCCGCCTCCCCGCCTGGGT

AGATCCAGACATGATAAGATACATTGATGAGTTTGGACAAACCACAACTAGAATGCAGTG

AAAAAAATGCTTTATTTGTGAAATTTGTGATGCTATTGCTTTATTTGTAACCATTATAAGC

TGCAATAAACAAGTTAACAACAACAATTGCATTCATTTTATGTTTCAGGTTCAGGGGGAG

GTGTGGGAGGTTTTTTAAAGCAAGTAA

SEQ ID NO: 79
CCACTACGGGTCTAGGCTGCCCATGTAAGGAGGCAAGGCCTGGGGACACCCGAGATGCCT

GGTTATAATTAACCCCAACACCTGCTGCCCCCCCCCCCCCAACACCTGCTGCCTGAGCCTG

AGCGGTTACCCCACCCCGGTGCCTGGGTCTTAGGCTCTGTACACCATGGAGGAGAAGCTC

GCTCTAAAAATAACCCTGTCCCTGGTGGATCCACTACGGGTCTAGGCTGCCCATGTAAGG

AGGCAAGGCCTGGGGACACCCGAGATGCCTGGTTATAATTAACCCCAACACCTGCTGCCC

CCCCCCCCCAACACCTGCTGCCTGAGCCTGAGCGGTTACCCCACCCCGGTGCCTGGGTCT

TAGGCTCTGTACACCATGGAGGAGAAGCTCGCTCTAAAAATAACCCTGTCCCTGGTGGAT

CCACTACGGGTCTAGGCTGCCCATGTAAGGAGGCAAGGCCTGGGGACACCCGAGATGCCT

GGTTATAATTAACCCCAACACCTGCTGCCCCCCCCCCCCCAACACCTGCTGCCTGAGCCTG

AGCGGTTACCCCACCCCGGTGCCTGGGTCTTAGGCTCTGTACACCATGGAGGAGAAGCTC

GCTCTAAAAATAACCCTGTCCCTGGTGGATCCTCCCTGGGGACAGCCCCTCCTGGCTAGTC

ACACCCTGTAGGCTCCTCTATATAACCCAGGGGCACAGGGGCTGCCCCCGGGTCACGCCA

CCATGGCACCGAAGAAGAAGCGCAAGGTGCATATGAATACAAAATATAATAAAGAGTTC

TTACTCTACTTAGCAGGGTTTGTAGACTCTGACGGTTCCATCATGGCCTTCATCATGCCTA

CTCAAACCGCAAAGTTCAAGCACCGTCTGAAGCTCCAGTTCGCGGTCGCACAGAAGACAC

AGCGCCGTTGGTTCCTCGACAAGCTGGTGGACGAGATCGGTGTGGGTTACGTGTATGACT

TCGGCAGCGTCTCCTACTACCGTCTGTCCGAGATCAAGCCTTTGCATAATTTTTTAACACA

ACTACAACCTTTTCTAAAACTAAAACAAAACAAGCAAATTTAGTTTTAAAAATTATTGA

ACAACTTCCGTCAGCAAAAGAATCCCCGGACAAATTCTTAGAAGTTTGTACATGGGTGGA

TCAAATTGCAGCTCTGAATGATTCGAAGACGCGTAAAACAACTTCTGAAACCGTTCGTGC

TGTGCTAGACAGTTTACCAGGCTCCGTGGGAGGTCTATCGCCATCTCAGGCATCCAGCGC

CGCATCCTCGGCTTCCTCAAGCCCGGGTTCAGGGATCTCCGAAGCACTCAGAGCTGGAGC

AGGTTCCGGCACTGGATACAACAAGGAATTCCTGCTCTACCTGGCGGGCTTCGTAGACGG

GGACGGCTCCATCTGTGCCTGTATCGTGCCTCGTCAAGATCGGAAGTTCAAGCACCAGCT

-continued

---

Sequence Listing

---

GCGGCTCTTTTTCGAGGTCGGTCAGAAGACACAGCGCCGTTGGTTCCTCGACAAGCTGGT

GGACGAGATCGGTGTGGGTTACGTGCGTGACCTGGGCTCCGCGAGCACGTACCGGCTGTC

CCAGATCAAGCCTCTGCACAACTTCCTGACCCAGCTCCAGCCCTTCCTGAAGCTCAAGCA

GAAGCAGGCCAACCTCGTGCTGAAGATCATCGAGCAGCTGCCCTCCGCCAAGGAATCCCC

GGACAAGTTCCTGGAGGTGTGCACCTGGGTGGACCAGATCGCCGCTCTGAACGACTCCAG

GACCCGCAAGACCACTTCCGAAACCGTCCGCGCCGTTCTAGACAGTCTCTCCGAGAAGAA

GAAGTCGTCCCCTTCGCCGGCCGCTAAGCGCGTGAAGCTGGACGGTAGAGCCAAGAGATC

TGGAAGCGGCGCCACAAATTTCTCACTGCTGAAACAGGCCGGCGACGTGGAAGAGAACC

CTGGACCTGCTAGCGGAATGGCACCGAAAAAAAAGCGCAAAGTACATATGAACACCAAG

TACAACAAGGAATTTCTCTTGTATCTCGCCGGCTTCGTCGATGCCGATGGGAGTATATACG

CGTGCATAAAGCCCCACCAACAGTTGAAATTTAAACATCAGTTACTCTTGTACTTTGAGGT

GTACCAAAAAACCCAAAGGAGGTGGTTTTTGGATAAGCTGGTCGATGAGATAGGAGTCG

GGTATGTCGCCGATCGCGGGTCGGTGAGTGAGTATCGTTTAAGTCAAATAAAACCGCTCC

ACAACTTCCTCACCCAGTTGCAGCCGTTCTTGAAGTTGAAGCAGAAGCAGGCCAACCTCG

TGCTCAAGATAATAGAGCAGTTGCCCAGCGCCAAGGAGAGTCCCGATAAGTTTCTGGAGG

TGTGTACCTGGGTGGACCAGATAGCCGCGTTAAACGACAGCAAAACCAGGAAAACCACG

AGCGAGACGGTGAGAGCGGTCTTGGATTCGCTCCCTGGCAGTGTCGGCGGATTGAGCCCA

AGCCAAGCCAGTTCGGCAGCCAGTAGCGCGAGTAGCTCGCCAGGAAGCGGCATAAGTGA

GGCTTTGAGAGCTGGAGCTGGAAGTGGTACCGGTTACAACAAGGAGTTCTTACTGTACTT

AGCCGGGTTCGTGGATGGCGATGGGAGTATATTCGCGTCCATAATCCCCAGCCAAGAGGT

GAAATTTAAACATACCTTACTCTTGCGATTTCGCGTGTGCCAAGCAACCAAAAGGAGGTG

GTTTTTGGATAAGCTGGTCGATGAGATAGGAGTCGGGTATGTCTCCGATCAGGGGTCGGC

CTCGTACTATACCTTAAGTGAGATAAAACCGTTACATAACTTCTTAACGCAATTGCAACCG

TTTCTGAAACTGAAGCAGAAGCAAGCGAATCTGGTCCTGAAGATCATCGAACAACTGCCG

AGTGCGAAGGAGTCCCCCGATAAGTTCCTCGAGGTCTGCACGTGGGTCGATCAAATAGCG

GCGTTAAATGATAGTAGGACGAGGAAAACGACGAGTGAGACGGTGAGGGCGGTGTTGGA

TTCGTTGAGTGAAAAGAAAAAGAGCAGTCCTTCGCCGGCAGCGAAGAGGGTTAAGCTCG

ACTAGTAAGCTTATCAACCTCTGGATTACAAAATTTGTGAAAGATTGACTGATATTCTTAA

CTATGTTGCTCCTTTTACGCTGTGTGGATATGCTGCTTTAATGCCTCTGTATCATGCTATTG

CTTCCCGTACGGCTTTCGTTTTCTCCTCCTTGTATAAATCCTGGTTGCTGTCTCTTTATGAG

GAGTTGTGGCCCGTTGTCCGTCAACGTGGCGTGGTGTGCTCTGTGTTTGCTGACGCAACCC

CCACTGGCTGGGGCATTGCCACCACCTGTCAACTCCTTTCTGGGACTTTCGCTTTCCCCCTC

CCGATCGCCACGGCAGAACTCATCGCCGCCTGCCTTGCCCGCTGCTGGACAGGGGCTAGG

TTGCTGGGCACTGATAATTCCGTGGTGTTGTCGGGGAAGCTGACGTCCTTTCCAGGGCTGC

TCGCCTGTGTTGCCAACTGGATCCTGCGCGGGACGTCCTTCTGCTACGTCCCTTCGGCTCT

CAATCCAGCGGACCTCCCTTCCCGAGGCCTTCTGCCGGTTCTGCGGCCTCTCCCGCGTCTT

CGCTTTCGGCCTCCGACGAGTCGGATCTCCCTTTGGGCCGCCTCCCCGCCTGGGTAGATCC

AGACATGATAAGATACATTGATGAGTTTGGACAAACCACAACTAGAATGCAGTGAAAAA

Sequence Listing

AATGCTTTATTTGTGAAATTTGTGATGCTATTGCTTTATTTGTAACCATTATAAGCTGCAAT

AAACAAGTTAACAACAACAATTGCATTCATTTTATGTTTCAGGTTCAGGGGGAGGTGTGG

GAGGTTTTTTAAAGCAAGTAA

SEQ ID NO: 80
CCACTACGGGTCTAGGCTGCCCATGTAAGGAGGCAAGGCCTGGGGACACCCGAGATGCCT

GGTTATAATTAACCCCAACACCTGCTGCCCCCCCCCCCCCAACACCTGCTGCCTGAGCCTG

AGCGGTTACCCCACCCCGGTGCCTGGGTCTTAGGCTCTGTACACCATGGAGGAGAAGCTC

GCTCTAAAAATAACCCTGTCCCTGGTGGATCCACTACGGGTCTAGGCTGCCCATGTAAGG

AGGCAAGGCCTGGGGACACCCGAGATGCCTGGTTATAATTAACCCCAACACCTGCTGCCC

CCCCCCCCCCAACACCTGCTGCCTGAGCCTGAGCGGTTACCCCACCCCGGTGCCTGGGTCT

TAGGCTCTGTACACCATGGAGGAGAAGCTCGCTCTAAAAATAACCCTGTCCCTGGTGGAT

CCACTACGGGTCTAGGCTGCCCATGTAAGGAGGCAAGGCCTGGGGACACCCGAGATGCCT

GGTTATAATTAACCCCAACACCTGCTGCCCCCCCCCCCCCCAACACCTGCTGCCTGAGCCTG

AGCGGTTACCCCACCCCGGTGCCTGGGTCTTAGGCTCTGTACACCATGGAGGAGAAGCTC

GCTCTAAAAATAACCCTGTCCCTGGTGGATCCTCCCTGGGGACAGCCCCTCCTGGCTAGTC

ACACCCTGTAGGCTCCTCTATATAACCCAGGGGCACAGGGGCTGCCCCCGGGTCACGCCA

CCATGGCACCGAAGAAGAAGCGCAAGGTGCATATGAATACAAAATATAATAAAGAGTTC

TTACTCTACTTAGCAGGGTTTGTAGACTCTGACGGTTCCATCATGGCCTTCATCATGCCTA

CTCAAACCGCAAAGTTCAAGCACCGTCTGAAGCTCCAGTTCGCGGTCGCACAGAAGACAC

AGCGCCGTTGGTTCCTCGACAAGCTGGTGGACGAGATCGGTGTGGGTTACGTGTATGACT

TCGGCAGCGTCTCCTACTACCGTCTGTCCGAGATCAAGCCTTTGCATAATTTTTTAACACA

ACTACAACCTTTTCTAAAACTAAAACAAAAACAAGCAAATTTAGTTTTAAAAATTATTGA

ACAACTTCCGTCAGCAAAAGAATCCCCGGACAAATTCTTAGAAGTTTGTACATGGGTGGA

TCAAATTGCAGCTCTGAATGATTCGAAGACGCGTAAAACAACTTCTGAAACCGTTCGTGC

TGTGCTAGACAGTTTACCAGGCTCCGTGGGAGGTCTATCGCCATCTCAGGCATCCAGCGC

CGCATCCTCGGCTTCCTCAAGCCCGGGTTCAGGGATCTCCGAAGCACTCAGAGCTGGAGC

AGGTTCCGGCACTGGATACAACAAGGAATTCCTGCTCTACCTGGCGGGCTTCGTAGACGG

GGACGGCTCCATCTGTGCCTGTATCGTGCCTCGTCAAGATCGGAAGTTCAAGCACCAGCT

GCGGCTCTTTTTCGAGGTCGGTCAGAAGACACAGCGCCGTTGGTTCCTCGACAAGCTGGT

GGACGAGATCGGTGTGGGTTACGTGCGTGACCTGGGCTCCGCGAGCACGTACCGGCTGTC

CCAGATCAAGCCTCTGCACAACTTCCTGACCCAGCTCCAGCCCTTCCTGAAGCTCAAGCA

GAAGCAGGCCAACCTCGTGCTGAAGATCATCGAGCAGCTGCCCTCCGCCAAGGAATCCCC

GGACAAGTTCCTGGAGGTGTGCACCTGGGTGGACCAGATCGCCGCTCTGAACGACTCCAG

GACCCGCAAGACCACTTCCGAAACCGTCCGCGCCGTTCTAGACAGTCTCTCCGAGAAGAA

GAAGTCGTCCCCTTCGCCGGCCGCTAAGCGCGTGAAGCTGGACGGTAGAGCCAAGAGATC

TGGAAGCGGCGCCACAAATTTCTCACTGCTGAAACAGGCCGGCGACGTGGAAGAGAACC

CTGGACCTGCTAGCGGAATGGCACCGAAAAAAAAGCGCAAAGTACATATGAACACCAAG

TACAACAAGGAATTTCTCTTGTATCTCGCCGGCTTCGTCGATGCCGATGGGAGTATATACG

CGTGCATAAAGCCCCACCAACAGTTGAAATTTAAACATCAGTTACTCTTGTACTTTGAGGT

-continued

| Sequence Listing |
| --- |

```
GTACCAAAAAACCCAAAGGAGGTGGTTTTTGGATAAGCTGGTCGATGAGATAGGAGTCG

GGTATGTCGCCGATCGCGGGTCGGTGAGTGAGTATCGTTTAAGTCAAATAAAACCGCTCC

ACAACTTCCTCACCCAGTTGCAGCCGTTCTTGAAGTTGAAGCAGAAGCAGGCCAACCTCG

TGCTCAAGATAATAGAGCAGTTGCCCAGCGCCAAGGAGAGTCCCGATAAGTTTCTGGAGG

TGTGTACCTGGGTGGACCAGATAGCCGCGTTAAACGACAGCAAAACCAGGAAAACCACG

AGCGAGACGGTGAGAGCGGTCTTGGATTCGCTCCCTGGCAGTGTCGGCGGATTGAGCCCA

AGCCAAGCCAGTTCGGCAGCCAGTAGCGCGAGTAGCTCGCCAGGAAGCGGCATAAGTGA

GGCTTTGAGAGCTGGAGCTGGAAGTGGTACCGGTTACAACAAGGAGTTCTTACTGTACTT

AGCCGGGTTCGTGGATGGCGATGGGAGTATATTCGCGTCCATAATCCCCAGCCAAGAGGT

GAAATTTAAACATACCTTACTCTTGCGATTTCGCGTGTGCCAAGCAACCAAAAGGAGGTG

GTTTTTGGATAAGCTGGTCGATGAGATAGGAGTCGGGTATGTCTCCGATCAGGGGTCGGC

CTCGTACTATACCTTAAGTGAGATAAAACCGTTACATAACTTCTTAACGCAATTGCAACCG

TTTCTGAAACTGAAGCAGAAGCAAGCGAATCTGGTCCTGAAGATCATCGAACAACTGCCG

AGTGCGAAGGAGTCCCCCGATAAGTTCCTCGAGGTCTGCACGTGGGTCGATCAAATAGCG

GCGTTAAATGATAGTAGGACGAGGAAAACGACGAGTGAGACGGTGAGGGCGGTGTTGGA

TTCGTTGAGTGAAAGAAAAAGAGCAGTCCTTCGCCGGCAGCGAAGAGGGTTAAGCTCG

ACTAGTAAGCTTATCAACCTCTGGATTACAAAATTTGTGAAAGATTGACTGATATTCTTAA

CTATGTTGCTCCTTTTACGCTGTGTGGATATGCTGCTTTAATGCCTCTGTATCATGCTATTG

CTTCCCGTACGGCTTTCGTTTTCTCCTCCTTGTATAAATCCTGGTTGCTGTCTCTTTATGAG

GAGTTGTGGCCCGTTGTCCGTCAACGTGGCGTGGTGTGCTCTGTGTTTGCTGACGCAACCC

CCACTGGCTGGGGCATTGCCACCACCTGTCAACTCCTTTCTGGGACTTTCGCTTTCCCCCTC

CCGATCGCCACGGCAGAACTCATCGCCGCCTGCCTTGCCCGCTGCTGGACAGGGGCTAGG

TTGCTGGGCACTGATAATTCCGTGGTGTTGTCGGGGAAGCTGACGTCCTTTCCAGGGCTGC

TCGCCTGTGTTGCCAACTGGATCCTGCGCGGGACGTCCTTCTGCTACGTCCCTTCGGCTCT

CAATCCAGCGGACCTCCCTTCCCGAGGCCTTCTGCCGGTTCTGCGGCCTCTCCCGCGTCTT

CGCTTTCGGCCTCCGACGAGTCGGATCTCCCTTTGGGCCGCCTCCCCGCCTGGGTAGATCC

AGACATGATAAGATACATTGATGAGTTTGGACAAACCACAACTAGAATGCAGTGAAAAA

AATGCTTTATTTGTGAAATTTGTGATGCTATTGCTTTATTTGTAACCATTATAAGCTGCAAT

AAACAAGTTAACAACAACAATTGCATTCATTTTATGTTTCAGGTTCAGGGGGAGGTGTGG

GAGGTTTTTTAAAGCAAGTAA
```

<div style="text-align: right">SEQ ID NO: 81</div>

```
CCACTACGGGTCTAGGCTGCCCATGTAAGGAGGCAAGGCCTGGGGACACCCGAGATGCCT

GGTTATAATTAACCCCAACACCTGCTGCCCCCCCCCCCCCCCAACACCTGCTGCCTGAGCCTG

AGCGGTTACCCCACCCCGGTGCCTGGGTCTTAGGCTCTGTACACCATGGAGGAGAAGCTC

GCTCTAAAAATAACCCTGTCCCTGGTGGATCCACTACGGGTCTAGGCTGCCCATGTAAGG

AGGCAAGGCCTGGGGACACCCGAGATGCCTGGTTATAATTAACCCCAACACCTGCTGCCC

CCCCCCCCCAACACCTGCTGCCTGAGCCTGAGCGGTTACCCCACCCCGGTGCCTGGGTCT

TAGGCTCTGTACACCATGGAGGAGAAGCTCGCTCTAAAAATAACCCTGTCCCTGGTGGAT

CCACTACGGGTCTAGGCTGCCCATGTAAGGAGGCAAGGCCTGGGGACACCCGAGATGCCT
```

-continued

Sequence Listing

```
GGTTATAATTAACCCCAACACCTGCTGCCCCCCCCCCCCCAACACCTGCTGCCTGAGCCTG

AGCGGTTACCCCACCCCGGTGCCTGGGTCTTAGGCTCTGTACACCATGGAGGAGAAGCTC

GCTCTAAAAATAACCCTGTCCCTGGTGGATCCTCCCTGGGGACAGCCCCTCCTGGCTAGTC

ACACCCTGTAGGCTCCTCTATATAACCCAGGGGCACAGGGGCTGCCCCCGGGTCACTACT

GCCACCATGGCACCGAAGAAGAAGCGCAAGGTGCATATGAATACAAAATATAATAAAGA

GTTCTTACTCTACTTAGCAGGGTTTGTAGACTCTGACGGTTCCATCATGGCCTTTATCTTGC

CTGAGCAGGGTCTGAAGTTCAAGCACCGTCTGAGGCTCCAGTTCGCGGTCGCTCAGAAGA

CACAGCGCCGTTGGTTCCTCGACAAGCTGGTGGACGAGATCGGTGTGGGTTACGTGTATG

ACTTTGGCAGCGTCTCCTATTACAGGCTGTCCCAGATCAAGCCTTTGCATAATTTTTTAAC

ACAACTACAACCTTTTCTAAAACTAAAACAAAAACAAGCAAATTTAGTTTTAAAAATTAT

TGAACAACTTCCGTCAGCAAAAGAATCCCCGGACAAATTCTTAGAAGTTTGTACATGGGT

GGATCAAATTGCAGCTCTGAATGATTCGAAGACGCGTAAAACAACTTCTGAAACCGTTCG

TGCTGTGCTAGACAGTTTACCAGGATCCGTGGGAGGTCTATCGCCATCTCAGGCATCCAG

CGCCGCATCCTCGGCTTCCTCAAGCCCGGGTTCAGGGATCTCCGAAGCACTCAGAGCTGG

AGCAGGTTCCGGCACCGGATACAACAAGGAATTCCTGCTCTACCTGGCGGGCTTCGTCGA

CGGGGACGGCTCCATCTGTGCCTGTATCGTGCCTCGTCAAGATCGGAAGTTCAAGCACCA

GCTGCGGCTCTTTTTCGAGGTCGGTCAGAAGACACAGCGCCGTTGGTTCCTCGACAAGCT

GGTGGACGAGATCGGTGTGGGTTACGTGAGGGACCTTGGCAGCGCGAGCACTTACCGTCT

GTCCCAGATCAAGCCTCTGCACAACTTCCTGACCCAGCTCCAGCCCTTCCTGAAGCTCAAG

CAGAAGCAGGCCAACCTCGTGCTGAAGATCATCGAGCAGCTGCCCTCCGCCAAGGAATCC

CCGGACAAGTTCCTGGAGGTGTGCACCTGGGTGGACCAGATCGCCGCTCTGAACGACTCC

AGGACCCGCAAGACCACTTCCGAAACCGTCCGCGCCGTTCTAGACAGTCTCTCCGAGAAG

AAGAAGTCGTCCCCTTCGCCGGCCGCTAAGCGCGTGAAGCTGGACGGTAGAGCCAAGAG

ATCTGGAAGCGGCGCCACAAATTTCTCACTGCTGAAACAGGCCGGCGACGTGGAAGAGA

ACCCTGGACCTGCTAGCGGAATGGCACCGAAAAAAAAGCGCAAAGTACATATGAACACC

AAGTACAACAAGGAATTTCTCTTGTATCTCGCCGGCTTCGTCGATGCAGATGGAAGTATAT

ACGCGTGCATAAAGCCCCACCAAGAGCTGAAGTTTAAACATCAGTTACTGTTGTACTTTG

AGGTGTACCAAAAGACCCAAAGAAGATGGTTCTTGGATAAGCTGGTCGATGAGATAGGA

GTCGGGTATGTCGCAGATCGCGGGTCGGTGAGTGAGTATCGGCTGAGTGAGATAAAACCG

CTCCACAACTTCCTCACCCAGTTGCAGCCGTTCTTGAAGTTGAAGCAGAAGCAGGCCAAC

CTCGTGCTCAAGATAATAGAGCAGTTGCCCAGCGCCAAGGAGAGTCCCGATAAGTTTCTG

GAGGTGTGTACCTGGGTGGACCAGATAGCCGCGTTAAACGACAGCAAAACCAGGAAAAC

CACGAGCGAAACCGTCAGAGCGGTCTTGGATTCGCTCCCTGGCAGTGTCGGCGGATTGAG

CCCAAGCCAAGCCAGTTCGGCAGCCAGTAGCGCGAGTAGCTCGCCAGGAAGCGGCATAA

GTGAGGCTTTGAGAGCTGGAGCTGGAAGTGGTACCGGTTACAACAAGGAGTTCTTACTGT

ACTTAGCCGGGTTCGTGGATGGCGATGGGAGTATATTCGCGTCCATCATCCCCAGCCAAG

AGGTGAAGTTCAAGCATACCTTACTCCTGAGGTTCCGCGTGTGCCAAGCAACCAAGAGGA

GGTGGTTCCTGGATAAACTGGTCGACGAGATCGGGGTCGGGTATGTCTCCGATCAGGGGT

CGGCCTCGTACTATACTCTGAGTCAGATCAAACCGTTACATAACTTCTTAACGCAATTGCA
```

-continued

Sequence Listing

```
ACCGTTTCTGAAACTGAAGCAGAAGCAAGCGAATCTGGTCCTGAAGATCATCGAACAACT

GCCGAGTGCGAAGGAGTCCCCCGATAAGTTCCTCGAGGTCTGCACGTGGGTCGATCAAAT

AGCGGCGTTAAACGATAGTAGGACGAGGAAAACGACGAGTGAGACGGTGCGGGCGGTGT

TGGATTCGTTGAGTGAAAAGAAAAAGAGCAGTCCTTCGCCGGCAGCGAAGAGGGTTAAG

CTCGACTAGTAAGCTTATCAACCTCTGGATTACAAAATTTGTGAAAGATTGACTGATATTC

TTAACTATGTTGCTCCTTTTACGCTGTGTGGATATGCTGCTTTAATGCCTCTGTATCATGCT

ATTGCTTCCCGTACGGCTTTCGTTTTCTCCTCCTTGTATAAATCCTGGTTGCTGTCTCTTTAT

GAGGAGTTGTGGCCCGTTGTCCGTCAACGTGGCGTGGTGTGCTCTGTGTTTGCTGACGCAA

CCCCCACTGGCTGGGGCATTGCCACCACCTGTCAACTCCTTTCTGGGACTTTCGCTTTCCC

CCTCCCGATCGCCACGGCAGAACTCATCGCCGCCTGCCTTGCCCGCTGCTGGACAGGGGC

TAGGTTGCTGGGCACTGATAATTCCGTGGTGTTGTCGGGGAAGCTGACGTCCTTTCCAGGG

CTGCTCGCCTGTGTTGCCAACTGGATCCTGCGCGGGACGTCCTTCTGCTACGTCCCTTCGG

CTCTCAATCCAGCGGACCTCCCTTCCCGAGGCCTTCTGCCGGTTCTGCGGCCTCTCCCGCG

TCTTCGCTTTCGGCCTCCGACGAGTCGGATCTCCCTTTGGGCCGCCTCCCCGCCTGGGTAG

ATCCAGACATGATAAGATACATTGATGAGTTTGGACAAACCACAACTAGAATGCAGTGAA

AAAAATGCTTTATTTGTGAAATTTGTGATGCTATTGCTTTATTTGTAACCATTATAAGCTGC

AATAAACAAGTTAACAACAACAATTGCATTCATTTTATGTTTCAGGTTCAGGGGGAGGTG

TGGGAGGTTTTTTAAAGCAAGTAA
```

SEQ ID NO: 82
```
CCACTACGGGTCTAGGCTGCCCATGTAAGGAGGCAAGGCCTGGGGACACCCGAGATGCCT

GGTTATAATTAACCCCAACACCTGCTGCCCCCCCCCCCCCAACACCTGCTGCCTGAGCCTG

AGCGGTTACCCCACCCCGGTGCCTGGGTCTTAGGCTCTGTACACCATGGAGGAGAAGCTC

GCTCTAAAAATAACCCTGTCCCTGGTGGATCCACTACGGGTCTAGGCTGCCCATGTAAGG

AGGCAAGGCCTGGGGACACCCGAGATGCCTGGTTATAATTAACCCCAACACCTGCTGCCC

CCCCCCCCCAACACCTGCTGCCTGAGCCTGAGCGGTTACCCCACCCCGGTGCCTGGGTCT

TAGGCTCTGTACACCATGGAGGAGAAGCTCGCTCTAAAAATAACCCTGTCCCTGGTGGAT

CCACTACGGGTCTAGGCTGCCCATGTAAGGAGGCAAGGCCTGGGGACACCCGAGATGCCT

GGTTATAATTAACCCCAACACCTGCTGCCCCCCCCCCCCCCCCAACACCTGCTGCCTGAGCCTG

AGCGGTTACCCCACCCCGGTGCCTGGGTCTTAGGCTCTGTACACCATGGAGGAGAAGCTC

GCTCTAAAAATAACCCTGTCCCTGGTGGATCCTCCCTGGGGACAGCCCCTCCTGGCTAGTC

ACACCCTGTAGGCTCCTCTATATAACCCAGGGGCACAGGGGCTGCCCCCGGGTCACTACT

GCCACCATGGCACCGAAGAAGAAGCGCAAGGTGCATATGAATACAAAATATAATAAAGA

GTTCTTACTCTACTTAGCAGGGTTTGTAGACTCTGACGGTTCCATCATGGCCTTTATCATGC

CTGATCAGGCGCCTAAGTTCAAGCACCGTCTGAGGCTCCAGTTCGCGGTCGCTCAGAAGA

CACAGCGCCGTTGGTTCCTCGACAAGCTGGTGGACGAGATCGGTGTGGGTTACGTGTATG

ACTTTGGCAGCGTCTCCTATTACAGGCTGTCCGAGATCAAGCCTTTGCATAATTTTTTAAC

ACAACTACAACCTTTTCTAAAACTAAAACAAAAACAAGCAAATTTAGTTTTAAAAATTAT

TGAACAACTTCCGTCAGCAAAAGAATCCCCGGACAAATTCTTAGAAGTTTGTACATGGGT

GGATCAAATTGCAGCTCTGAATGATTCGAAGACGCGTAAAACAACTTCTGAAACCGTTCG
```

-continued

Sequence Listing

TGCTGTGCTAGACAGTTTACCAGGATCCGTGGGAGGTCTATCGCCATCTCAGGCATCCAG

CGCCGCATCCTCGGCTTCCTCAAGCCCGGGTTCAGGGATCTCCGAAGCACTCAGAGCTGG

AGCAGGTTCCGGCACTGGATACAACAAGGAATTCCTGCTCTACCTGGCGGGCTTCGTCGA

CGGGGACGGCTCCATCTGTGCCTGTATCGTGCCTCGTCAAGATCGGAAGTTCAAGCACCA

GCTGCGGCTCTTTTTCGAGGTCGGTCAGAAGACACAGCGCCGTTGGTTCCTCGACAAGCT

GGTGGACGAGATCGGTGTGGGTTACGTGAGGGACCTTGGCAGCGCGAGCACTTACCGTCT

GTCCCAGATCAAGCCTCTGCACAACTTCCTGACCCAGCTCCAGCCCTTCCTGAAGCTCAAG

CAGAAGCAGGCCAACCTCGTGCTGAAGATCATCGAGCAGCTGCCCTCCGCCAAGGAATCC

CCGGACAAGTTCCTGGAGGTGTGCACCTGGGTGGACCAGATCGCCGCTCTGAACGACTCC

AGGACCCGCAAGACCACTTCCGAAACCGTCCGCGCCGTTCTAGACAGTCTCTCCGAGAAG

AAGAAGTCGTCCCCTTCGCCGGCCGCTAAGCGCGTGAAGCTGGACGGTAGAGCCAAGAG

ATCTGGAAGCGGCGCCACAAATTTCTCACTGCTGAAACAGGCCGGCGACGTGGAAGAGA

ACCCTGGACCTGCTAGCGGAATGGCACCGAAAAAAAAGCGCAAAGTACATATGAACACC

AAGTACAACAAGGAATTTCTCTTGTATCTCGCCGGCTTCGTCGATGCAGATGGAAGTATAT

ACGCGTGCATAAAGCCCCACCAAGAGCTGAAGTTTAAACATCAGTTACTGTTGTACTTTG

AGGTGTACCAAAAGACCCAAAGAAGATGGTTCTTGGATAAGCTGGTCGATGAGATAGGA

GTCGGGTATGTCGCAGATCGCGGGTCGGTGAGTGAGTATCGGCTGAGTGAGATAAAACCG

CTCCACAACTTCCTCACCCAGTTGCAGCCGTTCTTGAAGTTGAAGCAGAAGCAGGCCAAC

CTCGTGCTCAAGATAATAGAGCAGTTGCCCAGCGCCAAGGAGAGTCCCGATAAGTTTCTG

GAGGTGTGTACCTGGGTGGACCAGATAGCCGCGTTAAACGACAGCAAAACCAGGAAAAC

CACGAGCGAAACCGTCAGAGCGGTCTTGGATTCGCTCCCTGGCAGTGTCGGCGGATTGAG

CCCAAGCCAAGCCAGTTCGGCAGCCAGTAGCGCGAGTAGCTCGCCAGGAAGCGGCATAA

GTGAGGCTTTGAGAGCTGGAGCTGGAAGTGGTACCGGTTACAACAAGGAGTTCTTACTGT

ACTTAGCCGGGTTCGTGGATGGCGATGGGAGTATATTCGCGTCCATCATCCCCAGCCAAG

AGGTGAAGTTCAAGCATACCTTACTCCTGAGGTTCCGCGTGTGCCAAGCAACCAAGAGGA

GGTGGTTCCTGGATAAACTGGTCGACGAGATCGGGGTCGGGTATGTCTCCGATCAGGGGT

CGGCCTCGTACTATACTCTGAGTCAGATCAAACCGTTACATAACTTCTTAACGCAATTGCA

ACCGTTTCTGAAACTGAAGCAGAAGCAAGCGAATCTGGTCCTGAAGATCATCGAACAACT

GCCGAGTGCGAAGGAGTCCCCCGATAAGTTCCTCGAGGTCTGCACGTGGGTCGATCAAAT

AGCGGCGTTAAACGATAGTAGGACGAGGAAAACGACGAGTGAGACGGTGCGGGCGGTGT

TGGATTCGTTGAGTGAAAAGAAAAAGAGCAGTCCTTCGCCGGCAGCGAAGAGGGTTAAG

CTCGACTAGTAAGCTTATCAACCTCTGGATTACAAAATTTGTGAAAGATTGACTGATATTC

TTAACTATGTTGCTCCTTTTACGCTGTGTGGATATGCTGCTTTAATGCCTCTGTATCATGCT

ATTGCTTCCCGTACGGCTTTCGTTTTCTCCTCCTTGTATAAATCCTGGTTGCTGTCTCTTTAT

GAGGAGTTGTGGCCCGTTGTCCGTCAACGTGGCGTGGTGTGCTCTGTGTTTGCTGACGCAA

CCCCCACTGGCTGGGGCATTGCCACCACCTGTCAACTCCTTTCTGGGACTTTCGCTTTCCC

CCTCCCGATCGCCACGGCAGAACTCATCGCCGCCTGCCTTGCCCGCTGCTGGACAGGGGC

TAGGTTGCTGGGCACTGATAATTCCGTGGTGTTGTCGGGGAAGCTGACGTCCTTTCCAGGG

-continued

Sequence Listing

CTGCTCGCCTGTGTTGCCAACTGGATCCTGCGCGGGACGTCCTTCTGCTACGTCCCTTCGG

CTCTCAATCCAGCGGACCTCCCTTCCCGAGGCCTTCTGCCGGTTCTGCGGCCTCTCCCGCG

TCTTCGCTTTCGGCCTCCGACGAGTCGGATCTCCCTTTGGGCCGCCTCCCCGCCTGGGTAG

ATCCAGACATGATAAGATACATTGATGAGTTTGGACAAACCACAACTAGAATGCAGTGAA

AAAAATGCTTTATTTGTGAAATTTGTGATGCTATTGCTTTATTTGTAACCATTATAAGCTGC

AATAAACAAGTTAACAACAACAATTGCATTCATTTTATGTTTCAGGTTCAGGGGGAGGTG

TGGGAGGTTTTTTAAAGCAAGTAA

SEQ ID NO: 83
CCACTACGGGTCTAGGCTGCCCATGTAAGGAGGCAAGGCCTGGGGACACCCGAGATGCCT

GGTTATAATTAACCCCAACACCTGCTGCCCCCCCCCCCCCCAACACCTGCTGCCTGAGCCTG

AGCGGTTACCCCACCCCGGTGCCTGGGTCTTAGGCTCTGTACACCATGGAGGAGAAGCTC

GCTCTAAAAATAACCCTGTCCCTGGTGGATCCACTACGGGTCTAGGCTGCCCATGTAAGG

AGGCAAGGCCTGGGGACACCCGAGATGCCTGGTTATAATTAACCCCAACACCTGCTGCCC

CCCCCCCCCCAACACCTGCTGCCTGAGCCTGAGCGGTTACCCCACCCCGGTGCCTGGGTCT

TAGGCTCTGTACACCATGGAGGAGAAGCTCGCTCTAAAAATAACCCTGTCCCTGGTGGAT

CCACTACGGGTCTAGGCTGCCCATGTAAGGAGGCAAGGCCTGGGGACACCCGAGATGCCT

GGTTATAATTAACCCCAACACCTGCTGCCCCCCCCCCCCCCAACACCTGCTGCCTGAGCCTG

AGCGGTTACCCCACCCCGGTGCCTGGGTCTTAGGCTCTGTACACCATGGAGGAGAAGCTC

GCTCTAAAAATAACCCTGTCCCTGGTGGATCCTCCCTGGGGACAGCCCCTCCTGGCTAGTC

ACACCCTGTAGGCTCCTCTATATAACCCAGGGGCACAGGGGCTGCCCCCGGGTCACTACT

GCCACCATGGCACCGAAGAAGAAGCGCAAGGTGCATATGAATACAAAATATAATAAAGA

GTTCTTACTCTACTTAGCAGGGTTTGTAGACTCTGACGGTTCCATCATGGCCTTTATCTTGC

CTGAGCAGGGTCTGAAGTTCAAGCACCGTCTGAGGCTCCAGTTCGCGGTCGCTCAGAAGA

CACAGCGCCGTTGGTTCCTCGACAAGCTGGTGGACGAGATCGGTGTGGGTTACGTGTATG

ACTTTGGCAGCGTCTCCTATTACAGGCTGTCCCAGATCAAGCCTTTGCATAATTTTTTAAC

ACAACTACAACCTTTTCTAAAACTAAAACAAAAACAAGCAAATTTAGTTTTAAAAATTAT

TGAACAACTTCCGTCAGCAAAAGAATCCCCGGACAAATTCTTAGAAGTTTGTACATGGGT

GGATCAAATTGCAGCTCTGAATGATTCGAAGACGCGTAAAACAACTTCTGAAACCGTTCG

TGCTGTGCTAGACAGTTTACCAGGATCCGTGGGAGGTCTATCGCCATCTCAGGCATCCAG

CGCCGCATCCTCGGCTTCCTCAAGCCCGGGTTCAGGGATCTCCGAAGCACTCAGAGCTGG

AGCAGGTTCCGGCACCGGATACAACAAGGAATTCCTGCTCTACCTGGCGGGCTTCGTCGA

CGGGGACGGCTCCATCTGTGCCTGTATCGTGCCTCGTCAAGATCGGAAGTTCAAGCACCA

GCTGCGGCTCTTTTTCGAGGTCGGTCAGAAGACACAGCGCCGTTGGTTCCTCGACAAGCT

GGTGGACGAGATCGGTGTGGGTTACGTGAGGGACCTTGGCAGCGCGAGCACTTACCGTCT

GTCCCAGATCAAGCCTCTGCACAACTTCCTGACCCAGCTCCAGCCCTTCCTGAAGCTCAAG

CAGAAGCAGGCCAACCTCGTGCTGAAGATCATCGAGCAGCTGCCCTCCGCCAAGGAATCC

CCGGACAAGTTCCTGGAGGTGTGCACCTGGGTGGACCAGATCGCCGCTCTGAACGACTCC

AGGACCCGCAAGACCACTTCCGAAACCGTCCGCGCCGTTCTAGACAGTCTCTCCGAGAAG

AAGAAGTCGTCCCCTTCGCCGGCCGCTAAGCGCGTGAAGCTGGACGGTAGAGCCAAGAG

-continued

Sequence Listing

```
ATCTGGAAGCGGCGCCACAAATTTCTCACTGCTGAAACAGGCCGGCGACGTGGAAGAGA

ACCCTGGACCTGCTAGCGGAATGGCACCGAAAAAAAAGCGCAAAGTACATATGAACACC

AAGTACAACAAGGAATTTCTCTTGTATCTCGCCGGCTTCGTCGATTCCGATGGAAGTATAT

ACGCGTGCATAAAGCCCCACCAACAGCTGAAGTTTAAACATCAGTTACTGTTGTACTTTG

AGGTGTACCAAAAGACCCAAAGAAGATGGTTCTTGGATAAGCTGGTCGATGAGATAGGA

GTCGGGTATGTCGCAGATCGCGGGTCGGTGAGTGAGTATCGGCTGAGTCAAATAAAACCG

CTCCACAACTTCCTCACCCAGTTGCAGCCGTTCTTGAAGTTGAAGCAGAAGCAGGCCAAC

CTCGTGCTCAAGATAATAGAGCAGTTGCCCAGCGCCAAGGAGAGTCCCGATAAGTTTCTG

GAGGTGTGTACCTGGGTGGACCAGATAGCCGCGTTAAACGACAGCAAAACCAGGAAAAC

CACGAGCGAAACCGTCAGAGCGGTCTTGGATTCGCTCCCTGGCAGTGTCGGCGGATTGAG

CCCAAGCCAAGCCAGTTCGGCAGCCAGTAGCGCGAGTAGCTCGCCAGGAAGCGGCATAA

GTGAGGCTTTGAGAGCTGGAGCTGGAAGTGGTACCGGTTACAACAAGGAGTTCTTACTGT

ACTTAGCCGGGTTCGTGGATGGCGATGGGAGTATATTCGCGTCCATCATCCCCAGCCAAG

AGGTGAAGTTCAAGCATACCTTACTCCTGAGGTTCCGCGTGTGCCAAGCAACCAAGAGGA

GGTGGTTCCTGGATAAACTGGTCGACGAGATCGGGGTCGGGTATGTCTCCGATCGAGGGT

CGGCCTCGTACTATACTCTGAGTGAAATCAAACCGTTACATAACTTCTTAACGCAATTGCA

ACCGTTTCTGAAACTGAAGCAGAAGCAAGCGAATCTGGTCCTGAAGATCATCGAACAACT

GCCGAGTGCGAAGGAGTCCCCCGATAAGTTCCTCGAGGTCTGCACGTGGGTCGATCAAAT

AGCGGCGTTAAACGATAGTAGGACGAGGAAAACGACGAGTGAGACGGTGCGGGCGGTGT

TGGATTCGTTGAGTGAAAAGAAAAAGAGCAGTCCTTCGCCGGCAGCGAAGAGGGTTAAG

CTCGACTAGTAAGCTTATCAACCTCTGGATTACAAAATTTGTGAAAGATTGACTGATATTC

TTAACTATGTTGCTCCTTTTACGCTGTGTGGATATGCTGCTTTAATGCCTCTGTATCATGCT

ATTGCTTCCCGTACGGCTTTCGTTTTCTCCTCCTTGTATAAATCCTGGTTGCTGTCTCTTTAT

GAGGAGTTGTGGCCCGTTGTCCGTCAACGTGGCGTGGTGTGCTCTGTGTTTGCTGACGCAA

CCCCCACTGGCTGGGGCATTGCCACCACCTGTCAACTCCTTTCTGGGACTTTCGCTTTCCC

CCTCCCGATCGCCACGGCAGAACTCATCGCCGCCTGCCTTGCCCGCTGCTGGACAGGGGC

TAGGTTGCTGGGCACTGATAATTCCGTGGTGTTGTCGGGGAAGCTGACGTCCTTTCCAGGG

CTGCTCGCCTGTGTTGCCAACTGGATCCTGCGCGGGACGTCCTTCTGCTACGTCCCTTCGG

CTCTCAATCCAGCGGACCTCCCTTCCCGAGGCCTTCTGCCGGTTCTGCGGCCTCTCCCGCG

TCTTCGCTTTCGGCCTCCGACGAGTCGGATCTCCCTTTGGGCCGCCTCCCCGCCTGGGTAG

ATCCAGACATGATAAGATACATTGATGAGTTTGGACAAACCACAACTAGAATGCAGTGAA

AAAAATGCTTTATTTGTGAAATTTGTGATGCTATTGCTTTATTTGTAACCATTATAAGCTGC

AATAAACAAGTTAACAACAACAATTGCATTCATTTTATGTTTCAGGTTCAGGGGGAGGTG

TGGGAGGTTTTTTAAAGCAAGTAA
```

SEQ ID NO: 84
```
CCACTACGGGTCTAGGCTGCCCATGTAAGGAGGCAAGGCCTGGGGACACCCGAGATGCCT

GGTTATAATTAACCCCAACACCTGCTGCCCCCCCCCCCCCCAACACCTGCTGCCTGAGCCTG

AGCGGTTACCCCACCCCGGTGCCTGGGTCTTAGGCTCTGTACACCATGGAGGAGAAGCTC

GCTCTAAAAATAACCCTGTCCCTGGTGGATCCACTACGGGTCTAGGCTGCCCATGTAAGG
```

-continued

Sequence Listing

```
AGGCAAGGCCTGGGGACACCCGAGATGCCTGGTTATAATTAACCCCAACACCTGCTGCCC

CCCCCCCCCCAACACCTGCTGCCTGAGCCTGAGCGGTTACCCCACCCCGGTGCCTGGGTCT

TAGGCTCTGTACACCATGGAGGAGAAGCTCGCTCTAAAAATAACCCTGTCCCTGGTGGAT

CCACTACGGGTCTAGGCTGCCCATGTAAGGAGGCAAGGCCTGGGGACACCCGAGATGCCT

GGTTATAATTAACCCCAACACCTGCTGCCCCCCCCCCCCCCCCAACACCTGCTGCCTGAGCCTG

AGCGGTTACCCCACCCCGGTGCCTGGGTCTTAGGCTCTGTACACCATGGAGGAGAAGCTC

GCTCTAAAAATAACCCTGTCCCTGGTGGATCCTCCCTGGGGACAGCCCCTCCTGGCTAGTC

ACACCCTGTAGGCTCCTCTATATAACCCAGGGGCACAGGGGCTGCCCCCGGGTCACTACT

GCCACCATGGCACCGAAGAAGAAGCGCAAGGTGCATATGAATACAAAATATAATAAAGA

GTTCTTACTCTACTTAGCAGGGTTTGTAGACTCTGACGGTTCCATCATGGCCTTTATCATGC

CTGATCAGGCGCCTAAGTTCAAGCACCGTCTGAGGCTCCAGTTCGCGGTCGCTCAGAAGA

CACAGCGCCGTTGGTTCCTCGACAAGCTGGTGGACGAGATCGGTGTGGGTTACGTGTATG

ACTTTGGCAGCGTCTCCTATTACAGGCTGTCCGAGATCAAGCCTTTGCATAATTTTTTAAC

ACAACTACAACCTTTTCTAAAACTAAAACAAAAACAAGCAAATTTAGTTTTAAAAATTAT

TGAACAACTTCCGTCAGCAAAAGAATCCCCGGACAAATTCTTAGAAGTTTGTACATGGGT

GGATCAAATTGCAGCTCTGAATGATTCGAAGACGCGTAAAACAACTTCTGAAACCGTTCG

TGCTGTGCTAGACAGTTTACCAGGATCCGTGGGAGGTCTATCGCCATCTCAGGCATCCAG

CGCCGCATCCTCGGCTTCCTCAAGCCCGGGTTCAGGGATCTCCGAAGCACTCAGAGCTGG

AGCAGGTTCCGGCACTGGATACAACAAGGAATTCCTGCTCTACCTGGCGGGCTTCGTCGA

CGGGGACGGCTCCATCTGTGCCTGTATCGTGCCTCGTCAAGATCGGAAGTTCAAGCACCA

GCTGCGGCTCTTTTTCGAGGTCGGTCAGAAGACACAGCGCCGTTGGTTCCTCGACAAGCT

GGTGGACGAGATCGGTGTGGGTTACGTGAGGGACCTTGGCAGCGCGAGCACTTACCGTCT

GTCCCAGATCAAGCCTCTGCACAACTTCCTGACCCAGCTCCAGCCCTTCCTGAAGCTCAAG

CAGAAGCAGGCCAACCTCGTGCTGAAGATCATCGAGCAGCTGCCCTCCGCCAAGGAATCC

CCGGACAAGTTCCTGGAGGTGTGCACCTGGGTGGACCAGATCGCCGCTCTGAACGACTCC

AGGACCCGCAAGACCACTTCCGAAACCGTCCGCGCCGTTCTAGACAGTCTCTCCGAGAAG

AAGAAGTCGTCCCCTTCGCCGGCCGCTAAGCGCGTGAAGCTGGACGGTAGAGCCAAGAG

ATCTGGAAGCGGCGCCACAAATTTCTCACTGCTGAAACAGGCCGGCGACGTGGAAGAGA

ACCCTGGACCTGCTAGCGGAATGGCACCGAAAAAAAAGCGCAAAGTACATATGAACACC

AAGTACAACAAGGAATTTCTCTTGTATCTCGCCGGCTTCGTCGATTCCGATGGAAGTATAT

ACGCGTGCATAAAGCCCCACCAACAGCTGAAGTTTAAACATCAGTTACTGTTGTACTTTG

AGGTGTACCAAAAGACCCAAAGAAGATGGTTCTTGGATAAGCTGGTCGATGAGATAGGA

GTCGGGTATGTCGCAGATCGCGGGTCGGTGAGTGAGTATCGGCTGAGTCAAATAAAACCG

CTCCACAACTTCCTCACCCAGTTGCAGCCGTTCTTGAAGTTGAAGCAGAAGCAGGCCAAC

CTCGTGCTCAAGATAATAGAGCAGTTGCCCAGCGCCAAGGAGAGTCCCGATAAGTTTCTG

GAGGTGTGTACCTGGGTGGACCAGATAGCCGCGTTAAACGACAGCAAAACCAGGAAAAC

CACGAGCGAAACCGTCAGAGCGGTCTTGGATTCGCTCCCTGGCAGTGTCGGCGGATTGAG

CCCAAGCCAAGCCAGTTCGGCAGCCAGTAGCGCGAGTAGCTCGCCAGGAAGCGGCATAA

GTGAGGCTTTGAGAGCTGGAGCTGGAAGTGGTACCGGTTACAACAAGGAGTTCTTACTGT
```

-continued

Sequence Listing

ACTTAGCCGGGTTCGTGGATGGCGATGGGAGTATATTCGCGTCCATCATCCCCAGCCAAG

AGGTGAAGTTCAAGCATACCTTACTCCTGAGGTTCCGCGTGTGCCAAGCAACCAAGAGGA

GGTGGTTCCTGGATAAACTGGTCGACGAGATCGGGGTCGGGTATGTCTCCGATCGAGGGT

CGGCCTCGTACTATACTCTGAGTGAAATCAAACCGTTACATAACTTCTTAACGCAATTGCA

ACCGTTTCTGAAACTGAAGCAGAAGCAAGCGAATCTGGTCCTGAAGATCATCGAACAACT

GCCGAGTGCGAAGGAGTCCCCCGATAAGTTCCTCGAGGTCTGCACGTGGGTCGATCAAAT

AGCGGCGTTAAACGATAGTAGGACGAGGAAAACGACGAGTGAGACGGTGCGGGCGGTGT

TGGATTCGTTGAGTGAAAAGAAAAAGAGCAGTCCTTCGCCGGCAGCGAAGAGGGTTAAG

CTCGACTAGTAAGCTTATCAACCTCTGGATTACAAAATTTGTGAAAGATTGACTGATATTC

TTAACTATGTTGCTCCTTTTACGCTGTGTGGATATGCTGCTTTAATGCCTCTGTATCATGCT

ATTGCTTCCCGTACGGCTTTCGTTTTCTCCTCCTTGTATAAATCCTGGTTGCTGTCTCTTTAT

GAGGAGTTGTGGCCCGTTGTCCGTCAACGTGGCGTGGTGTGCTCTGTGTTTGCTGACGCAA

CCCCCACTGGCTGGGGCATTGCCACCACCTGTCAACTCCTTTCTGGGACTTTCGCTTTCCC

CCTCCCGATCGCCACGGCAGAACTCATCGCCGCCTGCCTTGCCCGCTGCTGGACAGGGGC

TAGGTTGCTGGGCACTGATAATTCCGTGGTGTTGTCGGGGAAGCTGACGTCCTTTCCAGGG

CTGCTCGCCTGTGTTGCCAACTGGATCCTGCGCGGGACGTCCTTCTGCTACGTCCCTTCGG

CTCTCAATCCAGCGGACCTCCCTTCCCGAGGCCTTCTGCCGGTTCTGCGGCCTCTCCCGCG

TCTTCGCTTTCGGCCTCCGACGAGTCGGATCTCCCTTTGGGCCGCCTCCCCGCCTGGGTAG

ATCCAGACATGATAAGATACATTGATGAGTTTGGACAAACCACAACTAGAATGCAGTGAA

AAAAATGCTTTATTTGTGAAATTTGTGATGCTATTGCTTTATTTGTAACCATTATAAGCTGC

AATAAACAAGTTAACAACAACAATTGCATTCATTTTATGTTTCAGGTTCAGGGGGAGGTG

TGGGAGGTTTTTTAAAGCAAGTAA

SEQ ID NO: 85

CTGTCTGAAAGGGAAGATATGAAAGGAATTTGTCGGTAAGTTTCTTATGATTGACTCACA

TGACGTGCTTTGTTTAACTCAGTGGAATCACGCTCATAAACCAAATATGTGCATGTGATCG

CGGCCGCCCTAGGCCACTACGGGTCTAGGCTGCCCATGTAAGGAGGCAAGGCCTGGGGAC

ACCCGAGATGCCTGGTTATAATTAACCCCAACACCTGCTGCCCCCCCCCCCCCCAACACCTG

CTGCCTGAGCCTGAGCGGTTACCCCACCCCGGTGCCTGGGTCTTAGGCTCTGTACACCATG

GAGGAGAAGCTCGCTCTAAAAATAACCCTGTCCCTGGTGGATCCACTACGGGTCTAGGCT

GCCCATGTAAGGAGGCAAGGCCTGGGGACACCCGAGATGCCTGGTTATAATTAACCCCAA

CACCTGCTGCCCCCCCCCCCCCCAACACCTGCTGCCTGAGCCTGAGCGGTTACCCCACCCCG

GTGCCTGGGTCTTAGGCTCTGTACACCATGGAGGAGAAGCTCGCTCTAAAAATAACCCTG

TCCCTGGTGGATCCACTACGGGTCTAGGCTGCCCATGTAAGGAGGCAAGGCCTGGGGACA

CCCGAGATGCCTGGTTATAATTAACCCCAACACCTGCTGCCCCCCCCCCCCCCAACACCTGC

TGCCTGAGCCTGAGCGGTTACCCCACCCCGGTGCCTGGGTCTTAGGCTCTGTACACCATGG

AGGAGAAGCTCGCTCTAAAAATAACCCTGTCCCTGGTGGATCCTCCCTGGGGACAGCCCC

TCCTGGCTAGTCACACCCTGTAGGCTCCTCTATATAACCCAGGGGCACAGGGGCTGCCCC

CGGGTCACGCCACCATGGCACCGAAGAAGAAGCGCAAGGTGCATATGAATACAAAATAT

AATAAAGAGTTCTTACTCTACTTAGCAGGGTTTGTAGACTCTGACGGTTCCATCATGGCCT

-continued

---
Sequence Listing
---

TCATCATGCCTACTCAAACCGCAAAGTTCAAGCACCGTCTGAAGCTCCAGTTCGCGGTCG

CACAGAAGACACAGCGCCGTTGGTTCCTCGACAAGCTGGTGGACGAGATCGGTGTGGGTT

ACGTGTATGACTTCGGCAGCGTCTCCTACTACCGTCTGTCCGAGATCAAGCCTTTGCATAA

TTTTTTAACACAACTACAACCTTTTCTAAAACTAAAACAAAAACAAGCAAATTTAGTTTTA

AAAATTATTGAACAACTTCCGTCAGCAAAAGAATCCCCGGACAAATTCTTAGAAGTTTGT

ACATGGGTGGATCAAATTGCAGCTCTGAATGATTCGAAGACGCGTAAAACAACTTCTGAA

ACCGTTCGTGCTGTGCTAGACAGTTTACCAGGCTCCGTGGGAGGTCTATCGCCATCTCAGG

CATCCAGCGCCGCATCCTCGGCTTCCTCAAGCCCGGGTTCAGGGATCTCCGAAGCACTCA

GAGCTGGAGCAGGTTCCGGCACTGGATACAACAAGGAATTCCTGCTCTACCTGGCGGGCT

TCGTAGACGGGGACGGCTCCATCTGTGCCTGTATCGTGCCTCGTCAAGATCGGAAGTTCA

AGCACCAGCTGCGGCTCTTTTTCGAGGTCGGTCAGAAGACACAGCGCCGTTGGTTCCTCG

ACAAGCTGGTGGACGAGATCGGTGTGGGTTACGTGCGTGACCTGGGCTCCGCGAGCACGT

ACCGGCTGTCCCAGATCAAGCCTCTGCACAACTTCCTGACCCAGCTCCAGCCCTTCCTGAA

GCTCAAGCAGAAGCAGGCCAACCTCGTGCTGAAGATCATCGAGCAGCTGCCCTCCGCCAA

GGAATCCCCGGACAAGTTCCTGGAGGTGTGCACCTGGGTGGACCAGATCGCCGCTCTGAA

CGACTCCAGGACCCGCAAGACCACTTCCGAAACCGTCCGCGCCGTTCTAGACAGTCTCTC

CGAGAAGAAGAAGTCGTCCCCTTCGCCGGCCGCTAAGCGCGTGAAGCTGGACGGTAGAG

CCAAGAGATCTGGAAGCGGCGCCACAAATTTCTCACTGCTGAAACAGGCCGGCGACGTGG

AAGAGAACCCTGGACCTGCTAGCGGAATGGCACCGAAAAAAAAGCGCAAAGTACATATG

AACACCAAGTACAACAAGGAATTTCTCTTGTATCTCGCCGGCTTCGTCGATGCCGATGGG

AGTATATACGCGTGCATAAAGCCCCACCAACAGTTGAAATTTAAACATCAGTTACTCTTGT

ACTTTGAGGTGTACCAAAAAACCCAAAGGAGGTGGTTTTTGGATAAGCTGGTCGATGAGA

TAGGAGTCGGGTATGTCGCCGATCGCGGGTCGGTGAGTGAGTATCGTTTAAGTCAAATAA

AACCGCTCCACAACTTCCTCACCCAGTTGCAGCCGTTCTTGAAGTTGAAGCAGAAGCAGG

CCAACCTCGTGCTCAAGATAATAGAGCAGTTGCCCAGCGCCAAGGAGAGTCCCGATAAGT

TTCTGGAGGTGTGTACCTGGGTGGACCAGATAGCCGCGTTAAACGACAGCAAAACCAGGA

AAACCACGAGCGAGACGGTGAGAGCGGTCTTGGATTCGCTCCCTGGCAGTGTCGGCGGAT

TGAGCCCAAGCCAAGCCAGTTCGGCAGCCAGTAGCGCGAGTAGCTCGCCAGGAAGCGGC

ATAAGTGAGGCTTTGAGAGCTGGAGCTGGAAGTGGTACCGGTTACAACAAGGAGTTCTTA

CTGTACTTAGCCGGGTTCGTGGATGGCGATGGGAGTATATTCGCGTCCATAATCCCCAGCC

AAGAGGTGAAATTTAAACATACCTTACTCTTGCGATTTCGCGTGTGCCAAGCAACCAAAA

GGAGGTGGTTTTTGGATAAGCTGGTCGATGAGATAGGAGTCGGGTATGTCTCCGATCAGG

GGTCGGCCTCGTACTATACCTTAAGTGAGATAAAACCGTTACATAACTTCTTAACGCAATT

GCAACCGTTTCTGAAACTGAAGCAGAAGCAAGCGAATCTGGTCCTGAAGATCATCGAACA

ACTGCCGAGTGCGAAGGAGTCCCCCGATAAGTTCCTCGAGGTCTGCACGTGGGTCGATCA

AATAGCGGCGTTAAATGATAGTAGGACGAGGAAAACGACGAGTGAGACGGTGAGGGCGG

TGTTGGATTCGTTGAGTGAAAAGAAAAAGAGCAGTCCTTCGCCGGCAGCGAAGAGGGTTA

AGCTCGACTAGTAAGCTTATCAACCTCTGGATTACAAAATTTGTGAAAGATTGACTGATAT

-continued

Sequence Listing

TCTTAACTATGTTGCTCCTTTTACGCTGTGTGGATATGCTGCTTTAATGCCTCTGTATCATG

CTATTGCTTCCCGTACGGCTTTCGTTTTCTCCTCCTTGTATAAATCCTGGTTGCTGTCTCTTT

ATGAGGAGTTGTGGCCCGTTGTCCGTCAACGTGGCGTGGTGTGCTCTGTGTTTGCTGACGC

AACCCCCACTGGCTGGGGCATTGCCACCACCTGTCAACTCCTTTCTGGGACTTTCGCTTTC

CCCCTCCCGATCGCCACGGCAGAACTCATCGCCGCCTGCCTTGCCCGCTGCTGGACAGGG

GCTAGGTTGCTGGGCACTGATAATTCCGTGGTGTTGTCGGGGAAGCTGACGTCCTTTCCAG

GGCTGCTCGCCTGTGTTGCCAACTGGATCCTGCGCGGGACGTCCTTCTGCTACGTCCCTTC

GGCTCTCAATCCAGCGGACCTCCCTTCCCGAGGCCTTCTGCCGGTTCTGCGGCCTCTCCCG

CGTCTTCGCTTTCGGCCTCCGACGAGTCGGATCTCCCTTTGGGCCGCCTCCCCGCCTGGGT

AGATCCAGACATGATAAGATACATTGATGAGTTTGGACAAACCACAACTAGAATGCAGTG

AAAAAAATGCTTTATTTGTGAAATTTGTGATGCTATTGCTTTATTTGTAACCATTATAAGC

TGCAATAAACAAGTTAACAACAACAATTGCATTCATTTTATGTTTCAGGTTCAGGGGGAG

GTGTGGGAGGTTTTTTAAAGCAAGTAA

SEQ ID NO: 86
CTGTCTGAAAGGGAAGATATGAAAGGAATTTGTCGGTAAGTTTCTTATGATTGACTCACA

TGACGTGCTTTGTTTAACTCAGTGGAATCACGCTCATAAACCAAATATGTGCATGTGATCT

CCCCCACTACGGGTCTAGGCTGCCCATGTAAGGAGGCAAGGCCTGGGGACACCCGAGATG

CCTGGTTATAATTAACCCCAACACCTGCTGCCCCCCCCCCCCCCAACACCTGCTGCCTGAGC

CTGAGCGGTTACCCCACCCCGGTGCCTGGGTCTTAGGCTCTGTACACCATGGAGGAGAAG

CTCGCTCTAAAAATAACCCTGTCCCTGGTGGATCCACTACGGGTCTAGGCTGCCCATGTAA

GGAGGCAAGGCCTGGGGACACCCGAGATGCCTGGTTATAATTAACCCCAACACCTGCTGC

CCCCCCCCCCCCAACACCTGCTGCCTGAGCCTGAGCGGTTACCCCACCCCGGTGCCTGGGT

CTTAGGCTCTGTACACCATGGAGGAGAAGCTCGCTCTAAAAATAACCCTGTCCCTGGTGG

ATCCACTACGGGTCTAGGCTGCCCATGTAAGGAGGCAAGGCCTGGGGACACCCGAGATGC

CTGGTTATAATTAACCCCAACACCTGCTGCCCCCCCCCCCCCCAACACCTGCTGCCTGAGCC

TGAGCGGTTACCCCACCCCGGTGCCTGGGTCTTAGGCTCTGTACACCATGGAGGAGAAGC

TCGCTCTAAAAATAACCCTGTCCCTGGTGGATCCTCCCTGGGGACAGCCCCTCCTGGCTAG

TCACACCCTGTAGGCTCCTCTATATAACCCAGGGGCACAGGGGCTGCCCCCGGGTCACTA

CTGCCACCATGGCACCTAAGAAAAAGAGAAAGGTCCATATGAATACCAAATACAATAAG

GAATTCCTCCTCTACTTGGCTGGGTTTGTGGACAGTGATGGCAGCATCATGGCCTTCATCC

TGCCTGAGCAGGGACTGAAGTTCAAGCACAGGCTGAGGCTGCAGTTTGCAGTGGCCCAGA

AAACCCAGAGAAGATGGTTTCTGGACAAGTTGGTGGATGAGATTGGGGTGGGGTATGTGT

ATGACTTTGGTTCAGTGAGCTACTACAGGCTCTCACAGATCAAGCCTCTGCATAACTTTCT

GACCCAGCTGCAGCCATTCCTCAAGCTGAAGCAGAAACAGGCCAACTTGGTCCTCAAGAT

CATTGAACAACTGCCCTCAGCTAAGGAGTCCCCAGACAAGTTCTTGGAGGTGTGTACCTG

GGTGGACCAGATAGCAGCACTTAATGACAGCAAGACTAGGAAAACCACCTCAGAGACTG

TCAGGGCTGTCCTGGACTCCCTCCCTGGTTCAGTTGGAGGGCTGTCCCCTAGCCAAGCCAG

CTCTGCAGCCTCCTCAGCCTCCAGCAGCCCAGGCTCAGGCATCTCAGAAGCCCTCAGAGC

TGGGGCAGGATCAGGCACTGGCTACAATAAGGAGTTCCTGCTGTACCTTGCTGGCTTTGTT

-continued

Sequence Listing

GATGGAGATGGAAGCATCTGTGCCTGCATTGTGCCCAGACAGGACAGAAAGTTCAAACAC

CAACTCAGACTGTTCTTTGAAGTGGGCCAAAAGACCCAGAGGAGATGGTTCTTGGACAAA

CTTGTGGATGAGATTGGAGTGGGCTATGTCAGGGATCTTGGTTCAGCCAGCACATACAGG

CTGTCCCAGATCAAACCCCTGCATAACTTCCTGACCCAACTGCAGCCATTCCTGAAGCTCA

AGCAGAAGCAGGCCAACTTGGTGCTGAAGATTATTGAACAGCTTCCTTCTGCCAAGGAAT

CCCCTGACAAGTTCCTGGAAGTGTGCACTTGGGTTGACCAGATTGCAGCCCTCAATGACA

GCAGGACCAGGAAGACCACTTCTGAGACTGTTAGAGCTGTGCTGGATAGCCTGTCAGAAA

AGAAGAAGTCCTCCCCTTCCCCTGCTGCCAAGAGGGTGAAGCTGGATGGTAGAGCCAAGA

GATCTGGAAGTGGAGCCACAAATTTCTCACTGCTGAAACAGGCTGGGGATGTGGAAGAG

AACCCTGGACCTGCTAGCGGAATGGCCCCCAAGAAGAAGAGGAAAGTGCACATGAACAC

CAAGTATAACAAGGAGTTCCTTCTGTATCTGGCTGGCTTTGTGGATTCTGATGGCTCCATC

TATGCCTGCATCAAGCCCCATCAGCAACTGAAGTTCAAACACCAGCTCCTCCTGTACTTTG

AGGTGTACCAAAAGACCCAGAGGAGATGGTTCTTGGACAAATTGGTAGATGAAATTGGA

GTGGGCTATGTGGCTGACAGGGGCTCAGTGTCAGAGTACAGGCTGTCCCAGATTAAGCCC

CTGCACAACTTCCTGACCCAACTGCAACCTTTCCTGAAACTCAAGCAGAAGCAGGCCAAC

CTGGTCCTGAAGATTATTGAACAGCTGCCATCAGCCAAGGAATCCCCTGACAAGTTCCTG

GAAGTCTGTACTTGGGTGGATCAGATTGCAGCCCTCAATGACTCCAAGACTAGAAAGACC

ACCTCTGAGACAGTCAGAGCTGTGCTGGATTCCCTGCCTGGATCAGTGGGAGGACTGAGC

CCAAGCCAGGCCTCCTCAGCTGCCAGCTCAGCCTCCTCCTCCCCTGGATCAGGAATCTCAG

AGGCCCTGAGAGCAGGGGCTGGCTCTGGTACTGGGTACAACAAGGAATTCCTGCTCTACC

TGGCTGGTTTTGTGGATGGGGATGGTTCCATCTTTGCCTCCATCATCCCTAGCCAGGAAGT

CAAGTTCAAGCATACCCTGCTCCTGAGATTCAGAGTGTGCCAGGCCACCAAGAGAAGATG

GTTCCTGGACAAGTTGGTGGATGAAATAGGAGTGGGATATGTGTCAGACAGGGGGAGTG

CCAGCTACTACACCCTGTCAGAGATCAAGCCCCTTCACAACTTTCTGACTCAACTCCAGCC

CTTCCTGAAATTGAAGCAAAAGCAGGCTAACCTGGTGCTCAAGATCATTGAGCAGCTCCC

CTCTGCCAAAGAGTCCCCTGATAAGTTCCTTGAAGTCTGCACCTGGGTGGACCAGATTGCT

GCCCTGAATGACTCCAGGACCAGAAAGACTACCTCAGAAACTGTCAGGGCAGTGCTGGAC

TCCCTGTCTGAGAAGAAAAAGTCCAGCCCAAGCCCTGCAGCCAAGAGAGTGAAGTTAGA

CTAGTAAGCTTATCAACCTCTGGATTACAAAATTTGTGAAAGATTGACTGATATTCTTAAC

TATGTTGCTCCTTTTACGCTGTGTGGATATGCTGCTTTAATGCCTCTGTATCATGCTATTGC

TTCCCGTACGGCTTTCGTTTTCTCCTCCTTGTATAAATCCTGGTTGCTGTCTCTTTATGAGG

AGTTGTGGCCCGTTGTCCGTCAACGTGGCGTGGTGTGCTCTGTGTTTGCTGACGCAACCCC

CACTGGCTGGGGCATTGCCACCACCTGTCAACTCCTTTCTGGGACTTTCGCTTTCCCCCTCC

CGATCGCCACGGCAGAACTCATCGCCGCCTGCCTTGCCCGCTGCTGGACAGGGGCTAGGT

TGCTGGGCACTGATAATTCCGTGGTGTTGTCGGGGAAGCTGACGTCCTTTCCAGGGCTGCT

CGCCTGTGTTGCCAACTGGATCCTGCGCGGGACGTCCTTCTGCTACGTCCCTTCGGCTCTC

AATCCAGCGGACCTCCCTTCCCGAGGCCTTCTGCCGGTTCTGCGGCCTCTCCCGCGTCTTC

GCTTTCGGCCTCCGACGAGTCGGATCTCCCTTTGGGCCGCCTCCCCGCCTGGGTAGATCCA

GACATGATAAGATACATTGATGAGTTTGGACAAACCACAACTAGAATGCAGTGAAAAAA

```
Sequence Listing
```

```
ATGCTTTATTTGTGAAATTTGTGATGCTATTGCTTTATTTGTAACCATTATAAGCTGCAATA

AACAAGTTAACAACAACAATTGCATTCATTTTATGTTTCAGGTTCAGGGGGAGGTGTGGG

AGGTTTTTTAAAGCAAGTAA
```

```
                                                SEQ ID NO: 87
CTGTCTGAAAGGGAAGATATGAAAGGAATTTGTCGGTAAGTTTCTTATGATTGACTCACA

TGACGTGCTTTGTTTAACTCAGTGGAATCACGCTCATAAACCAAATATGTGCATGTGATCT

CCCCCACTACGGGTCTAGGCTGCCCATGTAAGGAGGCAAGGCCTGGGGACACCCGAGATG

CCTGGTTATAATTAACCCCAACACCTGCTGCCCCCCCCCCCCCCAACACCTGCTGCCTGAGC

CTGAGCGGTTACCCCACCCCGGTGCCTGGGTCTTAGGCTCTGTACACCATGGAGGAGAAG

CTCGCTCTAAAAATAACCCTGTCCCTGGTGGATCCACTACGGGTCTAGGCTGCCCATGTAA

GGAGGCAAGGCCTGGGGACACCCGAGATGCCTGGTTATAATTAACCCCAACACCTGCTGC

CCCCCCCCCCCCAACACCTGCTGCCTGAGCCTGAGCGGTTACCCCACCCCGGTGCCTGGGT

CTTAGGCTCTGTACACCATGGAGGAGAAGCTCGCTCTAAAAATAACCCTGTCCCTGGTGG

ATCCACTACGGGTCTAGGCTGCCCATGTAAGGAGGCAAGGCCTGGGGACACCCGAGATGC

CTGGTTATAATTAACCCCAACACCTGCTGCCCCCCCCCCCCCCAACACCTGCTGCCTGAGCC

TGAGCGGTTACCCCACCCCGGTGCCTGGGTCTTAGGCTCTGTACACCATGGAGGAGAAGC

TCGCTCTAAAAATAACCCTGTCCCTGGTGGATCCTCCCTGGGGACAGCCCCTCCTGGCTAG

TCACACCCTGTAGGCTCCTCTATATAACCCAGGGGCACAGGGGCTGCCCCCGGGTCACTA

CTGCCACCATGGCACCGAAGAAGAAGCGCAAGGTGCATATGAATACAAAATATAATAAA

GAGTTCTTACTCTACTTAGCAGGGTTTGTAGACTCTGACGGTTCCATCATGGCCTTTATCTT

GCCTGAGCAGGGTCTGAAGTTCAAGCACCGTCTGAGGCTCCAGTTCGCGGTCGCTCAGAA

GACACAGCGCCGTTGGTTCCTCGACAAGCTGGTGGACGAGATCGGTGTGGGTTACGTGTA

TGACTTTGGCAGCGTCTCCTATTACAGGCTGTCCCAGATCAAGCCTTTGCATAATTTTTTA

ACACAACTACAACCTTTTCTAAAACTAAAACAAAAACAAGCAAATTTAGTTTTAAAAATT

ATTGAACAACTTCCGTCAGCAAAGAATCCCCGGACAAATTCTTAGAAGTTTGTACATGG

GTGGATCAAATTGCAGCTCTGAATGATTCGAAGACGCGTAAAACAACTTCTGAAACCGTT

CGTGCTGTGCTAGACAGTTTACCAGGATCCGTGGGAGGTCTATCGCCATCTCAGGCATCC

AGCGCCGCATCCTCGGCTTCCTCAAGCCCGGGTTCAGGGATCTCCGAAGCACTCAGAGCT

GGAGCAGGTTCCGGCACCGGATACAACAAGGAATTCCTGCTCTACCTGGCGGGCTTCGTC

GACGGGGACGGCTCCATCTGTGCCTGTATCGTGCCTCGTCAAGATCGGAAGTTCAAGCAC

CAGCTGCGGCTCTTTTTCGAGGTCGGTCAGAAGACACAGCGCCGTTGGTTCCTCGACAAG

CTGGTGGACGAGATCGGTGTGGGTTACGTGAGGGACCTTGGCAGCGCGAGCACTTACCGT

CTGTCCCAGATCAAGCCTCTGCACAACTTCCTGACCCAGCTCCAGCCCTTCCTGAAGCTCA

AGCAGAAGCAGGCCAACCTCGTGCTGAAGATCATCGAGCAGCTGCCCTCCGCCAAGGAAT

CCCCGGACAAGTTCCTGGAGGTGTGCACCTGGGTGGACCAGATCGCCGCTCTGAACGACT

CCAGGACCCGCAAGACCACTTCCGAAACCGTCCGCGCCGTTCTAGACAGTCTCTCCGAGA

AGAAGAAGTCGTCCCCTTCGCCGGCCGCTAAGCGCGTGAAGCTGGACGGTAGAGCCAAG

AGATCTGGAAGCGGCGCCACAAATTTCTCACTGCTGAAACAGGCCGGCGACGTGGAAGA

GAACCCTGGACCTGCTAGCGGAATGGCACCGAAAAAAAAGCGCAAAGTACATATGAACA
```

-continued

Sequence Listing

CCAAGTACAACAAGGAATTTCTCTTGTATCTCGCCGGCTTCGTCGATTCCGATGGAAGTAT

ATACGCGTGCATAAAGCCCCACCAACAGCTGAAGTTTAAACATCAGTTACTGTTGTACTTT

GAGGTGTACCAAAAGACCCAAAGAAGATGGTTCTTGGATAAGCTGGTCGATGAGATAGG

AGTCGGGTATGTCGCAGATCGCGGGTCGGTGAGTGAGTATCGGCTGAGTCAAATAAAACC

GCTCCACAACTTCCTCACCCAGTTGCAGCCGTTCTTGAAGTTGAAGCAGAAGCAGGCCAA

CCTCGTGCTCAAGATAATAGAGCAGTTGCCCAGCGCCAAGGAGAGTCCCGATAAGTTTCT

GGAGGTGTGTACCTGGGTGGACCAGATAGCCGCGTTAAACGACAGCAAAACCAGGAAAA

CCACGAGCGAAACCGTCAGAGCGGTCTTGGATTCGCTCCCTGGCAGTGTCGGCGGATTGA

GCCCAAGCCAAGCCAGTTCGGCAGCCAGTAGCGCGAGTAGCTCGCCAGGAAGCGGCATA

AGTGAGGCTTTGAGAGCTGGAGCTGGAAGTGGTACCGGTTACAACAAGGAGTTCTTACTG

TACTTAGCCGGGTTCGTGGATGGCGATGGGAGTATATTCGCGTCCATCATCCCCAGCCAA

GAGGTGAAGTTCAAGCATACCTTACTCCTGAGGTTCCGCGTGTGCCAAGCAACCAAGAGG

AGGTGGTTCCTGGATAAACTGGTCGACGAGATCGGGGTCGGGTATGTCTCCGATCGAGGG

TCGGCCTCGTACTATACTCTGAGTGAAATCAAACCGTTACATAACTTCTTAACGCAATTGC

AACCGTTTCTGAAACTGAAGCAGAAGCAAGCGAATCTGGTCCTGAAGATCATCGAACAAC

TGCCGAGTGCGAAGGAGTCCCCCGATAAGTTCCTCGAGGTCTGCACGTGGGTCGATCAAA

TAGCGGCGTTAAATGATAGTAGGACGAGGAAAACGACGAGTGAGACGGTGAGGGCGGTG

TTGGATTCGTTGAGTGAAAAGAAAAAGAGCAGTCCTTCGCCGGCAGCGAAGAGGGTTAA

GCTCGACTAGTAAGCTTATCAACCTCTGGATTACAAAATTTGTGAAAGATTGACTGATATT

CTTAACTATGTTGCTCCTTTTACGCTGTGTGGATATGCTGCTTTAATGCCTCTGTATCATGC

TATTGCTTCCCGTACGGCTTTCGTTTTCTCCTCCTTGTATAAATCCTGGTTGCTGTCTCTTTA

TGAGGAGTTGTGGCCCGTTGTCCGTCAACGTGGCGTGGTGTGCTCTGTGTTTGCTGACGCA

ACCCCCACTGGCTGGGGCATTGCCACCACCTGTCAACTCCTTTCTGGGACTTTCGCTTTCC

CCCTCCCGATCGCCACGGCAGAACTCATCGCCGCCTGCCTTGCCCGCTGCTGGACAGGGG

CTAGGTTGCTGGGCACTGATAATTCCGTGGTGTTGTCGGGGAAGCTGACGTCCTTTCCAGG

GCTGCTCGCCTGTGTTGCCAACTGGATCCTGCGCGGGACGTCCTTCTGCTACGTCCCTTCG

GCTCTCAATCCAGCGGACCTCCCTTCCCGAGGCCTTCTGCCGGTTCTGCGGCCTCTCCCGC

GTCTTCGCTTTCGGCCTCCGACGAGTCGGATCTCCCTTTGGGCCGCCTCCCCGCCTGGGTA

GATCCAGACATGATAAGATACATTGATGAGTTTGGACAAACCACAACTAGAATGCAGTGA

AAAAAATGCTTTATTTGTGAAATTTGTGATGCTATTGCTTTATTTGTAACCATTATAAGCT

GCAATAAACAAGTTAACAACAACAATTGCATTCATTTTATGTTTCAGGTTCAGGGGGAGG

TGTGGGAGGTTTTTTAAAGCAAGTAA

GGGTGGGTTGCTTTACCTCTCTAG
                                              SEQ ID NO: 88

TCACATCATGAGATTTAGTCACTTCC
                                              SEQ ID NO: 89

TTGCTACTTCACAGTAACCACATG
                                              SEQ ID NO: 90

TATGATCGCCTGTTCCTCCA
                                              SEQ ID NO: 91

-continued

| Sequence Listing |
| --- |

SEQ ID NO: 92

TAAGACCCAGCTTCACGGAG

SEQ ID NO: 93

AGGACAAAAGAGGACGGTCTGCCCTGG

SEQ ID NO: 94

CTCCATCACTAGGGGTTCCT

SEQ ID NO: 95

AGGAACCCCTAGTGATGGAG

SEQ ID NO: 96

ATGAATACAAAATATAATAAAGAGTTCTTACTCTACTTAGCAGGGTTTGTAGACGCTGAC

GGTTCCATCTATGCCTGTATCAAGCCTCATCAACAGCTTAAGTTCAAGCACCAGCTGTTGC

TCTATTTCGAGGTCTATCAGAAGACACAGCGCCGTTGGTTCCTCGACAAGCTGGTGGACG

AGATCGGTGTGGGTTACGTGGCTGACCGTGGCAGCGTCTCCGAGTACCGTCTGTCCCAGA

TCAAGCCTTTGCATAATTTTTTAACACAACTACAACCTTTTCTAAAACTAAAACAAAAACA

AGCAAATTTAGTTTTAAAAATTATTGAACAACTTCCGTCAGCAAAAGAATCCCCGGACAA

ATTCTTAGAAGTTTGTACATGGGTGGATCAAATTGCAGCTCTGAATGATTCGAAGACGCG

TAAAACAACTTCTGAAACCGTTCGTGCTGTGCTAGACAGTTTACCAGGATCCGTGGGAGG

TCTATCGCCATCTCAGGCATCCAGCGCCGCATCCTCGGCTTCCTCAAGCCCGGGTTCAGGG

ATCTCCGAAGCACTCAGAGCTGGAGCAGGTTCCGGCACTGGATACAACAAGGAATTCCTG

CTCTACCTGGCGGGCTTCGTCGACGGGGACGGCTCCATCTTTGCCTCTATCATTCCGTCGC

AGGAGGTTAAGTTCAAGCACACTCTGCTGCTCCGTTTCCGGGTCTGCCAGGCGACAAAGC

GCCGTTGGTTCCTCGACAAGCTGGTGGACGAGATTGGTGTGGGTTACGTGTCTGACCAGG

GCAGCGCGAGCTACTACACCCTGTCCGAGATCAAGCCTCTGCACAACTTCCTGACCCAGC

TCCAGCCCTTCCTGAAGCTCAAGCAGAAGCAGGCCAACCTCGTGCTGAAGATCATCGAGC

AGCTGCCCTCCGCCAAGGAATCCCCGGACAAGTTCCTGGAGGTGTGCACCTGGGTGGACC

AGATCGCCGCTCTGAACGACTCCAGGACCCGCAAGACCACTTCCGAAACCGTCCGCGCCG

TTCTAGACAGTCTCTCCGAGAAGAAGAAGTCGTCCCCC

SEQ ID NO: 97

ATGAATACAAAATATAATAAAGAGTTCTTACTCTACTTAGCAGGGTTTGTAGACTCTGAC

GGTTCCATCTATGCCTGTATCAAGCCTCATCAACAGCTTAAGTTCAAGCACCAGCTGTTGC

TCTATTTCGAGGTCTATCAGAAGACACAGCGCCGTTGGTTCCTCGACAAGCTGGTGGACG

AGATCGGTGTGGGTTACGTGGCTGACCGTGGCAGCGTCTCCGAGTACCGTCTGTCCCAGA

TCAAGCCTTTGCATAATTTTTTAACACAACTACAACCTTTTCTAAAACTAAAACAAAAACA

AGCAAATTTAGTTTTAAAAATTATTGAACAACTTCCGTCAGCAAAAGAATCCCCGGACAA

ATTCTTAGAAGTTTGTACATGGGTGGATCAAATTGCAGCTCTGAATGATTCGAAGACGCG

TAAAACAACTTCTGAAACCGTTCGTGCTGTGCTAGACAGTTTACCAGGATCCGTGGGAGG

TCTATCGCCATCTCAGGCATCCAGCGCCGCATCCTCGGCTTCCTCAAGCCCGGGTTCAGGG

ATCTCCGAAGCACTCAGAGCTGGAGCAGGTTCCGGCACTGGATACAACAAGGAATTCCTG

CTCTACCTGGCGGGCTTCGTCGACGGGGACGGCTCCATCTTTGCCTCTATCATTCCGTCGC

AGGAGGTTAAGTTCAAGCACACTCTGCTGCTCCGTTTCCGGGTCTGCCAGGCGACAAAGC

GCCGTTGGTTCCTCGACAAGCTGGTGGACGAGATTGGTGTGGGTTACGTGTCTGACCGTG

GCAGCGCGAGCTATTACACCCTGTCCGAGATCAAGCCTCTGCACAACTTCCTGACCCAGC

Sequence Listing

TCCAGCCCTTCCTGAAGCTCAAGCAGAAGCAGGCCAACCTCGTGCTGAAGATCATCGAGC

AGCTGCCCTCCGCCAAGGAATCCCCGGACAAGTTCCTGGAGGTGTGCACCTGGGTGGACC

AGATCGCCGCTCTGAACGACTCCAGGACCCGCAAGACCACTTCCGAAACCGTCCGCGCCG

TTCTAGACAGTCTCTCCGAGAAGAAGAAGTCGTCCCCC

SEQ ID NO: 98
ATGAATACAAAATATAATAAAGAGTTCTTACTCTACTTAGCAGGGTTTGTAGACGCTGAC

GGTTCCATCTATGCCTGTATCAAGCCTCATCAAGAGCTTAAGTTCAAGCACCAGCTGTTGC

TCTATTTCGAGGTCTATCAGAAGACACAGCGCCGTTGGTTCCTCGACAAGCTGGTGGACG

AGATCGGTGTGGGTTACGTGGCTGACCGTGGCAGCGTCTCCGAGTACCGTCTGTCCGAGA

TCAAGCCTTTGCATAATTTTTTAACACAACTACAACCTTTTCTAAAACTAAAACAAAAACA

AGCAAATTTAGTTTTAAAAATTATTGAACAACTTCCGTCAGCAAAAGAATCCCCGGACAA

ATTCTTAGAAGTTTGTACATGGGTGGATCAAATTGCAGCTCTGAATGATTCGAAGACGCG

TAAAACAACTTCTGAAACCGTTCGTGCTGTGCTAGACAGTTTACCAGGATCCGTGGGAGG

TCTATCGCCATCTCAGGCATCCAGCGCCGCATCCTCGGCTTCCTCAAGCCCGGGTTCAGGG

ATCTCCGAAGCACTCAGAGCTGGAGCAGGTTCCGGCACTGGATACAACAAGGAATTCCTG

CTCTACCTGGCGGGCTTCGTCGACGGGGACGGCTCCATCTTTGCCTCTATCATTCCGTCGC

AGGAGGTTAAGTTCAAGCACACTCTGCTGCTCCGTTTCCGGGTCTGCCAGGCGACAAAGC

GCCGTTGGTTCCTCGACAAGCTGGTGGACGAGATTGGTGTGGGTTACGTGTCTGACCAGG

GCAGCGCGAGCTACTACACCCTGTCCCAGATCAAGCCTCTGCACAACTTCCTGACCCAGC

TCCAGCCCTTCCTGAAGCTCAAGCAGAAGCAGGCCAACCTCGTGCTGAAGATCATCGAGC

AGCTGCCCTCCGCCAAGGAATCCCCGGACAAGTTCCTGGAGGTGTGCACCTGGGTGGACC

AGATCGCCGCTCTGAACGACTCCAGGACCCGCAAGACCACTTCCGAAACCGTCCGCGCCG

TTCTAGACAGTCTCTCCGAGAAGAAGAAGTCGTCCCCC

SEQ ID NO: 99
ATGAATACAAAATATAATAAAGAGTTCTTACTCTACTTAGCAGGGTTTGTAGACTCTGAC

GGTTCCATCATGGCCTTTATCTTGCCTGAGCAGGGTCTGAAGTTCAAGCACCGTCTGAGGC

TCCAGTTCGCGGTCGCTCAGAAGACACAGCGCCGTTGGTTCCTCGACAAGCTGGTGGACG

AGATCGGTGTGGGTTACGTGTATGACTTTGGCAGCGTCTCCTATTACAGGCTGTCCCAGAT

CAAGCCTTTGCATAATTTTTTAACACAACTACAACCTTTTCTAAAACTAAAACAAAAACAA

GCAAATTTAGTTTTAAAAATTATTGAACAACTTCCGTCAGCAAAAGAATCCCCGGACAAA

TTCTTAGAAGTTTGTACATGGGTGGATCAAATTGCAGCTCTGAATGATTCGAAGACGCGT

AAAACAACTTCTGAAACCGTTCGTGCTGTGCTAGACAGTTTACCAGGATCCGTGGGAGGT

CTATCGCCATCTCAGGCATCCAGCGCCGCATCCTCGGCTTCCTCAAGCCCGGGTTCAGGGA

TCTCCGAAGCACTCAGAGCTGGAGCAGGTTCCGGCACCGGATACAACAAGGAATTCCTGC

TCTACCTGGCGGGCTTCGTCGACGGGGACGGCTCCATCTGTGCCTGTATCGTGCCTCGTCA

AGATCGGAAGTTCAAGCACCAGCTGCGGCTCTTTTTCGAGGTCGGTCAGAAGACACAGCG

CCGTTGGTTCCTCGACAAGCTGGTGGACGAGATCGGTGTGGGTTACGTGAGGGACCTTGG

CAGCGCGAGCACTTACCGTCTGTCCCAGATCAAGCCTCTGCACAACTTCCTGACCCAGCTC

CAGCCCTTCCTGAAGCTCAAGCAGAAGCAGGCCAACCTCGTGCTGAAGATCATCGAGCAG

-continued

Sequence Listing

CTGCCCTCCGCCAAGGAATCCCCGGACAAGTTCCTGGAGGTGTGCACCTGGGTGGACCAG

ATCGCCGCTCTGAACGACTCCAGGACCCGCAAGACCACTTCCGAAACCGTCCGCGCCGTT

CTAGACAGTCTCTCCGAGAAGAAGAAGTCGTCCCCT

SEQ ID NO: 100
ATGAACACCAAGTACAACAAGGAATTTCTCTTGTATCTCGCCGGCTTCGTCGATTCCGATG

GAAGTATATACGCGTGCATAAAGCCCCACCAACAGCTGAAGTTTAAACATCAGTTACTGT

TGTACTTTGAGGTGTACCAAAAGACCCAAAGAAGATGGTTCTTGGATAAGCTGGTCGATG

AGATAGGAGTCGGGTATGTCGCAGATCGCGGGTCGGTGAGTGAGTATCGGCTGAGTCAAA

TAAAACCGCTCCACAACTTCCTCACCCAGTTGCAGCCGTTCTTGAAGTTGAAGCAGAAGC

AGGCCAACCTCGTGCTCAAGATAATAGAGCAGTTGCCCAGCGCCAAGGAGAGTCCCGATA

AGTTTCTGGAGGTGTGTACCTGGGTGGACCAGATAGCCGCGTTAAACGACAGCAAAACCA

GGAAAACCACGAGCGAAACCGTCAGAGCGGTCTTGGATTCGCTCCCTGGCAGTGTCGGCG

GATTGAGCCCAAGCCAAGCCAGTTCGGCAGCCAGTAGCGCGAGTAGCTCGCCAGGAAGC

GGCATAAGTGAGGCTTTGAGAGCTGGAGCTGGAAGTGGTACCGGTTACAACAAGGAGTTC

TTACTGTACTTAGCCGGGTTCGTGGATGGCGATGGGAGTATATTCGCGTCCATCATCCCCA

GCCAAGAGGTGAAGTTCAAGCATACCTTACTCCTGAGGTTCCGCGTGTGCCAAGCAACCA

AGAGGAGGTGGTTCCTGGATAAACTGGTCGACGAGATCGGGGTCGGGTATGTCTCCGATC

GAGGGTCGGCCTCGTACTATACTCTGAGTGAAATCAAACCGTTACATAACTTCTTAACGC

AATTGCAACCGTTTCTGAAACTGAAGCAGAAGCAAGCGAATCTGGTCCTGAAGATCATCG

AACAACTGCCGAGTGCGAAGGAGTCCCCCGATAAGTTCCTCGAGGTCTGCACGTGGGTCG

ATCAAATAGCGGCGTTAAATGATAGTAGGACGAGGAAAACGACGAGTGAGACGGTGAGG

GCGGTGTTGGATTCGTTGAGTGAAAAGAAAAAGAGCAGTCCT

SEQ ID NO: 101
ATGAATACCAAATACAATAAGGAATTCCTCCTCTACTTGGCTGGGTTTGTGGACAGTGAT

GGCAGCATCATGGCCTTCATCCTGCCTGAGCAGGGACTGAAGTTCAAGCACAGGCTGAGG

CTGCAGTTTGCAGTGGCCCAGAAAACCCAGAGAAGATGGTTTCTGGACAAGTTGGTGGAT

GAGATTGGGGGGGGTATGTGTATGACTTTGGTTCAGTGAGCTACTACAGGCTCTCACAG

ATCAAGCCTCTGCATAACTTTCTGACCCAGCTGCAGCCATTCCTCAAGCTGAAGCAGAAA

CAGGCCAACTTGGTCCTCAAGATCATTGAACAACTGCCCTCAGCTAAGGAGTCCCCAGAC

AAGTTCTTGGAGGTGTGTACCTGGGTGGACCAGATAGCAGCACTTAATGACAGCAAGACT

AGGAAAACCACCTCAGAGACTGTCAGGGCTGTCCTGGACTCCCTCCCTGGTTCAGTTGGA

GGGCTGTCCCCTAGCCAAGCCAGCTCTGCAGCCTCCTCAGCCTCCAGCAGCCCAGGCTCA

GGCATCTCAGAAGCCCTCAGAGCTGGGGCAGGATCAGGCACTGGCTACAATAAGGAGTTC

CTGCTGTACCTTGCTGGCTTTGTTGATGGAGATGGAAGCATCTGTGCCTGCATTGTGCCCA

GACAGGACAGAAAGTTCAAACACCAACTCAGACTGTTCTTTGAAGTGGGCCAAAAGACCC

AGAGGAGATGGTTCTTGGACAAACTTGTGGATGAGATTGGAGTGGGCTATGTCAGGGATC

TTGGTTCAGCCAGCACATACAGGCTGTCCCAGATCAAACCCCTGCATAACTTCCTGACCCA

ACTGCAGCCATTCCTGAAGCTCAAGCAGAAGCAGGCCAACTTGGTGCTGAAGATTATTGA

-continued

```
Sequence Listing
```

ACAGCTTCCTTCTGCCAAGGAATCCCCTGACAAGTTCCTGGAAGTGTGCACTTGGGTTGAC

CAGATTGCAGCCCTCAATGACAGCAGGACCAGGAAGACCACTTCTGAGACTGTTAGAGCT

GTGCTGGATAGCCTGTCAGAAAAGAAGAAGTCCTCCCCT

```
                                          SEQ ID NO: 102
```
ATGAACACCAAGTATAACAAGGAGTTCCTTCTGTATCTGGCTGGCTTTGTGGATTCTGATG

GCTCCATCTATGCCTGCATCAAGCCCCATCAGCAACTGAAGTTCAAACACCAGCTCCTCCT

GTACTTTGAGGTGTACCAAAAGACCCAGAGGAGATGGTTCTTGGACAAATTGGTAGATGA

AATTGGAGTGGGCTATGTGGCTGACAGGGGCTCAGTGTCAGAGTACAGGCTGTCCCAGAT

TAAGCCCCTGCACAACTTCCTGACCCAACTGCAACCTTTCCTGAAACTCAAGCAGAAGCA

GGCCAACCTGGTCCTGAAGATTATTGAACAGCTGCCATCAGCCAAGGAATCCCCTGACAA

GTTCCTGGAAGTCTGTACTTGGGTGGATCAGATTGCAGCCCTCAATGACTCCAAGACTAG

AAAGACCACCTCTGAGACAGTCAGAGCTGTGCTGGATTCCCTGCCTGGATCAGTGGGAGG

ACTGAGCCCAAGCCAGGCCTCCTCAGCTGCCAGCTCAGCCTCCTCCTCCCCTGGATCAGG

AATCTCAGAGGCCCTGAGAGCAGGGGCTGGCTCTGGTACTGGGTACAACAAGGAATTCCT

GCTCTACCTGGCTGGTTTTGTGGATGGGGATGGTTCCATCTTTGCCTCCATCATCCCTAGC

CAGGAAGTCAAGTTCAAGCATACCCTGCTCCTGAGATTCAGAGTGTGCCAGGCCACCAAG

AGAAGATGGTTCCTGGACAAGTTGGTGGATGAAATAGGAGTGGGATATGTGTCAGACAG

GGGGAGTGCCAGCTACTACACCCTGTCAGAGATCAAGCCCCTTCACAACTTTCTGACTCA

ACTCCAGCCCTTCCTGAAATTGAAGCAAAAGCAGGCTAACCTGGTGCTCAAGATCATTGA

GCAGCTCCCCTCTGCCAAAGAGTCCCCTGATAAGTTCCTTGAAGTCTGCACCTGGGTGGAC

CAGATTGCTGCCCTGAATGACTCCAGGACCAGAAAGACTACCTCAGAAACTGTCAGGGCA

GTGCTGGACTCCCTGTCTGAGAAGAAAAAGTCCAGCCCA

```
                                          SEQ ID NO: 103
```
RAKRSGSGATNFSLLKQAGDVEENPGP

```
                                          SEQ ID NO: 104
```
AGAGCCAAGAGATCTGGAAGCGGCGCCACAAATTTCTCACTGCTGAAACAGGCCGGCGA

CGTGGAAGAGAACCCTGGACCT

```
                                          SEQ ID NO: 105
```
AGAGCCAAGAGATCTGGAAGTGGAGCCACAAATTTCTCACTGCTGAAACAGGCTGGGGA

TGTGGAAGAGAACCCTGGACCT

```
                                          SEQ ID NO: 106
```
ATGGCACCGAAGAAGAAGCGCAAGGTGCAT

```
                                          SEQ ID NO: 107
```
ATGGCACCTAAGAAAAAGAGAAAGGTCCAT

```
                                          SEQ ID NO: 108
```
CCGGCCGCTAAGCGCGTGAAGCTGGAC

```
                                          SEQ ID NO: 109
```
CCTGCTGCCAAGAGGGTGAAGCTGGAT

```
                                          SEQ ID NO: 110
```
ATGGCACCGAAAAAAAAGCGCAAAGTACAT

```
                                          SEQ ID NO: 111
```
ATGGCCCCCAAGAAGAAGAGGAAAGTGCAC

```
                                          SEQ ID NO: 112
```
CCGGCAGCGAAGAGGGTTAAGCTCGAC

-continued

---
Sequence Listing
---

SEQ ID NO: 113

CCTGCAGCCAAGAGAGTGAAGTTAGAC

SEQ ID NO: 114

GATCCAGACATGATAAGATACATTGATGAGTTTGGACAAACCACAACTAGAATGCAGTGA

AAAAAATGCTTTATTTGTGAAATTTGTGATGCTATTGCTTTATTTGTAACCATTATAAGCT

GCAATAAACAAGTTAACAACAACAATTGCATTCATTTTATGTTTCAGGTTCAGGGGGAGG

TGTGGGAGGTTTTTTAAAGCAAGTAA

---

What is claimed is:

1. A polynucleotide comprising a muscle-specific expression cassette comprising the nucleic acid sequence of SEQ ID NO: 86, wherein said polynucleotide is a recombinant adeno-associated virus 9 (AAV9) viral genome, wherein said muscle-specific expression cassette is flanked by a 5' and inverted terminal repeat (ITR) sequence and a 3' ITR sequence, and wherein said 5' ITR sequence comprises a first D-sequence comprising the nucleic acid sequence of SEQ ID NO: 94 and said 3' ITR sequence comprises a second D-sequence comprising the nucleic acid sequence of SEQ ID NO: 95.

2. A recombinant AAV comprising said polynucleotide of claim 1, wherein said AAV has an AAV9 capsid.

3. A pharmaceutical composition comprising a pharmaceutically acceptable carrier and said polynucleotide of claim 1.

4. A pharmaceutical composition comprising a pharmaceutically acceptable carrier and said recombinant AAV of claim 2.

* * * * *

SEQUENCE LISTING

Sequence total quantity: 114
SEQ ID NO: 1              moltype = DNA   length = 120
FEATURE                   Location/Qualifiers
source                    1..120
                          mol_type = other DNA
                          organism = synthetic construct
SEQUENCE: 1
ctgtctgaaa gggaagatat gaaaggaatt tgtcggtaag tttcttatga ttgactcaca   60
tgacgtgctt tgtttaactc agtggaatca cgctcataaa ccaaatatgt gcatgtgatc   120

SEQ ID NO: 2              moltype = DNA   length = 365
FEATURE                   Location/Qualifiers
source                    1..365
                          mol_type = other DNA
                          organism = synthetic construct
SEQUENCE: 2
aatcaaggct gtgggggact gagggcaggc tgtaacaggc ttgggggcca gggcttatac   60
gtgcctggga ctcccaaagt attactgttc catgttcccg gcgaagggcc agctgtcccc   120
cgccagctag actcagcact tagtttagga accagtgagc aagtcagccc ttggggcagc   180
ccatacaagg ccatggggct gggcaagctg cacgcctggg tccggggtgg gcacggtgcc   240
cgggcaacga gctgaaagct catctgctct caggggcccc tccctgggga cagcccctcc   300
tggctagtca caccctgtag gctcctctat ataacccagg ggcacagggg ctgccccggg   360
gtcac                                                                365

SEQ ID NO: 3              moltype = DNA   length = 87
FEATURE                   Location/Qualifiers
source                    1..87
                          mol_type = other DNA
                          organism = synthetic construct
SEQUENCE: 3
cctccctggg gacagcccct cctggctagt cacaccctgt aggctcctct atataaccca   60
ggggcacagg ggctgccccc gggtcac                                       87

SEQ ID NO: 4              moltype = DNA   length = 12
FEATURE                   Location/Qualifiers
source                    1..12
                          mol_type = other DNA
                          organism = synthetic construct
SEQUENCE: 4
aacacctgct gc                                                        12

SEQ ID NO: 5              moltype = DNA   length = 10
FEATURE                   Location/Qualifiers
source                    1..10
                          mol_type = other DNA
                          organism = synthetic construct
SEQUENCE: 5
aacaggtgct                                                           10

SEQ ID NO: 6              moltype = DNA   length = 10
FEATURE                   Location/Qualifiers
source                    1..10
                          mol_type = other DNA
                          organism = synthetic construct
SEQUENCE: 6
aacacgtgct                                                           10

SEQ ID NO: 7              moltype = DNA   length = 10

-continued

```
FEATURE                Location/Qualifiers
source                 1..10
                       mol_type = other DNA
                       organism = synthetic construct
SEQUENCE: 7
aacagctgct                                                          10

SEQ ID NO: 8           moltype = DNA   length = 10
FEATURE                Location/Qualifiers
source                 1..10
                       mol_type = other DNA
                       organism = synthetic construct
SEQUENCE: 8
aacacctgca                                                          10

SEQ ID NO: 9           moltype = DNA   length = 10
FEATURE                Location/Qualifiers
source                 1..10
                       mol_type = other DNA
                       organism = synthetic construct
SEQUENCE: 9
aacaggtgca                                                          10

SEQ ID NO: 10          moltype = DNA   length = 10
FEATURE                Location/Qualifiers
source                 1..10
                       mol_type = other DNA
                       organism = synthetic construct
SEQUENCE: 10
aacacgtgca                                                          10

SEQ ID NO: 11          moltype = DNA   length = 10
FEATURE                Location/Qualifiers
source                 1..10
                       mol_type = other DNA
                       organism = synthetic construct
SEQUENCE: 11
aacagctgca                                                          10

SEQ ID NO: 12          moltype = DNA   length = 12
FEATURE                Location/Qualifiers
source                 1..12
                       mol_type = other DNA
                       organism = synthetic construct
SEQUENCE: 12
aacaggtgct gc                                                       12

SEQ ID NO: 13          moltype = DNA   length = 12
FEATURE                Location/Qualifiers
source                 1..12
                       mol_type = other DNA
                       organism = synthetic construct
SEQUENCE: 13
aacacgtgct gc                                                       12

SEQ ID NO: 14          moltype = DNA   length = 12
FEATURE                Location/Qualifiers
source                 1..12
                       mol_type = other DNA
                       organism = synthetic construct
SEQUENCE: 14
aacagctgct gc                                                       12

SEQ ID NO: 15          moltype = DNA   length = 12
FEATURE                Location/Qualifiers
source                 1..12
                       mol_type = other DNA
                       organism = synthetic construct
SEQUENCE: 15
aacacctgca gc                                                       12

SEQ ID NO: 16          moltype = DNA   length = 12
FEATURE                Location/Qualifiers
source                 1..12
                       mol_type = other DNA
                       organism = synthetic construct
SEQUENCE: 16
aacaggtgca gc                                                       12
```

-continued

```
SEQ ID NO: 17          moltype = DNA  length = 12
FEATURE                Location/Qualifiers
source                 1..12
                       mol_type = other DNA
                       organism = synthetic construct
SEQUENCE: 17
aacacgtgca gc                                                         12

SEQ ID NO: 18          moltype = DNA  length = 3357
FEATURE                Location/Qualifiers
source                 1..3357
                       mol_type = genomic DNA
                       organism = Mus musculus
SEQUENCE: 18
ccatcctggt ctatagagag agttccagaa cagccagggc tacagataaa cccatctgga   60
aaaacaaagt tgaatgaccc aagaggggtt ctcagagggt ggcgtgtgct ccctggcaag  120
cctatgacat ggccgggggcc tgcctctctc tgcctctgac cctcagtggc tcccatgaac  180
tccttgccca atggcatctt tttcctgcgc tccttgggtt attccagtct cccctcagca  240
ttccttcctc agggcctcgc tcttctctct gctccctcct tgcacagctg gctctgtcca  300
cctcagatgt cacagtgctc tctcagagga ggaaggcacc atgtaccctc tgtttcccag  360
gtaagggttc aattttaa  aatggttttt tgtttgtttg tttgtttgtt tgtttgtttg  420
tttttcaaga cagggctcct ctgtgtagtc ctaactgtct tgaaactccc tctgtagacc  480
aggtcgacct cgaactcttg aaacctgcca cggaccaccc agtcaggtat ggaggtccct  540
ggaatgagcg tcctcgaagc taggtgggta agggttcggc ggtgacaaac agaaacaaac  600
acagaggcag tttgaatctg agtgtatttt gcagctctca agcaggggat tttatacata  660
aaaaaaaaaa aaaaaaaaaa accaaacatt acatctctta gaaactatat ccaatgaaac  720
aatcacagat accaaccaaa accattgggc agagtaaagc acaaaaatca tccaagcatt  780
acaactctga aaccatgtat tcagtgaatc acaaacagaa caggtaacat cattattaat  840
ataaatcacc aaaatataac aattctaaaa ggatgtatcc agtgggggct gtcgtccaag  900
gctagtggca gatttccagg agcaggttag taaatcttaa ccactgaact aactctccag  960
ccccatggtc aattattatt tagcatctag tgcctaattt ttttttataa atcttcacta 1020
tgtaatttaa aactattta  attcttccta attaaggctt tctttaccat ataccaaaat 1080
tcacctccaa tgcacacgc  gtagccatat gaaattttat tgttgggaaa atttgtacct 1140
atcataatag ttttgtaaat gatttaaaaa gcaaagtgtt agccgggcgt ggtggcacac 1200
gcctttaatc cctgcactcg ggaggcaggg gcaggaggat ttctgagttt gaggccagcc 1260
tggtctacag agtgagttcc aggacagcca gggctacaca gagaaaccct gtctcgaacc 1320
ccccaccccc caaaaaaagc aaagtgttgg tttccttggg gataaagtca tgttagtggc 1380
ccatctctag gcccatctca cccattattc tcgcttaaga tcttggccta ggctaccagg 1440
aacatgtaaa taagaaaagg aataagagaa aacaaaacag agagattgcc atgagaacta 1500
cggctcaata ttttttctct ccggcgaaga gttccacaac catctccagg aggcctccac 1560
gttttgaggt caatggcctc agtctgtgga acttgtcaca cagatcttac tggaggtggt 1620
gtggcagaaa cccattcctt ttagtgtctt gggctaaaag taaaaggccc agaggaggcc 1680
tttgctcatc tgaccatgct gacaaggaac acgggtgcca ggacagaggc tggaccccag 1740
gaacaccta  aacacttctt cccttctccg cccctagag  caggctccc  tcaccagcct 1800
gggcagaaat gggggaagat ggagtgaagc catactggct actccagaat caacagaggg 1860
agccggggggc aatactggag aagctggtct ccccccaggg gcaatcctgg cacctcccag 1920
gcagaagagg aaacttccac agtgcatctc acttccatga atccccctcct cggactctga 1980
ggtccttggt cacagctgag gtgcaaaagg ctcctgtcat attgtgtcct gctctggtct 2040
gccttccaca gcttggggggc cacctagccc acctctccct agggatgaga gcagccacta 2100
cgggtctagg ctgcccatgt aaggaggcaa ggcctgggga cacccgagat gcctggttat 2160
aattaaccca gacatgtggc tgccccccccc ccccaacac ctgctgcctg agcctcaccc 2220
ccaccccggt gcctgggtct taggctctgt acaccatgga ggagaagctc gctctaaaaa 2280
taaccctgtc cctggtggat ccagggtgag gggcaggctg agggcggcca cttccctcag 2340
ccgcaggttt gttttcccaa gaatggtttt tctgcttctg tagcttttcc tgtcaattct 2400
gccatggtgg agcagcctgc actgggcttc tgggagaaac caaaccggggt tctaaccttt 2460
cagctacagt tattgccttt cctgtagatg ggcgactaca gccccacccc caccccgtc 2520
tcctgtatcc ttcctgggcc tggggatcct aggcttcac  tggaaatttc ccccaggtg  2580
ctgtaggcta gagtcacggc tcccaagaac agtgcttgcc tggcatgcat ggttctgaac 2640
ctccaactgc aaaaaatgac acataccttg acccttggaa ggctgaggca gggggattgc 2700
catgagtgca aagccagact gggtggcata gttagaccct gtctcaaaaa accaaaaaca 2760
attaaataac taaagtcagg caagtaatcc tactcgggag actgaggcag agggattgtt 2820
acatgtctga ggccagcctg gactacatag ggtttcaggc tagccctgtc tacagagtaa 2880
ggccctattt caaaaacaca aacaaaatgg ttctcccagc tgctaatgct caccaggcaa 2940
tgaagcctgg tgagcattag caatgaaggc aatgaacaagg ggtgctggtc acaatcaagg 3000
ctgtgggggga ctgagggcag gctgtaacag gcttgggggc cagggcttat acgtgcctgg 3060
gactcccaaa gtattactgt tccatgttcc cggcgaaggg ccagctgtcc cccgccagct 3120
agactcagca cttagtttag gaaccagtga gcaagtcagc ccttgggca gcccatacaa 3180
ggccatgggg ctgggcaagc tgcacgcctg ggtccggggt gggcacggtg cccgggcaac 3240
gagctgaaag ctcatctgct ctcagggggcc cctccctggg gacagccct  cctggctagt 3300
cacaccctgt aggctcctct atataaccca gggggcacagg ggctgccccc gggtcac      3357

SEQ ID NO: 19          moltype = DNA  length = 655
FEATURE                Location/Qualifiers
source                 1..655
                       mol_type = genomic DNA
                       organism = Homo sapiens
SEQUENCE: 19
cctgagtttg aatctctcca actcagccag cctcagtttc ccctccactc agtccctagg   60
aggaagggggc gcccaagcgg gtttctgggg ttagactgcc ctccattgca attggtcctt  120
```

-continued

```
ctcccggcct ctgcttcctc cagctcacag ggtatctgct cctcctggag ccacaccttg    180
gttccccgag gtgccgctgg gactcgggta ggggtgaggg cccaggggcg acagggggag    240
ccgagggcca caggaagggc tggtggctga aggagactca ggggccaggg gacggtggct    300
tctacgtgct tgggacgttc ccagccaccg tcccatgttc ccggcggggg ccagctgtcc    360
ccaccgccag cccaactcag cacttggtta gggtatcagc ttggtggggg cgtgagccca    420
gccctggggc gctcagccca tacaaggcca tggggctggg cgcaaagcat gcctgggttc    480
agggtgggta tggtgccgga gcagggaggt gagaggctca gctgccctcc agaactcctc    540
cctggggaca acccctccca gccaatagca cagcctaggt cccccatat aaggccacgg    600
ctgctggccc ttcctttggg tcagtgtcac ctccaggata cagacagccc ccctt         655
```

SEQ ID NO: 20          moltype = DNA   length = 206
FEATURE                Location/Qualifiers
source                 1..206
                       mol_type = genomic DNA
                       organism = Mus musculus
SEQUENCE: 20
```
ccactacggg tctaggctgc ccatgtaagg aggcaaggcc tggggacacc cgagatgcct    60
ggttataatt aacccagaca tgtggctgcc cccccccccc caacacctgc tgcctgagcc    120
tcacccccac cccggtgcct gggtcttagg ctctgtacac catggaggag aagctcgctc    180
taaaaataac cctgtccctg gtggat                                         206
```

SEQ ID NO: 21          moltype = DNA   length = 211
FEATURE                Location/Qualifiers
source                 1..211
                       mol_type = other DNA
                       organism = synthetic construct
SEQUENCE: 21
```
ccactacggg tctaggctgc ccatgtaagg aggcaaggcc tggggacacc cgagatgcct    60
ggttataatt aaccccaaca cctgctgccc cccccccccc aacacctgct gcctgagcct    120
gagcggttac cccaccccgg tgcctgggtc ttaggtctg tacaccatgg aggagaagct    180
cgctctaaaa ataaccctgt ccctggtgga t                                   211
```

SEQ ID NO: 22          moltype = DNA   length = 720
FEATURE                Location/Qualifiers
source                 1..720
                       mol_type = other DNA
                       organism = synthetic construct
SEQUENCE: 22
```
ccactacggg tctaggctgc ccatgtaagg aggcaaggcc tggggacacc cgagatgcct    60
ggttataatt aaccccaaca cctgctgccc cccccccccc aacacctgct gcctgagcct    120
gagcggttac cccaccccgg tgcctgggtc ttaggtctg tacaccatgg aggagaagct    180
cgctctaaaa ataaccctgt ccctggtgga tccactacgg gtctaggctg cccatgtaag    240
gaggcaaggc ctggggacac ccgagatgcc tggttataat taaccccaac acctgctgcc    300
cccccccccc caacacctgc tgcctgagcc tgagcggtta ccccaccccg gtgcctgggt    360
cttaggctct gtacaccatg gaggagaagc tcgctctaaa aataaccctg tccctggtgg    420
atccactacg ggtctaggct gcccatgtaa ggaggcaagg cctgggggaca cccgagatgc    480
ctggttataa ttaaccccaa cacctgctgc ccccccccc ccaacacctg ctgcctgagc    540
ctgagcggtt accccacccc ggtgcctggg tcttaggctc tgtacaccat ggaggagaag    600
ctcgctctaa aaataaccct gtccctggtg gatcctccct ggggcagcc cctcctggct    660
agtcacaccc tgtaggctcc tctatataac ccaggggcac aggggctgcc cccgggtcac    720
```

SEQ ID NO: 23          moltype = DNA   length = 792
FEATURE                Location/Qualifiers
source                 1..792
                       mol_type = other DNA
                       organism = synthetic construct
SEQUENCE: 23
```
aagcttgcat gtctaagcta gacccttcag attaaaaata actgaggtaa gggcctgggt    60
aggggaggtg gtgtgagacg ctcctgtctc tcctctatct gcccatcggc cctttgggga    120
ggaggaatgt gcccaaggac taaaaaaagg ccatggagcc agaggggcga gggcaacaga    180
cctttcatgg gcaaaccttg gggccctgct gtctagcatg ccccactacg ggtctaggct    240
gcccatgtaa ggaggcaagg cctggggaca cccgagatgc ctggttataa ttaacccaga    300
catgtggctg cccccccccc cccaacacct gctgcctcta aaaataaccc tgtccctggt    360
ggatcccctg catgcgaaga tcttcgaaca aggctgtggg ggactgaggg caggctgtaa    420
caggcttggg ggccagggct tatacgtgcc tgggactccc aaagtattac tgttccatgt    480
tcccggcgaa gggccagctg tccccgcca gctagactca gcacttagtt taggaaccag    540
tgagcaagtc agcccttggg gcagcccata caaggccatg gggctgggca agctgcacgc    600
ctgggtccgg ggtgggcacg gtgcccgggc aacgagctga aagctcatct gctctcaggg    660
gcccctccct ggggacagcc cctcctggct agtcacaccc tgtaggctcc tctatataac    720
ccaggggcac aggggctgcc ctcattctac caccacctcc acagcacaga cagacactca    780
ggagcagcca gc                                                        792
```

SEQ ID NO: 24          moltype = DNA   length = 591
FEATURE                Location/Qualifiers
source                 1..591
                       mol_type = other DNA
                       organism = synthetic construct
SEQUENCE: 24
```
atcaacctct ggattacaaa atttgtgaaa gattgactga tattcttaac tatgttgctc    60
```

-continued

```
cttttacgct gtgtggatat gctgctttaa tgcctctgta tcatgctatt gcttcccgta   120
cggctttcgt tttctcctcc ttgtataaat cctggttgct gtctctttat gaggagttgt   180
ggcccgttgt ccgtcaacgt ggcgtggtgt gctctgtgtt tgctgacgca accccactg    240
gctgggcat  tgccaccacc tgtcaactcc tttctgggac tttcgctttc ccctcccga    300
tcgccacggc agaactcatc gccgcctgcc ttgcccgctg ctggacaggg gctaggttgc   360
tgggcactga taattccgtg gtgttgtcgg ggaagctgac gtcctttcca gggctgctcg   420
cctgtgttgc caactggatc ctgcgcggga cgtcctttctg ctacgtccct tcggctctca   480
atccagcgga cctcccttcc cgaggccttc tgccggttct gcggcctctc ccgcgtcttc   540
gctttcggcc tccgacgagt cggatctccc tttgggccgc ctccccgcct g            591
```

SEQ ID NO: 25          moltype = AA   length = 10
FEATURE                Location/Qualifiers
source                 1..10
                       mol_type = protein
                       organism = synthetic construct
SEQUENCE: 25
MAPKKKRKVH                                                           10

SEQ ID NO: 26          moltype = AA   length = 9
FEATURE                Location/Qualifiers
source                 1..9
                       mol_type = protein
                       organism = synthetic construct
SEQUENCE: 26
RAAKRPRTT                                                            9

SEQ ID NO: 27          moltype = AA   length = 9
FEATURE                Location/Qualifiers
source                 1..9
                       mol_type = protein
                       organism = synthetic construct
SEQUENCE: 27
PAAKRVKLD                                                            9

SEQ ID NO: 28          moltype = AA   length = 9
FEATURE                Location/Qualifiers
source                 1..9
                       mol_type = protein
                       organism = synthetic construct
SEQUENCE: 28
HHPKKKRKV                                                            9

SEQ ID NO: 29          moltype = DNA   length = 135
FEATURE                Location/Qualifiers
source                 1..135
                       mol_type = other DNA
                       organism = synthetic construct
SEQUENCE: 29
gatccagaca tgataagata cattgatgag tttggacaaa ccacaactag aatgcagtga   60
aaaaaatgct ttatttgtga aatttgtgat gctattgctt tatttgtaac cattataagc   120
tgcaataaac aagtt                                                     135

SEQ ID NO: 30          moltype = AA   length = 738
FEATURE                Location/Qualifiers
source                 1..738
                       mol_type = protein
                       organism = synthetic construct
SEQUENCE: 30
MAADGYLPDW LEDNLSEGIR EWWDLKPGAP KPKANQQKQD NGRGLVLPGY KYLGPFNGLD    60
KGEPVNAADA AALEHDKAYD QQLQAGDNPY LRYNHADAEF QERLQEDTSF GGNLGRAVFQ    120
AKKRVLEPLG LVESPVKTAP GKKRPVEPSP QRSPDSSTGI GKKGQQPAKK RLNFGQTGDS    180
ESVPDPQPIG EPPAGPSGLQ SGTMAAGGGA PMADNNEGAD GVGSSSGNWH CDSTWLGDRV    240
ITTSTRTWAL PTYNNHLYKQ ISNGTSGGST NDNTYFGYST PWGYFDFNRF HCHFSPRDWQ    300
RLINNNWGFR PKRLNFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFEFSYNFED    420
VPFHSSYAHS QSLDRLMNPL IDQYLYYLSR TQSTGGTAGT QQLLFSQAGP NNMSAQAKNW    480
LPGPCYRQQR VSTTLSQNNN SNFAWTGATK YHLNGRDSLV NPGVAMATHK DDEERFFPSS    540
GVLMFGKQGA GKDNVDYSSV MLTSEEEIKT TNPVATEQYG VVADNLQQQN AAPIVGAVNS    600
QGALPGMVWQ NRDVYLQGPI WAKIPHTDGN FHPSPLMGGF GLKHPPPQIL IKNTPVPADP    660
PTTFNQAKLA SFITQYSTGQ VSVEIEWELQ KENSKRWNPE IQYTSNYYKS TNVDFAVNTE    720
GTYSEPRPIG TRYLTRNL                                                  738

SEQ ID NO: 31          moltype = AA   length = 736
FEATURE                Location/Qualifiers
source                 1..736
                       mol_type = protein
                       organism = synthetic construct
SEQUENCE: 31
MAADGYLPDW LEDNLSEGIR EWWALKPGAP QPKANQQHQD NARGLVLPGY KYLGPGNGLD    60
```

-continued

```
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736
```

```
SEQ ID NO: 32          moltype = DNA  length = 10
FEATURE                Location/Qualifiers
source                 1..10
                       mol_type = other DNA
                       organism = synthetic construct
SEQUENCE: 32
gccaccatgg                                                           10
```

```
SEQ ID NO: 33          moltype = AA  length = 163
FEATURE                Location/Qualifiers
source                 1..163
                       mol_type = protein
                       organism = Chlamydomonas reinhardtii
SEQUENCE: 33
MNTKYNKEFL LYLAGFVDGD GSIIAQIKPN QSYKFKHQLS LAFQVTQKTQ RRWFLDKLVD    60
EIGVGYVRDR GSVSDYILSE IKPLHNFLTQ LQPFLKLKQK QANLVLKIIW RLPSAKESPD    120
KFLEVCTWVD QIAALNDSKT RKTTSETVRA VLDSLSEKKK SSP                      163
```

```
SEQ ID NO: 34          moltype = AA  length = 9
FEATURE                Location/Qualifiers
source                 1..9
                       mol_type = protein
                       organism = Chlamydomonas reinhardtii
SEQUENCE: 34
LAGLIDADG                                                            9
```

```
SEQ ID NO: 35          moltype = AA  length = 3685
FEATURE                Location/Qualifiers
source                 1..3685
                       mol_type = protein
                       organism = Homo sapiens
SEQUENCE: 35
MLWWEEVEDC YEREDVQKKT FTKWVNAQFS KFGKQHIENL FSDLQDGRRL LDLLEGLTGQ    60
KLPKEKGSTR VHALNNVNKA LRVLQNNNVD LVNIGSTDIV DGNHKLTLGL IWNIILHWQV    120
KNVMKNIMAG LQQTNSEKIL LSWVRQSTRN YPQVNVINFT TSWSDGLALN ALIHSHRPDL    180
FDWNSVVCQQ SATQRLEHAF NIARYQLGIE KLLDPEDVDT TYPDKKSILM YITSLFQVLP    240
QQVSIEAIQE VEMLPRPPKV TKEEHFQLHH QMHYSQQITV SLAQGYERTS SPKPRFKSYA    300
YTQAAYVTTS DPTRSPFPSQ HLEAPEDKSF GSSLMESEVN LDRYQTALEE VLSWLLSAED    360
TLQAQGEISN DVEVVKDQFH THEGYMMDLT AHQGRVGNIL QLGSKLIGTG KLSEDEETEV    420
QEQMNLLNSR WECLRVASME KQSNLHRVLM DLQNQKLKEL NDWLTKTEER TRKMEEEPLG    480
PDLEDLKRQV QQHKVLQEDL EQEQVRVNSL THMVVVVDES SGDHATAALE EQLKVLGDRW    540
ANICRWTEDR WVLLQDILLK WQRLTEEQCL FSAWLSEKED AVNKIHTTGF KDQNEMLSSL    600
QKLAVLKADL EKKKQSMGKL YSLKQDLLST LKNKSVTQKT EAWLDNFARC WDNLVQKLEK    660
STAQISQAVT TTQPSLTQTT VMETVTTVTT REQILVKHAQ EELPPPPPQK KRQITVDSEI    720
RKRLDVDITE LHSWITRSEA VLQSPEFAIF RKEGNFSDLK EKVNAIEREK AEKFRKLQDA    780
SRSAQALVEQ MVNEGVNADS IKQASEQLNS RWIEFCQLLS ERLNWLEYQN NIIAFYNQLQ    840
QLEQMTTTAE NWLKIQPTTP SEPTAIKSQL KICKDEVNRL SDLQPQIERL KIQSIALKEK    900
GQGPMFLDAD FVAFTNHFKQ VFSDVQAREK ELQTIFDTLP PMRYQETMSA IRTWVQQSET    960
KLSIPQLSVT DYEIMEQRLG ELQALQSSLQ EQQSGLYYLS TTVKEMSKKA PSEISRKYQS    1020
EFEEIEGRWK KLSSQLVEHC QKLEEQMNKL RKIQNHIQTL KKWMAEVDVF LKEEWPALGD    1080
SEILKKQLKQ CRLLVSDIQT IQPSLNSVNE GGQKIKNEAE PEFASRLETE LKELNTQWDH    1140
MCQQVYARKE ALKGGLEKTV SLQKDLSEMH EWMTQAEEEY LERDFEYKTP DELQKAVEEM    1200
KRAKEEAQQK EAKVKLLTES VNSVIAQAPP VAQEALKKEL ETLTTNYQWL CTRLNGKCKT    1260
LEEVWACWHE LLSYLEKANK WLNEVEFKLK TTENIPGGAE EISEVLDSLE NLMRHSEDNP    1320
NQIRILAQTL TDGGVMDELI NEELETFNSR WRELHEEAVR RQKLLEQSIQ SAQETEKSLH    1380
LIQESLTFID KQLAAYIADK VDAAQMPQEA QKIQSDLTSH EISLEEMKKH NQGKEAAQRV    1440
LSQIDVAQKK LQDVSMKFRL FQKPANFEQR LQESKMILDE VKMHLPALET KSVEQEVVQS    1500
QLNHCVNLYK SLSEVKSEVE MVIKTGRQIV QKKQTENPKE LDERVTALKL HYNELGAKVT    1560
ERKQQLEKCL KLSRKMRKEM NVLTEWLAAT DMELTKRSAV EGMPSNLDSE VAWGKATQKE    1620
IEKQKVHLKS ITEVGEALKT DKLSLLNSNW IAVTSRAEEW LNLLLEYQKH    1680
METFDQNVDH ITKWIIQADT LLDESEKKKP QQKEDVLKRL KAELNDIRPK VDSTRDQAAN    1740
LMANRGDHCR KLVEPQISEL NHRFAAISHR IKTGKASIPL KELEQFNSDI QKLLEPLEAE    1800
IQQGVNLKEE DFNKDMNEDN EGTVKELLQR GDNLQQRITD ERKREEIKIK QQLLQTKHNA    1860
LKDLRSQRRK KALEISHQWY QYKRQADDLL KCLDDIEKKL ASLPEPRDER KIKEIDRELQ    1920
KKKEELNAVR RQAEGLSEDG AAMAVEPTQI QLSKRWREIE SKFAQFRRLN FAQIHTVREE    1980
TMMVMTEDMP LEISYVPSTY LTEITHVSQA LLEVEQLLNA PDLCAKDFED LFKQEESLKN    2040
```

-continued

```
IKDSLQQSSG RIDIIHSKKT AALQSATPVE RVKLQEALSQ LDFQWEKVNK MYKDRQGRFD    2100
RSVEKWRRFH YDIKIFNQWL TEAEQFLRKT QIPENWEHAK YKWYLKELQD GIGQRQTVVR    2160
TLNATGEEII QQSSKTDASI LQEKLGSLNL RWQEVCKQLS DRKKRLEEQK NILSEFQRDL    2220
NEFVLWLEEA DNIASIPLEP GKEQQLKEKL EQVKLLVEEL PLRQGILKQL NETGGPVLVS    2280
APISPEEQDK LENKLKQTNL QWIKVSRALP EKQGEIEAQI KDLGQLEKKL EDLEEQLNHL    2340
LLWLSPIRNQ LEIYNQPNQE GPFDVKETEI AVQAKQPDVE EILSKGQHLY KEKPATQPVK    2400
RKLEDLSSEW KAVNRLLQEL RAKQPDLAPG LTTIGASPTQ TVTLVTQPVV TKETAISKLE    2460
MPSSLMLEVP ALADFNRAWT ELTDWLSLLD QVIKSQRVMV GDLEDINEMI IKQKATMQDL    2520
EQRRPQLEEL ITAAQNLKNK TSNQEARTII TDRIERIQNQ WDEVQEHLQN RRQQLNEMLK    2580
DSTQWLEAKE EAEQVLGQAR AKLESWKEGP YTVDAIQKKI TETKQLAKDL RQWQTNVDVA    2640
NDLALKLLRD YSADDTRKVH MITENINASW RSIHKRVSER EAALEETHRL LQQFPLDLEK    2700
FLAWLTEAET TANVLQDATR KERLLEDSKG VKELMKQWQD LQGEIEAHTD VYHNLDENSQ    2760
KILRSLEGSD DAVLLQRRLD NMNFKWSELR KKSLNIRSHL EASSDQWKRL HLSLQELLVW    2820
LQLKDDELSR QAPIGGDFPA VQKQNDVHRA FKRELKTKEP VIMSTLETVR IFLTEQPLEG    2880
LEKLYQEPRE LPPEERAQNV TRLLRKQAEE VNTEWEKLNL HSADWQRKID ETLERLRELQ    2940
EATDELDLKL RQAEVIKGSW QPVGDLLIDS LQDHLEKVKA LRGEIAPLKE NVSHVNDLAR    3000
QLTTLGIQLS PYNLSTLEDL NTRWKLLQVA VEDRVRQLHE AHRDFGPASQ HFLSTSVQGP    3060
WERAISPNKV PYYINHETQT TCWDHPMKTE LYQSLADLNN VRFSAYRTAM KLRRLQKALC    3120
LDLLSLSAAC DALDQHNLKQ NDQPMDILQI INCLTTIYDR LEQEHNNLVN VPLCVDMCLN    3180
WLLNVYDTGR TGRIRVLSFK TGIISLCKAH LEDKYRYLFK QVASSTGFCD QRRLGLLLHD    3240
SIQIPRQLGE VASFGGSNIE PSVRSCFQFA NNKPEIEAAL FLDWMRLEPQ SMVWLPVLHR    3300
VAAAETAKHQ AKCNICKECP IIGFRYRSLK HFNYDICQSC FFSGRVAKGH KMHYPMVEYC    3360
TPTTSGEDVR DFAKVLKNKF RTKRYFAKHP RMGYLPVQTV LEGDNMETPV TLINFWPVDS    3420
APASSPQLSH DDTHSRIEHY ASRLAEMENS NGSYLNDSIS PNESIDDEHL LIQHYCQSLN    3480
QDSPLSQPRS PAQILISLES EERGELERIL ADLEEENRNL QAEYDRLKQQ HEHKGLSPLP    3540
SPPEMMPTSP QSPRDAELIA EAKLLRQHKG RLEARMQILE DHNKQLESQL HRLRQLLEQP    3600
QAEAKVNGTT VSSPSTSLQR SDSSQPMLLR VVGSQTSDSM GEEDLLSPPQ DTSTGLEEVM    3660
EQLNNSFPSS RGRNTPGKPM REDTM                                         3685
```

```
SEQ ID NO: 36          moltype = AA  length = 3092
FEATURE                Location/Qualifiers
source                 1..3092
                       mol_type = protein
                       organism = Homo sapiens
SEQUENCE: 36
MLWWEEVEDC YEREDVQKKT FTKWVNAQFS KFGKQHIENL FSDLQDGRRL LDLLEGLTGQ    60
KLPKEKGSTR VHALNNVNKA LRVLQNNNVD LVNIGSTDIV DGNHKLTLGL IWNIILHWQV    120
KNVMKNIMAG LQQTNSEKIL LSWVRQSTRN YPQVNVINFT TSWSDGLALN ALIHSHRPDL    180
FDWNSVVCQQ SATQRLEHAF NIARYQLGIE KLLDPEDVDT TYPDKKSILM YITSLFQVLP    240
QQVSIEAIQE VEMLPRPPKV TKEEHFQLHH QMHYSQQITV SLAQGYERTS SPKPRFKSYA    300
YTQAAYVTTS DPTRSPFPSQ HLEAPEDKSF GSSLMESEVN LDRYQTALEE VLSWLLSAED    360
TLQAQGEISN DVEVVKDQFH THEGYMMDLT AHQGRVGNIL QLGSKLIGTG KLSEDEETEV    420
QEQMNLLNSR WECLRVASME KQSNLHRVLM DLQNQKLKEL NDWLTKTEER TRKMEEEPLG    480
PDLEDLKRQV QQHKVLQEDL EQEQVRVNSL THMVVVVDES SGDHATAALE EQLKVLGDRW    540
ANICRWTEDR WVLLQDILLK WQRLTEEQCL FSAWLSEKED AVNKIHTTGF KDQNEMLSSL    600
QKLAVLKADL EKKKQSMGKL YSLKQDLLST LKNKSVTQKT EAWLDNFARC WDNLVQKLEK    660
STAQISQAVT TTQPSLTQTT VMETVTTVTT REQILVKHAQ LEPPPPPQK KRQITVDSEI    720
RKRLDVDITE LHSWITRSEA VLQSPEFAIF RKEGNFSDLK EKVNAIEREK AEKFRKLQDA    780
SRSAQALVEQ MVNEGVNADS IKQASEQLNS RWIEFCQLLS ERLNWLEYQN NIIAFYNQLQ    840
QLEQMTTTAE NWLKIQPTTP SEPTAIKSQL KICKDEVNRL SDLQPQIERL KIQSIALKEK    900
GQGPMFLDAD FVAFTNHFKQ VFSDVQAREK ELQTIFDTLP PMRYQETMSA IRTWVQQSET    960
KLSIPQLSVT DYEIMEQRLG ELQALQSSLQ EQQSGLYYLS TTVKEMSKKA PSEISRKYQS    1020
EFEEIEGRWK KLSSQLVEHC QKLEEQMNKL RKIQNHIQTL KKWMAEVDVF LKEEWPALGD    1080
SEILKKQLKQ CRLLVSDIQT IQPSLNSVNE GGQKIKNEAE PEFASRLETE LKELNTQWDH    1140
MCQQVYARKE ALKGGLEKTV SLQKDLSEMH EWMTQAEEEY KRDFEYKTP DELQKAVEEM    1200
KRAKEEAQQK EAKVKLLTES VNSVIAQAPP VAQEALKKEL ETLTTNYQWL CTRLNGKCKT    1260
LEEVWACWHE LLSYLEKANK WLNEVEFKLK TTENIPGGAE EISEVLDSLE NLMRHSEDNP    1320
NQIRILAQTL TDGGVMDELI NEELETFNSR WRELHEEAVR RQKLLEQSIQ SAQETEKSLH    1380
LIQESLTFID KQLAAYIADK VDAAQMPQEA QKIQSDLTSH EISLEEMKKH NQGKEAAQRV    1440
LSQIDVAQKK LQDVSMKFRL FQKPANFEQR LQESKMILDE VKMHLPALET KSVEQEVVQS    1500
QLNHCVNLYK SLSEVKSEVE MVIKTGRQIV QKKQTENPKE LDERVTALKL HYNELGAKVT    1560
ERKQQLEKCL KLSRKMRKEM NVLTEWLAAT DMELTKRSAV EGMPSNLDSE VAWGKATQKE    1620
IEKQKVHLKS ITEVGEALKT VGKKETLVE DKLSLLNSNW IAVTSRAEEW LNLLLEYQKH    1680
METFDQNVDH ITKWIIQADT LLDESEKKKP QQKEDVLKRL KAELNDIRPK VDSTRDQAAN    1740
LMANRGDHCR KLVEPQISEL NHRFAAISHR IKTGKASIPL KELEQFNSDI QKLLEPLEAE    1800
IQQGVNLKEE DFNKDMNEDN EGTVKELLQR GDNLQQRITD ERKREEIKIK QQLLQTKHNA    1860
LKDLRSQRRK KALEISHQWY QYKRQADDLL KCLDDIEKKL ASLPEPRDER KIKEIDRELQ    1920
KKKEELNAVR RQAEGLSEDG AAMAVEPTQI QLSKRWREIE SKFAQFRRLN FAQIHTVREE    1980
TMMVMTEDMP LEISYVPSTY LTEITHVSQA LLEVEQLLNA PDLCAKDFED LFKQEESLKN    2040
IKDSLQQSSG RIDIIHSKKT AALQSATPVE RVKLQEALSQ LDFQWEKVNK MYKDRQGRFD    2100
RSVEKWRRFH YDIKIFNQWL TEAEQFLRKT QIPENWEHAK YKWYLKDLQG EIEAHTDVYH    2160
NLDENSQKIL RSLEGSDDAV LLQRRLDNMN FKWSELRKKS LNIRSHLEAS SDQWKRLHLS    2220
LQELLVWLQL KDDELSRQAP IGGDFPAVQK QNDVHRAFKR ELKTKEPVIM STLETVRIFL    2280
TEQPLEGLEK LYQEPRELPP EERAQNVTRL LRKQAEEVNT EWEKLNLHSA DWQRKIDETL    2340
ERLRELQEAT DELDLKLRQA EVIKGSWQPV GDLLIDSLQD HLEKVKALRG EIAPLKENVS    2400
HVNDLARQLT TLGIQLSPYN LSTLEDLNTR WKLLQVAVED RVRQLHEAHR DFGPASQHFL    2460
STSVQGPWER AISPNKVPYY INHETQTTCW DHPKMTELYQ SLADLNNVRF SAYRTAMKLR    2520
RLQKALCLDL LSLSAACDAL DQHNLKQNDQ PMDILQIINC LTTIYDRLEQ EHNNLVNVPL    2580
CVDMCLNWLL NVYDTGRTGR IRVLSFKTGI ISLCKAHLED KYRYLFKQVA SSTGFCDQRR    2640
```

-continued

```
LGLLLHDSIQ IPRQLGEVAS FGGSNIEPSV RSCFQFANNK PEIEAALFLD WMRLEPQSMV   2700
WLPVLHRVAA AETAKHQAKC NICKECPIIG FRYRSLKHFN YDICQSCFFS GRVAKGHKMH   2760
YPMVEYCTPT TSGEDVRDFA KVLKNKFRTK RYFAKHPRMG YLPVQTVLEG DNMETPVTLI   2820
NFWPVDSAPA SSPQLSHDDT HSRIEHYASR LAEMENSNGS YLNDSISPNE SIDDEHLLIQ   2880
HYCQSLNQDS PLSQPRSPAQ ILISLESEER GELERILADL EEENRNLQAE YDRLKQQHEH   2940
KGLSPLPSPP EMMPTSPQSP RDAELIAEAK LLRQHKGRLE ARMQILEDHN KQLESQLHRL   3000
RQLLEQPQAE AKVNGTTVSS PSTSLQRSDS SQPMLLRVVG SQTSDSMGEE DLLSPPQDTS   3060
TGLEEVMEQL NNSFPSSRGR NTPGKPMRED TM                                3092

SEQ ID NO: 37              moltype = DNA   length = 22
FEATURE                    Location/Qualifiers
source                     1..22
                           mol_type = genomic DNA
                           organism = Homo sapiens
SEQUENCE: 37
aaggattatg tattacctcc cg                                             22

SEQ ID NO: 38              moltype = DNA   length = 22
FEATURE                    Location/Qualifiers
source                     1..22
                           mol_type = genomic DNA
                           organism = Homo sapiens
SEQUENCE: 38
ttcctaatac ataatggagg gc                                             22

SEQ ID NO: 39              moltype = DNA   length = 22
FEATURE                    Location/Qualifiers
source                     1..22
                           mol_type = genomic DNA
                           organism = Homo sapiens
SEQUENCE: 39
ctacatggtg tatctgacta ag                                             22

SEQ ID NO: 40              moltype = DNA   length = 22
FEATURE                    Location/Qualifiers
source                     1..22
                           mol_type = genomic DNA
                           organism = Homo sapiens
SEQUENCE: 40
gatgtaccac atagactgat tc                                             22

SEQ ID NO: 41              moltype = DNA   length = 22
FEATURE                    Location/Qualifiers
source                     1..22
                           mol_type = other DNA
                           organism = synthetic construct
SEQUENCE: 41
aaggattatg tatctgacta ag                                             22

SEQ ID NO: 42              moltype = DNA   length = 22
FEATURE                    Location/Qualifiers
source                     1..22
                           mol_type = other DNA
                           organism = synthetic construct
SEQUENCE: 42
ttcctaatac atagactgat tc                                             22

SEQ ID NO: 43              moltype = AA   length = 354
FEATURE                    Location/Qualifiers
source                     1..354
                           mol_type = protein
                           organism = synthetic construct
SEQUENCE: 43
MNTKYNKEFL LYLAGFVDSD GSIYATIRPV QSTKFKHTLR LWFAVTQKTQ RRWFLDKLVD   60
EIGVGYVYDN GSVSWYYLSE IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSICACIVP RQDRKFKHQL RLFFEVGQKT   240
KRRWFLDKLV DEIGVGYVED TGRASRYRLS QIKPLHNFLT QLQPFLKLKQ KQANLVLKII   300
EQLPSAKESP DKFLEVCTWV DQIAALNDSR TRKTTSETVR AVLDSLSEKK KSSP         354

SEQ ID NO: 44              moltype = AA   length = 354
FEATURE                    Location/Qualifiers
source                     1..354
                           mol_type = protein
                           organism = synthetic construct
SEQUENCE: 44
MNTKYNKEFL LYLAGFVDSD GSIFAVIEPV QSAKFKHRLK LSFVVTQKTQ RRWFLDKLVD   60
EIGVGYVYDQ GSVSFYRLSE IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
```

```
GISEALRAGA GSGTGYNKEF LLYLAGFVDG DGSICACIVP RQDRKFKHQL RLFFEVGQTT    240
RRRWFLDKLV DEIGVGYVFD KGSASMYRLS EIKPLHNFLT QLQPFLKLKQ KQANLVLKII    300
EQLPSAKESP DKFLEVCTWV DQIAALNDSR TRKTTSETVR AVLDSLSEKK KSSP          354

SEQ ID NO: 45            moltype = AA   length = 354
FEATURE                  Location/Qualifiers
source                   1..354
                         mol_type = protein
                         organism = synthetic construct
SEQUENCE: 45
MNTKYNKEFL LYLAGFVDSD GSIYASIMPI QTAKFKHRLK LQFAVAQKTQ RRWFLDKLVD    60
EIGVGYVYDF GSVSYYRLSQ IKPLHNFLTQ LQPFLKLKQK QANLVLKIIE QLPSAKESPD    120
KFLEVCTWVD QIAALNDSKT RKTTSETVRA VLDSLPGSVG GLSPSQASSA ASSASSSPGS    180
GISEALRAGA GSGTGYNKEF LLYLAGFVDG DGSICACIVP RQDRKFKHQL RLFFEVGQKT    240
QRRWFLDKLV DEIGVGYVRD LGSASTYRLS EIKPLHNFLT QLQPFLKLKQ KQANLVLKII    300
EQLPSAKESP DKFLEVCTWV DQIAALNDSR TRKTTSETVR AVLDSLSEKK KSSP          354

SEQ ID NO: 46            moltype = AA   length = 354
FEATURE                  Location/Qualifiers
source                   1..354
                         mol_type = protein
                         organism = synthetic construct
SEQUENCE: 46
MNTKYNKEFL LYLAGFVDSD GSIIAFIMPS QTAKFKHRLK LQFAVAQKTQ RRWFLDKLVD    60
EIGVGYVYDF GSVSYYRLSQ IKPLHNFLTQ LQPFLKLKQK QANLVLKIIE QLPSAKESPD    120
KFLEVCTWVD QIAALNDSKT RKTTSETVRA VLDSLPGSVG GLSPSQASSA ASSASSSPGS    180
GISEALRAGA GSGTGYNKEF LLYLAGFVDG DGSICACIVP RQDRKFKHQL RLFFEIGQKT    240
QRRWFLDKLV DEIGVGYVRD LGSASTYRLS QIKPLHNFLT QLQPFLKLKQ KQANLVLKII    300
EQLPSAKESP DKFLEVCTWV DQIAALNDSK TRKTTSETVR AVLDSLSEKK KSSP          354

SEQ ID NO: 47            moltype = AA   length = 354
FEATURE                  Location/Qualifiers
source                   1..354
                         mol_type = protein
                         organism = synthetic construct
SEQUENCE: 47
MNTKYNKEFL LYLAGFVDSD GSIMAFIMPT QTAKFKHRLK LQFAVAQKTQ RRWFLDKLVD    60
EIGVGYVYDF GSVSYYRLSE IKPLHNFLTQ LQPFLKLKQK QANLVLKIIE QLPSAKESPD    120
KFLEVCTWVD QIAALNDSKT RKTTSETVRA VLDSLPGSVG GLSPSQASSA ASSASSSPGS    180
GISEALRAGA GSGTGYNKEF LLYLAGFVDG DGSICACIVP RQDRKFKHQL RLFFEVGQKT    240
QRRWFLDKLV DEIGVGYVRD LGSASTYRLS QIKPLHNFLT QLQPFLKLKQ KQANLVLKII    300
EQLPSAKESP DKFLEVCTWV DQIAALNDSR TRKTTSETVR AVLDSLSEKK KSSP          354

SEQ ID NO: 48            moltype = AA   length = 354
FEATURE                  Location/Qualifiers
source                   1..354
                         mol_type = protein
                         organism = synthetic construct
SEQUENCE: 48
MNTKYNKEFL LYLAGFVDSD GSIMAFILPE QHMKFKHRLR LQFAVAQKTQ RRWFLDKLVD    60
EIGVGYVYDF GSVSYYRLSE IKPLHNFLTQ LQPFLKLKQK QANLVLKIIE QLPSAKESPD    120
KFLEVCTWVD QIAALNDSKT RKTTSETVRA VLDSLPGSVG GLSPSQASSA ASSASSSPGS    180
GISEALRAGA GSGTGYNKEF LLYLAGFVDG DGSICACIVP RQDRKFKHQL RLFFEVGQKT    240
QRRWFLDKLV DEIGVGYVRD LGSASTYRLS EIKPLHNFLT QLQPFLKLKQ KQANLVLKII    300
EQLPSAKESP DKFLEVCTWV DQIAALNDSR TRKTTSETVR AVLDSLSEKK KSSP          354

SEQ ID NO: 49            moltype = AA   length = 354
FEATURE                  Location/Qualifiers
source                   1..354
                         mol_type = protein
                         organism = synthetic construct
SEQUENCE: 49
MNTKYNKEFL LYLAGFVDSD GSIMAFILPE QHLKFKHRLR LQFAVAQKTQ RRWFLDKLVD    60
EIGVGYVYDF GSVSYYRLSE IKPLHNFLTQ LQPFLKLKQK QANLVLKIIE QLPSAKESPD    120
KFLEVCTWVD QIAALNDSKT RKTTSETVRA VLDSLPGSVG GLSPSQASSA ASSASSSPGS    180
GISEALRAGA GSGTGYNKEF LLYLAGFVDG DGSICACIVP RQDRKFKHQL RLFFEVGQKT    240
QRRWFLDKLV DEIGVGYVRD LGSASTYRLS EIKPLHNFLT QLQPFLKLKQ KQANLVLKII    300
EQLPSAKESP DKFLEVCTWV DQIAALNDSR TRKTTSETVR AVLDSLSEKK KSSP          354

SEQ ID NO: 50            moltype = AA   length = 354
FEATURE                  Location/Qualifiers
source                   1..354
                         mol_type = protein
                         organism = synthetic construct
SEQUENCE: 50
MNTKYNKEFL LYLAGFVDSD GSIMAFILPE QGLKFKHRLR LQFAVAQKTQ RRWFLDKLVD    60
EIGVGYVYDF GSVSYYRLSQ IKPLHNFLTQ LQPFLKLKQK QANLVLKIIE QLPSAKESPD    120
KFLEVCTWVD QIAALNDSKT RKTTSETVRA VLDSLPGSVG GLSPSQASSA ASSASSSPGS    180
GISEALRAGA GSGTGYNKEF LLYLAGFVDG DGSICACIVP RQDRKFKHQL RLFFEVGQKT    240
```

-continued

```
QRRWFLDKLV DEIGVGYVRD LGSASTYRLS QIKPLHNFLT QLQPFLKLKQ KQANLVLKII   300
EQLPSAKESP DKFLEVCTWV DQIAALNDSR TRKTTSETVR AVLDSLSEKK KSSP          354

SEQ ID NO: 51              moltype = AA   length = 354
FEATURE                    Location/Qualifiers
source                     1..354
                           mol_type = protein
                           organism = synthetic construct
SEQUENCE: 51
MNTKYNKEFL LYLAGFVDSD GSIMAFIMPD QAPKFKHRLR LQFAVAQKTQ RRWFLDKLVD   60
EIGVGYVYDF GSVSYYRLSE IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSICACIVP RQDRKFKHQL RLFFEVQKT    240
QRRWFLDKLV DEIGVGYVRD LGSASTYRLS QIKPLHNFLT QLQPFLKLKQ KQANLVLKII   300
EQLPSAKESP DKFLEVCTWV DQIAALNDSR TRKTTSETVR AVLDSLSEKK KSSP          354

SEQ ID NO: 52              moltype = AA   length = 354
FEATURE                    Location/Qualifiers
source                     1..354
                           mol_type = protein
                           organism = synthetic construct
SEQUENCE: 52
MNTKYNKEFL LYLAGFVDAD GSIYACIKPH QQLKFKHQLL LYFEVYQKTQ RRWFLDKLVD   60
EIGVGYVADR GSVSEYRLSQ IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSIFASIMP TQWTKFKHSL LLRFRVTQST   240
RRRWFLDKLM DEIGVGYVSD QGRASYYTLS EIKPLHNFLT QLQPFLKLKQ KQANLVLKII   300
EQLPSAKESP DKFLEVCTWV DQIAALNDSR TRKTTSETVR AVLDSLSEKK KSSP          354

SEQ ID NO: 53              moltype = AA   length = 354
FEATURE                    Location/Qualifiers
source                     1..354
                           mol_type = protein
                           organism = synthetic construct
SEQUENCE: 53
MNTKYNKEFL LYLAGFVDAD GSIYACIKPH QQLKFKHQLL LYFEVYQKTQ RRWFLDKLVD   60
EIGVGYVIDS GSVSTYRLSQ IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSIFASIIP SQLVKFKHTL LLRFRVTQAT   240
RRRWFLDKLV DEIGVGYVTD NGRASYYTLS EIKPLHNFLT QLQPFLKLKQ KQANLVLKII   300
EQLPSAKESP DKFLEVCTWV DQIAALNDSR TRKTTSETVR AVLDSLSEKK KSSP          354

SEQ ID NO: 54              moltype = AA   length = 354
FEATURE                    Location/Qualifiers
source                     1..354
                           mol_type = protein
                           organism = synthetic construct
SEQUENCE: 54
MNTKYNKEFL LYLAGFVDAD GSIYACIKPH QQLKFKHQLL LYFEVYQKTQ RRWFLDKLVD   60
EIGVGYVADR GSVSEYRLSQ IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSIFASIIP SQLVKFKHTL LLRFRVCQAT   240
KRRWFLDKLV DEIGVGYVSD QGSASYYTLS EIKPLHNFLT QLQPFLKLKQ KQANLVLKII   300
EQLPSAKESP DKFLEVCTWV DQIAALNDSR TRKTTSETVR AVLDSLSEKK KSSP          354

SEQ ID NO: 55              moltype = AA   length = 354
FEATURE                    Location/Qualifiers
source                     1..354
                           mol_type = protein
                           organism = synthetic construct
SEQUENCE: 55
MNTKYNKEFL LYLAGFVDSD GSIYACIKPH QQLKFKHQLL LYFEVYQKTQ RRWFLDKLVD   60
EIGVGYVADR GSVSEYRLSQ IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSIFASIIP SQEVKFKHTL LLRFRVCQAT   240
KRRWFLDKLV DEIGVGYVSD QGSASYYTLS EIKPLHNFLT QLQPFLKLKQ KQANLVLKII   300
EQLPSAKESP DKFLEVCTWV DQIAALNDSR TRKTTSETVR AVLDSLSEKK KSSP          354

SEQ ID NO: 56              moltype = AA   length = 354
FEATURE                    Location/Qualifiers
source                     1..354
                           mol_type = protein
                           organism = synthetic construct
SEQUENCE: 56
MNTKYNKEFL LYLAGFVDAD GSIYACIKPH QQLKFKHQLL LYFEVYQKTQ RRWFLDKLVD   60
EIGVGYVADR GSVSEYRLSQ IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSIFASIIP SQEVKFKHTL LLRFRVCQAT   240
KRRWFLDKLV DEIGVGYVSD QGSASYYTLS EIKPLHNFLT QLQPFLKLKQ KQANLVLKII   300
```

```
EQLPSAKESP DKFLEVCTWV DQIAALNDSR TRKTTSETVR AVLDSLSEKK KSSP          354

SEQ ID NO: 57              moltype = AA   length = 354
FEATURE                    Location/Qualifiers
source                     1..354
                           mol_type = protein
                           organism = synthetic construct
SEQUENCE: 57
MNTKYNKEFL LYLAGFVDAD GSIYACIKPH QQLKFKHQLL LYFEVYQKTQ RRWFLDKLVD   60
EIGVGYVADR GSVSEYRLSQ IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSIFASIIP SQEVKFKHTL LLRFRVTQAT   240
KRRWFLDKLV DEIGVGYVSD VGSASYYTLS EIKPLHNFLT QLQPFLKLKQ KQANLVLKII   300
EQLPSAKESP DKFLEVCTWV DQIAALNDSR TRKTTSETVR AVLDSLSEKK KSSP          354

SEQ ID NO: 58              moltype = AA   length = 354
FEATURE                    Location/Qualifiers
source                     1..354
                           mol_type = protein
                           organism = synthetic construct
SEQUENCE: 58
MNTKYNKEFL LYLAGFVDSD GSIYACIKPH QQLKFKHQLL LYFEVYQKTQ RRWFLDKLVD   60
EIGVGYVADR GSVSEYRLSQ IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSIFASIIP SQEVKFKHTL LLRFRVCQAT   240
KRRWFLDKLV DEIGVGYVSD RGSASYYTLS EIKPLHNFLT QLQPFLKLKQ KQANLVLKII   300
EQLPSAKESP DKFLEVCTWV DQIAALNDSR TRKTTSETVR AVLDSLSEKK KSSP          354

SEQ ID NO: 59              moltype = AA   length = 354
FEATURE                    Location/Qualifiers
source                     1..354
                           mol_type = protein
                           organism = synthetic construct
SEQUENCE: 59
MNTKYNKEFL LYLAGFVDAD GSIYACIKPH QELKFKHQLL LYFEVYQKTQ RRWFLDKLVD   60
EIGVGYVADR GSVSEYRLSE IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSIFASIIP SQEVKFKHTL LLRFRVCQAT   240
KRRWFLDKLV DEIGVGYVSD QGSASYYTLS QIKPLHNFLT QLQPFLKLKQ KQANLVLKII   300
EQLPSAKESP DKFLEVCTWV DQIAALNDSR TRKTTSETVR AVLDSLSEKK KSSP          354

SEQ ID NO: 60              moltype = DNA   length = 1062
FEATURE                    Location/Qualifiers
source                     1..1062
                           mol_type = other DNA
                           organism = synthetic construct
SEQUENCE: 60
atgaatacaa aatataataa agagttctta ctctacttag cagggtttgt agactctgac   60
ggttccatct atgccacgat ccggcctgtt caaagtacta agttcaagca cactctgcgg   120
ctctggttcg cggtcacgca gaagacacag cgccgttggt tcctcgacaa gctggtggac   180
gagatcggtg tgggttacgt gtatgacaat ggcagcgtct cctggtacta tctgtccgag   240
atcaagcctt tgcataattt tttaacacaa ctacaacctt ttctaaaact aaaacaaaaa   300
caagcaaatt tagtttttaaa aattattgaa caacttccgt cagcaaaaga atccccggac   360
aaaattcttag aagtttgtac atgggtggat caaattgcag ctctgaatga ttcgaagacg   420
cgtaaaacaa cttctgaaac cgttcgtgct gtgctagaca gtttaccagg atccgtggga   480
ggtctatcgc catctcaggc atccagcgcc gcatcctcgg cttcctcaag cccgggttca   540
gggatctccg aagcactcag agctggagca ggttccggca ctggatacaa caaggaattc   600
ctgctctacc tggcgggctt cgtcgacggg gacggctcca tctgtgcctg tatcgtgcct   660
cgtcaagatc ggaagttcaa gcaccagctg cggctctttt tcgaggtcgg tcagaagaca   720
aagcgcgtt ggttcctcga caagctggtg gacgagatcg gtgtgggtta cgtggaggac   780
acgggcaggg cgagcaggta ccggctgtcc cagatcaagc ctctgcacaa cttcctgacc   840
cagctccagc ccttcctgaa gctcaagcag aagcaggcca acctcgtgct gaagatcatc   900
gagcagctgc cctccgccaa ggaatccccg gacaagttcc tggaggtgtg cacctgggtg   960
gaccagatcg ccgctctgaa cgactccagg acccgcaaga ccacttccga aaccgtcgc   1020
gccgttctag acagtctctc cgagaagaag aagtcgtccc cc                      1062

SEQ ID NO: 61              moltype = DNA   length = 1062
FEATURE                    Location/Qualifiers
source                     1..1062
                           mol_type = other DNA
                           organism = synthetic construct
SEQUENCE: 61
atgaatacaa aatataataa agagttctta ctctacttag cagggtttgt agactctgac   60
ggttccatct ttgccgttat cgagcctgtt caaagtgcta agttcaagca ccggctgaag   120
ctctcgttcg ttgtcactca gaagacacag cgccgttggt tcctcgacaa gctggtggac   180
gagatcggtg tgggttacgt gtatgaccag ggcagcgtct ccttttacag gctgtccgag   240
atcaagcctt tgcataattt tttaacacaa ctacaacctt ttctaaaact aaaacaaaaa   300
caagcaaatt tagtttttaaa aattattgaa caacttccgt cagcaaaaga atccccggac   360
aaaattcttag aagtttgtac atgggtggat caaattgcag ctctgaatga ttcgaagacg   420
```

```
cgtaaaacaa cttctgaaac cgttcgtgct gtgctagaca gtttaccagg atccgtggga   480
ggtctatcgc catctcaggc atccagcgcc gcatcctcgg cttcctcaag cccgggttca   540
gggatctccg aagcactcag agctggagca ggttccggca ctggatacaa caaggaattc   600
ctgctctacc tggcgggctt cgtcgacggg gacggctcca tctgtgcctg tatcgtgcct   660
cgtcaagatc ggaagttcaa gcaccagctg cggctctttt tcgaggtcgg gcagacgaca   720
aggcgccgtt ggttcctcga caagctggtg gacgagatcg gtgtgggtta cgtgtttgac   780
aagggcagcg cgagcatgta ccggctgtcc gagatcaagc ctctgcacaa cttcctgacc   840
cagctccagc ccttcctgaa gctcaagcag aagcaggcca acctcgtgct gaagatcatc   900
gagcagctgc cctccgccaa ggaatccccg gacaagttcc tggaggtgtg cacctgggtg   960
gaccagatcg ccgctctgaa cgactccagg acccgacaaga ccacttccga aaccgtccgc  1020
gccgttctag acagtctctc cgagaagaag aagtcgtccc cc                     1062

SEQ ID NO: 62         moltype = DNA   length = 1062
FEATURE               Location/Qualifiers
source                1..1062
                      mol_type = other DNA
                      organism = synthetic construct
SEQUENCE: 62
atgaatacaa aatataataa agagttctta ctctacttag cagggtttgt agactctgac   60
ggttccatct atgccagtat catgcctatt caaacggcta agttcaagca ccgtctgaag   120
ctccagttcg cggtcgctca gaagacacag cgccgttggt tcctcgacaa gctggtggac   180
gagatcggtg tgggttacgt gtatgacttt ggcagcgtct cctattacag gctgtcccag   240
atcaagcctt tgcataattt tttaacacaa ctacaacctt ttctaaaact aaaacaaaaa   300
caagcaaatt tagttttaaa aattattgaa caacttccgt cagcaaaaga atccccggac   360
aaaattcttag aagtttgtac atgggtggat caaattgcag ctctgaatga ttcgaagacg   420
cgtaaaacaa cttctgaaac cgttcgtgct gtgctagaca gtttaccagg atccgtggga   480
ggtctatcgc catctcaggc atccagcgcc gcatcctcgg cttcctcaag cccgggttca   540
gggatctccg aagcactcag agctggagca ggttccggca ctggatacaa caaggaattc   600
ctgctctacc tggcgggctt cgtcgacggg gacggctcca tctgtgcctg tatcgtgcct   660
cgtcaagatc ggaagttcaa gcaccagctg cggctctttt tcgaggtcgg tcagaagaca   720
cagcgccgtt ggttcctcga caagctggtg gacgagatcg gtgtgggtta cgtgagggac   780
cttggcagcg cgagcactta ccgtctgtcc gagatcaagc ctctgcacaa cttcctgacc   840
cagctccagc ccttcctgaa gctcaagcag aagcaggcca acctcgtgct gaagatcatc   900
gagcagctgc cctccgccaa ggaatccccg gacaagttcc tggaggtgtg cacctgggtg   960
gaccagatcg ccgctctgaa cgactccagg acccgcaaga ccacttccga aaccgtccgc  1020
gccgttctag acagtctctc cgagaagaag aagtcgtccc cc                     1062

SEQ ID NO: 63         moltype = DNA   length = 1062
FEATURE               Location/Qualifiers
source                1..1062
                      mol_type = other DNA
                      organism = synthetic construct
SEQUENCE: 63
atgaatacaa aatataataa agagttctta ctctacttag cagggtttgt agactctgac   60
ggttccatca ttgcctttat catgcctagt cagacggcta agttcaagca ccgtctgaag   120
ctccagttcg cggtcgctca gaagacacag cgccgttggt tcctcgacaa gctggtggac   180
gagatcggtg tgggttacgt gtatgacttt ggcagcgtct cctattacag gctgtcccag   240
atcaagcctt tgcataattt tttaacacaa ctacaacctt ttctaaaact aaaacaaaaa   300
caagcaaatt tagttttaaa aattattgaa caacttccgt cagcaaaaga atccccggac   360
aaaattcttag aagtttgtac atgggtggat caaattgcag ctctgaatga ttcgaagacg   420
cgtaaaacaa cttctgaaac cgttcgtgct gtgctagaca gtttaccagg atccgtggga   480
ggtctatcgc catctcaggc atccagcgcc gcatcctcgg cttcctcaag cccgggttca   540
gggatctccg aagcactcag agctggagca ggttccggca ctggatacaa caaggaattc   600
ctgctctacc tggcgggctt cgtcgacggg gacggctcca tctgtgcctg tatcgtgcct   660
cgtcaagatc ggaagttcaa gcaccagctg cggctctttt tcgagatcgg tcagaagaca   720
cagcgccgtt ggttcctcga caagctggtg gacgagatcg gtgtgggtta cgtgagggac   780
cttggcagcg cgagcactta ccgtctgtcc cagatcaagc ctctgcacaa cttcctgacc   840
cagctccagc ccttcctgaa gctcaagcag aagcaggcca acctcgtgct gaagatcatc   900
gagcagctgc cctccgccaa ggaatccccg gacaagttcc tggaggtgtg cacctgggtg   960
gaccagatcg ccgctctgaa cgactccagg acccgcaaga ccacttccga aaccgtccgc  1020
gccgttctag acagtctctc cgagaagaag aagtcgtccc cc                     1062

SEQ ID NO: 64         moltype = DNA   length = 1062
FEATURE               Location/Qualifiers
source                1..1062
                      mol_type = other DNA
                      organism = synthetic construct
SEQUENCE: 64
atgaatacaa aatataataa agagttctta ctctacttag cagggtttgt agactctgac   60
ggttccatca tggcctttat catgcctact cagacggcta agttcaagca ccgtctgaag   120
ctccagttcg cggtcgctca gaagacacag cgccgttggt tcctcgacaa gctggtggac   180
gagatcggtg tgggttacgt gtatgacttt ggcagcgtct cctattacag gctgtccgag   240
atcaagcctt tgcataattt tttaacacaa ctacaacctt ttctaaaact aaaacaaaaa   300
caagcaaatt tagttttaaa aattattgaa caacttccgt cagcaaaaga atccccggac   360
aaaattcttag aagtttgtac atgggtggat caaattgcag ctctgaatga ttcgaagacg   420
cgtaaaacaa cttctgaaac cgttcgtgct gtgctagaca gtttaccagg atccgtggga   480
ggtctatcgc catctcaggc atccagcgcc gcatcctcgg cttcctcaag cccgggttca   540
gggatctccg aagcactcag agctggagca ggttccggca ctggatacaa caaggaattc   600
ctgctctacc tggcgggctt cgtcgacggg gacggctcca tctgtgcctg tatcgtgcct   660
```

```
cgtcaagatc ggaagttcaa gcaccagctg cggctctttt tcgaggtcgg tcagaagaca  720
cagcgccgtt ggttcctcga caagctggtg gacgagatcg gtgtgggtta cgtgagggac  780
cttggcagcg cgagcactta ccgtctgtcc cagatcaagc ctctgcacaa cttcctgacc  840
cagctccagc ccttcctgaa gctcaagcag aagcaggcca acctcgtgct gaagatcatc  900
gagcagctgc cctccgccaa ggaatccccg gacaagttcc tggaggtgtg cacctgggtg  960
gaccagatcg ccgctctgaa cgactccagg acccgcaaga ccacttccga aaccgtccgc  1020
gccgttctag acagtctctc cgagaagaag aagtcgtccc cc  1062

SEQ ID NO: 65           moltype = DNA  length = 1062
FEATURE                 Location/Qualifiers
source                  1..1062
                        mol_type = other DNA
                        organism = synthetic construct
SEQUENCE: 65
atgaatacaa aatataataa agagttctta ctctacttag cagggtttgt agactctgac  60
ggttccatca tggcctttat cttgcctgag cagcatatga agttcaagca ccgtctgagg  120
ctccagttcg cggtcgctca gaagacacag cgccgttggt tcctcgacaa gctggtggac  180
gagatcggtg tgggttacgt gtatgacttt ggcagcgtct cctattacag gctgtccgag  240
atcaagcctt tgcataattt tttaacacaa ctacaacctt ttctaaaact aaaaacaaaaa  300
caagcaaatt tagtttttaaa aattattgaa caacttccgt cagcaaaaga atccccggac  360
aaaattcttag aagtttgtac atgggtggat caaattgcag ctctgaatga ttcgaagacg  420
cgtaaaacaa cttctgaaac cgttcgtgct gtgctagaca gtttaccagg atccgtggga  480
ggtctatcgc catctcaggc atccagcgcc gcatcctcgg cttcctcaag cccgggttca  540
gggatctccg aagcactcag agctggagca ggttccggca ctggatacaa caaggaattc  600
ctgctctacc tggcgggctt cgtcgacggg gacggctcca tctgtgcctg tatcgtgcct  660
cgtcaagatc ggaagttcaa gcaccagctg cggctctttt tcgaggtcgg tcagaagaca  720
cagcgccgtt ggttcctcga caagctggtg gacgagatcg gtgtgggtta cgtgagggac  780
cttggcagcg cgagcactta ccgtctgtcc cagatcaagc ctctgcacaa cttcctgacc  840
cagctccagc ccttcctgaa gctcaagcag aagcaggcca acctcgtgct gaagatcatc  900
gagcagctgc cctccgccaa ggaatccccg gacaagttcc tggaggtgtg cacctgggtg  960
gaccagatcg ccgctctgaa cgactccagg acccgcaaga ccacttccga aaccgtccgc  1020
gccgttctag acagtctctc cgagaagaag aagtcgtccc cc  1062

SEQ ID NO: 66           moltype = DNA  length = 1062
FEATURE                 Location/Qualifiers
source                  1..1062
                        mol_type = other DNA
                        organism = synthetic construct
SEQUENCE: 66
atgaatacaa aatataataa agagttctta ctctacttag cagggtttgt agactctgac  60
ggttccatca tggcctttat cttgcctgag cagcatctta agttcaagca ccgtctgagg  120
ctccagttcg cggtcgctca gaagacacag cgccgttggt tcctcgacaa gctggtggac  180
gagatcggtg tgggttacgt gtatgacttt ggcagcgtct cctattacag gctgtccgag  240
atcaagcctt tgcataattt tttaacacaa ctacaacctt ttctaaaact aaaaacaaaaa  300
caagcaaatt tagtttttaaa aattattgaa caacttccgt cagcaaaaga atccccggac  360
aaaattcttag aagtttgtac atgggtggat caaattgcag ctctgaatga ttcgaagacg  420
cgtaaaacaa cttctgaaac cgttcgtgct gtgctagaca gtttaccagg atccgtggga  480
ggtctatcgc catctcaggc atccagcgcc gcatcctcgg cttcctcaag cccgggttca  540
gggatctccg aagcactcag agctggagca ggttccggca ctggatacaa caaggaattc  600
ctgctctacc tggcgggctt cgtcgacggg gacggctcca tctgtgcctg tatcgtgcct  660
cgtcaagatc ggaagttcaa gcaccagctg cggctctttt tcgaggtcgg tcagaagaca  720
cagcgccgat ggttcctcga caagctggtg gacgagatcg gtgtgggtta cgtgagggac  780
cttggcagcg cgagcactta ccgtctgtcc cagatcaagc ctctgcacaa cttcctgacc  840
cagctccagc ccttcctgaa gctcaagcag aagcaggcca acctcgtgct gaagatcatc  900
gagcagctgc cctccgccaa ggaatccccg gacaagttcc tggaggtgtg cacctgggtg  960
gaccagatcg ccgctctgaa cgactccagg acccgcaaga ccacttccga aaccgtccgc  1020
gccgttctag acagtctctc cgagaagaag aagtcgtccc cc  1062

SEQ ID NO: 67           moltype = DNA  length = 1062
FEATURE                 Location/Qualifiers
source                  1..1062
                        mol_type = other DNA
                        organism = synthetic construct
SEQUENCE: 67
atgaatacaa aatataataa agagttctta ctctacttag cagggtttgt agactctgac  60
ggttccatca tggcctttat cttgcctgag cagggtctga agttcaagca ccgtctgagg  120
ctccagttcg cggtcgctca gaagacacag cgccgttggt tcctcgacaa gctggtggac  180
gagatcggtg tgggttacgt gtatgacttt ggcagcgtct cctattacag gctgtccgag  240
atcaagcctt tgcataattt tttaacacaa ctacaacctt ttctaaaact aaaaacaaaaa  300
caagcaaatt tagtttttaaa aattattgaa caacttccgt cagcaaaaga atccccggac  360
aaaattcttag aagtttgtac atgggtggat caaattgcag ctctgaatga ttcgaagacg  420
cgtaaaacaa cttctgaaac cgttcgtgct gtgctagaca gtttaccagg atccgtggga  480
ggtctatcgc catctcaggc atccagcgcc gcatcctcgg cttcctcaag cccgggttca  540
gggatctccg aagcactcag agctggagca ggttccggca ccggatacaa caaggaattc  600
ctgctctacc tggcgggctt cgtcgacggg gacggctcca tctgtgcctg tatcgtgcct  660
cgtcaagatc ggaagttcaa gcaccagctg cggctctttt tcgaggtcgg tcagaagaca  720
cagcgccgtt ggttcctcga caagctggtg gacgagatcg gtgtgggtta cgtgagggac  780
cttggcagcg cgagcactta ccgtctgtcc cagatcaagc ctctgcacaa cttcctgacc  840
cagctccagc ccttcctgaa gctcaagcag aagcaggcca acctcgtgct gaagatcatc  900
```

-continued

```
gagcagctgc cctccgccaa ggaatccccg gacaagttcc tggaggtgtg cacctgggtg    960
gaccagatcg ccgctctgaa cgactccagg acccgcaaga ccacttccga aaccgtccgc    1020
gccgttctag acagtctctc cgagaagaag aagtcgtccc cc                       1062

SEQ ID NO: 68          moltype = DNA  length = 1062
FEATURE                Location/Qualifiers
source                 1..1062
                       mol_type = other DNA
                       organism = synthetic construct
SEQUENCE: 68
atgaatacaa aatataataa agagttctta ctctacttag cagggtttgt agactctgac    60
ggttccatca tggcctttat catgcctgat caggcgccta agttcaagca ccgtctgagg    120
ctccagttcg cggtcgctca gaagacacag cgccgttggt tcctcgacaa gctggtggac    180
gagatcggtg tgggttacgt gtatgacttt ggcagcgtct cctattacag gctgtccgag    240
atcaagcctt tgcataattt tttaacacaa ctacaacctt ttctaaaact aaaacaaaaa    300
caagcaaatt tagtttttaaa aattattgaa caacttccgt cagcaaaaga atccccggac    360
aaaattcttag aagtttgtac atgggtggat caaattgcag ctctgaatga ttcgaagacg    420
cgtaaaacaa cttctgaaac cgttcgtgtc gtgctagaca gtttaccagg atccgtggga    480
ggtctatcgc catctcaggc atccagcgcc gcatcctcgg cttcctcaag cccgggttca    540
gggatccccg aagcactcag agctggagca ggttccggca ctggatacaa caaggaattc    600
ctgctctacc tggcgggctt cgtcgacggg gacggctcca tctgtgcctg tatcgtgcct    660
cgtcaagatc ggaagttcaa gcaccagctg cggctctttt tcgaggtcac tcagaagaca    720
cagcgccgtt ggttcctcga caagctggtg gacgagatcg gtgtgggtta cgtgagggac    780
cttggcagcg cgagcactta ccgtctgtcc cagatcaagc ctctgcacaa cttcctgacc    840
cagctccagc ccttcctgaa gctcaagcag aagcaggcca acctcgtgct gaagatcatc    900
gagcagctgc cctccgccaa ggaatccccg gacaagttcc tggaggtgtg cacctgggtg    960
gaccagatcg ccgctctgaa cgactccagg acccgcaaga ccacttccga aaccgtccgc    1020
gccgttctag acagtctctc cgagaagaag aagtcgtccc cc                       1062

SEQ ID NO: 69          moltype = DNA  length = 1062
FEATURE                Location/Qualifiers
source                 1..1062
                       mol_type = other DNA
                       organism = synthetic construct
SEQUENCE: 69
atgaatacaa aatataataa agagttctta ctctacttag cagggtttgt agacgctgac    60
ggttccatct atgcctgtat caagcctcat caacagctta agttcaagca ccagctgttg    120
ctctatttcg aggtctatca gaagacacag cgccgttggt tcctcgacaa gctggtggac    180
gagatcggtg tgggttacgt ggctgaccgt ggcagcgtct ccgagtaccg tctgtcccag    240
atcaagcctt tgcataattt tttaacacaa ctacaacctt ttctaaaact aaaacaaaaa    300
caagcaaatt tagtttttaaa aattattgaa caacttccgt cagcaaaaga atccccggac    360
aaaattcttag aagtttgtac atgggtggat caaattgcag ctctgaatga ttcgaagacg    420
cgtaaaacaa cttctgaaac cgttcgtgct gtgctagaca gtttaccagg atccgtggga    480
ggtctatcgc catctcaggc atccagcgcc gcatcctcgg cttcctcaag cccgggttca    540
gggatccccg aagcactcag agctggagca ggttccggca ctggatacaa caaggaattc    600
ctgctctacc tggcgggctt cgtcgacggg gacggctcca tctttgcctc tatcatgccg    660
acgcagtgga cgaagttcaa gcactcgctg ttgctccgat ttgctccggt cac ccagtcgaca    720
aggcgccgtt ggttcctcga caagctgatg gacgagattg gtgtgggtta cgtgtctgac    780
cagggcaggg cgagctacta caccctgtcc cagatcaagc ctctgcacaa cttcctgacc    840
cagctccagc ccttcctgaa gctcaagcag aagcaggcca acctcgtgct gaagatcatc    900
gagcagctgc cctccgccaa ggaatccccg gacaagttcc tggaggtgtg cacctgggtg    960
gaccagatcg ccgctctgaa cgactccagg acccgcaaga ccacttccga aaccgtccgc    1020
gccgttctag acagtctctc cgagaagaag aagtcgtccc cc                       1062

SEQ ID NO: 70          moltype = DNA  length = 1062
FEATURE                Location/Qualifiers
source                 1..1062
                       mol_type = other DNA
                       organism = synthetic construct
SEQUENCE: 70
atgaatacaa aatataataa agagttctta ctctacttag cagggtttgt agacgctgac    60
ggttccatct atgcctgtat caagcctcat caacagctta agttcaagca ccagctgttg    120
ctctatttcg aggtctatca gaagacacag cgccgttggt tcctcgacaa gctggtggac    180
gagatcggtg tgggttacgt gattgactcg ggcagcgtct ccacgtaccg gctgtcccag    240
atcaagcctt tgcataattt tttaacacaa ctacaacctt ttctaaaact aaaacaaaaa    300
caagcaaatt tagtttttaaa aattattgaa caacttccgt cagcaaaaga atccccggac    360
aaaattcttag aagtttgtac atgggtggat caaattgcag ctctgaatga ttcgaagacg    420
cgtaaaacaa cttctgaaac cgttcgtgct gtgctagaca gtttaccagg atccgtggga    480
ggtctatcgc catctcaggc atctagcgcc gcatcctcgg cttcctcaag cccgggttca    540
gggatccccg aagcactcag agctggagca ggttccggca ctggatacaa caaggaattc    600
ctgctctacc tggcgggctt cgtcgacggg gacggctcca tctttgcctc tatcattccg    660
tcgcagctgg ttaagttcaa gcacactctg ctgctccgtt ccgggtcac ccaggcgaca      720
aggcgccgtt ggttcctcga caagctggtg gacgagatcg gtgtgggtta cgtgacggac    780
aacggcaggg cgagctacta caccctgtcc gagatcaagc ctctgcacaa cttcctgacc    840
cagctccagc ccttcctgaa gctcaagcag aagcaggcca acctcgtgct gaagatcatc    900
gagcagctgc cctccgccaa ggaatccccg gacaagttcc tggaggtgtg cacctgggtg    960
gaccagatcg ccgctctgaa cgactccagg acccgcaaga ccacttccga aaccgtccgc    1020
gccgttctag acagtctctc cgagaagaag aagtcgtccc cc                       1062
```

```
SEQ ID NO: 71          moltype = DNA  length = 1062
FEATURE                Location/Qualifiers
source                 1..1062
                       mol_type = other DNA
                       organism = synthetic construct
SEQUENCE: 71
atgaatacaa aatataataa agagttctta ctctacttag cagggtttgt agacgctgac   60
ggttccatct atgcctgtat caagcctcat caacagctta agttcaagca ccagctgttg  120
ctctatttcg aggtctatca gaagacacag cgccgttggt tcctcgacaa gctggtggac  180
gagatcggtg tgggttacgt ggctgaccgt ggcagcgtct ccgagtaccg tctgtcccag  240
atcaagcctt tgcataattt tttaacacaa ctacaacctt ttctaaaact aaaacaaaaa  300
caagcaaatt tagtttttaaa aattattgaa caacttccgt cagcaaaaga atccccggac  360
aaaattcttag aagtttgtac atgggtggat caaattgcag ctctgaatga ttcgaagacg  420
cgtaaaacaa cttctgaaac cgttcgtgct gtgctagaca gtttaccagg atccgtggga  480
ggtctatcgc catctcaggc atccagcgcc gcatcctcgg cttcctcaag cccgggttca  540
gggatctccg aagcactcag agctggagca ggttccggca ctggatacaa caaggaattc  600
ctgctctacc tggcgggctt cgtcgacggg gacggctcca tctttgcctc tatcattccg  660
tcgcagctgg ttaagttcaa gcacactctg ctgctccgtt tccgggtctg ccaggcgaca  720
aagcgccgtt ggttcctcga caagctggtg gacgagattg gtgtgggtta cgtgtctgac  780
cagggcagcg cgagctacta caccctgtcc gagatcaagc ctctgcacaa cttcctgacc  840
cagctccagc ccttcctgaa gctcaagcag aagcaggcca acctcgtgct gaagatcatc  900
gagcagctgc cctccgccaa ggaatccccg gacaagttcc tggaggtgtg cacctgggtg  960
gaccagatcg ccgctctgaa cgactccagg acccgcaaga ccacttccga aaccgtccgc 1020
gccgttctag acagtctctc cgagaagaag aagtcgtccc cc                     1062

SEQ ID NO: 72          moltype = DNA  length = 1062
FEATURE                Location/Qualifiers
source                 1..1062
                       mol_type = other DNA
                       organism = synthetic construct
SEQUENCE: 72
atgaatacaa aatataataa agagttctta ctctacttag cagggtttgt agactctgac   60
ggttccatct atgcctgtat caagcctcat caacagctta agttcaagca ccagctgttg  120
ctctatttcg aggtctatca gaagacacag cgccgttggt tcctcgacaa gctggtggac  180
gagatcggtg tgggttacgt ggctgaccgt ggcagcgtct ccgagtaccg tctgtcccag  240
atcaagcctt tgcataattt tttaacacaa ctacaacctt ttctaaaact aaaacaaaaa  300
caagcaaatt tagtttttaaa aattattgaa caacttccgt cagcaaaaga atccccggac  360
aaaattcttag aagtttgtac atgggtggat caaattgcag ctctgaatga ttcgaagacg  420
cgtaaaacaa cttctgaaac cgttcgtgct gtgctagaca gtttaccagg atccgtggga  480
ggtctatcgc catctcaggc atccagcgcc gcatcctcgg cttcctcaag cccgggttca  540
gggatctccg aagcactcag agctggagca ggttccggca ctggatacaa caaggaattc  600
ctgctctacc tggcgggctt cgtcgacggg gacggctcca tctttgcctc tatcattccg  660
tcgcaggagg ttaagttcaa gcacactctg ctgctccgtt tccgggtctg ccaggcgaca  720
aagcgccgtt ggttcctcga caagctggtg gacgagattg gtgtgggtta cgtgtctgac  780
cagggcagcg cgagctacta caccctgtcc gagatcaagc ctctgcacaa cttcctgacc  840
cagctccagc ccttcctgaa gctcaagcag aagcaggcca acctcgtgct gaagatcatc  900
gagcagctgc cctccgccaa ggaatccccg gacaagttcc tggaggtgtg cacctgggtg  960
gaccagatcg ccgctctgaa cgactccagg acccgcaaga ccacttccga aaccgtccgc 1020
gccgttctag acagtctctc cgagaagaag aagtcgtccc cc                     1062

SEQ ID NO: 73          moltype = DNA  length = 1062
FEATURE                Location/Qualifiers
source                 1..1062
                       mol_type = other DNA
                       organism = synthetic construct
SEQUENCE: 73
atgaatacaa aatataataa agagttctta ctctacttag cagggtttgt agacgctgac   60
ggttccatct atgcctgtat caagcctcat caacagctta agttcaagca ccagctgttg  120
ctctatttcg aggtctatca gaagacacag cgccgttggt tcctcgacaa gctggtggac  180
gagatcggtg tgggttacgt ggctgaccgt ggcagcgtct ccgagtaccg tctgtcccag  240
atcaagcctt tgcataattt tttaacacaa ctacaacctt ttctaaaact aaaacaaaaa  300
caagcaaatt tagtttttaaa aattattgaa caacttccgt cagcaaaaga atccccggac  360
aaaattcttag aagtttgtac atgggtggat caaattgcag ctctgaatga ttcgaagacg  420
cgtaaaacaa cttctgaaac cgttcgtgct gtgctagaca gtttaccagg atccgtggga  480
ggtctatcgc catctcaggc atccagcgcc gcatcctcgg cttcctcaag cccgggttca  540
gggatctccg aagcactcag agctggagca ggttccggca ctggatacaa caaggaattc  600
ctgctctacc tggcgggctt cgtcgacggg gacggctcca tctttgcctc tatcattccg  660
tcgcaggagg ttaagttcaa gcacactctg ctgctccgtt tccgggtctg ccaggcgaca  720
aagcgccgtt ggttcctcga caagctggtg gacgagattg gtgtgggtta cgtgtctgac  780
cagggcagcg cgagctacta caccctgtcc gagatcaagc ctctgcacaa cttcctgacc  840
cagctccagc ccttcctgaa gctcaagcag aagcaggcca acctcgtgct gaagatcatc  900
gagcagctgc cctccgccaa ggaatccccg gacaagttcc tggaggtgtg cacctgggtg  960
gaccagatcg ccgctctgaa cgactccagg acccgcaaga ccacttccga aaccgtccgc 1020
gccgttctag acagtctctc cgagaagaag aagtcgtccc cc                     1062

SEQ ID NO: 74          moltype = DNA  length = 1062
FEATURE                Location/Qualifiers
source                 1..1062
                       mol_type = other DNA
```

-continued

```
                           organism = synthetic construct
SEQUENCE: 74
atgaatacaa aatataataa agagttctta ctctacttag cagggtttgt agacgctgac    60
ggttccatct atgcctgtat caagcctcat caacagctta agttcaagca ccagctgttg   120
ctctatttcg aggtctatca gaagacacag cgccgttggt tcctcgacaa gctggtggac   180
gagatcggtg tgggttacgt ggctgaccgt ggcagcgtct ccgagtaccg tctgtcccga   240
atcaagcctt tgcataattt tttaacacaa ctacaacctt ttctaaaact aaaacaaaaa   300
caagcaaatt tagtttttaaa aattattgaa caacttccgt cagcaaaaga atccccggac   360
aaattcttag aagtttgtac atgggtggat caaattgcag ctctgaatga ttcgaagacg   420
cgtaaaacaa cttctgaaac cgttcgtgct gtgctagaca gtttaccagg atccgtggga   480
ggtctatcgc catctcaggc atccagcgcc gcatcctcgg cttcctcaag cccgggttca   540
gggatctccg aagcactcag agctggagca ggttccggca ctggatacaa caaggaattc   600
ctgctctacc tggcgggctt cgtcgacggg gacggctcca tctttgcctc tatcattccg   660
tcgcaggagg ttaagttcaa gcacactctg ctgctccgtt tcaggtcac tcaggcgaca   720
aagcgccgtt ggttcctcga caagctggtg gacgagattg gtgtgggtta cgtgtctgac   780
gttggcagcg cgagctatta caccctgtcc gagatcaagc ctctgcacaa cttcctgacc   840
cagctccagc ccttcctgaa gctcaagcag aagcaggcca acctcgtgct gaagatcatc   900
gagcagctgc cctccgccaa ggaatccccg gacaagttcc tggaggtgtg cacctgggtg   960
gaccagatcg ccgctctgaa cgactccagg acccgcaaga ccacttccga aaccgtccgc  1020
gccgttctag acagtctctc cgagaagaag aagtcgtccc cc                      1062

SEQ ID NO: 75            moltype = DNA  length = 1062
FEATURE                  Location/Qualifiers
source                   1..1062
                         mol_type = other DNA
                         organism = synthetic construct
SEQUENCE: 75
atgaatacaa aatataataa agagttctta ctctacttag cagggtttgt agactctgac    60
ggttccatct atgcctgtat caagcctcat caacagctta agttcaagca ccagctgttg   120
ctctatttcg aggtctatca gaagacacag cgccgttggt tcctcgacaa gctggtggac   180
gagatcggtg tgggttacgt ggctgaccgt ggcagcgtct ccgagtaccg tctgtcccag   240
atcaagcctt tgcataattt tttaacacaa ctacaacctt ttctaaaact aaaacaaaaa   300
caagcaaatt tagtttttaaa aattattgaa caacttccgt cagcaaaaga atccccggac   360
aaattcttag aagtttgtac atgggtggat caaattgcag ctctgaatga ttcgaagacg   420
cgtaaaacaa cttctgaaac cgttcgtgct gtgctagaca gtttaccagg atccgtggga   480
ggtctatcgc catctcaggc atccagcgcc gcatcctcgg cttcctcaag cccgggttca   540
gggatctccg aagcactcag agctggagca ggttccggca ctggatacaa caaggaattc   600
ctgctctacc tggcgggctt cgtcgacggg gacggctcca tctttgcctc tatcattccg   660
tcgcaggagg ttaagttcaa gcacactctg ctgctccgtt tcaggtctg ccaggcgaca   720
aagcgccgtt ggttcctcga caagctggtg gacgagattg gtgtgggtta cgtgtctgac   780
cgtggcagcg cgagctatta caccctgtcc gagatcaagc ctctgcacaa cttcctgacc   840
cagctccagc ccttcctgaa gctcaagcag aagcaggcca acctcgtgct gaagatcatc   900
gagcagctgc cctccgccaa ggaatccccg gacaagttcc tggaggtgtg cacctgggtg   960
gaccagatcg ccgctctgaa cgactccagg acccgcaaga ccacttccga aaccgtccgc  1020
gccgttctag acagtctctc cgagaagaag aagtcgtccc cc                      1062

SEQ ID NO: 76            moltype = DNA  length = 1062
FEATURE                  Location/Qualifiers
source                   1..1062
                         mol_type = other DNA
                         organism = synthetic construct
SEQUENCE: 76
atgaatacaa aatataataa agagttctta ctctacttag cagggtttgt agacgctgac    60
ggttccatct atgcctgtat caagcctcat caagagctta agttcaagca ccagctgttg   120
ctctatttcg aggtctatca gaagacacag cgccgttggt tcctcgacaa gctggtggac   180
gagatcggtg tgggttacgt ggctgaccgt ggcagcgtct ccgagtaccg tctgtccgag   240
atcaagcctt tgcataattt tttaacacaa ctacaacctt ttctaaaact aaaacaaaaa   300
caagcaaatt tagtttttaaa aattattgaa caacttccgt cagcaaaaga atccccggac   360
aaattcttag aagtttgtac atgggtggat caaattgcag ctctgaatga ttcgaagacg   420
cgtaaaacaa cttctgaaac cgttcgtgct gtgctagaca gtttaccagg atccgtggga   480
ggtctatcgc catctcaggc atccagcgcc gcatcctcgg cttcctcaag cccgggttca   540
gggatctccg aagcactcag agctggagca ggttccggca ctggatacaa caaggaattc   600
ctgctctacc tggcgggctt cgtcgacggg gacggctcca tctttgcctc tatcattccg   660
tcgcaggagg ttaagttcaa gcacactctg ctgctccgtt tcaggtctg ccaggcgaca   720
aagcgccgtt ggttcctcga caagctggtg gacgagattg gtgtgggtta cgtgtctgac   780
cagggcagcg cgagctacta caccctgtcc cagatcaagc ctctgcacaa cttcctgacc   840
cagctccagc ccttcctgaa gctcaagcag aagcaggcca acctcgtgct gaagatcatc   900
gagcagctgc cctccgccaa ggaatccccg gacaagttcc tggaggtgtg cacctgggtg   960
gaccagatcg ccgctctgaa cgactccagg acccgcaaga ccacttccga aaccgtccgc  1020
gccgttctag acagtctctc cgagaagaag aagtcgtccc cc                      1062

SEQ ID NO: 77            moltype = AA  length = 42
FEATURE                  Location/Qualifiers
source                   1..42
                         mol_type = protein
                         organism = synthetic construct
SEQUENCE: 77
SLPGSVGGLS PSQASSAASS ASSSPGSGIS EALRAGAGSG TG                        42
```

-continued

```
SEQ ID NO: 78          moltype = DNA   length = 3947
FEATURE                Location/Qualifiers
source                 1..3947
                       mol_type = other DNA
                       organism = synthetic construct
SEQUENCE: 78
aagcttgcat gtctaagcta gacccttcag attaaaaata actgaggtaa gggcctgggt   60
aggggaggtg gtgtgagacg ctcctgtctc tcctctatct gcccatcggc cctttgggga   120
ggaggaatgt gcccaaggac taaaaaaagg ccatggagcc agaggggcga gggcaacaga   180
cctttcatgg gcaaaccttg gggccctgct gtctagcatg ccccactacg ggtctaggct   240
gcccatgtaa ggaggcaagg cctgggaca cccgagatgc ctggttataa ttaacccaga   300
catgtggctg ccccccccccc cccaacacct gctgcctcta aaaataaccc tgtccctggt   360
ggatcccctg catgcgaaga tcttcgaaca aggctgtggg ggactgaggg caggctgtaa   420
caggcttggg ggccagggct tatacgtgcc tgggactccc aaagtattac tgttccatgt   480
tcccggcgaa gggccagctg tcccccgcca gctagactca gcacttagtt taggaaccag   540
tgagcaagtc agcccttggg gcagcccata caaggccatg gggctgggca agctgcacgc   600
ctgggtccgg ggtgggcacg gtgcccgggc aacgagctga aagctcatct gctctcaggg   660
gcccctccct ggggacagcc cctcctggct agtcacaccc tgtaggctcc tctatataac   720
ccaggggcac aggggctgcc ctcattctac caccacctcc acagcacaga cagacactca   780
ggagcagcca gcgccaccat ggcaccgaag aagaagcgca aggtgcatat gaatacaaaa   840
tataataaag agttcttact ctacttagca gggtttgtag actctgacgg ttccatcatg   900
gccttcatca tgcctactca aaccgcaaag ttcaagcacc gtctgaagct ccagttcgcg   960
gtcgcacaga agacacagcg ccgttggttc ctcgacaagc tggtggacga gatcggtgtg   1020
ggttacgtgt atgacttcgg cagcgtctcc tactaccgtc tgtccgagat caagcctttg   1080
cataattttt taacacaact acaaccttt ctaaaactaa aacaaaaaca agcaaattta   1140
gttttaaaaa ttattgaaca acttccgtca gcaaaagaat ccccggacaa attcttagaa   1200
gtttgtacat gggtggatca aattgcagct ctgaatgatt cgaagacgcg taaaacaact   1260
tctgaaaccg ttcgtgctgt gctagacagt ttaccaggct ccgtgggagg tctatcgcca   1320
tctcaggcat ccagcgccgc atcctcggct tcctcaagcc cgggttcagg gatctccgaa   1380
gcactcagag ctggagcagg ttccggcact ggatacaaca aggaattcct gctctacctg   1440
gcgggcttcg tagacgggga cggctccatc tgtgcctgta tcgtgcctcg tcaagatcgg   1500
aagttcaagc accagctgcg gctctttttc gaggtcggtc agaagacaca gcgccgttgg   1560
ttcctcgaca agctggtgga cgagatcggt gtgggttacg tgcgtgacct gggctccgcg   1620
agcacgtacc ggctgtccca gatcaagcct ctgcacaact cctgaccca gctccagccc   1680
ttcctgaagc tcaagcagaa gcaggccaac ctcgtgctga agatcatcga gcagctgccc   1740
tccgccaagg aatccccgga caagttcctg gaggtgtgca cctgggtgga ccagatcgcc   1800
gctctgaacg actccaggac ccgcaagacc acttccgaaa ccgtccgcgc cgttctagac   1860
agtctctccg agaagaagaa gtcgtcccct tcgccggccg ctaagcgcgt gaagctggac   1920
ggtagagcca agagatctgg aagcggcgcc acaaatttct cactgctgaa acaggccggc   1980
gacgtggaag agaaccctgg acctgctagc ggaatggcac cgaaaaaaaa gcgcaaagta   2040
catatgaaca ccaagtacaa caaggaattt ctcttgtatc tcgccggctt cgtcgatgcc   2100
gatgggagta tacgcgtg cataaagccc caccaacagt tgaaatttaa acatcagtta   2160
ctcttgtact ttgaggtgta ccaaaaaacc caaggaggt cgttttgga taagctggtc   2220
gatgagatag gagtcgggta tgtcgccgat cgcgggtcgg tgagtgagta tcgtttaagt   2280
caaataaaac cgctccacaa cttcctcacc cagttgcagc cgttcttgaa gttgaagcag   2340
aagcaggcca acctcgtgct caagataata gagcagttgc ccagcgccaa ggagagtccc   2400
gataagtttc tggaggtgtg tacctgggtg gaccagatag ccgcgttaaa cgacagcaaa   2460
accaggaaaa ccacgagcga gacggtgaga gcggtcttgg attcgctccc tggcagtgtc   2520
ggcggattga gcccaagcca agccagttcg gcagccagta gcgcgagtag ctcgccagga   2580
agcggcataa gtgaggcttt gagagctgga gctggaagtg gtaccggtta caacaaggag   2640
ttcttactgt acttagccgg gttcgtggat ggcgatggga gtatattcgc gtccataatc   2700
cccagccaag aggtgaaatt taaacatacc ttactcttgc gatttcgcgt gtgccaagca   2760
accaaaagga ggtggttttt ggataagctg gtcgatgaga taggagtcgg gtatgtctcc   2820
gatcagggg cggcctcgta ctataccta agtgagataa aaccgttaca taacttctta   2880
acgcaattgc aaccgtttct gaaactgaag cagaagcaag cgaatctggt cctgaagatc   2940
atcgaacaac tgccgagtgc gaaggagtcc cccgataagt tcctcgaggt ctgcacgtc   3000
gtcgatcaaa tagcggcgtt aaatgatagt aggacgagga aaacgacgag tgagacggtg   3060
agggcggtgt tggattcgtt gagtgaaaag aaaagagca gtccttcgcc ggcagcgaag   3120
agggttaagc tcgactagta agcttatcaa cctctggatt acaaaatttg tgaaagattg   3180
actgatattc ttaactatgt tgctcctttt acgctgtgtg gatatgctgc tttaatgcct   3240
ctgtatcatg ctattgcttc ccgtacggct ttcgttttct cctccttgta taaatcctgg   3300
ttgctgtctc tttatgagga gttgtggccc gttgtccgtc aacgtggcgt ggtgtgctct   3360
gtgtttgctg acgcaacccc cactggctgg ggcattgcca ccacctgtca actcctttct   3420
gggactttcg ctttcccct cccgatcgcc acggcagaac tcatcgccgc ctgccttgcc   3480
cgctgctgga caggggctag gttgctgggc actgataatt ccgtggtgtt gtcggggaag   3540
ctgacgtcct ttcagggct gctcgcctgt gttgccaact ggatcctgcg cgggacgtcc   3600
ttctgctacg tcccttcggc tctcaatcca gcggacctcc cttcccgagg ccttctgccg   3660
gttctgcggc ctctcccgcg tcttcgcttt cggcctccga cgagtcggat ctccctttgg   3720
gccgcctccc cgcctgggta gatccagaca tgataagata cattgatgag tttggacaaa   3780
ccacaactag aatgcagtga aaaaaatgct ttatttgtga aatttgtgat gctattgctt   3840
tatttgtaac cattataagc tgcaataaac aagttaacaa caacaattgc attcatttta   3900
tgtttcaggt tcaggggag gtgtgggagg ttttttaaag caagtaa             3947

SEQ ID NO: 79          moltype = DNA   length = 3875
FEATURE                Location/Qualifiers
source                 1..3875
                       mol_type = other DNA
                       organism = synthetic construct
SEQUENCE: 79
```

```
ccactacggg tctaggctgc ccatgtaagg aggcaaggcc tggggacacc cgagatgcct    60
ggttataatt aaccccaaca cctgctgccc cccccccccc aacacctgct gcctgagcct   120
gagcggttac cccaccccgg tgcctgggtc ttaggctctg tacaccatgg aggagaagct   180
cgctctaaaa ataaccctgt ccctggtgga tccactacgg gtctaggctg cccatgtaag   240
gaggcaaggc ctggggacac ccgagatgcc tggttataat taaccccaac acctgctgcc   300
cccccccccc caacacctgc tgcctgagcc tgagcggtta ccccaccccg gtgcctgggt   360
cttaggctct gtacaccatg gaggagaagc tcgctctaaa ataaccctg tccctggtgg   420
atccactacg ggtctaggct gcccatgtaa ggaggcaagg cctggggaca cccgagatgc   480
ctggttataa ttaaccccaa cacctgctgc cccccccccc ccaacacctg ctgcctgagc   540
ctgagcggtt accccacccc ggtgcctggg tcttaggctc tgtacaccat ggaggagaag   600
ctcgctctaa aaataaccct gtccctggtg gatcctccct ggggacagcc cctcctggct   660
agtcacaccc tgtaggctcc tctatataac ccaggggcac aggggctgcc cccgggtcac   720
gccaccatgg caccgaagaa gaagcgcaag gtgcatatga atacaaaata taataaagag   780
ttcttactct acttagcagg gtttgtagac tctgacggtt ccatcatggc cttcatcatg   840
cctactcaaa ccgcaaagtt caagcaccgt ctgaagctcc agttcgcggt cgcacagaag   900
acacagcgcc gttggttcct cgacaagctg gtggacgaga tcggtgtggg ttacgtgtat   960
gacttcggca gcgtctccta ctaccgtctg tccgagatca agcctttgca taatttttta  1020
acacaactac aacctttct aaaactaaaa caaaaacaag caaatttagt tttaaaaatt  1080
attgaacaac ttccgtcagc aaaagaatcc ccggacaaat tcttagaagt ttgtacatgg  1140
gtggatcaaa ttgcagctct gaatgattcg aagacgcgta aaacaacttc tgaaaccgtt  1200
cgtgctgtgc tagacagttt accaggctcc gtgggaggtc tatcgccatc tcaggcatcc  1260
agcgccgcat cctcggcttc ctcaagcccg ggttcaggga tctccgaagc actcagagct  1320
ggagcaggtt ccggcactgg atacaacaag gaattcctgc tctacctggc gggcttcgta  1380
gacgggacg gctccatctg tgcctgtatc gtgcctcgtc aagatcggaa gttcaagcac  1440
cagctgcggc tcttttttcga ggtcggtcag aagacacagc gccgttggtt cctcgacaag  1500
ctggtggacg agatcggtgt gggttacgtg cgtgacctgg gctccgcgag cacgtaccgg  1560
ctgtcccaga tcaagcctct gcacaacttc ctgacccagc tccagccctt cctgaagctc  1620
aagcagaagc aggccaacct cgtgctgaag atcatcgagc agctgccctc cgccaaggaa  1680
tccccggaca agttcctgga ggtgtgcacc tgggtggacc agatcgccgc tctgaacgac  1740
tccaggaccc gcaagaccac ttccgaaacc gtccgcgccg ttctagacag tctctccgga  1800
aagaagaagt cgtcccctc gccggccgct aagcgcgtga agctggacg tagagccaag  1860
agatctggaa gcggcgccac aaatttctca ctgctgaaac aggccggcga cgtggaagag  1920
aaccctggac ctgctagcgg aatggcaccg aaaaaaaagc gcaaagtaca tatgaacacc  1980
aagtacaaca aggaatttct cttgtatctc gccggcttcg tcgatgccga tgggagtata  2040
tacgcgtgca taaagcccca ccaacagttg aaatttaaac atcagttact cttgtacttt  2100
gaggtgtacc aaaaaaccca aaggaggtgg ttttttggata agctggtcga tgagatagga  2160
gtcgggtatg tcgccgatcg cgggtcggtg agtgagtatc gtttaagtca aataaaaccg  2220
ctccacaact tcctcaccca gttgcagccg ttcttgaagt tgaagcagaa gcaggccaac  2280
ctcgtgctca agataataga gcagttgccc agcgccaagg agagtcccga taagtttctg  2340
gaggtgtgta cctgggtgga ccagatagcc gcgttaaacg acagcaaaac caggaaaacc  2400
acgagcgaga cggtgagagc ggtcttggat tcgctccctg gcagtgtcgg cggattgagc  2460
ccaagccaag ccagttcggc agccagtagc gcgagtagct cgccaggaag cggcataagt  2520
gaggctttga gagctggagc tggaagtggt accggttaca acaaggagtt cttactgtac  2580
ttagccgggt tcgtggatgg cgatgggagt atattcgcgt ccataatccc cagccaagag  2640
gtgaaattta aacataccett actcttgcga tttcgcgtgt gccaagcaac caaaaggagg  2700
tggtttttg ataagctggt cgatgagata ggagtcgggg atgtctccga tcaggggtcg  2760
gcctcgtact ataccttaag tgagataaaa ccgttacata acttcttaac gcaattgcaa  2820
ccgtttctga aactgaagca gaagcaagcg aatctggtcc tgaagatcat cgaacaactg  2880
ccgagtgcga aggagtcccc cgataagttc ctcgaggtct gcacgtgggt cgatcaaata  2940
gcggcgttaa atgatagtag gacgaggaaa acgacgagtg agacggtgag ggcggtgttg  3000
gattcgttga gtgaaaagaa aaagagcagt ccttcgccgg cagcgaagag ggttaagctc  3060
gactagtaag cttatcaacc tctggattac aaaatttgtg aaagattgac tgatattctt  3120
aactatgttg ctccttttac gctgtgtgga tatgctgctt taatgcctct gtatcatgct  3180
attgcttccc gtacggcttt cgttttctcc tccttgtata aatcctggtt gctgtctctt  3240
tatgaggagt tgtggcccgt tgtccgtcaa cgtggcgtgg tgtgctctgt gtttgctgac  3300
gcaacccca ctggctgggg cattgccacc acctgtcaac tcctttctgg gactttcgct  3360
ttccccctcc cgatcgccac ggcagaactc atcgccgcct gccttgcccg ctgctggaca  3420
ggggctaggt tgctgggcac tgataattcc gtggtgttgt cggggaagct gacgtccttt  3480
ccagggctgc tcgcctgtgt tgccaactgg atcctgcgcg ggacgtcctt ctgctacgtc  3540
ccttcggctc tcaatccagc ggacctccct tcccgaggcc ttctgccggt tctgcggcct  3600
ctcccgcgtc ttcgctttcg gcctccgacg agtcggatct cccttgggc cgcctccccg  3660
cctgggtaga tccagacatg ataagataca ttgatgagtt tggacaaacc acaactagaa  3720
tgcagtgaaa aaaatgcttt atttgtgaaa tttgtgatgc tattgcttta tttgtaacca  3780
ttataagctg caataaacaa gttaacaaca caattgcat tcattttatg tttcaggttc  3840
aggggaggt gtgggaggtt ttttaaagca agtaa                              3875
```

```
SEQ ID NO: 80          moltype = DNA   length = 3875
FEATURE                Location/Qualifiers
source                 1..3875
                       mol_type = other DNA
                       organism = synthetic construct
SEQUENCE: 80
ccactacggg tctaggctgc ccatgtaagg aggcaaggcc tggggacacc cgagatgcct    60
ggttataatt aaccccaaca cctgctgccc cccccccccc aacacctgct gcctgagcct   120
gagcggttac cccaccccgg tgcctgggtc ttaggctctg tacaccatgg aggagaagct   180
cgctctaaaa ataaccctgt ccctggtgga tccactacgg gtctaggctg cccatgtaag   240
gaggcaaggc ctgggacac ccgagatgcc tggttataat taaccccaac acctgctgcc   300
cccccccccc caacacctgc tgcctgagcc tgagcggtta ccccaccccg gtgcctgggt   360
cttaggctct gtacaccatg gaggagaagc tcgctctaaa ataaccctg tccctggtgg   420
```

```
atccactacg ggtctaggct gcccatgtaa ggaggcaagg cctgggaca cccgagatgc   480
ctggttataa ttaaccccaa cacctgctgc ccccccccc ccaacacctg ctgcctgagc   540
ctgagcggtt accccacccc ggtgcctggg tcttaggctc tgtacaccat ggaggagaag   600
ctcgctctaa aaataaccct gtccctggtg gatcctccct ggggacagcc cctcctggct   660
agtcacaccc tgtaggctcc tctatataac ccaggggcac aggggctgcc cccgggtcac   720
gccaccatgg caccgaagaa gaagcgcaag gtgcatatga atacaaaata taataaaagag   780
ttcttactct acttagcagg gtttgtagac tctgacggtt ccatcatggc cttcatcatg   840
cctactcaaa ccgcaaagtt caagcaccgt ctgaagctcc agttcgcggt cgcacagaag   900
acacagcgcc gttggttcct cgacaagctg gtggacgaga tcggtgtggg ttacgtgtat   960
gacttcggca gcgtctccta ctaccgtctg tccgagatca agcctttgca taatttttta  1020
acacaactac aacctttct aaaactaaaa caaaaacaag caaatttagt tttaaaaatt  1080
attgaacaac ttccgtcagc aaaagaatcc ccggacaaat tcttagaagt ttgtacatgg  1140
gtggatcaaa ttgcagctct gaatgattcg aagacgcgta aaacaacttc tgaaaccgtt  1200
cgtgctgtgc tagacagttt accaggctcc gtgggaggtc tatcgccatc tcaggcatcc  1260
agcgccgcat cctcggcttc ctcaagcccg ggtcaggga tctccgaagc actcagagct  1320
ggagcaggtt ccggcactgg atacaacaag gaattcctgc tctacctggc gggcttcgta  1380
gacgggggacg gctccatctg tgcctgtatc gtgcctcgtc aagatcggaa gttcaagcac  1440
cagctgcggc tcttttcga ggtcggtcag aagacacagc gccgttggtt cctcgacaag  1500
ctggtggacg agatcggtgt gggttacgtg cgtgacctgg gctccgcgag cacgtaccgg  1560
ctgtcccaga tcaagcctct gcacaacttc ctgacccagc tccagccctt cctgaagctc  1620
aagcagaagc aggccaacct cgtgctgaag atcatcgagc agctgccctc cgccaaggaa  1680
tccccgacga agttcctgga ggtgtgcacc tgggtggacc agatcgccgc tctgaacgac  1740
tccaggaccc gcaagaccac ttccgaaacc gtccgcgccg ttctagacag tctctccgag  1800
aagaagaagt cgtcccttc gccggccgct aagcgcgtga agctggacgg tagagccaag  1860
agatctggaa gcggcgccac aaatttctca ctgctgaaac aggccggcga cgtggaagag  1920
aaccctggac ctgctagcgg aatggccacg aaaaaaaagc gcaaagtaca tatgaacacc  1980
aagtacaaca aggaatttct cttgtatctc gccggcttcg tcgatgccga tgggagtata  2040
tacgcgtgca taaagcccca ccaacagttg aaatttaaac atcagttact cttgtacttt  2100
gaggtgtacc aaaaaaccca aaggaggtgg ttttttggata agctggtcga tgagatagga  2160
gtcgggtatg tcgccgatcg cgggtcggtg agtgagtatc gtttaagtca aataaaaccg  2220
ctccacaact tcctcaccca gttgcagccg ttcttgaagt tgaagcagaa gcaggccaac  2280
ctcgtgctca agataataga gcagttgccc agcgccaagg agagtcccga taagtttctg  2340
gaggtgtgta cctgggtgga ccagatagcc gcgttaaacg acagcaaaac caggaaaacc  2400
acgagcgaga cggtgagagc ggtcttggat tcgctccctg gcagtgtcgg cggattgagc  2460
ccaagccaag ccagttcggc agccagtagc gcgagtagct cgccaggaag cggcataagt  2520
gaggctttga gagctggagc tggaagtggt accggttaca acaaggagtt cttactgtac  2580
ttagccgggt tcgtggatgg cgatgggagt atattcgcgt ccataatccc cagccaagag  2640
gtgaaattta aacataccct actcttgcga tttcgcgtgt gccaagcaac caaaaggagg  2700
tggtttttgg ataagctggt cgatgagata ggagtcgggt atgtctccga tcaggggtcg  2760
gcctcgtact ataccttaag tgagataaaa ccgttacata acttcttaac gcaattgcaa  2820
ccgtttctga aactgaagca gaagcaagcg aatctggtcc tgaagatcat cgaacaactg  2880
ccgagtgcga aggagtcccc cgataagttc ctcgaggtct gcacgtgggt cgatcaaata  2940
gcggcgttaa atgatagtag gacgaggaaa acgacgagtg agcgttggtt cctcgacaag  3000
gattcgttga gtgaaaagaa aaagagcagt ccttcgccgg cagcgaagag ggttaagctc  3060
gactagtaag cttatcaacc tctggattac aaaatttgtg aaagattgac tgatattctt  3120
aactatgttg ctccttttac gctgtgtgga tatgctgctt taatgcctct gtatcatgct  3180
attgcttccc gtacggcttt cgttttctct tccttgtata aatcctggtt gctgtctctt  3240
tatgaggagt tgtggcccgt tgtccgtcaa cgtggcgtgg tgtgctctgt gtttgctgac  3300
gcaacccca ctggctgggg cattgccacc acctgtcaac tcctttctgg actttcgct  3360
ttccccctcc cgatcgccac ggcagaactc atcgccgcct gccttgcccg ctgctggaca  3420
ggggctaggt tgctgggcac tgataattcc gtggtgttgt cggggaagct gacgtccttt  3480
ccagggctgc tcgcctgtgt tgccaactgg atcctgcgcg ggacgtcctt ctgctacgtc  3540
ccttcggctc tcaatccagc ggacctccct tcccgaggcc ttctgccggt tctgcggcct  3600
ctcccgcgtc ttcgctttcg cctccgacg agtcggatct ccctttgggc cgcctccccg  3660
cctgggtaga tccagacatg ataagataca ttgatgagtt tggacaaacc acaactagaa  3720
tgcagtgaaa aaaatgcttt atttgtgaaa tttgtgatgc tattgcttta tttgtaacca  3780
ttataagctg caataaacaa gttaacaaca caattgcat tcattttatg tttcaggttc  3840
aggggggagg gtgggaggtt ttttaaagca agtaa                             3875
```

```
SEQ ID NO: 81          moltype = DNA  length = 3879
FEATURE                Location/Qualifiers
source                 1..3879
                       mol_type = other DNA
                       organism = synthetic construct
SEQUENCE: 81
ccactacggg tctaggctgc ccatgtaagg aggcaaggcc tggggacacc cgagatgcct   60
ggttataatt aaccccaaca cctgctgccc cccccccc aacacctgct gcctgagcct  120
gagcggttac cccacccgg tgcctgggtc ttaggtctg tacaccatgg aggagaagct  180
cgctctaaaa ataaccctgt ccctggtgga tccactacgg gtctaggctg cccatgtaag  240
gaggcaaggc ctgggacac ccgagatgcc tggttataat taaccccaac acctgctgcc  300
cccccccc caacacctgc tgcctgagcc tgagcggtta ccccacccg gtgcctgggt  360
cttaggctct gtacaccatg gaggagaagc tcgctctaaa ataaccctg tccctggtgg  420
atccactacg ggtctaggct gcccatgtaa ggaggcaagg cctgggaca cccgagatgc  480
ctggttataa ttaaccccaa cacctgctgc ccccccccc ccaacacctg ctgcctgagc  540
ctgagcggtt accccacccc ggtgcctggg tcttaggctc tgtacaccat ggaggagaag  600
ctcgctctaa aaataaccct gtccctggtg gatcctccct ggggacagcc cctcctggct  660
agtcacaccc tgtaggctcc tctatataac ccaggggcac aggggctgcc cccgggtcac  720
tactgccacc atggcaccga agaagaagcg caaggtgcat atgaatacaa aatataataa  780
agagttctta ctctacttag cagggtttgt agactctgac ggttccatca tggcctttat  840
```

-continued

```
cttgcctgag cagggtctga agttcaagca ccgtctgagg ctccagttcg cggtcgctca    900
gaagacacag cgccgttggt tcctcgacaa gctggtggac gagatcggtg tgggttacgt    960
gtatgacttt ggcagcgtct cctattacag gctgtcccag atcaagcctt tgcataattt   1020
tttaacacaa ctacaacctt ttctaaaact aaaacaaaaa caagcaaatt tagttttaaa   1080
aattattgaa caacttccgt cagcaaaaga atccccggac aaattcttag aagtttgtac   1140
atgggtggat caaattgcag ctctgaatga ttcgaagacg cgtaaaacaa cttctgaaac   1200
cgttcgtgct gtgctagaca gtttaccagg atccgtggga ggtctatcgc catctcaggc   1260
atccagcgcc gcatcctcgg cttcctcaag cccgggttca gggatctccg aagcactcag   1320
agctggagca ggttccggca ccggatacaa caaggaattc ctgctctacc tggcgggctt   1380
cgtcgacggg gacggctcca tctgtgcctg tatcgtgcct cgtcaagatc ggaagttcaa   1440
gcaccagctg cggctctttt tcgaggtcgg tcagaagaca cagcgccgtt ggttcctcga   1500
caagctggtg gacgagatcg gtgtgtgggtta cgtgagggac cttggcagcg cgagcactta   1560
ccgtctgtcc cagatcaagc ctctgcacaa cttcctgacc cagctccagc ccttcctgaa   1620
gctcaagcag aagcaggcca acctcgtgct gaagatcatc gagcagctgc cctccgccaa   1680
ggaatccccg gacaagttcc tggaggtgtg cacctgggtg gaccagatcg ccgctctgaa   1740
cgactccagg acccgcaaga ccacttccga aaccgtccgc gccgttctag acagtctctc   1800
cgagaagaag aagtcgtccc cttcgccggc cgctaagcgc gtgaagctgg acggtagagc   1860
caagagatct ggaagcggcg ccacaaattt ctcactgctg aaacaggccg gcgacgtgga   1920
agagaaccct ggacctgcta gcggaatggc accgaaaaaa aagcgcaaag tacatatgaa   1980
caccaagtac aacaaggaat ttctcttgta tctcgccggc ttcgtcgatg cagatggaag   2040
tatatacgcg tgcataaagc cccaccaaga gctgaagttt aaacatcagt tactgttgta   2100
ctttgaggtg taccaaaaga cccaaagaag atggttcttg gataagctgg tcgatgagat   2160
aggagtcggg tatgtcgcag atcgcgggtc ggtgagtgag tatcggctga gtgagataaa   2220
accgctccac aacttcctca cccagttgca gccgttcttg aagttgaagc agaagcaggc   2280
caacctcgtg ctcaagataa tagagcagtt gcccagcgcc aaggagagtc ccgataagtt   2340
tctggaggtg tgtacctggg tggaccagat agccgcgtta aacgacagca aaaccaggaa   2400
aaccacgagc gaaaccgtca gagcggtctt ggattcgctc cctggcagtg tcggcgcgatt   2460
gagcccaagc caagccagtt cggcagccag tagcgcgagt agctcgccag gaagcggcat   2520
aagtgaggct ttgagagctg gagctggaag tggtaccggt tacaacaagg agttcttact   2580
gtacttagcc gggttcgtgg atggcgatgg gagtatattc gagtccatca tccccagcca   2640
agaggtgaag ttcaagcata ccttactcct gaggttccgc gtgtgccaag caaccaagag   2700
gaggtggttc ctggataaac tggtcgacga gatcggggtc gggtatgtct ccgatcaggg   2760
gtcggcctcg tactatactc tgagtcagat caaaccgtta cataacttct taacgcaatt   2820
gcaaccgttt ctgaaactga agcagaagca agcgaatctg gtcctgaaga tcatcgaaca   2880
actgccgagt gcgaaggagt cccccgataa gttcctcgag gtctgcacgt gggtcgatca   2940
aatagcggcg ttaaacgata gtaggacgag gaaaacgacg agtgagacgg tgcgggcggt   3000
gttggattcg ttgagtgaaa agaaaaagag cagtccttcg ccggcagcga agagggttaa   3060
gctcgactag taagcttatc aacctctgga ttacaaaatt tgtgaaagat tgactgatat   3120
tcttaactat gttgctcctt ttacgctgtg tggatatgct gctttaatgc ctctgtatca   3180
tgctattgct tcccgtacgg cttttcgttt ctcctccttg tataaatcct ggttgctgtc   3240
tctttatgag gagttgtggc ccgttgtccg tcaacgtggc gtggtgtgct ctgtgtttgc   3300
tgacgcaacc cccactggct ggggcattgc caccacctgt caactccttt ctgggacttt   3360
cgctttcccc ctccccgatcg ccacggcaga actcatcgcc gcctgccttg cccgctgctg a  3420
gacaggggct aggttgctgg gcactgataa ttccgtggtg ttgtcgggga agctgacgtc   3480
ctttccaggt ctgctcgcct gtgttgccaa ctggatcctg cgcgggacgt ccttctgcta   3540
cgtcccttcg gctctcaatc cagcggacct cccttcccga ggccttctgc cggttctgcg   3600
gcctctcccg cgtcttcgct ttcggcctcc gacgagtcgg atctcccttt gggccgcctc   3660
cccgcctggg tagatccaga catgataaga tacattgatg agtttggaca aaccacaact   3720
agaatgcagt gaaaaaaatg ctttatttgt gaaatttgtg atgctattgc tttatttgta   3780
accattataa gctgcaataa acaagttaac aacaacaatt gcattcattt tatgtttcag   3840
gttcaggggg aggtgtggga ggttttttaa agcaagtaa            3879
```

```
SEQ ID NO: 82       moltype = DNA  length = 3879
FEATURE             Location/Qualifiers
source              1..3879
                    mol_type = other DNA
                    organism = synthetic construct
SEQUENCE: 82
ccactacggg tctaggctgc ccatgtaagg aggcaaggcc tggggacacc cgagatgcct     60
ggttataatt aaccccaaca cctgctgccc cccccccccc aacacctgct gcctgagcct    120
gagcggttac cccaccccgg tgcctgggtc ttaggctctg tacaccatgg aggagaagct    180
cgctctaaaa ataaccctgt ccctggtgga tccactacgg gtctaggctg cccatgtaag    240
gaggcaaggc ctggggacac ccgagatgcc tggttataat taaccccaac acctgctgcc    300
cccccccccc caacacctgc tgcctgagcc tgagcggtt accccaccccg gtgcctgggt    360
cttaggctct gtacaccatg gaggagaagc tcgctctaaa aataaccctg tccctggtgg    420
atccactacg ggtctaggct gcccatgtaa ggaggcaagg cctggggaca cccgagatgc    480
ctggttataa ttaaccccaa cacctgctgc ccccccccc caacacctg ctgcctgagc    540
ctgagcggtt accccacccc ggtgcctggg tcttaggctc tgtacaccat ggaggagaag    600
ctcgctctaa aaataaccct gtccctggtg gatcctcgac agcc cctcctggct    660
agtcacaccc tgtaggctcc tctatataac ccagggggcac aggggctgcc cccgggtcac    720
tactgccacc atggcaccga gaagaagcg caaggtgcat atgaatacaa aatataataa    780
agagttctta ctctacttag cagggtttgt agactctgac ggttccatca tggcctttat    840
catgcctgat caggcgccta agttcaagca ccgtctgagg ctccagttcg cggtcgctca    900
gaagacacag cgccgttggt tcctcgacaa gctggtggac gagatcggtg tgggttacgt    960
gtatgacttt ggcagcgtct cctattacag gctgtcccag atcaagcctt tgcataattt   1020
tttaacacaa ctacaacctt ttctaaaact aaaacaaaaa caagcaaatt tagttttaaa   1080
aattattgaa caacttccgt cagcaaaaga atccccggac aaattcttag aagtttgtac   1140
atgggtggat caaattgcag ctctgaatga ttcgaagacg cgtaaaacaa cttctgaaac   1200
cgttcgtgct gtgctagaca gtttaccagg atccgtggga ggtctatcgc catctcaggc   1260
```

-continued

```
atccagcgcc gcatcctcgg cttcctcaag cccgggttca gggatctccg aagcactcag   1320
agctggagca ggttccggca ctggatacaa caaggaattc ctgctctacc tggcgggctt   1380
cgtcgacggg gacggctcca tctgtgcctg tatcgtgcct cgtcaagatc ggaagttcaa   1440
gcaccagctg cggctctttt tcgaggtcgg tcagaagaca cagcgccgtt ggttcctcga   1500
caagctggtg gacgagatcg gtgtgggtta cgtgagggac cttggcagcg cgagcactta   1560
ccgtctgtcc cagatcaagc ctctgcacaa cttcctgacc cagctccagc ccttcctgaa   1620
gctcaagcag aagcaggcca acctcgtgct gaagatcatc gagcagctgc cctccgccaa   1680
ggaatccccg gacaagttcc tggaggtgtg cacctgggtg gaccagatcg ccgctctgaa   1740
cgactccagg acccgcaaga ccacttccga aaccgtccgc gccgttctag acagtctctc   1800
cgagaagaag aagtcgtccc cttcgccggc cgctaagcgc gtgaagctgg acggtagagc   1860
caagagatct ggaagcggcg ccacaaattt ctcactgctg aaacaggccg cgcacgtgga   1920
agagaaccct ggacctgcta gcggaatggc accgaaaaaa aagcgcaaag tacatatgaa   1980
caccaagtac aacaaggaat ttctcttgta tctcgccggc ttcgtcgatg cagatggaag   2040
tatatacgcg tgcataaagc cccaccaaga gctgaagttt aaacatcagt tactgttgta   2100
ctttgaggtg taccaaaaga cccaagaag atggttcttg gataagctgg tcgatgagat   2160
aggagtcggg tatgtcgcag atcgcgggtc ggtgagtgag tatcggctga gtgagataaa   2220
accgctccac aacttcctca cccagttgca gccgttcttg aagttgaagc agaagcaggc   2280
caacctcgtg ctcaagataa tagagcagtt gcccagcgcc aaggagagtc ccgataagtt   2340
tctggaggtg tgtacctggg tggaccagat agccgcgtta aacgacagca aaaccaggaa   2400
aaccacgagc gaaaccgtca gagcggtctt ggattcgctc cctggcagtg tcggcggatt   2460
gagcccaagc caagccagtt cggcagccag tagcgcgagt agctcgccag gaagcggcat   2520
aagtgaggct ttgagagctg gagctggaag tggtaccggt tacaacaagg agttcttact   2580
gtacttagcc gggttcgtgg atggcgatgg gagtatattc gcgtccatca tccccagcca   2640
agaggtgaag ttcaagcata ccttactcct gaggttccgc gtgtgccaag caaccaagag   2700
gaggtggttc ctggataaac tggtcgacga gatcggggtc gggtatgtct ccgatcaggg   2760
gtcggcctcg tactatactc tgagtcagat caaaccgtta cataacttct taacgcaatt   2820
gcaaccgttt ctgaaactga agcagaagca agcgaatctg gtcctgaaga tcatcgaaca   2880
actgccgagt gcgaaggagt cccccgataa gttcctcgag gtctgcacgt gggtcgatca   2940
aatagcggcg ttaaacgata gtaggacgag gaaaacgacg agtgagacgg tgcgggcggt   3000
gttggattcg ttgagtgaaa agaaaaagag cagtccttcg ccggcagcga agagggttaa   3060
gctcgactag taagcttatc aacctctgga ttacaaaatt tgtgaaagat tgactgatat   3120
tcttaactat gttgctcctt ttacgctgtg tggatatgct gctttaatgc ctctgtatca   3180
tgctattgct tcccgtacgg ctttcgtttt ctcctccttg tataaatcct ggttgctgtc   3240
tctttatgag gagttgtggc ccgttgtccg tcaacgtggc gtggtgtgct ctgtgtttgc   3300
tgacgcaacc cccactggct ggggcattgc caccacctgt caactccttt ctgggacttt   3360
cgctttcccc ctccccgatcg ccacggcaga actcatcgcc gcctgccttg cccgctgctg   3420
gacaggggct aggttgctgg gcactgataa ttccgtggtg ttgtcgggga agctgacgtc   3480
ctttccaggg ctgctcgcct gtgttgccaa ctggatcctg cgcgggacgt ccttctgcta   3540
cgtcccttcg gctctcaatc cagcggacct cccttcccga ggccttctgc cggttctgcg   3600
gcctctcccg cgtcttcgct ttcggcctcc gacgagtcgg atctcccttt gggccgcctc   3660
cccgcctggg tagatccaga catgataaga tacattgatg agtttggaca aaccacaact   3720
agaatgcagt gaaaaaaatg ctttatttgt gaaatttgtg atgctattgc tttatttgta   3780
accattataa gctgcaataa acaagttaac aacaacaatt gcattcattt tatgtttcag   3840
gttcaggggg aggtgtggga ggttttttaa agcaagtaa                           3879
```

SEQ ID NO: 83          moltype = DNA   length = 3879
FEATURE                Location/Qualifiers
source                 1..3879
                       mol_type = other DNA
                       organism = synthetic construct
SEQUENCE: 83

```
ccactacggg tctaggctgc ccatgtaagg aggcaaggcc tggggacacc cgagatgcct   60
ggttataatt aaccccaaca cctgctgccc ccccccccc aacacctgct gcctgagcct   120
gagcggttac cccaccccgg tgcctgggtc ttaggctctg tacaccatgg aggagaagct   180
cgctctaaaa ataaccctgt ccctggtgga tccactacgg gtctaggctg cccatgtaag   240
gaggcaaggc ctggggacac ccgagatgcc tggttataat taaccccaac acctgctgcc   300
cccccccccc caacacctgc tgcctgagcc tgagcggtta ccccaccccg gtgcctgggt   360
cttaggctct gtacaccatg gaggagaagc tcgctctaaa aataaccctg tccctggtgg   420
atccactacg ggtctaggct gcccatgtaa ggaggcaagg cctgggggaca cccgagatgc   480
ctggttataa ttaaccccaa cacctgctgc cccccccccc caacacctgc ctgctgagc   540
ctgagcggtt accccacccc ggtgcctggg tcttaggctc tgtacaccat ggaggagaag   600
ctcgctctaa aaataaccct gtccctggtg gatcctccct ggggacagcc cctcctggct   660
agtcacaccc tgtaggctcc tctatataac ccaggggcac aggggctgcc cccgggtcac   720
tactgccacc atggcaccga agaagaagcg caaggtgcat atgaatacaa aatataataa   780
agagttctta ctctacttag cagggtttgt agactctgac ggttccatca tggcctttat   840
cttgcctgag cagggtctga agttcaagca ccgtctgagg ctccagttcg cggtcgctca   900
gaagacacag cgccgttggt tcctcgacaa gctggtggac gagatcggtg tgggttacgt   960
gtatgacttt ggcagcgtct cctattacag gctgtcccag atcaagcctt tgcataattt   1020
tttaacacaa ctacaacctt ttctaaaact aaaacaaaaa caagcaaatt tagttttaaa   1080
aattattgaa caacttccgt cagcaaaaga atccccggac aaattcttag aagtttgtac   1140
atgggtggat caaattgcag ctctgaatga ttcgaagacg cgtaaaacaa cttctgaaac   1200
cgttcgtgct gtgctagaca gtttaccagg atccgtggga ggtctatcgc catctcaggc   1260
atccagcgcc gcatcctcgg cttcctcaag cccgggttca gggatctccg aagcactcag   1320
agctggagca ggttccggca ccggatacaa caaggaattc ctgctctacc tggcgggctt   1380
cgtcgacggg gacggctcca tctgtgcctg tatcgtgcct cgtcaagatc ggaagttcaa   1440
gcaccagctg cggctctttt tcgaggtcgg tcagaagaca cagcgccgtt ggttcctcga   1500
caagctggtg gacgagatcg gtgtgggtta cgtgagggac cttggcagcg cgagcactta   1560
ccgtctgtcc cagatcaagc ctctgcacaa cttcctgacc cagctccagc ccttcctgaa   1620
gctcaagcag aagcaggcca acctcgtgct gaagatcatc gagcagctgc cctccgccaa   1680
```

```
ggaatccccg dacaagttcc tggaggtgtg cacctgggtg gaccagatcg ccgctctgaa   1740
cgactccagg acccgcaaga ccacttccga aaccgtccgc gccgttctag acagtctctc   1800
cgagaagaag aagtcgtccc cttcgccggc cgctaagcgc gtgaagctgg acggtagagc   1860
caagagatct ggaagcggcg ccacaaattt ctcactgctg aaacaggccg cgacgtgga    1920
agagaaccct ggacctgcta gcggaatggc accgaaaaaa aagcgcaaag tacatatgaa   1980
caccaagtac aacaaggaat ttctcttgta tctcgccggc ttcgtcgatt ccgatggaag   2040
tatatacgcg tgcataaagc cccaccaaca gctgaagttt aaacatcagt tactgttgta   2100
ctttgaggtg taccaaaaga cccaagaag atggttcttg gataagctgg tcgatgagat   2160
aggagtcggg tatgtcgcag atcgcgggtc ggtgagtgag tatcggctga gtcaaataaa   2220
accgctccac aacttcctca cccagttgca gccgttcttg aagttgaagc agaagcaggc   2280
caacctcgtg ctcaagataa tagagcagtt gcccagcgcc aaggagagtc ccgataagtt   2340
tctgaggtg tgtacctggg tggaccagat agccgcgtta aacgacagca aaaccaggaa   2400
aaccacgagc gaaaccgtca gagcggtctt ggattcgctc cctggcagtg tcggcggatt   2460
gagcccaagc caagccagtt cggcagccag tagcgcgagt agctcgccag gaagcggcat   2520
aagtgaggct ttgagagctg gagctggaag tggtaccggt tacaacaagg agttcttact   2580
gtacttagcc gggttcgtgg atggcgatgg gagtatattc gcgtccatca tccccagcca   2640
agaggtgaag ttcaagcata ccttactcct gaggttccgc gtgtgccaag caaccaagag   2700
gaggtggttc ctggataaac tggtcgacga gatcgggctg gggtatgtct ccgatcgagg   2760
gtcggcctcg tactactctc tgagtgaaat caaaccgtta cataacttct taacgcaatt   2820
gcaaccgttt ctgaaactga agcagaagca agcgaatctg gtcctgaaga tcatcgaaca   2880
actgccgagt gcgaaggagt cccccgataa gttcctcgag gtctgcacgt gggtcgatca   2940
aatagcggcg ttaaacgata gtaggacgag gaaaacgacg agtgagacgg tgcgggcggt   3000
gttggattcg ttgagtgaaa agaaaaaagag cagtccttcg ccggcagcga agagggttaa   3060
gctcgactag taagcttatc aacctctgga ttacaaaatt tgtgaaagat tgactgatat   3120
tcttaactat gttgctcctt ttacgctgtg tggatatgct gctttaatgc ctctgtatca   3180
tgctattgct tcccgtacgg ctttcgtttt ctcctccttg tataaatcct ggttgctgtc   3240
tctttatgag gagttgtggc ccgttgtccg tcaacggtgc gtggtgtgct ctgtgtttgc   3300
tgacgcaacc cccactggct ggggcattgc caccacctgt caactccttt ctgggacttt   3360
cgctttcccc ctccccgatcg ccacggcaga actcatcgcc gcctgccttg cccgctgctg   3420
gacaggggct aggttgctgg gcactgataa ttccgtggga ttgtcggggga agctgacgtc   3480
ctttccaggg ctgctcgcct gtgttgccaa ctggatcctg cgcgggacgt ccttctgcta   3540
cgtcccttcg gctctcaatc cagcggacct cccttcccga ggccttctgc cggttctgcg   3600
gcctctcccg cgtcttcgct ttcggcctcc gacgagtcgg atctcccttt gggccgcctc   3660
cccgcctggg tagatccaga catgataaga tacattgatg agtttggaca aaccacaact   3720
agaatgcagt gaaaaaaatg ctttatttgt gaaatttgtg atgctattgc tttatttgta   3780
accattataa gctgcaataa acaagttaac aacaacaatt gcattcattt tatgtttcag   3840
gttcaggggg aggtgtggga ggttttttaa agcaagtaa                          3879
```

```
SEQ ID NO: 84          moltype = DNA   length = 3879
FEATURE                Location/Qualifiers
source                 1..3879
                       mol_type = other DNA
                       organism = synthetic construct
SEQUENCE: 84
ccactacggg tctaggctgc ccatgtaagg aggcaaggcc tggggacacc cgagatgcct   60
ggttataatt aaccccaaca cctgctgccc cccccccccc aacacctgct gcctgagcct   120
gagcggttac cccaccccgg tgcctgggtc ttaggctctg tacaccatgg aggagaagct   180
cgctctaaaa ataaccctgt ccctggtgga tccactacgg gtctaggctg cccatgtaag   240
gaggcaaggc ctggggacac ccgagatgcc tggttataat taaccccaac acctgctgcc   300
cccccccccc aacacctgc tgcctgagcc tgagcggtta ccccaccccg gtgcctgggt   360
cttaggctct gtacaccatg gaggagaagc tcgctctaaa ataaccctg tccctggtgg   420
atccactacg ggtctaggct gcccatgtaa ggaggcaagg cctggggaca cccgagatgc   480
ctggttataa ttaaccccaa cacctgctgc cccccccccc ccaacacctg ctgcctgagc   540
ctgagcggtt accccaccccc ggtgcctggg tcttaggctc tgtacaccat ggaggagaag   600
ctcgctctaa aataaccct gtccctggtg gatcctcccc ggggacagcc cctcctggct   660
agtcacaccc tgtaggctcc tctatataac ccaggggcac aggggctgcc cccgggtcac   720
tactgccacc atggcaccga agaagaagcg caaggtgcat atgaatacaa aatataataa   780
agagttctta ctctacttag cagggtttgt agactctgac ggttccatca tggcctttat   840
catgcctgat caggcgccta agttcaagca accgtctgagg ctccagttcg cggtcgctca   900
gaagacacag cgccgttggt tcctcgacaa gctggtgagc gagatcggtg tgggttacgt   960
gtatgacttt ggcagcgtct cctattacag gctgtccgag atcaagcctt tgcataattt   1020
tttaacacaa ctacaacctt ttctaaaact aaaacaaaaa caagcaaatt tagttttaaa   1080
aattattgaa caacttccgt cagcaaaaga atccccggac aaattcttag aagtttgtac   1140
atgggtggat caaattgcag ctctgaatga ttcgaaacg cgtaaaacaa cttctgaaac   1200
cgttcgtgct gtgctagaca gtttaccagg atccgtggga ggtctatcgc catctcaggc   1260
atccagcgcc gcatcctcgg cttcctcaag cccgggttca gggatctccg aagcactcag   1320
agctggagca ggttccggca ctggatacaa caaggaattc ctgctctacc tggcgggctt   1380
cgtcgacggg gacggctcca tctgtgcctg tatcgtgcct cgtcaagatc ggaagttcaa   1440
gcaccagctg cggctctttt tcgaggtcgg tcagaagaca cagccgcgtt ggttcctcga   1500
caagctggtg gacgagatcg gtgtgggtta cgtgagggac cttggcagcg cgagcactta   1560
ccgtctgtcc cagatcaagc ctctcgcaca cttcctgacc cagctccagc ccttcctgaa   1620
gctcaagcag aagcaggcca acctcgtgct gaagatcatc gagcagctgc cctccgccaa   1680
ggaatccccg gacaagttcc tggaggtgtg cacctgggtg gaccagatcg ccgctctgaa   1740
cgactccagg acccgcaaga ccacttccga aaccgtccgc gccgttctag acagtctctc   1800
cgagaagaag aagtcgtccc cttcgccggc cgctaagcgc gtgaagctgg acggtagagc   1860
caagagatct ggaagcggcg ccacaaattt ctcactgctg aaacaggccg cgacgtgga    1920
agagaaccct ggacctgcta gcggaatggc accgaaaaaa aagcgcaaag tacatatgaa   1980
caccaagtac aacaaggaat ttctcttgta tctcgccggc ttcgtcgatt ccgatggaag   2040
tatatacgcg tgcataaagc cccaccaaca gctgaagttt aaacatcagt tactgttgta   2100
```

```
ctttgaggtg taccaaaaga cccaaagaag atggttcttg gataagctgg tcgatgagat    2160
aggagtcggg tatgtcgcag atcgcgggtc ggtgagtgag tatcggctga gtcaaataaa    2220
accgctccac aacttcctca cccagttgca gccgttcttg aagttgaagc agaagcaggc    2280
caacctcgtg ctcaagataa tagagcagtt gcccagcgcc aaggagagtc ccgataagtt    2340
tctggaggtg tgtacctggg tggaccagat agccgcgtta aacgacagca aaaccaggaa    2400
aaccacgagc gaaaccgtca gagcggtctt ggattcgctc cctggcagtg tcggcggatt    2460
gagcccaagc caagccagtt cggcagccag tagcgcgagt agctcgccag gaagcggcat    2520
aagtgaggct ttgagagctg gagctggaag tggtaccggt tacaacaagg agttcttact    2580
gtacttagcc gggttcgtgg atggcgatgg gagtatattc gcgtccatca tccccagcca    2640
agaggtgaag ttcaagcata ccttactcct gaggttccgc gtgtgccaag caaccaagag    2700
gaggtggttc ctggataaac tggtcgacga gatcggggtc gggtatgtct ccgatcgagg    2760
gtcggcctcg tactatactc tgagtgaaat caaaccgtta cataacttct taacgcaatt    2820
gcaaccgttt ctgaaactga agcagaagca agcgaatctg gtcctgaaga tcatcgaaca    2880
actgccgagt gcgaaggagt cccccgataa gttcctcgag gtctgcacgt gggtcgatca    2940
aatagcggcg ttaaacgata gtaggacgag gaaaacgacg agtgagacgg tgcgggcggt    3000
gttggattcg ttgagtgaaa agaaaaagag cagtccttcg ccggcagcga agagggttaa    3060
gctcgactag taagcttatc aacctctgga ttacaaaatt tgtgaaagat tgactgatat    3120
tcttaactat gttgctcctt ttacgctgtg tggatatgct gctttaatgc ctctgtatca    3180
tgctattgct tcccgtacgg cttttcgttt ctcctccttg tataaatcct ggttgctgtc    3240
tctttatgag gagttgtggc ccgttgtccg tcaacgttgg cgtggtgtgct ctgtgtttgc    3300
tgacgcaacc cccactggct ggggcattgc caccacctgt caactccttt ctgggacttt    3360
cgctttcccc ctccccgatcg ccacggcaga actcatcgcc gcctgccttg ccccgctgctg    3420
gacaggggct aggttgctgg gcactgataa ttccgtggtg ttgtcgggga agctgacgtc    3480
ctttccaggg ctgctcgcct gtgttgccaa ctggatcctg cgcgggacgt ccttctgcta    3540
cgtcccttcg gctctcaatc cagcggacct cccttcccga ggccttctgc cggttctgcg    3600
gcctctcccg cgtcttcgct ttcggcctcc gacgagtcgg atctcccttt ggccgcctc    3660
cccgcctggg tagatccaga catgataaga tacattgatg agtttggaca aaccacaact    3720
agaatgcagt gaaaaaaatg ctttatttgt gaaatttgtg atgctattgc tttatttgta    3780
accattataa gctgcaataa acaagttaac aacaacaatt gcattcattt tatgtttcag    3840
gttcagggggg aggtgtggga ggttttttaa agcaagtaa                          3879
```

```
SEQ ID NO: 85          moltype = DNA   length = 4009
FEATURE                Location/Qualifiers
source                 1..4009
                       mol_type = other DNA
                       organism = synthetic construct
SEQUENCE: 85
ctgtctgaaa gggaagatat gaaaggaatt tgtcggtaag tttcttatga ttgactcaca    60
tgacgtgctt tgtttaactc agtggaatca cgctcataaa ccaaatatgt gcatgtgatc    120
gcggccgccc taggccacta cgggtctagg ctgcccatgt aaggaggcaa ggcctgggga    180
cacccgagat gcctggttat aattaacccc aacacctgct gccccccccc ccaacacc    240
tgctgcctga gcctgagcgg ttaccccacc ccggtgcctg ggtcttaggc tctgtacacc    300
atggaggaga agctcgctct aaaaataacc ctgtccctgg tggatccact acgggtctag    360
gctgcccatg taaggaggca aggcctgggg acacccgaga tgcctggtta taattaaccc    420
caacacctgc tgccccccccc ccccaacac ctgctgcctg agcctgagcg gttaccccac    480
cccggtgcct gggtcttagg ctctgtacac catggaggag aagctcgctc taaaaataac    540
cctgtccctg gtggatccac tacgggtcta ggctgcccat gtaaggaggc aaggcctggg    600
gacacccgag atgcctggtt ataattaacc ccaacacctg ctgccccccc ccccccaaca    660
cctgctgcct gagcctgagc ggttacccca ccccggtgcc tgggtcttag gctctgtaca    720
ccatggagga gaagctcgct ctaaaaataa ccctgtccct ggtggatcct ccctggggac    780
agcccctcct ggctagtcac accctgtagg ctcctctata taacccaggg gcacaggggac    840
tgcccccggg tcacgccacc atggcaccga agaagaagcg caaggtgcat atgaatacaa    900
aatataataa agagttctta ctctacttag cagggtttgt agactctgac ggttccatca    960
tggccttcat catgcctact caaaccgcaa agttcaagca ccgtctgaag ctccagttcg    1020
cggtcgcaca gaagacacag cgccgttggt tcctcgacaa gctggtggac gagatcggtg    1080
tgggttacgt gtatgacttc ggcagcgtct cctactaccg tctgtccgag atcaagcctt    1140
tgcataattt tttaacacaa ctacaacctt ttctaaaact aaaacaaaaa caagcaaatt    1200
tagttttaaa aattattgaa caacttccgt cagcaaaaga atccccggac aaattcttag    1260
aagtttgtac atgggtggat caaattgcag ctctgaatga ttcgaagacg cgtaaaacaa    1320
cttctgaaac cgttcgtgct gtgctagaca gtttaccagg ctccgtggga ggtctatcgc    1380
catctcaggc atccagcgcc gcatcctcgg cttcctcaag cccgggttca gggatctccg    1440
aagcactcag agctggagca ggttccggca ctggatacaa caaggaattc ctgctctacc    1500
tggcgggctt cgtagacggg gacggctcca tctgtgcctg tatcgtgcct cgtcaagatc    1560
ggaagttcaa gcaccagctg cggctctttt tcgaggtcgg tcagaagaca cagcgccgtt    1620
ggttcctcga caagctggtg gacgagatcg gtgtgggtta cgtcgtgac ctgggctccg    1680
cgagcacgta ccggctgtcc cagatcaagc ctctgcacaa cttcctgacc cagctccagc    1740
ccttcctgaa gctcaagcag aagcaggcca acctcgtgct gaagatcatc gagcagctgc    1800
cctccgccaa ggaatccccg gacaagttcc tggaggtgtg cacctgggtg gaccagatcg    1860
ccgctctgaa cgactccagg acccgccaag ccacttccga aaccgtccgc gccgttctag    1920
acagtctctc cgagaagaag aagtcgtccc cttcgccggc cgctaagcgc gtgaagctgg    1980
acggtagagc caagagatct ggaagcggcg ccacaaattt ctcactgctg aaacaggccg    2040
gcgacgtgga agagaaccct ggacctgcta gcggaatggc accgaaaaaa aagcgcaaag    2100
tacatatgaa caccaagtac aacaaggaat ttctcttgta tctcgccggc ttcgtcgatg    2160
ccgatgggag tatatcgcg tgcataaagc cccaccaaca gttgaaattt aaacatcagt    2220
tactcttgta ctttgaggtg taccaaaaaa cccaaaggag gtggtttttg gataagctgg    2280
tcgatgagat aggagtcggg tatgtcgccg atcgcgggtc ggtgagtgag tatcgtttaa    2340
gtcaaataaa accgctccac aacttcctca cccagttgca gccgttcttg aagttgaagc    2400
agaagcaggc caacctcgtg ctcaagataa tagagcagtt gcccagcgcc aaggagagtc    2460
ccgataagtt tctggaggtg tgtacctggg tggaccagat agccgcgtta aacgacagca    2520
```

-continued

```
aaaccaggaa aaccacgagc gagacggtga gagcggtctt ggattcgctc cctggcagtg  2580
tcggcggatt gagcccaagc caagccagtt cggcagccag tagcgcgagt agctcgccag  2640
gaagcggcat aagtgaggct ttgagagctg gagctggaag tggtaccggt tacaacaagg  2700
agttcttact gtacttagcc gggttcgtgg atggcgatgg gagtatattc gcgtccataa  2760
tccccagcca agaggtgaaa tttaaacata ccttactctt gcgatttcgc gtgtgccaag  2820
caaccaaaag gaggtggttt ttggataagc tggtcgatga gataggagtc gggtatgtct  2880
ccgatcaggg gtcggcctcg tactatacct taagtgagat aaaaccgtta cataacttct  2940
taacgcaatt gcaaccgttt ctgaaactga agcagaagca agcgaatctg gtcctgaaga  3000
tcatcgaaca actgccgagt gcgaaggagt cccccgataa gttcctcgag gtctgcacgt  3060
gggtcgatca aatagcggcg ttaaatgata gtaggacgag gaaaacgacg agtgagacgg  3120
tgagggcggt gttggattcg ttgagtgaaa agaaaaagag cagtccttcg ccggcagcga  3180
agagggttaa gctcgactag taagcttatc aacctctgga ttacaaaatt tgtgaaagat  3240
tgactgatat tcttaactat gttgctcctt ttacgctgtg tggatatgct gctttaatgc  3300
ctctgtatca tgctattgct tcccgtacgg ctttcgtttt ctcctccttg tataaatcct  3360
ggttgctgtc tctttatgag gagttgtggc ccgttgtccg tcaacgtggc gtggtgtgct  3420
ctgtgtttgc tgacgcaacc cccactggct ggggcattgc caccacctgt caactccttt  3480
ctgggacttt cgctttcccc ctccccgatcg ccacggcaga actcatcgcc gcctgccttg  3540
cccgctgctg gacaggggct aggttgctgg gcactgataa ttccgtggtg ttgtcgggga  3600
agctgacgtc ctttccaggg ctgctcgcct gtgttgccaa ctggatcctg cgcgggacgt  3660
ccttctgcta cgtcccttcg gctctcaatc cagcggacct cccttcccga ggccttctgc  3720
cggttctgcg gcctctcccg cgtcttcgct ttcggcctcc gacgagtcgg atctcccttt  3780
gggccgcctc cccgcctggg tagatccaga catgataaga tacattgatg agtttggaca  3840
aaccacaact agaatgcagt gaaaaaaatg ctttatttgt gaaatttgtg atgctattgc  3900
tttatttgta accattataa gctgcaataa acaagttaac aacaacaatt gcattcattt  3960
tatgtttcag gttcaggggg aggtgtggga ggttttttaa agcaagtaa         4009
```

SEQ ID NO: 86          moltype = DNA  length = 4003
FEATURE                Location/Qualifiers
source                 1..4003
                       mol_type = other DNA
                       organism = synthetic construct
SEQUENCE: 86

```
ctgtctgaaa gggaagatat gaaaggaatt tgtcggtaag tttcttatga ttgactcaca  60
tgacgtgctt tgtttaactc agtggaatca cgctcataaa ccaaatatgt gcatgtgatc  120
tcccccacta cgggtctagg ctgcccatgt aaggaggcaa ggcctgggca cacccgagat  180
gcctggttat aattaacccc aacacctgct gcccccccccc ccccaacacc tgctgcctga  240
gcctgagcgg ttaccccacc ccggtgcctg ggtcttaggc tctgtacacc atggaggaga  300
agctcgctct aaaaataacc ctgtccctgg tggatccact acgggtctag gctgcccatg  360
taaggaggca aggcctgggg acacccgaga tgcctggtta taattaaccc caacacctgc  420
tgccccccccc ccccaacacc ctgctgcctg agcctgagcg gttaccccac cccggtgcct  480
gggtcttagg ctctgtacac catggaggag aagctcgctc taaaaataac cctgtccctg  540
gtggatccac tacgggtcta ggctgcccat gtaaggaggc aaggcctggg acacccgag  600
atgcctggtt ataattaacc ccaacacctg ctgcccccccc cccccaacca cctgctgcct  660
gagcctgagc ggttaccccca ccccggtgcc tgggtcttag gctctgtaca ccatggagga  720
gaagctcgct ctaaaaataa ccctgtccct ggtggatcct ccctggggac agcccctcct  780
ggctagtcac accctgtagg ctcctctata taacccaggg gcacagggggc tgcccccggg  840
tcactactgc caccatggca cctaagaaaa agagaaaggt ccatatgaat accaaatca  900
ataaggaatt cctcctctac ttggctgggt ttgtggacag tgatggcagc atcatggcct  960
tcatcctgcc tgagcaggga ctgaagttca gcacaggct gaggctgcag tttgcagtgg  1020
cccagaaaac ccagagaaga tggtttctgg acaagttggt ggatgagatt ggggtggggt  1080
atgtgatga ctttggttca gtgagctact acaggctctc acagatcaag cctctgcata  1140
actttctgac ccagctgcag ccattcctca agctgaagca gaaacaggcc aacttggtcc  1200
tcaagatcat tgaacaactg ccctcagcta aggagtcccc agacaagttc ttggaggtgt  1260
gtacctgggt ggaccagata gcagcactta atgacagcaa gactaggaaa accacctcag  1320
agactgtcag ggctgtcctg gactccctcc ctggttcagt tggagggggctg tccctagcc  1380
aagccagctc tgcagcctcc tcagcctcca gcagcccagg ctcaggcatc tcagaagccc  1440
tcagagctgg ggcaggatca ggcactggct acaataagga gttcctgctg taccttgctg  1500
gctttgttga tggagatgga agcatctgtg cctgcattgt gcccagacag gacagaaagt  1560
tcaaacacca actcagactg ttctttgaag tggggcccaaa gacccagagg agatggttct  1620
tggacaaact tgtggatgag attggagtgg gctatgtcag ggatcttgag tcagccagca  1680
catacaggct gtcccagatc aaaccccctg ataacttcct gacccaactg cagccattcc  1740
tgaagctcaa gcagaagcag gccaacttgg tgctgaagat tattgaacag cttccttctg  1800
ccaaggaatc ccctgacaag ttcctggaag tgtgcacttg ggttgaccag attgcagccc  1860
tcaatgacag caggaccagg aagaccactt ctgagactgt tagagctgtg tcggtagagc  1920
tgtcagaaaa gaagagtcc tccccttccc ctgctgccaa gagggtgaag ctggatggta  1980
gagccaagag atctggaagt ggagccacaa atttctcact gctgaaacag gctggggatg  2040
tggaagagaa ccctggacct gctagcggaa tggcccccaa gaagaagagg aaagtgcaca  2100
tgaacaccaa gtataacaag gagttccttc tgtatctggc tggctttgtg gattctgatg  2160
gctccatcta tgcctgcatc aagcccatc agcaactgaa gttcaaacac cagctcctcc  2220
tgtactttga ggtgtaccaa aagacccaga ggagatggtt cttggacaaa ttggtagatg  2280
aaaattggag gggctatgtg gctgacaggg gctcagtgtc agagtacagg ctgtcccaga  2340
ttaagcccct gcacaacttc ctgacccaac tgcaaccttt cctgaaactc aagcagaagc  2400
aggccaacct ggtcctgaag attattgaac agctgccatc agccaggaa tcccctgaca  2460
agttcctgga agttctgtact tgggtgatc agattgccgc tccaagacta  2520
gaaagaccac ctctgagaca gtcagagctg tgctggattc cctgcctgga tcagtgggag  2580
gactgagccc aagccaggcc tcctcagctg ccagctcagc ctcctcctcc cctggatcag  2640
gaatctcaga ggccctgaga gcaggggctg gctctggtac tgggtacaac aaggaattcc  2700
tgctctacct ggctggtttt gtggatgggg atggttccat ctttgcctcc atcatcccta  2760
gccaggaagt caagttcaag catacccctgc tcctgagatt cagagtgtgc caggccacca  2820
```

-continued

```
agagaagatg gttcctggac aagttggtgg atgaaatagg agtgggatat gtgtcagaca    2880
gggggagtgc cagctactac accctgtcag agatcaagcc ccttcacaac tttctgactc    2940
aactccagcc cttcctgaaa ttgaagcaaa agcaggctaa cctggtgctc aagatcattg    3000
agcagctccc ctctgccaaa gagtcccctg ataagttcct tgaagtctgc acctgggtgg    3060
accagattgc tgccctgaat gactccagga ccagaaagac tacctcagaa actgtcaggg    3120
cagtgctgga ctccctgtct gagaagaaaa agtccagccc aagccctgca gccaagagag    3180
tgaagttaga ctagtaagct tatcaacctc tggattacaa aatttgtgaa agattgactg    3240
atattcttaa ctatgttgct cctttttacgc tgtgtgtggata tgctgctttta atgcctctgt    3300
atcatgctat tgcttcccgt acggctttcg ttttctcctc cttgtataaa tcctggttgc    3360
tgtctcttta tgaggagttg tggcccgttg tccgtcaacg tggcgtggtg tgctctgtgt    3420
ttgctgacgc aaccccact ggctggggca ttgccaccac ctgtcaactc ctttctggga    3480
ctttcgcttt ccccctcccg atcgccacg cagaactcat cgccgcctgc cttgcccgct    3540
gctggacagg ggctaggttg ctgggcactg ataattccgt ggtgttgtcg gggaagctga    3600
cgtcctttcc agggctgctc gcctgtgttg ccaactggat cctgcgcggg acgtccttct    3660
gctacgtccc ttcggctctc aatccagcgg acctcccttc ccgaggccctt ctgccggttc    3720
tgcggcctct cccgcgtctt cgctttcggc ctccgacgag tcggatcctcc ctttgggccg    3780
cctccccgcc tgggtagatc cagacatgat aagatacatt gatgagtttg gacaaaccac    3840
aactagaatg cagtgaaaaa aatgctttat ttgtgaaatt tgtgatgcta ttgctttatt    3900
tgtaaccatt ataagctgca ataaacaagt taacaacaac aattgcattc attttatgtt    3960
tcaggttcag ggggaggtgt gggaggtttt ttaaagcaag taa                     4003
```

SEQ ID NO: 87         moltype = DNA   length = 4003
FEATURE               Location/Qualifiers
source                1..4003
                      mol_type = other DNA
                      organism = synthetic construct
SEQUENCE: 87

```
ctgtctgaaa gggaagatat gaaaggaatt tgtcggtaag tttcttatga ttgactcaca    60
tgacgtgctt tgtttaactc agtggaatca cgctcataaa ccaaatatgt gcatgtgatc    120
tccccacta cgggtctagg ctgcccatgt aaggaggcaa ggcctgggga cacccgagat    180
gcctggttat aattaacccc aacacctgct gccccccccc ccccaacacc tgctgcctga    240
gcctgagcgg ttaccccacc ccggtgcctg ggtcttaggc tctgtacacc atggaggaga    300
agctcgctct aaaaataacc ctgtccctgg tggatccact acgggtctag gctgcccatg    360
taaggaggca aggcctgggg acacccgaga tgcctggtta taattaaccc caacacctgc    420
tgcccccccc ccccaacac ctgctgcctg agcctgagcg gttaccccac cccggtgcct    480
gggtcttagg ctctgtacac catggaggag aagctcgctc taaaaataac cctgtccctg    540
gtggatccac tacgggtcta ggctgcccat gtaaggaggc aaggcctggg gacacccgag    600
atgcctggtt ataattaacc ccaacacctg ctgcccccccc ccccaaca cctgctgcct    660
gagcctgagc ggttaccccca cccggtgcc tgggtcttag gctctgtaca ccatggagga    720
gaagctcgct ctaaaaataa ccctgtccct ggtggatcct ccctggggac agcccctcct    780
ggctagtcac accctgtagg ctcctctata taacccaggg gcacaggggc tgcccccggg    840
tcactactgc caccatggca ccgaagaaga agcgcaaggt gcatatgaat acaaaatata    900
ataaagagtt cttactctac ttagcagggt ttgtagactc tgacggttcc atcatggcct    960
ttatcttgcc tgagcagggt ctgaagttca agcaccgtcg gaggctccag ttcgcggtcg    1020
ctcagaagac acagcgccgt tggttcctcg acaagctggt ggacgagatc ggtgtgggtt    1080
acgtgtatga ctttggcagc gtctcctatt acaggctgtc ccagatcaag cctttgcata    1140
attttttaac acaactacaa ccttttctaa aactaaaaca aaaacaagca aatttagttt    1200
taaaaattat tgaacaactt ccgtcagcaa aagaatcccc ggacaaattc ttagaagttt    1260
gtacatgggt ggatcaaatt gcagctctga atgattcgaa gacgcgtaaa acaacttctg    1320
aaaccgttcg tgctgtgcta gacagtttac caggatccgt gggaggtcta tcgccatctc    1380
aggcatccag cgccgcatcc tcggcttcct caagcccggg ttcagggatc tccgaagcac    1440
tcagagctgg agcaggttcc ggcaccggat acaacaagga attcctgctc tacctgtgcg    1500
gcttcgtcga cggggacggc tccatctgtg cctgtatcgt gcctcgtcaa gatcggaagt    1560
tcaagcacca gctgcggctc tttttcgagg tcggtcagaa gacacagcgc cgttggttcc    1620
tcgacaagct ggtggacgag atcggtgtgg gttacgtgag ggaccttggc agcgcgagca    1680
cttaccgtct gtcccagatc aagcctctgc acaacttcct gacccagctc cagcccttcc    1740
tgaagctcaa gcagaagcag gccaacctcg tgctgaagat catcgagcag ctgccctccg    1800
ccaaggaatc cccggacaag ttcctggagg tgtgcacctg ggtggaccag atcgccgctc    1860
tgaacgactc caggaccgc aagaccactt ccgaaaccgt ccgcgccgtt ctagacagtc    1920
tctccgagaa gaagaagtcg tcccttcgc cggccgctaa gcgcgtgaag ctggacggta    1980
gagccaagag atctggaagc ggcgccacaa atttctcact gctgaaacag gccggcgacg    2040
tggaagagaa ccctggacct gctagcggaa tggcaccgaa aaaaaagcgc aaagtacata    2100
tgaacaccaa gtacaacaag gaatttctct tgtatctcgc cggcttcgtc gattccgatg    2160
gaagtatata cgcgtgcata aagcccccacc aacagctgaa cattaaacat cagttactgt    2220
tgtactttga ggtgtaccaa aagacccaaa gaagatggtt cttggataag ctggtcgatg    2280
agataggagt cgggtatgtc gcagatcgcg ggtcggtgag tgagtatcgg ctgagtcaaa    2340
taaaaccgct ccacaacttc ctcacccagt tgcagccgtt cttgaagttg aagcagaagc    2400
aggccaacct cgtgctcaag ataatagagc agttgcccag cgccaaggag agtcccgata    2460
agtttctgga ggtgtgtacc tgggtggacc agatagccgc gttaaacgac agcaaaacca    2520
ggaaaaccac gagcgaaacc gtcagagcgg tcttggattc gctccctggc agtgtcggcg    2580
gattgagccc aagccaagcc agttcggcag ccagtagcgc gagtagctcg ccaggaagcg    2640
gcataagtga ggctttgaga gctggagctg gaagtggtac cggttacaac aaggagttct    2700
tactgtactt agccggggttc gtggatggcg atgggagtat attcgcgtcc atcatcccca    2760
gccaagaggt gaagttcaag cataccttac tcctgaggtt ccggcttgtgc caagcaacca    2820
agaggaggtg gttcctggat aaaactggtc acgagatcgg ggtcgggtat gtctccgatc    2880
gagggtcggc ctcgtactat actctgagtg aaatcaaacc gttacataac ttcttaacgc    2940
aattgcaacc gtttctgaaa ctgaagcaga agcaagcgaa tctggtcctg aagatcatcg    3000
aacaactgcc gagtgcgaag gagtcccccg ataagttcct cgaggtctgc acgtgggtcg    3060
atcaaatagc ggcgttaaat gatagtagga cgaggaaaac gacgagtgag acggtgaggg    3120
```

```
cggtgttgga ttcgttgagt gaaaagaaaa agagcagtcc ttcgccggca gcgaagaggg   3180
ttaagctcga ctagtaagct tatcaacctc tggattacaa aatttgtgaa agattgactg   3240
atattcttaa ctatgttgct ccttttacgc tgtgtggata tgctgcttta atgcctctgt   3300
atcatgctat tgcttcccgt acggctttcg ttttctcctc cttgtataaa tcctggttgc   3360
tgtctcttta tgaggagttg tggcccgttg tccgtcaacg tggcgtggtg tgctctgtgt   3420
ttgctgacgc aacccccact ggctggggca ttgccaccac ctgtcaactc ctttctggga   3480
ctttcgcttt cccctcccg atcgccacgg cagaactcat cgccgcctgc cttgcccgct   3540
gctggacagg ggctaggttg ctgggcactg ataattccgt ggtgttgtcg gggaagctga   3600
cgtcctttcc agggctgctc gcctgtgttg ccaactggat cctgcgcggg acgtccttct   3660
gctacgtccc ttcggctctc aatccagcgg acctcccttc ccgaggcctt ctgccggttc   3720
tgcggcctct cccgcgtctt cgctttcggc ctccgacgag tcggatcctcc ctttgggccg   3780
cctccccgcc tgggtagatc cagacatgat aagatacatt gatgagtttg gacaaaccac   3840
aactagaatg cagtgaaaaa aatgctttat ttgtgaaatt tgtgatgcta ttgctttatt   3900
tgtaaccatt ataagctgca ataaacaagt taacaacaac aattgcattc attttatgtt   3960
tcaggttcag ggggaggtgt gggaggtttt ttaaagcaag taa                      4003
```

```
SEQ ID NO: 88          moltype = DNA   length = 24
FEATURE                Location/Qualifiers
source                 1..24
                       mol_type = other DNA
                       organism = synthetic construct
SEQUENCE: 88
gggtgggttg ctttacctct ctag                                            24

SEQ ID NO: 89          moltype = DNA   length = 26
FEATURE                Location/Qualifiers
source                 1..26
                       mol_type = other DNA
                       organism = synthetic construct
SEQUENCE: 89
tcacatcatg agatttagtc acttcc                                          26

SEQ ID NO: 90          moltype = DNA   length = 24
FEATURE                Location/Qualifiers
source                 1..24
                       mol_type = other DNA
                       organism = synthetic construct
SEQUENCE: 90
ttgctacttc acagtaacca catg                                            24

SEQ ID NO: 91          moltype = DNA   length = 20
FEATURE                Location/Qualifiers
source                 1..20
                       mol_type = other DNA
                       organism = synthetic construct
SEQUENCE: 91
tatgatcgcc tgttcctcca                                                 20

SEQ ID NO: 92          moltype = DNA   length = 20
FEATURE                Location/Qualifiers
source                 1..20
                       mol_type = other DNA
                       organism = synthetic construct
SEQUENCE: 92
taagacccag cttcacggag                                                 20

SEQ ID NO: 93          moltype = DNA   length = 27
FEATURE                Location/Qualifiers
source                 1..27
                       mol_type = other DNA
                       organism = synthetic construct
SEQUENCE: 93
aggacaaaag aggacggtct gccctgg                                         27

SEQ ID NO: 94          moltype = DNA   length = 20
FEATURE                Location/Qualifiers
source                 1..20
                       mol_type = other DNA
                       organism = synthetic construct
SEQUENCE: 94
ctccatcact aggggttcct                                                 20

SEQ ID NO: 95          moltype = DNA   length = 20
FEATURE                Location/Qualifiers
source                 1..20
                       mol_type = other DNA
                       organism = synthetic construct
SEQUENCE: 95
aggaacccct agtgatggag                                                 20
```

```
SEQ ID NO: 96          moltype = DNA  length = 1062
FEATURE                Location/Qualifiers
source                 1..1062
                       mol_type = other DNA
                       organism = synthetic construct
SEQUENCE: 96
atgaatacaa aatataataa agagttctta ctctacttag cagggtttgt agacgctgac   60
ggttccatct atgcctgtat caagcctcat caacagctta agttcaagca ccagctgttg  120
ctctatttcg aggtctatca gaagacacag cgccgttggt tcctcgacaa gctggtggac  180
gagatcggtg tgggttacgt ggctgaccgt ggcagcgtct ccgagtaccg tctgtcccag  240
atcaagcctt tgcataattt tttaacacaa ctacaacctt ttctaaaact aaaacaaaaa  300
caagcaaatt tagtttttaaa aattattgaa caacttccgt cagcaaaaga atccccggac  360
aaattcttag aagtttgtac atgggtggat caaattgcag ctctgaatga ttcgaagacg  420
cgtaaaacaa cttctgaaac cgttcgtgct gtgctagaca gtttaccagg atccgtggga  480
ggtctatcgc catctcaggc atccagcgcc gcatcctcgg cttcctcaag cccgggttca  540
gggatctccg aagcactcag agctggagca ggttccggca ctggatacaa caaggaattc  600
ctgctctacc tggcgggctt cgtcgacggg gacggctcca tctttgcctc tatcattccg  660
tcgcaggagg ttaagttcaa gcacactctg ctgctccgtt tccgggtctg ccaggcgaca  720
aagcgccgtt ggttcctcga caagctggtg gacgagattg gtgtgggtta cgtgtctgac  780
cagggcagcg cgagctacta caccctgtcc gagatcaagc ctctgcacaa cttcctgacc  840
cagctccagc ccttcctgaa gctcaagcag aagcaggcca acctcgtgct gaagatcatc  900
gagcagctgc cctccgccaa ggaatccccg gacaagttcc tggaggtgtg cacctgggtg  960
gaccagatcg ccgctctgaa cgactccagg acccgcaaga ccacttccga aaccgtccgc 1020
gccgttctag acagtctctc cgagaagaag aagtcgtccc cc                    1062

SEQ ID NO: 97          moltype = DNA  length = 1062
FEATURE                Location/Qualifiers
source                 1..1062
                       mol_type = other DNA
                       organism = synthetic construct
SEQUENCE: 97
atgaatacaa aatataataa agagttctta ctctacttag cagggtttgt agactctgac   60
ggttccatct atgcctgtat caagcctcat caacagctta agttcaagca ccagctgttg  120
ctctatttcg aggtctatca gaagacacag cgccgttggt tcctcgacaa gctggtggac  180
gagatcggtg tgggttacgt ggctgaccgt ggcagcgtct ccgagtaccg tctgtcccag  240
atcaagcctt tgcataattt tttaacacaa ctacaacctt ttctaaaact aaaacaaaaa  300
caagcaaatt tagtttttaaa aattattgaa caacttccgt cagcaaaaga atccccggac  360
aaattcttag aagtttgtac atgggtggat caaattgcag ctctgaatga ttcgaagacg  420
cgtaaaacaa cttctgaaac cgttcgtgct gtgctagaca gtttaccagg atccgtggga  480
ggtctatcgc catctcaggc atccagcgcc gcatcctcgg cttcctcaag cccgggttca  540
gggatctccg aagcactcag agctggagca ggttccggca ctggatacaa caaggaattc  600
ctgctctacc tggcgggctt cgtcgacggg gacggctcca tctttgcctc tatcattccg  660
tcgcaggagg ttaagttcaa gcacactctg ctgctccgtt tccgggtctg ccaggcgaca  720
aagcgccgtt ggttcctcga caagctggtg gacgagattg gtgtgggtta cgtgtctgac  780
cgtggcagcg cgagctatta caccctgtcc gagatcaagc ctctgcacaa cttcctgacc  840
cagctccagc ccttcctgaa gctcaagcag aagcaggcca acctcgtgct gaagatcatc  900
gagcagctgc cctccgccaa ggaatccccg gacaagttcc tggaggtgtg cacctgggtg  960
gaccagatcg ccgctctgaa cgactccagg acccgcaaga ccacttccga aaccgtccgc 1020
gccgttctag acagtctctc cgagaagaag aagtcgtccc cc                    1062

SEQ ID NO: 98          moltype = DNA  length = 1062
FEATURE                Location/Qualifiers
source                 1..1062
                       mol_type = other DNA
                       organism = synthetic construct
SEQUENCE: 98
atgaatacaa aatataataa agagttctta ctctacttag cagggtttgt agacgctgac   60
ggttccatct atgcctgtat caagagctta agttcaagca ccagctgttg              120
ctctatttcg aggtctatca gaagacacag cgccgttggt tcctcgacaa gctggtggac  180
gagatcggtg tgggttacgt ggctgaccgt ggcagcgtct ccgagtaccg tctgtccgag  240
atcaagcctt tgcataattt tttaacacaa ctacaacctt ttctaaaact aaaacaaaaa  300
caagcaaatt tagtttttaaa aattattgaa caacttccgt cagcaaaaga atccccggac  360
aaattcttag aagtttgtac atgggtggat caaattgcag ctctgaatga ttcgaagacg  420
cgtaaaacaa cttctgaaac cgttcgtgct gtgctagaca gtttaccagg atccgtggga  480
ggtctatcgc catctcaggc atccagcgcc gcatcctcgg cttcctcaag cccgggttca  540
gggatctccg aagcactcag agctggagca ggttccggca ctggatacaa caaggaattc  600
ctgctctacc tggcgggctt cgtcgacggg gacggctcca tctttgcctc tatcattccg  660
tcgcaggagg ttaagttcaa gcacactctg ctgctccgtt tccgggtctg ccaggcgaca  720
aagcgccgtt ggttcctcga caagctggtg gacgagattg gtgtgggtta cgtgtctgac  780
cagggcagcg cgagctacta caccctgtcc cagatcaagc ctctgcacaa cttcctgacc  840
cagctccagc ccttcctgaa gctcaagcag aagcaggcca acctcgtgct gaagatcatc  900
gagcagctgc cctccgccaa ggaatccccg gacaagttcc tggaggtgtg cacctgggtg  960
gaccagatcg ccgctctgaa cgactccagg acccgcaaga ccacttccga aaccgtccgc 1020
gccgttctag acagtctctc cgagaagaag aagtcgtccc cc                    1062

SEQ ID NO: 99          moltype = DNA  length = 1062
FEATURE                Location/Qualifiers
source                 1..1062
```

-continued

```
                         mol_type = other DNA
                         organism = synthetic construct
SEQUENCE: 99
atgaatacaa aatataataa agagttctta ctctacttag cagggtttgt agactctgac   60
ggttccatca tggcctttat cttgcctgag cagggtctga agttcaagca ccgtctgagg  120
ctccagttcg cggtcgctca gaagacacag cgccgttggt tcctcgacaa gctggtggac  180
gagatcggtg tgggttacgt gtatgacttt ggcagcgtct cctattacag gctgtcccag  240
atcaagcctt tgcataattt tttaacacaa ctacaacctt ttctaaaact aaaacaaaaa  300
caagcaaatt tagtttttaaa aattattgaa caacttccgt cagcaaaaga atccccggac  360
aaattcttag aagtttgtac atgggtggat caaattgcag ctctgaatga ttcgaagacg  420
cgtaaaacaa cttctgaaac cgttcgtgct gtgctagaca gtttaccagg atccgtggga  480
ggtctatcgc catctcaggc atccagcgcc gcatcctcgg cttcctcaag cccgggttca  540
gggatctccg aagcactcag agctggagca ggttccggca ccggatacaa caaggaattc  600
ctgctctacc tggcgggctt cgtcgacggg gacggctcca tctgtgcctg tatcgtgcct  660
cgtcaagatc ggaagttcaa gcaccagctg cggctctttt tcgaggtcgg tcagaagaca  720
cagcgccgtt ggttcctcga caagctggtg gacgagatcg gtgtgggtta cgtgagggac  780
cttggcagcg cgagcactta ccgtctgtcc cagatcaagc ctctgcacaa cttcctgacc  840
cagctccagc ccttcctgaa gctcaagcag aagcaggcca acctcgtgct gaagatcatc  900
gagcagctgc cctccgccaa ggaatccccg gacaagttcc tggaggtgtg cacctgggtg  960
gaccagatcg ccgctctgaa cgactccagg acccgcaaga ccacttccga aaccgtccgc 1020
gccgttctag acagtctctc cgagaagaag aagtcgtccc ct                    1062

SEQ ID NO: 100        moltype = DNA  length = 1062
FEATURE               Location/Qualifiers
source                1..1062
                      mol_type = other DNA
                      organism = synthetic construct
SEQUENCE: 100
atgaacacca agtacaacaa ggaatttctc ttgtatctcg ccggcttcgt cgattccgat   60
ggaagtatat acgcgtgcat aaagccccac caacagctga agtttaaaca tcagttactg  120
ttgtactttg aggtgtacca aaagacccaa agaagatggt tcttggataa gctggtcgat  180
gagataggag tcgggtatgt cgcagatcgc gggtcggtga gtgagtatcg gctgagtcaa  240
ataaaaccgc tccacaactt cctcacccag ttgcagccgt tcttgaagtt gaagcagaag  300
caggccaacc tcgtgctcaa gataatagag cagttgccca gcgcaaagga gagtcccgat  360
aagtttctgg aggtgtgtac ctgggtggac cagatagccg cgttaaacga cagcaaaacc  420
aggaaaacca cgagcgaaac cgtcagagcg gtcttggatt cgctccctgg cagtgtcggc  480
ggattgagcc caagccaagc cagttcggca gccagtagcg cgagtagctc gccaggaagc  540
ggcataagtg aggctttgag agctggagct ggaagtggta ccggttacaa caaggagttc  600
ttactgtact tagccgggtt cgtggatggc gatgggagta tattcgcgtc catcatcccc  660
agccaagagg tgaagttcaa gcatacctta ctcctgaggt tccgcgtgtg ccaagcaacc  720
aagaggaggt ggttcctgga taaactggtc gacgagatcg gggtcgggta tgtctccgat  780
cgagggtcgg cctcgtacta tactctgagt gaaatcaaac cgttacataa cttcttaacg  840
caattgcaac cgtttctgaa actgaagcag aagcaagcga atctggtcct gaagatcatc  900
gaacaactgc cgagtgcgaa ggagtccccc gataagttcc tcgaggtctg cacgtgggtc  960
gatcaaatag cggcgttaaa tgatagtagg acgaggaaaa cgacgagtga gacggtgagg 1020
gcggtgttgg attcgttgag tgaaaagaaa aagagcagtc ct                    1062

SEQ ID NO: 101        moltype = DNA  length = 1062
FEATURE               Location/Qualifiers
source                1..1062
                      mol_type = other DNA
                      organism = synthetic construct
SEQUENCE: 101
atgaatacca aatacaataa ggaattcctc ctctacttgg ctgggtttgt ggacagtgat   60
ggcagcatca tggccttcat cctgcctgag cagggactga agttcaagca caggctgagg  120
ctgcagtttg cagtggccca gaaaacccag agaagatggt ttctggacaa gttggtggat  180
gagattgggg tggggtatgt gtatgacttt ggttcagtga gctactacag gctctcacag  240
atcaagcctc tgcataactt tctgacccag ctgcagccat tcctcaagct gaagcagaaa  300
caggccaact tggtcctcaa gatcattgaa caactgcct cagctaagga gtcccagac   360
aagtttcttg gaggtgtgtac ctgggtggac cagatagcag cacttaatga cagcaagact  420
aggaaaacca cctcagagac tgtcagggct gtcctggact ccctccctgg ttcagttgga  480
gggctgtccc ctagccaagc cagctctgca gcctcctcag cctccagcag cccaggctca  540
ggcatctcag aagccctcag agctggggca ggatcaggca ctggctacaa taaggagttc  600
ctgctgtacc ttgctggctt tgttgatgga gatggaagca tctgtgcctg cattgtgcc   660
agacaggaca gaaagttcaa acaccaactc agactgttct ttgaagtggg ccaaaagacc  720
cagaggagat ggttcttgga caacttgtgt gatgagattg gagtgggcta tgtcagggat  780
cttggttcag ccagcacata caggctgtcc cagatcaaac ccctgcataa cttcctgacc  840
caactgcagc cattcctgaa gctcaagcag aagcaggcca acttggtgct gaagattatt  900
gaacagcttc cttctgccaa ggaatccct gacaagttcc tggaagtgtg cacttgggtt  960
gaccagattg cagccctcaa tgacagcagg accaggaaga ccacttctga gactgttaga 1020
gctgtgctgg atagcctgtc agaaaagaag aagtcctccc ct                    1062

SEQ ID NO: 102        moltype = DNA  length = 1062
FEATURE               Location/Qualifiers
source                1..1062
                      mol_type = other DNA
                      organism = synthetic construct
SEQUENCE: 102
atgaacacca agtataacaa ggagttcctt ctgtatctgg ctggctttgt ggattctgat   60
```

-continued

___

```
ggctccatct atgcctgcat caagccccat cagcaactga agttcaaaca ccagctcctc    120
ctgtactttg aggtgtacca aaagacccag aggagatggt tcttggacaa attggtagat    180
gaaattggag tgggctatgt ggctgacagg ggctcagtgt cagagtacag gctgtcccag    240
attaagcccc tgcacaactt cctgacccaa ctgcaacctt tcctgaaact caagcagaag    300
caggccaacc tggtcctgaa gattattgaa cagctgccat cagccaagga atcccctgac    360
aagttcctgg aagtctgtac ttgggtggat cagattgcag ccctcaatga ctccaagact    420
agaaagacca cctctgagac agtcagagct gtgctggatt ccctgcctgg atcagtggga    480
ggactgagcc caagccaggc ctcctcagct gccagctcag cctcctcctc ccctggatca    540
ggaatctcag aggccctgag agcaggggct ggctctggta ctgggtacaa caaggaattc    600
ctgctctacc tggctggttt tgtggatggg gatggttcca tctttgcctc catcatccct    660
agccaggaag tcaagttcaa gcataccctg ctcctgagat tcagagtgtg ccaggccacc    720
aagagaagat ggttcctgga caagttggtg gatgaaatag gagtgggata tgtgtcagac    780
aggggggagtg ccagctacta caccctgtca gagatcaagc cccttcacaa ctttctgact    840
caactccagc ccttcctgaa attgaagcaa aagcaggcta acctggtgct caagatcatt    900
gagcagctcc cctctgccaa agagtcccct gataagttcc ttgaagtctg cacctggggt    960
gaccagattg ctgccctgaa tgactccagg accagaaaga ctacctcaga aactgtcagg   1020
gcagtgctgg actccctgtc tgagaagaaa aagtccagcc ca                       1062
```

```
SEQ ID NO: 103             moltype = AA   length = 27
FEATURE                    Location/Qualifiers
source                     1..27
                           mol_type = protein
                           organism = synthetic construct
SEQUENCE: 103
RAKRSGSGAT NFSLLKQAGD VEENPGP                                          27

SEQ ID NO: 104             moltype = DNA   length = 81
FEATURE                    Location/Qualifiers
source                     1..81
                           mol_type = other DNA
                           organism = synthetic construct
SEQUENCE: 104
agagccaaga gatctggaag cggcgccaca aatttctcac tgctgaaaca ggccggcgac    60
gtggaagaga accctggacc t                                               81

SEQ ID NO: 105             moltype = DNA   length = 81
FEATURE                    Location/Qualifiers
source                     1..81
                           mol_type = other DNA
                           organism = synthetic construct
SEQUENCE: 105
agagccaaga gatctggaag tggagccaca aatttctcac tgctgaaaca ggctggggat    60
gtggaagaga accctggacc t                                               81

SEQ ID NO: 106             moltype = DNA   length = 30
FEATURE                    Location/Qualifiers
source                     1..30
                           mol_type = other DNA
                           organism = synthetic construct
SEQUENCE: 106
atggcaccga agaagaagcg caaggtgcat                                       30

SEQ ID NO: 107             moltype = DNA   length = 30
FEATURE                    Location/Qualifiers
source                     1..30
                           mol_type = other DNA
                           organism = synthetic construct
SEQUENCE: 107
atggcaccta agaaaaagag aaaggtccat                                       30

SEQ ID NO: 108             moltype = DNA   length = 27
FEATURE                    Location/Qualifiers
source                     1..27
                           mol_type = other DNA
                           organism = synthetic construct
SEQUENCE: 108
ccggccgcta agcgcgtgaa gctggac                                          27

SEQ ID NO: 109             moltype = DNA   length = 27
FEATURE                    Location/Qualifiers
source                     1..27
                           mol_type = other DNA
                           organism = synthetic construct
SEQUENCE: 109
cctgctgcca agagggtgaa gctggat                                          27

SEQ ID NO: 110             moltype = DNA   length = 30
FEATURE                    Location/Qualifiers
source                     1..30
```

-continued

```
                        mol_type = other DNA
                        organism = synthetic construct
SEQUENCE: 110
atggcaccga aaaaaaagcg caaagtacat                              30

SEQ ID NO: 111         moltype = DNA  length = 30
FEATURE                Location/Qualifiers
source                 1..30
                       mol_type = other DNA
                       organism = synthetic construct
SEQUENCE: 111
atggccccca agaagaagag gaaagtgcac                              30

SEQ ID NO: 112         moltype = DNA  length = 27
FEATURE                Location/Qualifiers
source                 1..27
                       mol_type = other DNA
                       organism = synthetic construct
SEQUENCE: 112
ccggcagcga agagggttaa gctcgac                                 27

SEQ ID NO: 113         moltype = DNA  length = 27
FEATURE                Location/Qualifiers
source                 1..27
                       mol_type = other DNA
                       organism = synthetic construct
SEQUENCE: 113
cctgcagcca agagagtgaa gttagac                                 27

SEQ ID NO: 114         moltype = DNA  length = 207
FEATURE                Location/Qualifiers
source                 1..207
                       mol_type = other DNA
                       organism = synthetic construct
SEQUENCE: 114
gatccagaca tgataagata cattgatgag tttggacaaa ccacaactag aatgcagtga   60
aaaaaatgct ttatttgtga aatttgtgat gctattgctt tatttgtaac cattataagc  120
tgcaataaac aagttaacaa caacaattgc attcattta tgtttcaggt tcagggggag   180
gtgtgggagg tttttaaag caagtaa                                        207
```